US008952025B2

(12) United States Patent
Hecht et al.

(10) Patent No.: US 8,952,025 B2
(45) Date of Patent: Feb. 10, 2015

(54) MULTIFUNCTIONAL RADICAL QUENCHERS AND THEIR USES

(71) Applicants: Sidney Hecht, Phoenix, AZ (US); Omar Khdour, Tempe, AZ (US); Jun Lu, Tempe, AZ (US); Pablo Arce, Tempe, AZ (US)

(72) Inventors: Sidney Hecht, Phoenix, AZ (US); Omar Khdour, Tempe, AZ (US); Jun Lu, Tempe, AZ (US); Pablo Arce, Tempe, AZ (US)

(73) Assignee: Arizona Board of Regents, A Body Corporate of the State of Arizona Acting for and on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/855,133

(22) Filed: Apr. 2, 2013

(65) Prior Publication Data
US 2013/0267546 A1 Oct. 10, 2013

Related U.S. Application Data

(63) Continuation of application No. 13/520,642, filed as application No. PCT/US2011/025613 on Feb. 21, 2011, now abandoned.

(60) Provisional application No. 61/306,036, filed on Feb. 19, 2010.

(51) Int. Cl.
| | | |
|---|---|---|
| A01N 43/54 | (2006.01) | |
| A61K 31/505 | (2006.01) | |
| C07D 239/47 | (2006.01) | |
| C07D 213/74 | (2006.01) | |
| C07D 237/22 | (2006.01) | |
| C07D 239/42 | (2006.01) | |
| C07D 213/73 | (2006.01) | |
| C07D 239/52 | (2006.01) | |
| C07D 403/04 | (2006.01) | |
| C07D 471/04 | (2006.01) | |

(52) U.S. Cl.
CPC ............ *C07D 239/47* (2013.01); *C07D 213/74* (2013.01); *C07D 237/22* (2013.01); *C07D 239/42* (2013.01); *C07D 213/73* (2013.01); *C07D 239/52* (2013.01); *C07D 403/04* (2013.01); *C07D 471/04* (2013.01)
USPC ........... 514/269; 514/272; 514/351; 544/319; 544/320; 546/300; 546/303

(58) Field of Classification Search
CPC .. C07D 213/02; C07D 237/14; C07D 237/16; C07D 239/36; C07D 239/52
USPC ........... 544/319, 320; 546/300, 303; 514/345, 514/351, 269, 272
See application file for complete search history.

(56) References Cited

U.S. PATENT DOCUMENTS

| | | | | | |
|---|---|---|---|---|---|
| 5,340,815 | A | * | 8/1994 | Connor et al. | 514/269 |
| 5,356,898 | A | * | 10/1994 | Belliotti et al. | 514/269 |
| 5,849,761 | A | * | 12/1998 | Yaksh | 514/327 |
| 6,835,216 | B2 | * | 12/2004 | Pratt et al. | 44/335 |
| 7,547,709 | B2 | * | 6/2009 | Pratt et al. | 514/300 |

FOREIGN PATENT DOCUMENTS

| | | |
|---|---|---|
| WO | 0200683 A2 | 1/2002 |
| WO | WO 03007950 A1 * | 1/2003 |

OTHER PUBLICATIONS

B.R. Kim et al., 30 Bulletin of the Korean Chemical Society, 2107-2110 (2009).*
B.E. Fisher et al., 29 Journal of Organic Chemistry, 776-781 (1964).*
R.F. Brown et al., Journal of Organic Chemistry, 388-389 (1946).*
S. A. Harris et al., 61 Journal of the American Chemical Society 1245-1247 (1939).*
K.H. Chung et al., 44 Zeitschrift fuer Naturforschung, C: Journal of Biosciences 609-616 (1989).*
S.D. L'vova et al., 11 Zhurnal Organicheskoi Khimii, 1537-1540 (1975).*
S.D. L'voya et al., 11 Zhurnal Organicheskoi Khimii, 1537-1540 (1975).*
P. Calza et al., 86 International Journal of Environmental Analytical Chemistry, 265-275 (2006).*
W. Korytnyk et al., 15 Biochemistry, 5458-5466 (1976).*
Abe, K., et al., "Marked Reduction in CSF Lactate and Pyruvate Levels After CoQ Therapy in a Patient with Mitochondrial Myopathy, Encephalopathy, Lactic Acidosis and Stroke-like Episodes (MELAS)," Acta Neurol. Scand., 1991, pp. 356-359, vol. 83.
Armstrong, Jeffrey S., et al., "Glutathione depletion enforces the mitochondrial permeability transition and causes cell death in Bcl-2 overexpressing HL60 cells," FASEB J., Aug. 2002, pp. 1263-1265, vol. 16, No. 10.
Armstrong, Jeffrey S., et al., "The coenzyme Q10 analog decylubiquinone inhibits the redox-activated mitochondrial permeability transition: role of mitochondrial respiratory chain complex III," J. Biol. Chem., Dec. 2003, pp. 49079-49084, vol. 278, No. 49.
Armstrong, Jeffrey S., et al., "Cysteine starvation activates the redox-dependent mitochondrial permeability transition in retinal pigment epithelial cells," Invest. Ophthalmol. Vis. Sci., Nov. 2004, pp. 4183-4189, vol. 45, No. 11.
Armstrong, Jeffrey S., et al., "Does Oxidative Stress Contribute to the Pathology of Friedreich's Ataxia? A Radical Question," FASEB J., Jul. 2010, pp. 2152-2163, vol. 24, No. 7.

(Continued)

*Primary Examiner* — James O Wilson
*Assistant Examiner* — Alexander R Pagano
(74) *Attorney, Agent, or Firm* — McDonnell Boehnen Hulbert & Berghoff LLP

(57) ABSTRACT

The present disclosure provides biologically active compounds of formula (I): and pharmaceutically acceptable salts thereof: compositions comprising these compounds, and methods of using these compounds in a variety of applications, such as treatment or suppression of diseases associated with decreased mitochondrial function resulting in diminished ATP production and/or oxidative stress and/or lipid peroxidation.

31 Claims, 26 Drawing Sheets

(56) References Cited

OTHER PUBLICATIONS

Asin-Cayuela, Jordi, et al., "Fine-tuning the hydrophobicity of a mitochondria-targeted antioxidant," FEBS Lett., Jul. 2004, pp. 9-16, vol. 571, Nos. 1-3.

Atamna, Hani, et al., "Methylene blue delays cellular senescence and enhances key mitochondrial biochemical pathways," FASEB J., Mar. 2008, pp. 703-712, vol. 22, No. 3.

Barbiroli, B. et al., "Coenzyme Q10 Improves Mitochondrial Respiration in Patients with Mitochondrial Mytopathies. An in Vivo Study on Brain and Skeletal Muscle by Phosphorous Magnetic Resonance Spectroscopy," Cell. Mol. Biol., Jul. 1997, pp. 741-749, vol. 43.

Barnham, Kevin J., et al., "Neurodegenerative diseases and oxidative stress," Nat. Rev. Drug Discovery, Mar. 2004, pp. 205-214, vol. 3.

Benard, Giovanni, et al., "Ultrastructure of the mitochondrion and its bearing on function and bioenergetics," Antioxid. Redox. Signal., Nov. 2008, pp. 1312-1342, vol. 18, No. 8.

Bencze, Krisztina Z., et al., "Human Fraxatin: Iron and Ferrochelatase Binding Surface," Chem. Commun., May 2007, pp. 1798-1800, vol. 18.

Bendahan, D., et al., "31P NMR Spectroscopy and Ergometer Exercise Test as Evidence for Muscle Oxidative Performance Improvement with Coenzyme Q in Mitochondrial Myopathies," Neurology, Jun. 1992, pp. 1203-1208, vol. 42, No. 6.

Boduszek, Bogdan, et al., "A new method for the preparation of pyridine-4-phasphonic acids," Synthesis, 1979, pp. 452-453, vol. 1979, No. 6.

Bradley, J. L., et al., "Clinical, Biochemical and Molecular Genetic Correlations in Friedreich's Ataxia," Hum. Mol. Genet., 2000, pp. 275-282. vol. 9, No. 2.

Bresolin, N., et al., "Clinical and Biochemical Correlations in Mitochondrial Myopathies Treated with Coenzyme Q10," Neurology, Jun. 1988, pp. 892-899, vol. 38, No. 6.

Bresolin, N., et al., "Ubidecarenone in the Treatment of Mitochondrial Myopathies: a Multi-Center Double-Blind Trial," J. Neurol. Sci., Dec. 1990, pp. 70-78, vol. 100, Nos. 1-2.

Brigelius-Flohe, Regina, et al., "Vitamin E: function and metabolism," FASEB J., Jul. 1999, pp. 1145-1155, vol. 13, No. 10.

Bulteau, Anne-Laure, et al., "Frataxin Acts as an Iron Chaperone Protein to Modulate Mitochondrial Aconitase Activity," Science, Jul. 2004, pp. 242-245, vol. 305.

Burton, G. W., et al., "Vitamin E: application of the principles of physical organic chemistry to the exploration of its structure and function," Acc. Chem. Res., 1986, pp. 194-201, vol. 19.

Cadenas, Enrique, et al., "Mitochondrial free radical generation, oxidative stress and aging," Free Radic. Biol. Med., Aug. 2000, pp. 222-230, vol. 29, Nos. 3-4.

Cadenas, Enrique, "Mitochondrial free radical production and cell signaling," Mol. Aspects Med., Feb.-Apr. 2004, pp. 17-26, vol. 25, Nos. 1-2.

Calabrese, Vittorio, et al., "Oxidative stress, mitochondrial dysfunction and cellular stress response in Friedreich's ataxia," J. Neurol. Sci., Jun. 2005, pp. 145-162, vol. 233, Nos. 1-2.

Campuzano, Victoria, et al., "Friedreich's Ataxia: Autosomal Recessive Disease Caused by an Intronic GAA Triplet Repeat Expansion," Science , Mar. 1996, pp. 1423-1427, vol. 271, No. 5254.

Campuzano, Victoria, et al., "Frataxin is Reduced in Friedreich Ataxia Patients and is Associated with Mitochondrial Membranes," Hum. Mol. Genet., 1997, pp. 1771-1780, vol. 6, No. 11.

Castilho, Roger F., et al., "Oxidative damage of mitochondria induced by Fe(II)citrate is potentiated by Ca and includes lipid peroxidation and alterations in membrane proteins," Arch. Biochem. Biophys., Jan. 1994, pp. 158-163, vol. 308, No. 1.

Chua, Yee Liu, et al., "Oltipraz-induced phase 2 enzyme response conserved in cells lacking mitochondrial DNA," Biochem. Biophys. Res. Commun., Nov. 2005, pp. 375-381, vol. 337, No. 1.

Corey, Elias James, et al., "New and highly effective method for the oxidation of primary and secondary alcohols to carbonyl compound," J. Am. Chem. Soc., 1972, pp. 7586-7587, vol. 94, No. 21.

Corey, Elias James, et al., "Pyridinium Chlorochromate, An Efficient Reagent for Oxidation of Primary and Secondary Alcohols to Carbonyl Compounds," Tetrahedron Lett., 1975, pp. 2647-2650, vol. 31.

Crompton, Martin, "The mitochondrial permeability transition pore and its role in cell death," Biochem. J., 1999, pp. 233-249, vol. 341.

D'Alessio, M., et al., "Apoptotic GSH extrusion is associated with free radical generation," Ann. N.Y. Acad. Sci., Dec. 2003, pp. 449-452, vol. 1010.

De Hingh, Yvette C., et al., "Direct Measurement of Lipid Peroxidation in Submitochondrial Particles," Biochemistry, 1995, pp. 12755-12760, vol. 34.

Dimauro, Salvatore, et al., "Mitochondrial DNA mutations in human disease," Am. J. Med. Genet, Spr. 2001, pp. 18-26, vol. 106, No. 1.

Dimauro, Salvatore, et al., "Mitochondrial disorders in the nervous system," Annu. Rev. Neurosci., Jul. 2008, pp. 91-123, vol. 31.

Dröge, Wulf, "Free radicals in the physiological control of cell function," Physiol. Rev., Jan. 2002, pp. 47-95, vol. 82, No. 1.

Drummen, Gregor P., et al., "C11-BODIPY (581/591), an oxidation-sensitive fluorescent lipid peroxidation probe: (micro)spectroscopic characterization and validation of methodology," Free Radical Biol. Med., Aug. 2002, pp. 473-490, vol. 33, No. 4.

Durr, M.D., Alexandra, et al., "Clinical and Genetic Abnormalities in Patients with Friedreich's Ataxia," New Engl. J. Med., Oct. 1996, pp. 1169-1175, vol. 335, No. 16.

Ehrenberg, Benjamin, et al., "Membrane potential can be determined in individual cells from the Nernstian distribution of cationic dye," Biophys. J., May 1988, pp. 785-794, vol. 53, No. 5.

Finkel, Toren, "Oxidant signals and oxidative stress," Curr. Opin. Cell Biol., Apr. 2003, pp. 247-254, vol. 15, No. 2.

Fridovich, Irwin, "Fundamental aspect of reactive oxygen species, or what's the matter with oxygen?" Ann. N.Y. Acad. Sci., Nov. 1999, pp. 13-18, vol. 893.

Frigerio, Marco, et al., "A User-Friendly Entry to 2-Iodoxybenzoic Acid (IBX)," J. Org. Chem., Jun. 1999, pp. 4537-4538, vol. 64, No. 12.

Gaetani, Gian Franco, et al., "Catalase and glutathione peroxidase are equally active in detoxification of hydrogen peroxide in human erythrocytes," Blood, Jan. 1989, pp. 334-339, vol. 73, No. 1.

Garcia-Rivas, G De J, et al., "Ru360, a specific mitochondrial calcium uptake inhibitor, improves cardiac post-ischaemic functional recovery in rats in vivo," Br. J. Pharmacol., Dec. 2006, pp. 829-837, vol. 149, No. 7.

Genova, Maria L., et al, "Mitochondrial production of oxygen radical species and the role of Coenzyme Q as an antioxidant," Exp. Biol. Med., May 2003, pp. 506-513, vol. 228, No. 5.

Gille, Lars, et al., "Redox-Interaction of Alpha-Tocopheryl Quinone with Isolated Mictochondrial Cytochrome bc1 Complex," Biochem. Pharmacol., Jul. 2004, pp. 373-381, vol. 68, No. 2.

Gillis, J.C., et al., "Idebenone. A review of its pharmacodynamic and pharmacokinetic properties, and therapeutic use in age-related cognitive disorders," Drugs Aging, Aug. 1994, pp. 133-152, vol. 5, No. 2.

Goda, S., et al., "Clinical improvement after administration of coenzyme Q10 in a patient with mitochondrial encephalomyopathy," J. Neurol., Jan. 1985, pp. 62-63, vol. 234, No. 1.

Gold, R., et al., "Phosphorus Magnetic Resonance Spectroscopy in the Evaluation of Mitochondrial Myopathies: Results of a 6-Month Therapy Study with Coenzyme Q," Eur. Neurol., 1996, pp. 191-196, vol. 36, No. 4.

Gonzalez-Cabo, Pilar, et al., "Frataxin Interacts Functionally with Mitochondrial Electron Transport Chain Proteins," Hum. Mol. Genet., 2005, pp. 2091-2098. vol. 14, No. 15.

Green, Douglas R., et al., "Mitochondria and apoptosis," Science, Aug. 1998, pp. 1309-1312, vol. 281, No. 5381.

Gregor, Wolfgang, et al., "Distribution of Tocopheryl Quinone in Mitochondrial Membranes and Interference with Ubiquinone-Mediated Electron Transfer," Biochem. Pharmacol., May 2006, pp. 1589-1601, vol. 71, No. 11.

Zhang, Dawei, et al., "The mitochondrial permeability transition regulates cytochrome c release for apoptosis during endoplasmic reticulum stress by remodeling the cristae junction," J. Biol. Chem., Feb. 2008, pp. 3476-3486, vol. 283, No. 6.

(56) References Cited

OTHER PUBLICATIONS

Zierz, Stephan, et al., "Exogenous Coenzyme Q (Coq) fails to increase Coq in Skeletal Muscle of Two Patients with Mitochondrial Myopathies," J. Neurol. Sci., Mar. 1990, pp. 283-290, vol. 95, No. 3.
Zimmerman, Matthew C., et al., "Mitochondrial Dysfunction and Mitochondrial-Produced Reactive Oxygen Species: New Targets for Neurogenic Hypertension?" Hypertension, 2008, 53, pp. 112-114, vol. 53.
International Search Report and Written Opinion for PCT/US2011/025613, 14 pages. Jul. 25, 2011.
International Preliminary Report on Patentability for PCT/US2011/025613, 8 pages. Aug. 12, 2012.
Niki, Etsuo, et al., "Dynamics of antioxidant action of vitamin E," Acc. Chem. Res., Jan. 2004, pp. 45-51, vol. 37, No. 1.
Omura, Kanji, et al., "Oxidation of alcohols by 'activated' dimethyl sulfoxide. a preparative, steric and mechanistic study," Tetrahedron, 1978, pp. 1651-1660, vol. 34, No. 11.
Ogasahara, Saburo, et al., "Improvement of Abnormal Pyruvate Metabolism and Cardiac Conduction Defect with Coenzyme Q10 in Kearns-Sayre Syndrome," Neurology, 1985, pp. 372-377, vol. 35, No. 3.
Osakada, Fumitaka, et al., "Neuroprotective effects of a-tocopherol on oxidative stress in rat striatal cultures," Eur. J. Pharmacol., Mar. 2003, pp. 15-22, vol. 465, Nos. 1-2.
Osakada, Fumitaka, et al., "Alpha-Tocotrienol provides the most potent neuroprotection among vitamin E analogs on cultured striatal neurons," Neuropharmacology, Nov. 2004, pp. 904-915, vol. 47, No. 6.
Ouahchi, Karim, et al., "Ataxia with Isolated Vitamin E Deficiency is Caused by Mutations in the Alpha-Tocopherol Transfer Protein," Nat. Genet., Feb. 1995, pp. 141-145, vol. 9.
Palozza, Paola, et al., "Design, synthesis, and antioxidant potency of novel alpha-tocopherol analogues in isolated membranes and intact cells," Free Radic. Biol. Med., Apr. 2008, pp. 1452-1464, vol. 44, No. 7.
Pap, E.H.W., et al., "Ratio-fluorescence microscopy of lipid peroxidation in living cells using C11-BODIPY581/591," FEBS Lett., Jun. 1999, pp. 278-282, vol. 453, No. 3.
Park, Sungjo, et al., "Yeast Frataxin Sequentially Chaperones and Stores Iron by Coupling Protein Assembly with Iron Oxidation," J. Biol. Chem., Aug. 2003, pp. 31340-31351, vol. 278, No. 33.
Piancatelli, G., et al., "Pyridinium chlorochromate: A versatile oxidant in organic synthesis," Synthesis, 1982, pp. 245-258, vol. 1982, No. 4.
Pisano, R, et al., "Plasma Concentrations and Pharmacokinetics of Idebenone and its Metabolites Following Single and Repeated Doses in Young Patients with Mitochondrial Encephalomyopathy," Eur. J. Clin. Pharmacol., Oct. 1996, 167-169, vol. 51, No. 2.
Pratt, Derek A., et al., 5-Pyrimidinols: novel chain-breaking antioxidants more effective than phenols, J. Am. Chem. Soc., 2001, pp. 4625-4626, vol. 123.
Quinzii, Catarina M., et al., "Respiratory chain dysfunction and oxidative stress correlate with severity of primary COQ10 deficiency," FASEB J., Jun. 2008, pp. 1874-1885, vol. 22, No. 6.
Reddy, P. Hemachandra, "Amyloid precursor protein-mediated free radicals and oxidative damage: implications for the development and progression of Alzheimer's disease," J. Neurochem., Jan. 2006, pp. 1-13, vol. 96, No. 1.
Reddy, P. Hemachandra, et al., "Are mitochondria critical in the pathogenesis of Alzheimer's disease?" Brain Res. Rev., Nov. 2005, pp. 618-632, vol. 49, No. 3.
Robinson, B.H., et al., "Nonviability of cells with oxidative defects in galactose medium: A screening test for affected patient fibroblast," Biochem. Med. Metab. Biol., Oct. 1992, pp. 122-126, vol. 48, No. 2.
Rotig, Agnes, et al., Molecular Insights into Friedreich's Ataxia and Antioxidant-Based Therapies, Trends Mol. Med., May 2002, pp. 221-224, vol. 8, No. 5.
Rustin, Pierre, et al., "Idebenone Treatment in Friedreich Patients: One-year-long Randomized Placebo-controlled Trial," Neurology, Feb. 2004, pp. 524-525, vol. 62, No. 3.
Scavo, Frank, et al., "Preparation of alpha,beta-dehydro-beta-amino acid derivatives by tin-promoted addition of malonates to simple nitriles," Tetrahedron Lett., 1985, pp. 2603-2606, vol. 26, No. 22.
Shue, Shey-Shing, et al., "Targeting antioxidants to mitochondria: a new therapeutic direction," Biochim. Biophys. Acta, Feb. 2006, pp. 256-265, vol. 1762, No. 2.
Smith, Archie L., "Preparation, properties, and conditions for assay of mitochondria: slaughterhouse material, small-scale," Methods Enzymol., 1967, pp. 81-86, vol. 10.
Smith, P. K., "Measurement of protein using bicinchoninic acid," Anal. Biochem., Oct. 1985, pp. 76-85, vol. 150, No. 1.
Smith, Robin A., et al., "Delivery of bioactive molecules to mitochondria in vivo," Proc. Natl. Acad. Sci., Apr. 2003, pp. 5407-5412, vol. 100, No. 9.
Smith, Robin A., et al., "Using mitochondria-targeted molecules to study mitochondrial radical production and its consequences," Biochem. Soc. Trans., 2003, pp. 1295-1299, vol. 31, Part 6.
Syper, Ludwik, "The Baeyer-Villiger Oxidation of Aromatic Aldehydes and Ketones with Hydrogen Peroxide Catalyzed by Selenium Compounds. A Convenient Method for the Preparation of Phenols," Synthesis, Mar. 1989, pp. 167-172, No. 3.
Takano, Seiichi, et al., "Asymmetric construction of optically active 3-hydroxyalkyne functionalities," J. Chem. Soc., Chem. Commun., Sep. 1989, pp. 1344-1345, No. 18.
Takano, Seiichi, et al., "An Efficient Stereoselective Preparation of Vitamin E (Alpha-Tocopherol) from Phytol," Synlett, Aug. 1990, pp. 451-452, No. 8.
Takenaka, Yoshito, et al., "The effect of alpha-tocopherol as an antioxidant on the oxidation of membrane protein thiols induced by free radicals generated in different sites," Arch. Biochem. Biophys., Mar. 1991, pp. 344-350, vol. 285, No. 2.
Tallman, Keri A., et al., "Kinetic products of linoleate peroxidation: rapid beta-fragmentation of nonconjugated peroxyls," J. Am. Chem. Soc., Nov. 2001, pp. 11827-11828, vol. 123, No. 47.
Tirmenstein, M. A., et al., "Glutathione depletion and the production of reactive oxygen species in isolated hepatocyte suspensions," Chem. Biol. Interact., Jul. 2000, pp. 201-217, vol. 127, No. 3.
Traber, Maret G., et al., "Preferential incorporation of alpha-tocopherol vs gamma-tocopherol in human lipoproteins," J. Am. Clin. Nutr., Mar. 1989, pp. 517-526, vol. 49, No. 3.
Traber, Maret G., et al., "Human plasma vitamin E kinetics demonstrate rapid recycling of plasma RRR-alphatocopherol," Proc. Natl. Acad. Sci., Oct. 1994, pp. 10005-10008, vol. 91, No. 21.
Trnka, Jan, et al., "Antioxidant properties of MitoTEMPOL and its hydroxylamine," Free Radic. Res., Jan. 2009, pp. 4-12, vol. 43, No. 1.
Trounce, Ian A., et al., "Assessment of mitochondrial oxidative phosphorylation in patient muscle biopsies, lymphoblasts, and transmitochondrial cell lines," Methods Enzymol., 1996, pp. 484-509, vol. 264.
Turrens, Julio F., "Mitochondrial formation of reactive oxygen species," J. Physiol., Oct. 2003, pp. 335-344, vol. 552, No. 2.
Van Haaften, Rachel I.M., et al, "No Reduction of Alpha-Tocopherol Quinone by Glutathione in Rat Liver," Biochem. Pharmacol., 2001, pp. 715-719, vol. 61.
Viehe, Heinz G., et al., "The Captodative Effect," Acc. Chem. Res., 1985, pp. 148-154, vol. 18.
Wallace, Douglas C., "Mouse Models for Mitochondrial Disease," Am. J. Med. Genet., Spr. 2001, pp. 71-93, vol. 106, No. 1.
Wijtmans, Maikel, et al., "6-Amino-3-pyridinols: towards diffusion-controlled chain-breaking antioxidants," Angew. Chem. Int. Ed. Engl., Sep. 2003, pp. 4370-4373, vol. 42, No. 36.
Wijtmans, Maikel, et al., "Synthesis and Reactivity of Some 6-Substituted-2,4-dimethyl-3-pyridinols, a Novel Class of Chain-Breaking Antioxidants," J. Org. Chem., 2004, pp. 9215-9223, vol. 69, No. 26.
Wilson, Robert B., et al., "Respiratory Deficiency Due to Loss of Mitochondrial DNA in Yeast Lacking the Frataxin Homologue," Nat. Genet., Aug. 1997, pp. 352-357, vol. 16.
Wilson, Robert B., "Frataxin and Frataxin Deficiency in Friedreich's Ataxia," J. Neurol. Sci., 2003, pp. 103-105, vol. 207.
Wright, Alan F., et al., "Lifespan and mitochondrial control of Neurodegeneration," Nat. Genet., 2004, pp. 1153-1158, vol. 36.
Wu, Guey-Shuang, et al., "Autoxidation of phosphatidylcholine liposomes," Lipids, Jun. 1982, pp. 403-413, vol. 17, No. 6.

(56) References Cited

OTHER PUBLICATIONS

Yamada, Satoshi, et al., "Immunochemical Detection of a Lipofuscin-like Fluorophore Derived from Malondialdehyde and Lysine," J. Lipid Res., Aug. 2001, pp. 1187-1196, vol. 42.

Yin, Dazhong, "Biochemical Basis of Lipofuscin, Ceroid and Age Pigment-like Fluorophores," Free Radical Biol. Med., 1996, pp. 871-888, vol. 21, No. 6.

Ying, Wen Long, et al., "Inhibition of mitochondrial calcium ion transport by an oxo-bridged dinuclear ruthenium ammine complex," Biochemistry, May 1991, pp. 4949-4952, vol. 30, No. 20.

Yoon, Taejin, et al., "Iron-Sulfur Cluster Biosynthesis. Characterization of Frataxin as an Iron Donor for Assembly of [2Fe-2S] Clusters in ISU-Type Proteins," J. Am Chem. Soc., 2003, pp. 6078-6084, vol. 125.

Yoon, Taejin, et al., "Frataxin-Mediated Iron Delivery to Ferrochelatase in the Final Step of Heme Biosynthesis," J. Biol. Chem., Jun. 2004, pp. 25943-25946, vol. 279, No. 25.

Zhang, Dawei, et al., "Bax and the mitochondrial permeability transition cooperate in the release of cytochrome c during endoplasmic reticulum-stress-induced apoptosis," Cell Death Differ., 2007, pp. 703-715, vol. 14.

Griffith, Owen W., et al., "Potent and specific inhibition of glutathione synthesis by buthionine sulfoximine (S-n-butyl homocysteine sulfoximine)," J. Biol. Chem., Aug. 1979, pp. 7558-7560, vol. 254.

Hart, Paul E., et al., "Antioxidant treatment of patients with Friedreich ataxia: four-year follow-up," Arch. Neurol., Apr. 2005, pp. 621-626, vol. 62, No. 4.

Henze, Katrin, et al., "Evolutionary Biology: Essence of Mitochondria," Nature, Nov. 2003, pp. 127-28, vol. 426, No. 6963.

Ihara, Yuetsu, et al., "Mitochondrial Encephalomyopathy (MELAS): Pathological Study and Successful Therapy with Coenzyme Q10 and Idebenone," J. Neurol. Sci., May 1989, pp. 263-271, vol. 90, No. 3.

Ikejiri, M.D., Y., et al., "Idebenone Improves Cerebral Mitochondrial Oxidative Metabolism in a Patient with MELAS," Neurology, Aug. 1996, pp. 583-585, vol. 47, No. 2.

Infante, Juan P., "A Function for the Vitamin E metabolite [alpha]-Tocopherol Quinone as an Essential Enzyme Cofactor for the Mitochondrial Fatty Acid Desaturases," FEBS Lett., Mar. 1999, pp. 1-5, vol. 446, No. 1.

Ingold, K. U., et al., "A new vitamin E analogue more active than a-tocopherol in the rat curative myopathy bioassay," FEBS Lett., Sep. 1986, pp. 117-120, vol. 205, No. 1.

Inoue, Seiichi, et al., "Improved General Method of Ortho Alkylation of Phenols Using Alkyl Isopropyl Sulfide, Sulfuryl Chloride, and Triethylamine. An Expedient Synthesis of Representative Oxygen Heterocycles and (2R ,4'R,8'R)-alpha-Tocopherol," J. Org. Chem., 1987, 52, 5495.

Itoh, Takashi, et al., "The substitution of 5-halo-1, 2, 3-triazines with electrolytically generated superoxide," Tetrahedron, 1991, pp. 4317-4324, vol. 47, No. 25.

Iuliano, Luigi, et al., "Protection of low density lipoprotein oxidation by the antioxidant agent IRFI005, a new synthetic hydrophilic vitamin E analogue," Free Radic. Biol. Med., Apr. 1999, pp. 858-868, vol. 26, Nos. 7-8.

James, Andrew M., et al., "Interactions of Mitochondria-Targeted and Untargeted Ubiquinones with the Mitochondrial Respiratory Chain and Reactive Oxygen Species," J. Biol. Chem., Jun. 2005, pp. 21295-21312, vol. 280, No. 22.

Jauslin, Mathias L., et al., "A cellular model for Friedreich Ataxia reveals small-molecule glutathione peroxidase mimetics as novel treatment strategy," Hum. Mol. Genet, 2002, pp. 3055-3063, vol. 11, No. 24.

Jenner, Peter, "Oxidative Stress in Parkinson's Disease," Ann. Neurol., 2003, pp. S26-S38, vol. 53, Supp. 3.

Jurma, Octavian P., et al., "Decreased glutathione results in calcium-mediated cell death in PC12," Free Radic. Biol. Med., 1997, pp. 1055-1066, vol. 23, No. 7.

Kamal-Eldin, Afaf, et al., "The chemistry and antioxidant properties of tocopherols and tocotrienols," Lipids, Jul. 1996, pp. 671-701, vol. 31, No. 7.

Kao, J.P., "Practical aspects of measuring [Ca2+] with fluorescent indicators," Methods Cell Biol.. 1994, pp. 155-181. vol. 40.

Katsuki, Tsutomu, e al., "The First Practical Method for Symmetric Epoxidation," J. Am. Chem. Soc., 1980, pp. 5974-5976, vol. 102.

Kelso, Geoffrey F., et al., "Selective Targeting of a Redox-active Ubiquinone to Mitochondria within Cells," J. Biol. Chem., Feb. 2001, pp. 4588-4596, vol. 276, No. 7.

Kim, Hye-Young, et al., "Lipid-soluble 3-pyridinol antioxidants spare alpha-tocopherol and do not efficiently mediate peroxidation of cholesterol esters in human low-density lipoprotein," J. Med. Chem., Nov. 2005, pp. 6787-6789, vol. 48, No. 22.

Kohar, Indra, et al., "Is Alpha-Tocopherol a Reservoir for Alpha-Tocopheryl Hydroquinone?" Free Radical Biol. Med., Aug. 1995, pp. 197-207, vol. 19, No. 2.

Kowaltowski, Alicia J., et al., "The thiol-specific antioxidant enzyme prevents mitochondrial permeability transition," J. Biol. Chem., May 1998, pp. 12766-12769, vol. 273, No. 21.

Kowaltowski, Alicia J., et al., "Mitochondrial damage induced by conditions of oxidative stress," Free Radic. Biol. Med., Feb. 1999, pp. 436-471, vol. 26, Nos. 3-4.

Kowaltowski, Alicia J., et al., "Mitochondrial permeability transition and oxidative stress," FEBS Lett., Apr. 2001, pp. 12-15, vol. 495, Nos. 1-2.

Kuypers, Fras A., et al., "Parinaric acid as a sensitive fluorescent probe for the determination of lipid peroxidation," Biochim Biophys Acta., 1987, pp. 266-274, vol. 921.

La Marche, J.B., et al., "The Cardiomyopathy of Friedreich's Ataxia morphological observations in three cases," Can. J. Neurol. Sci., Nov. 1980, pp. 389-396, vol. 7, No. 4.

Lebel, Carl P., et al., "Evaluation of the probe 2',7'—dichlorofluorescin as an indicator of reactive oxygen species formation and oxidative stress," Chem. Res. Toxicol., 1992, pp. 227-231, vol. 5.

Leonard, J.V., et al., "Mitochondrial respiratory chain disorders I: mitochondrial DNA defects," Lancet, Jan. 2000, pp. 299-304, vol. 355, No. 9200.

Lerman-Sagie, T., et al., "Dramatic Improvement in Mitochondrial Cardiomyopathy Following Treatment with Idebenone," J. Inherit. Metab. Dis., 2001, pp. 28-34, vol. 24.

Ley, Steven V., et al., "Tetrapropylammonium Perruthenate, Pr4N+RuO4−, TPAP: A Catalytic Oxidant for Organic Synthesis," Synthesis, 1994, pp. 639-666, vol. 1994, No. 7.

Lin, Michael T., et al., "Mitochondrial dysfunction and oxidative stress in neurodegenerative diseases," Nature, Oct. 2006, pp. 787-795, vol. 443.

Lowes, Damon a., et al., "The mitochondria-targeted antioxidant MitoQ protects against organ damage in a lipopolysaccharide-peptidoglycan model of sepsis," Free Radical Biol. Med., 2008, pp. 1559-1565, vol. 45, No. 11.

Lu, C., et al., "Role of calcium and cyclophilin D in the regulation of mitochondrial permeabilization induced by glutathione depletion," Biochem. Biophys. Res. Commun., Nov. 2007, pp. 572-577, vol. 363, No. 3.

Lu, Jun, et al. "Design, synthesis and evaluation of an alpha-tocopherol analogue as a mitochondrial antioxidant," Bioorg. Med. Chem., Nov. 2010, pp. 7628-7638, vol. 18, No. 21.

MacCoubrey, I. C., et al., "Quantitative fluorescence measurements of cell viability (cytotoxicity) with a multi-well plate scanner," J. Cell Biol., p. 58a, vol. 111, No. 5, Part 2, (1990).

MacKenzie, Julia B., et al., "The Biological Activity of Alpha-Tocopherylhydroquinone and Alpha-Tocopherylquinone," J. Biol. Chem., 1950, pp. 655-662, vol. 183.

Manfredini, Stefano, et al., "Novel antioxidant agents deriving from molecular combinations of vitamins C and E analogues: 3,4-dihydroxy-5(R)-[2(R,S)-(6-hydroxy-2,5,7,8-tetramethyl-chroman-2(R,S)-yl-methyl)-[1,3]-dioxolan-4(S)-yl]-5H-furan-2-one and 3-O-octadecyl derivatives." Bioorg. Med. Chem., Dec. 2000, pp. 2791-2801, vol. 8, No. 12.

(56) References Cited

OTHER PUBLICATIONS

Manton, Kenneth G., et al., "ROS effects of on neurodegeneration in Alzheimer's disease and related disorders: on environmental stresses of ionizing radiation," Curr. Alzheimer Res. Nov. 2004, pp. 277-293, vol. 1, No. 4.

Markesbery, William R., et al., "Oxidative Alterations in Alzheimer's Disease," Brain Pathol., Jan. 1999, pp. 133-146, vol. 9. No. 1.

Markovits, Judith, et al., "Ethidium dimer: a new reagent for fluorimetric determination of nucleic acids," Anal. Biochem., Apr. 1979, pp. 259-264. vol. 94, No. 2.

Mates, Jose M., et al., "Antioxidant enzymes and human diseases," Clin. Biochem., Nov. 1999, pp. 595-603, vol. 32, No. 8.

Matlib, Mohammed A., et al., "Oxygen-bridged dinuclear ruthenium amine complex specifically inhibits Ca2+ uptake into mitochondria in vitro and in situ in single cardiac myocytes," J. Biol. Chem., Apr. 1998, pp. 10223-10231, vol. 273, No. 17.

Matthews, P.M., et al., "Coenzyme Q10 with Multiple Vitamins is Generally Ineffective in Treatment of Mitochondrial Disease," Neurology, May 1993, pp. 884-890, vol. 43, No. 5.

Matsuno-Yagi, Akemi, et al., "Studies on the Mechanism of Oxidative Phosphorylation: Catalytic Site Cooperativity in Atp Synthesis," J. Biol. Chem., Nov. 1985, pp. 14424-14427, vol. 260, No. 27.

Mcbride, Lincoln J., et al., "Amidine Protecting Groups for Oligonucleotide Synthesis," J. Am. Chem. Soc., 1986, pp. 2040-2048, vol. 108.

Minta, Akwasi, et al., "Fluorescent indicators for cytosolic calcium based on rhodamine and fluorescein chromophores," J. Biol. Chem., May 1989, pp. 8171-8178, vol. 264, No. 14.

Moore, Andrew N.J., et al., "Alpha-Tocopheryl Quinone is Converted into Vitamin E in Man," Free Radical Biol. Med., 1997, pp. 931-934, vol. 22, No. 2.

Moore, P. L., et al., "A rapid pH insensitive, two color fluorescence viability (cytotoxicity) assay," J. Cell Biol., 1990, p. 58a, vol. 111, Part 2.

Murphy, Michael P., et al., "Drug delivery to mitochondria: the key to mitochondrial medicine," J. Adv. Drug Deliv. Rev., Mar. 2000, pp. 235-250, vol. 41, No. 2.

Murphy, Michael P., "Development of lipophilic cations as therapies for disorders due to mitochondrial dysfunction," Expert Opin. Biol. Ther., Sep. 2001, pp. 753-764, vol. 1, No. 5.

Nam, Tae-Gyu, et al., "Tetrahydro-1,8-naphthyridinol analogues of alpha-tocopherol as antioxidants in lipid membranes and low-density lipoproteins," J. Am. Chem. Soc., Aug. 2007, pp. 10211-10219, vol. 129, No. 33.

\* cited by examiner

MULTIFUNCTIONAL RADICAL QUENCHERS AND THEIR USES

CROSS-REFERENCE TO RELATED APPLICATIONS

This application claims the benefit of the U.S. Provisional Application No. 61/306,036, filed Feb. 19, 2010, which is incorporated by reference herein in its entirety.

FIELD OF THE INVENTION

The present disclosure provides biologically active compounds multifunctional radical quenchers of formula (I) and pharmaceutically acceptable salts thereof, compositions comprising these compounds, and methods of using these compounds in a variety of applications, such as treatment or suppression of diseases associated with decreased mitochondrial function resulting in diminished ATP production and/or oxidative stress and/or lipid peroxidation.

SUMMARY OF THE INVENTION

Mitochondria are intracellular organelles responsible for a number of metabolic transformations and regulatory functions. They produce much of the ATP employed by eukaryotic cells. They are also the major source of free radicals and reactive oxygen species that cause oxidative stress. Consequently, mitochondrial defects are damaging, particularly to neural and muscle tissues which have high energy level demands. Thus, energetic defects have been implicated in forms of movement disorders, cardiomyopathy, myopathy, blindness, and deafness (DiMauro et al. (2001) *Am. J. Med. Genet.* 106, 18-26; Leonard et al. (2000) *Lancet.* 355, 299-304). There are a number of mitochondrial diseases resulting from both nuclear and mitochondrial genetic defects, and the underlying biochemistries of these diseases tend to be rather similar. They include increased lactate production, diminished respiration and ATP production, and reflect the consequences of oxidative stress. This invention describes novel compounds for the treatment or suppression of diseases associated with decreased mitochondrial function resulting in diminished ATP production and/or oxidative stress and/or lipid peroxidation. The invention also describes use of these compounds for the treatment of mitochondrial disorders, including but not limited to Friedreich's ataxia, Leber's Hereditary Optic Neuropathy, Kearns-Sayre Syndrome, Mitochondrial Encephalomyopathy with Lactic Acidosis and Stroke-Like Episodes and more generally, any disease associated with impairment of energy production and mitochondrial function.

Thus, in one aspect, the disclosure provides compounds of formula (I):

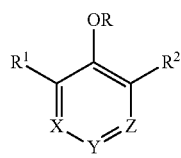

(I)

and pharmaceutically acceptable salts thereof.

Another aspect of the disclosure provides pharmaceutical compositions comprising the compounds and salts of the disclosure and an appropriate carrier, excipient or diluent. The exact nature of the carrier, excipient or diluent will depend upon the desired use for the composition, and may range from being suitable for veterinary uses to being suitable for human use. The compositions may optionally include one or more additional compounds suitable for a use.

Another aspect of the disclosure provides methods of treating or suppressing diseases associated with decreased mitochondrial function resulting in diminished ATP production and/or oxidative stress and/or lipid peroxidation, comprising administering an effective amount of the compound and salts of the disclosure.

Another aspect of the disclosure provides a method of treating or suppressing one or more of Friedreich's ataxia, Leber's Hereditary Optic Neuropathy, Kearns-Sayre Syndrome, Mitochondrial Encephalomyopathy with Lactic Acidosis and Stroke-Like Episodes, or Leigh syndrome, comprising administering an effective amount of the compound and salts of the disclosure.

Another aspect of the disclosure provides a method of treating or suppressing one or more of obesity, atherosclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, and Leigh syndrome, comprising administering an effective amount of the compound and salts of the disclosure.

The compounds of the invention increase ATP concentration in $CoQ_{10}$ deficient cells. In addition, the compounds of the invention inhibit lipid peroxidation and prevent reactive oxygen species (ROS) production in cells depleted of the antioxidant glutathione (GSH) using the chemical diethyl maleate. Moreover, these compounds all prevented ROS-dependent cell death after the cells were depleted of GSH. The antioxidant potential of the compounds described above is significantly increased compared to that of α-tocopherol and idebenone; therefore, these compounds have the potential of improved efficacy in clinical applications compared to α-tocopherol and idebenone.

DESCRIPTION OF THE SEVERAL VIEWS OF THE DRAWINGS

FIG. 1A, Comparison of the antioxidant activities of compound C and α-tocopherol. Compound C prevent lipid peroxidation in a concentration-dependent fashion with scavenging activity much higher than α-tocopherol. FIG. 1B, Compound C redox core lacking the phytol side chain (1,4,6-trimethyl-2,3-dihydro-1H-pyrrolo[2,3-b]pyridin-5-ol) is less effective than compound C itself. FIG. 1C, Compound A shows complete protection at 15 μM, and more effective in preventing lipid peroxidation than idebenone and its reduced form (Idebenol). The redox core of compound A, which is compound 12, is less active than compound A (with aliphatic side chain).

diethylmaleate (5 mM)+idebenone (5 µM); diethylmaleate (5 mM)+MRQ compound C; diethylmaleate (5 mM)+idebenone (5 µM) or diethylmaleate (5 mM)+α-tocopherol for 30 min, washed in HSSB buffer. The cells were loaded with dichlorofluorescein diacetate (10 µM) for 20 min, and the green fluorescence was measured by flow cytometry using the FL1-H channel. The figure shows a representative example of three independent experiments. In each analysis, 10,000 events were recorded. Increased DCF fluorescence, a measure of intracellular oxidation and ROS production, was determined by a shift in DCF fluorescence to the right on the X-axis of the FACS histogram. Results after gating cell populations for increased DCF fluorescence show that those MRQs A and B are significantly more effective in blocking diethylmaleate-induced ROS production compared to idebenone or its reduced form (Idebenol), while α-tocopherol-analog type compound C was more effective in protecting glutathione depleted CEM cells than α-tocopherol.

Figure 3:
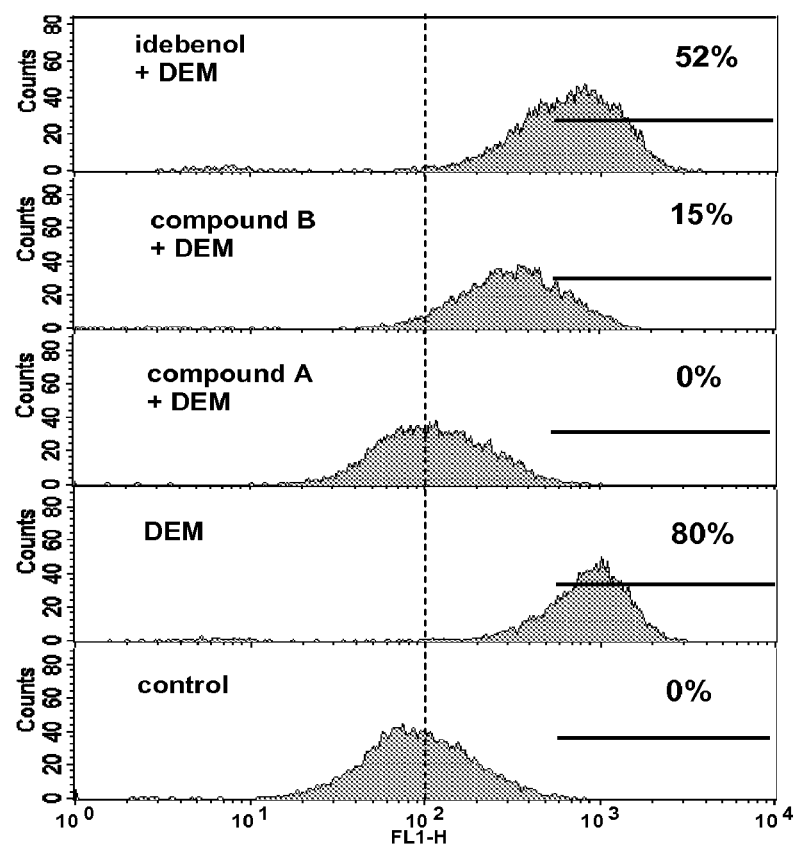

FIG. 3. Representative flow cytometric histograms showing ROS production in CEM cells. CEM cells were treated with media alone control (basal ROS level); diethylmaleate (DEM) (5 mM) (oxidative stress induced by glutathione depletion), diethylmaleate (5 mM)+MRQ compound A (1 µM); diethylmaleate (5 mM)+MRQ compound B (1 µM); diethylmaleate (5 mM)+idebenol (1 µM); for 30 min, washed in HSSB buffer. The cells were loaded with dichlorofluorescein diacetate (10 µM) for 20 min, and the green fluorescence was measured by flow cytometry using the FL1-H channel. The figure shows a representative example of three independent experiments. In each analysis, 10,000 events were recorded. Increased DCF fluorescence, a measure of intracellular oxidation and ROS production, was determined by a shift in DCF fluorescence to the right on the X-axis of the FACS histogram. Compound A again afforded complete protection when used at 1 µM concentration while compound B and idebenol were less effective at this concentration.

Figure 4:
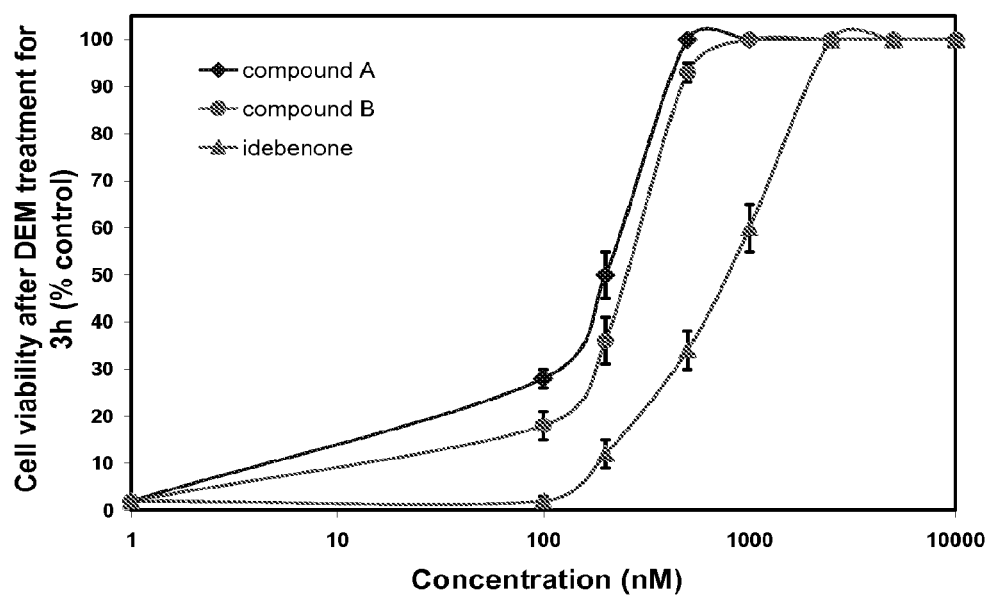

FIG. 4. Comparison of the cytoprotective effects of MRQs A and B (structures shown in FIG. 2) compared to idebenone. Viability of CEM cells treated with diethylmaleate for 3 h after pre-treatment with various concentrations of idebenone or MRQs A and B for 2 h. Cytotoxicity assay determined by trypan blue exclusion. The $EC_{50}$ (effective concentration that prevents 50% of cell death) for compound A, compound B and idebenone were 203±23 nM, 300±22 nM and 765±36 nM, respectively. Data are expressed as mean±S.E.M (n=3).

Figure 5:
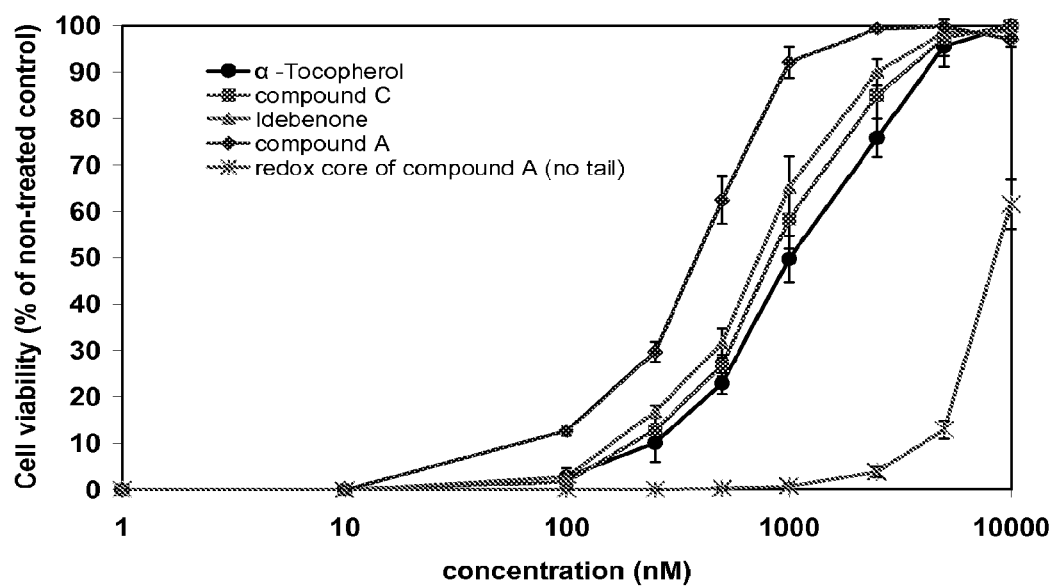

FIG. 5. Typical dose/response curves for idebenone, α-tocopherol, compound A, compound A redox core (compound 12), and compound C. Cellular viability after BSO treatment was measured by calcein-AM fluorescence of live cell. Cell viability is relative to non-BSO treated FRDA fibroblasts and is plotted against concentration. The $EC_{50}$ (effective concentration that prevents 50% of cell death) for compound A, compound C, idebenone and α-tocopherol were 390±28 nM, 833±75 nM, 710±80 nM and 1030±116 nM respectively. Data shown are from a typical experiment, repeated at least 3 times, and each point represents the mean±SD of three determinations.

Figure 6:
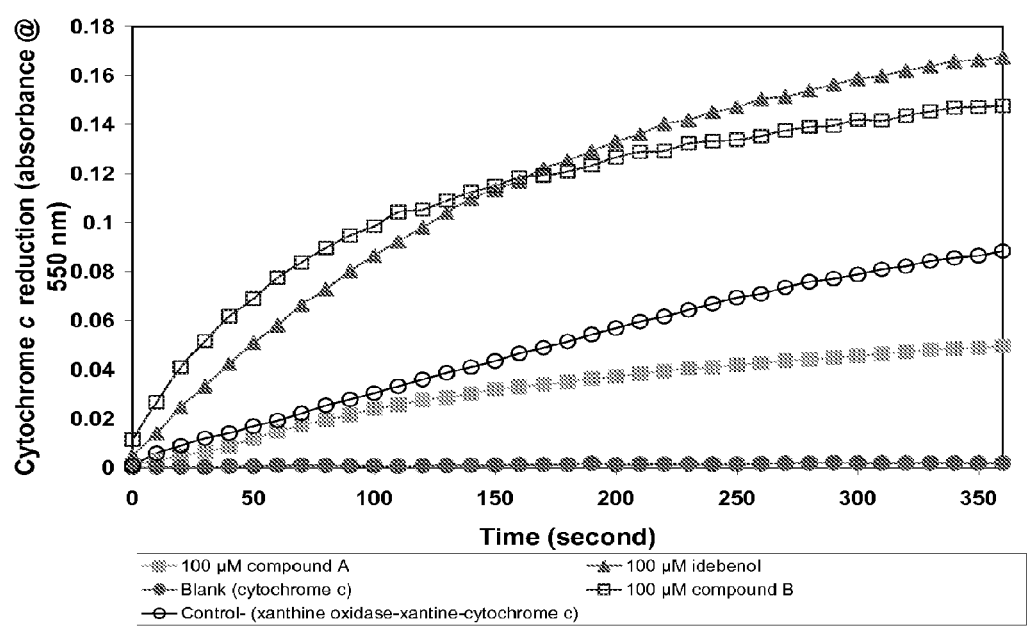

FIG. 6. Reduction of cytochrome c by superoxide (generated by xanthine oxidase) (opened circle), Idebenol (solid triangle), compound A (solid square) and compound B (open square).

FIG. 7A. Representative flow cytometric histograms overlay profile showing ROS production in CEM cells following pretreatment with the indicated compounds (0.5, 1 or 5 µM) The figure shows a representative example of three independent experiments. Increased DCF fluorescence, a measure of intracellular oxidation and ROS production, was determined by a shift in DCF fluorescence to the right on the x-axis of the FACS histogram. The data show that compounds A and B were more effective than idebenone at all tested concentrations.

FIG. 7B. A bar graph representation of the quantitation of the % mean fluorescence intensity in treated control (DEM) and drug-treated CEM cells calculated using CellQuest software. Data are expressed as means±SE (n=3). The data show that compounds A and B were more effective than idebenone at all tested concentrations.

Figure 8:
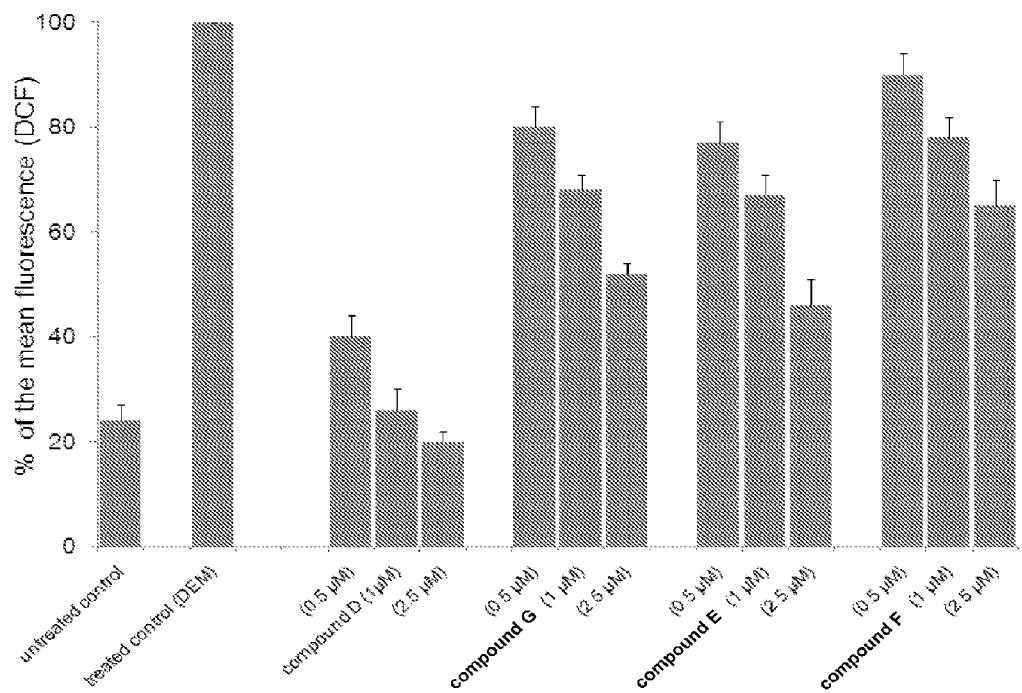

FIG. 8. A bar graph representation of the ROS production as the % mean fluorescence intensity in treated control (DEM) and drug-treated CEM cells following pretreatment with the indicated compounds (0.5, 1 or 5 µM). The fluorescence intensities in treated control cells are expressed as 100%. The figure shows a representative example of three independent experiments. Data are expressed as means±SE (n=3). The most effective compound in suppressing ROS was D.

Figure 9:
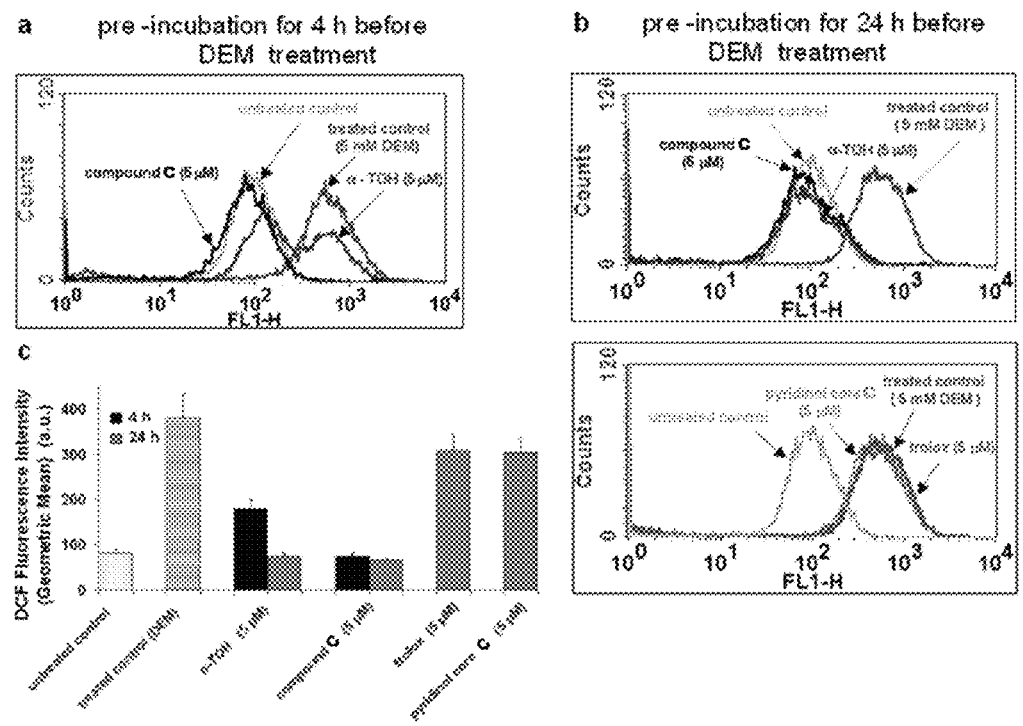

FIG. 9. Representative flow cytometric histograms overlay showing ROS production in CEM cells. Following pretreatment with the indicated compounds (5 µM) for 4 (panel a) or 24 h (panel b). Bottom left panel (c) shows a bar graph of mean DCF fluorescence values (a.u.) recorded by FACS and represents the geometric means of the above flow cytogram profiles calculated using CellQuest software. Data are expressed as means±SE (n=3). Compound C shows better protection against ROS production than α-tocopherol after a 4-hour preincubation while the redox cores of compound C (pyridinol core C) and α-tocopherol (trolox) lacking the phytyl side chain showed no protection FIG. 10. Representative flow cytometric histogram overlays showing ROS production in CEM cells following pretreatment with the indicated compounds (at 1 µM concentration) for 1, 3 or 6 hours, with or without 5 mM diethylmaleate (DEM). The figure shows a representative example of three independent experiments. Increased DCF fluorescence, a measure of intracellular oxidation and ROS production, was determined by a shift in DCF fluorescence to the right on the x-axis of the FACS histogram. Also shown is a bar graph of mean DCF fluorescence (a.u.) recorded by FACS and represents the geometric means of the above flow cytogram profiles calculated using CellQuest software. Data are expressed as means±SE (n=3) Compound C was clearly more effective than α-tocopherol in suppressing ROS.

Figure 11:
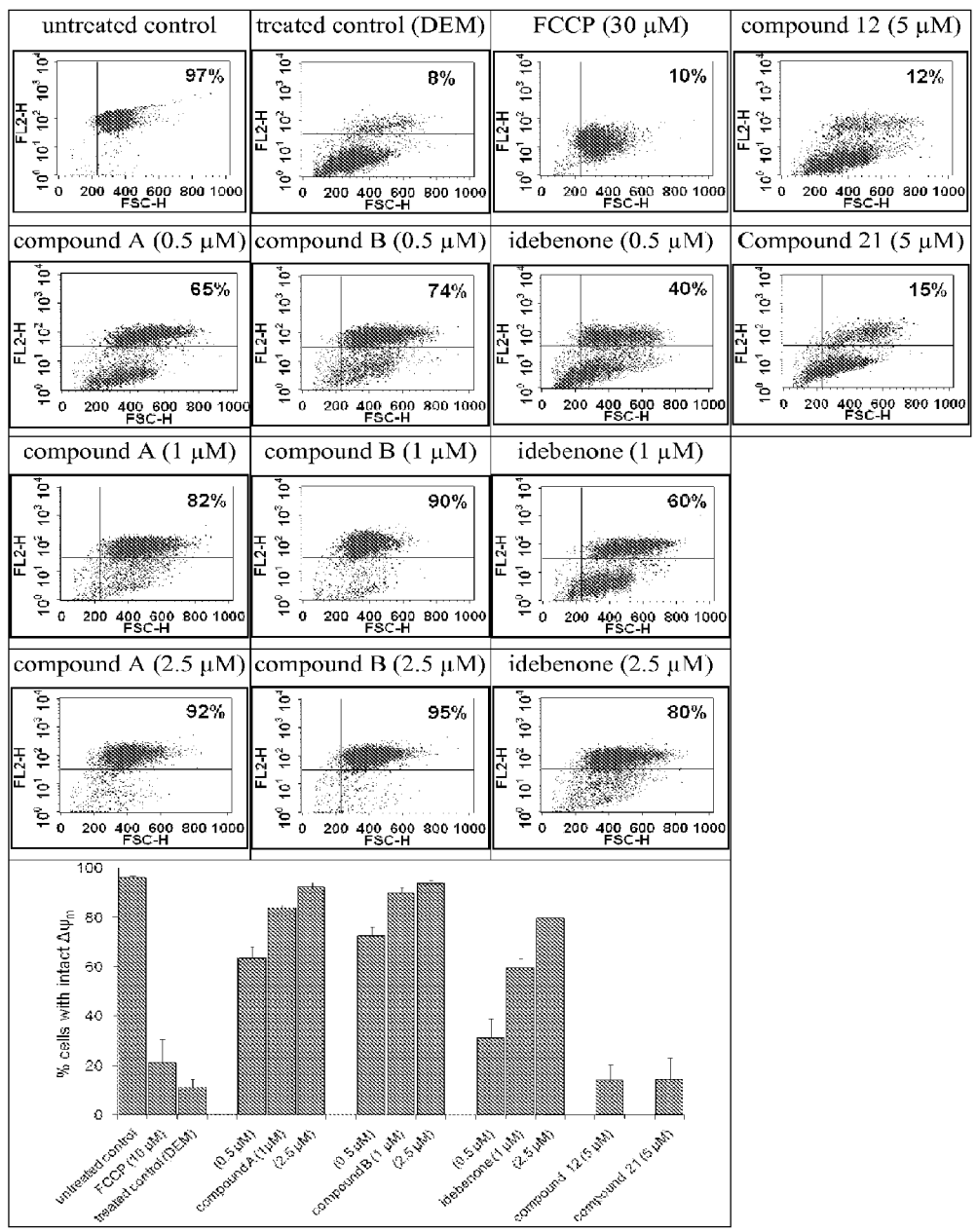

FIG. 11. Representative flow cytometric two dimensional color density dot plot analyses of mitochondrial membrane potential $\Delta_{\psi m}$ in CEM cells following pretreatment with the indicated compounds (0.5, 1, or 2.5 µM) overnight. The percentage of cells with intact $\Delta_{\psi m}$ is indicated in the top right quadrant of captions. Bottom of the figure shows a bar graph of means the percentage of cells with intact $\Delta_{\psi m}$ recorded by FACS. Data are expressed as means±SE (n=3). Compounds A and B were clearly more effective in maintaining mitochondrial membrane potential from oxidative than were idebenone, or the redox cores of A and B (i.e. the compounds lacking the side chains).

Figure 12:
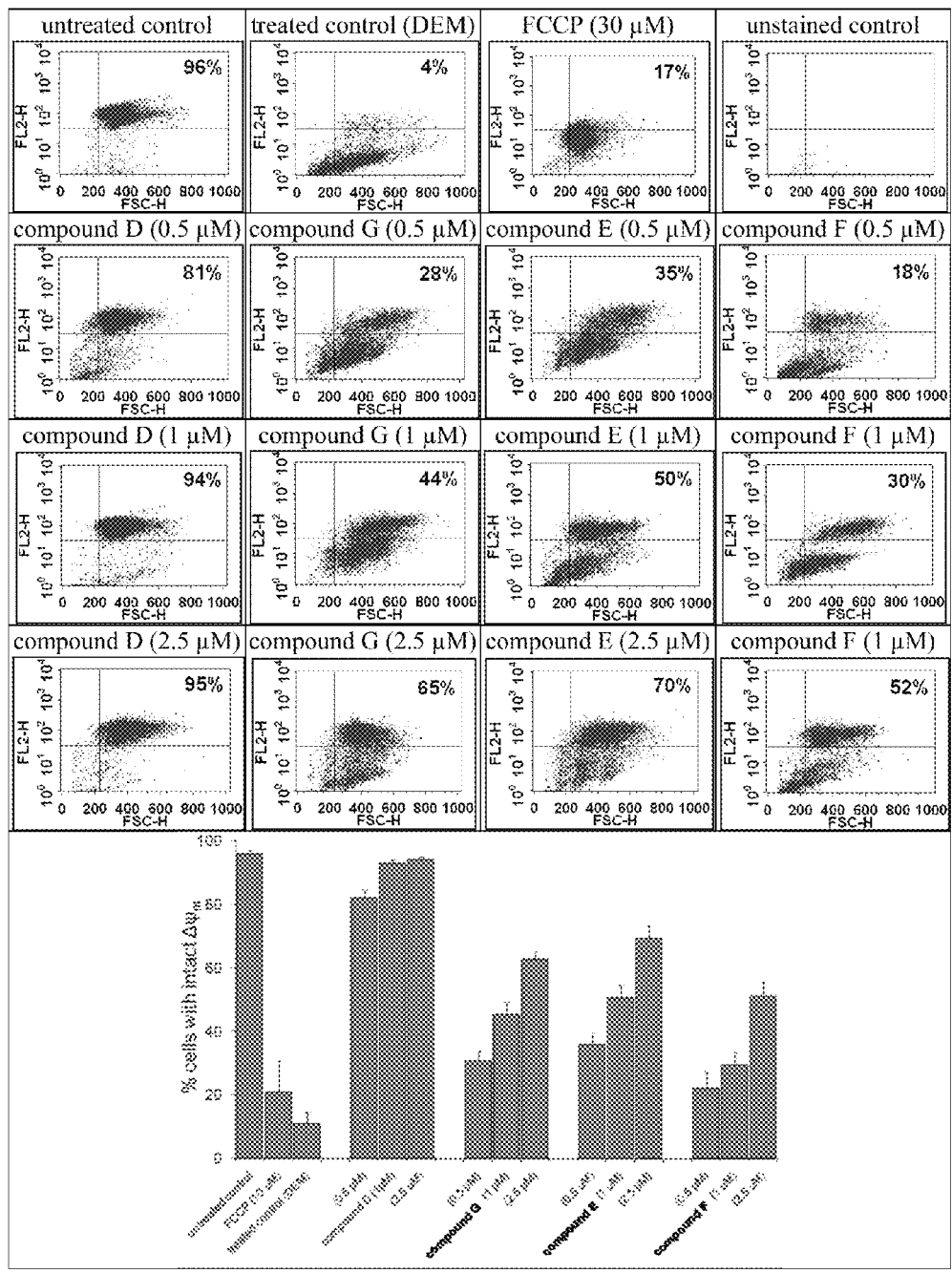

FIG. 12. Representative flow cytometric two dimensional color density dot plot analyses of mitochondrial membrane potential $\Delta_{\psi m}$ in CEM cells following pretreatment with the indicated compounds (0.5, 1, or 2.5 µM) overnight. The percentage of cells with intact $\Delta_{\psi m}$ is indicated in the top right quadrant of captions. Bottom of the figure shows a bar graph of means the percentage of cells with intact $\Delta_{\psi m}$ recorded by FACS. Data are expressed as means±SE (n=3). Compounds D was the most effective in maintaining mitochondrial membrane potential from oxidative.

Figure 13:
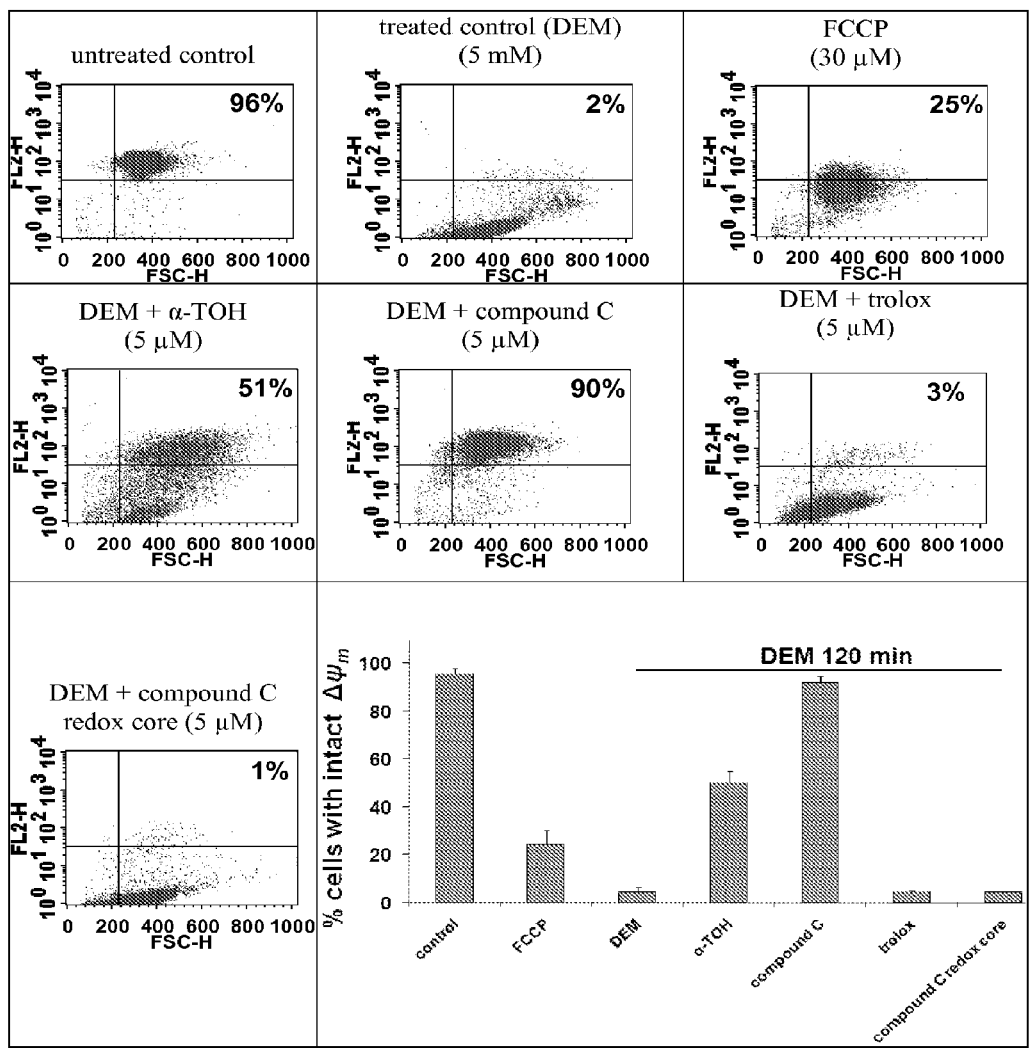
Figure 13:
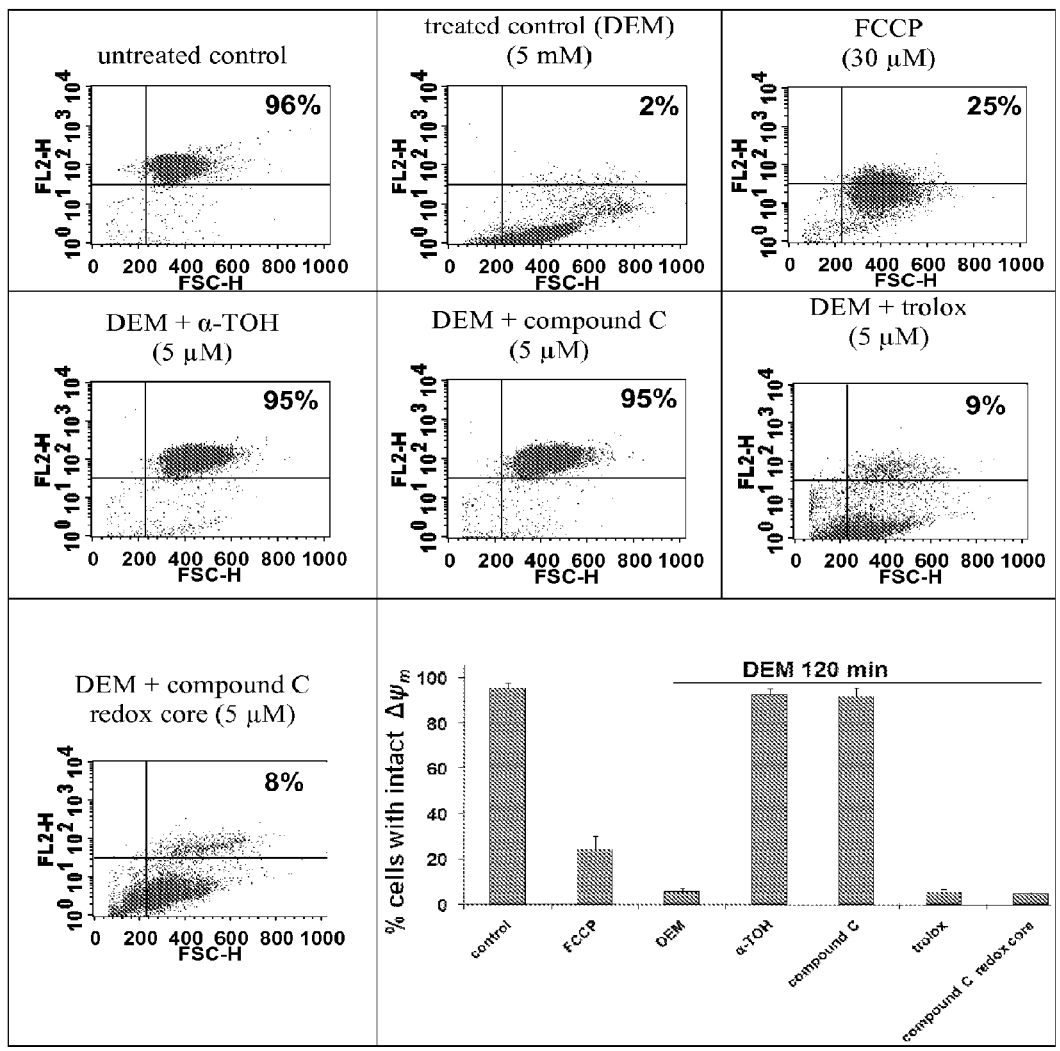
Figure 13:
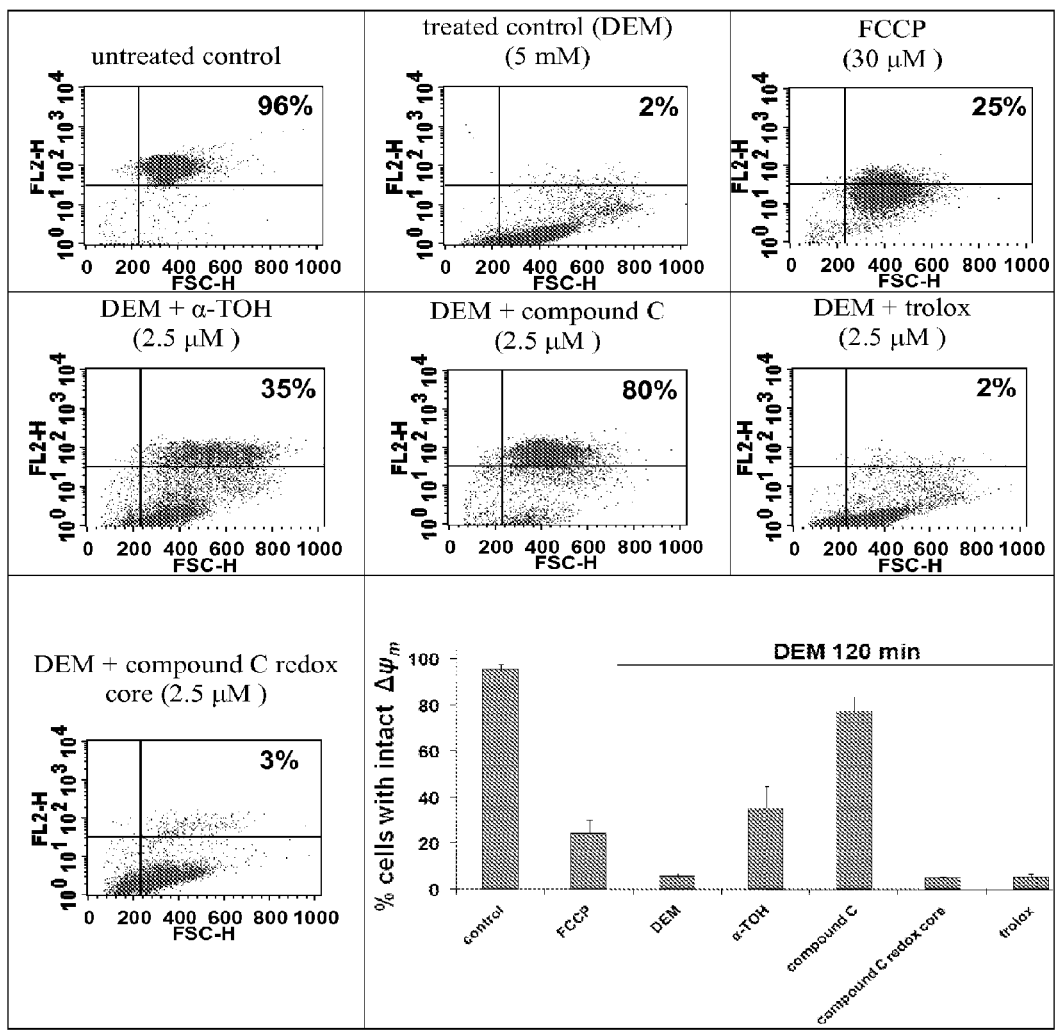
Figure 13:
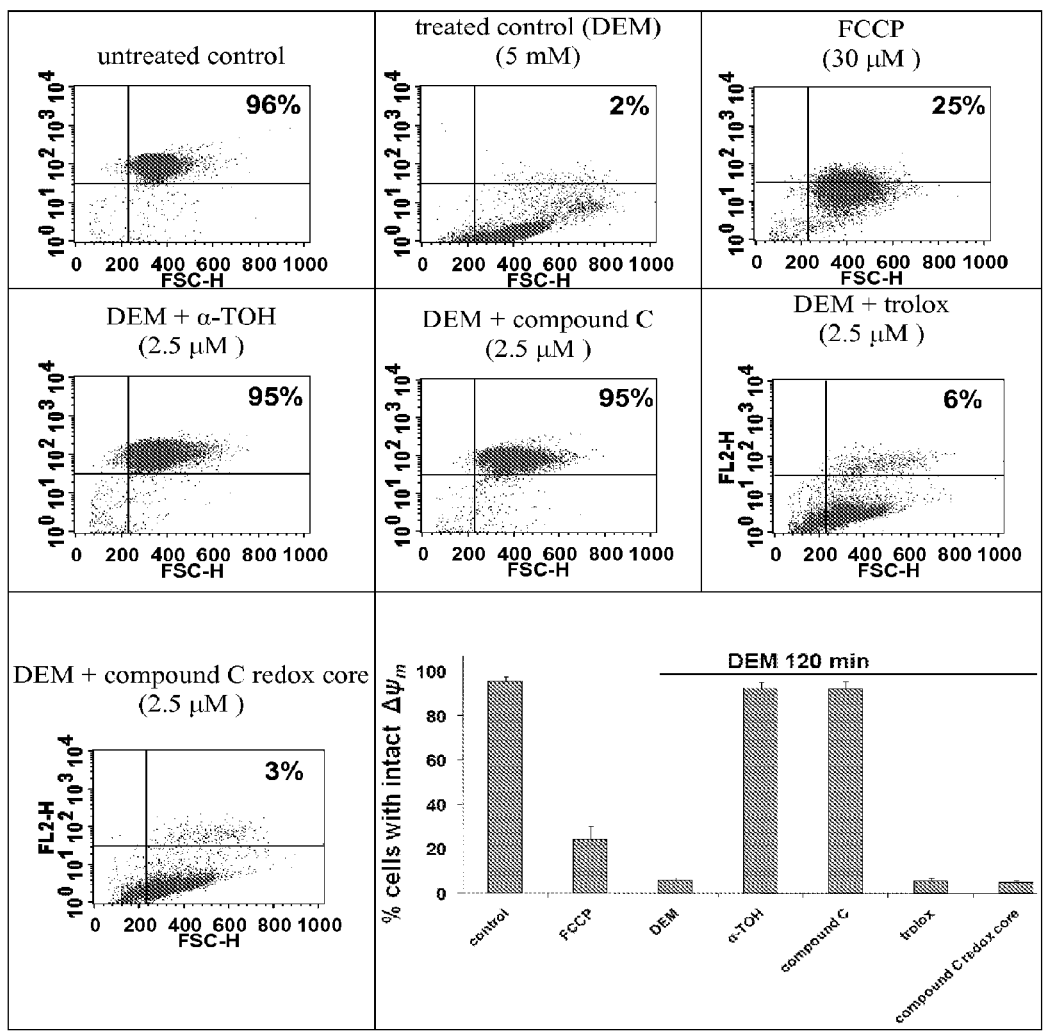
Figure 13:
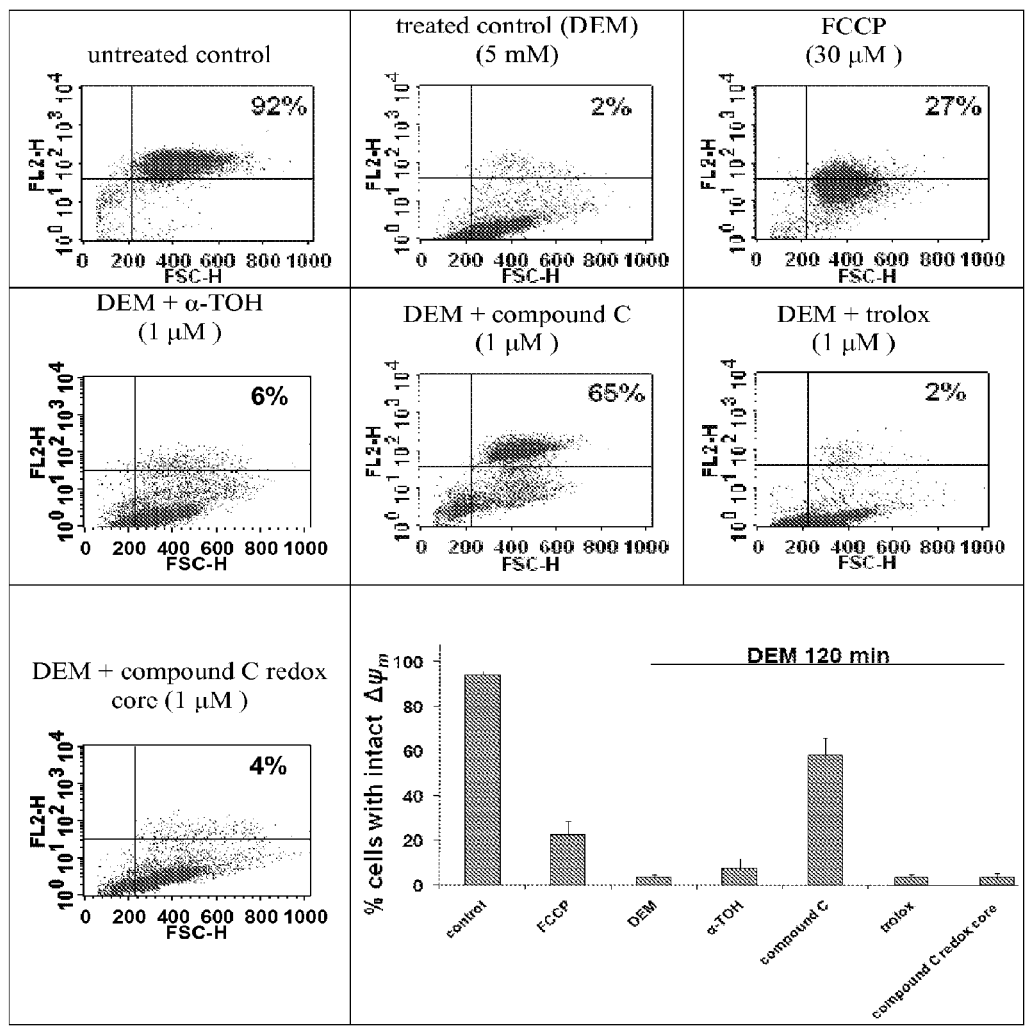
Figure 13:
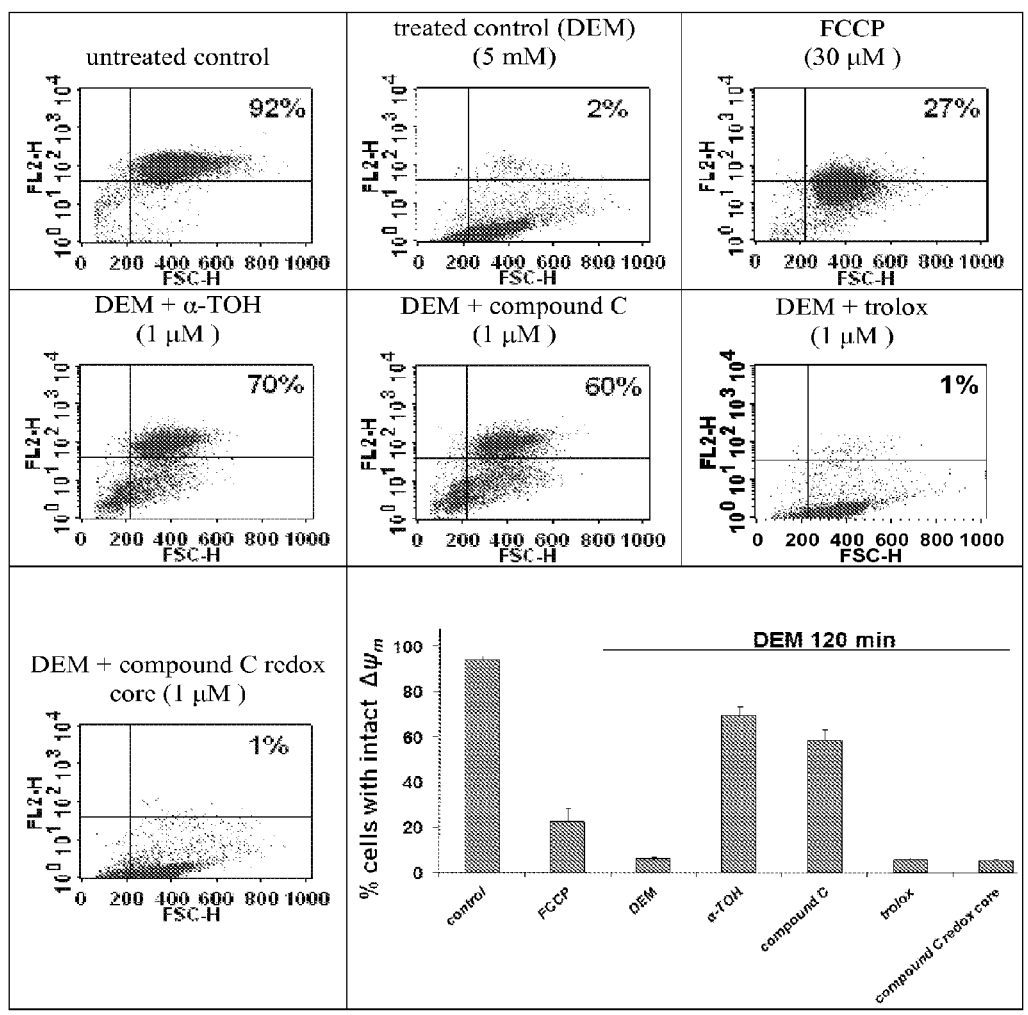

FIGS. 13 A-F. Representative flow cytometric two dimensional color density dot plot analyses of mitochondrial membrane potential $\Delta_{\psi m}$ in CEM cells following pretreatment with the indicated compounds (1, 2.5 or 5 μM) for 4 hours (FIG. 13 A, FIG. 13 C, FIG. 13 E) or 24 hours (FIG. 13 B, FIG. 13 D, FIG. 13 F). The percentage of cells with intact $\Delta_{\psi m}$ is indicated in the top right quadrant of captions. Bottom right of each figure shows a bar graph of means the percentage of cells with intact $\Delta_{\psi m}$ recorded by FACS. Data are expressed as means±SE (n=3). Compound C was more effective than tocopherol in preserving mitochondrial membrane potential after 4-hour pretreatment, and comparable to tocopherol after 24-hour pretreatment.

Figure 14:
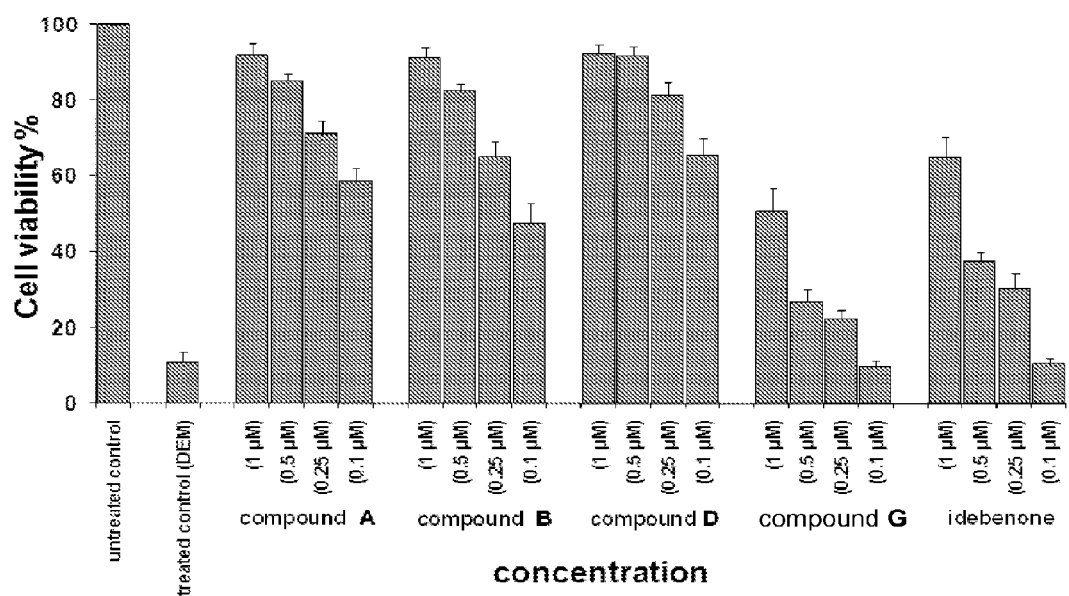

FIG. 14. Trypan blue exclusion test. CEM cells were incubated in RPMI medium (control)±compound A, compound B, compound D, compound G, or idebenone for overnight followed by 5 mM diethylmaleate (DEM) treatment. Cell viability was determined by trypan blue exclusion analysis at 3 h after DEM treatment. Compounds A, B and D were all quite effective in maintaining cell viability following DEM treatment, with D being the most effective.

Figure 15:
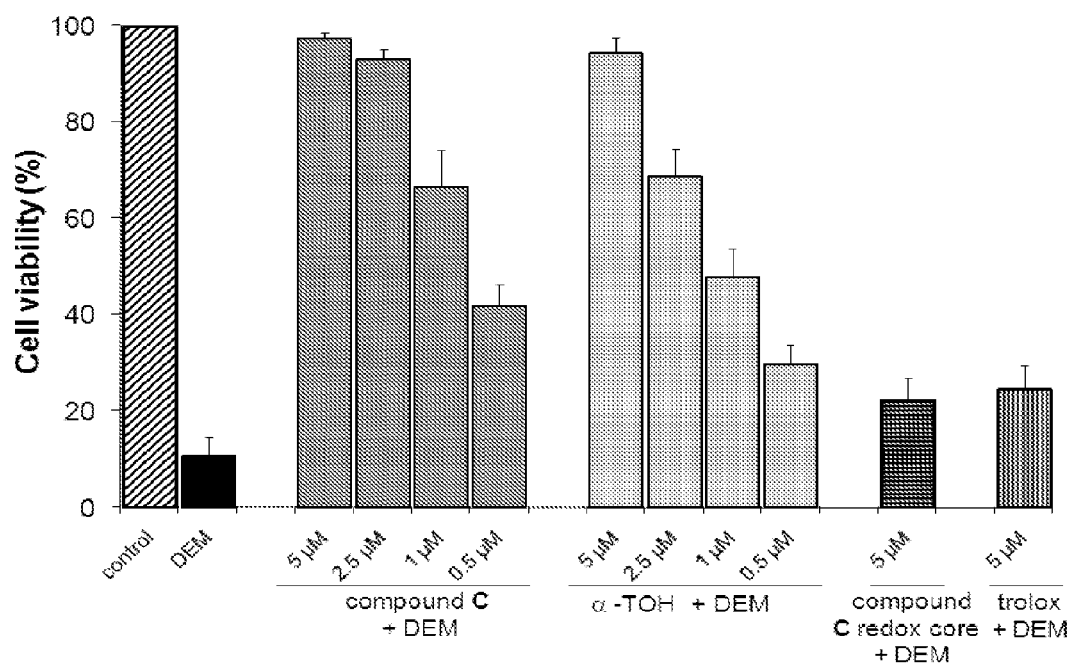

FIG. 15. Trypan blue exclusion test. CEM cells were incubated in RPMI medium (control)±compound C, compound redox core, α-tocopherol or trolox for overnight followed by 5 mM diethylmaleate (DEM) treatment. Cell viability was determined by trypan blue exclusion analysis at 3 h after DEM treatment. Compounds C and tocopherol were both effective in maintaining cell viability following treatment with DEM, with compound C being somewhat more effective. The redox cores of these compounds were quite ineffective.

Figure 16:
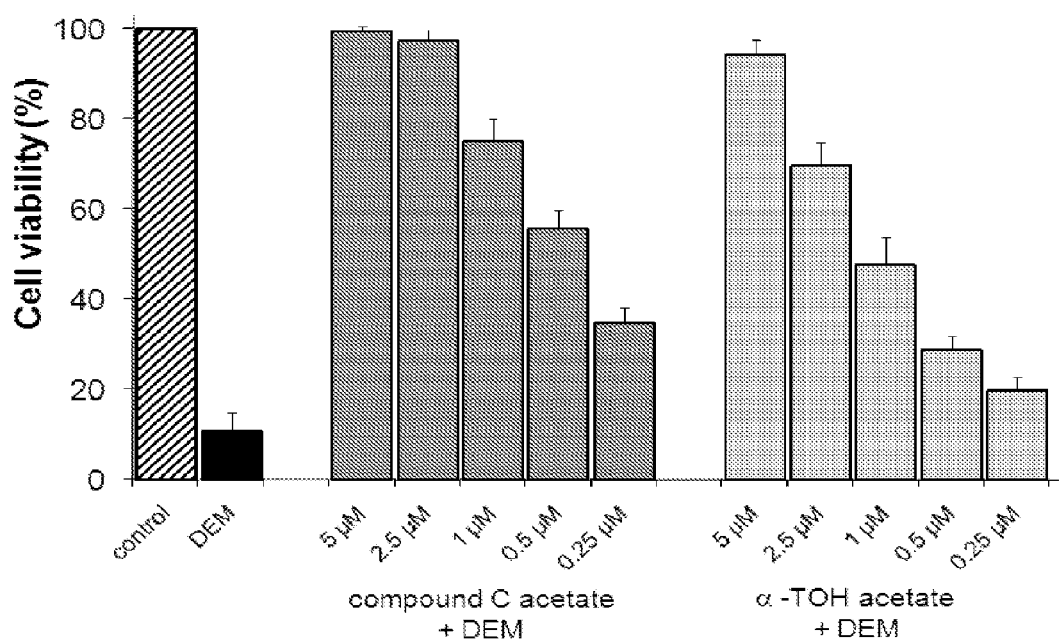

FIG. 16. Trypan blue exclusion test. CEM cells were incubated in RPMI medium (control)±compound C acetate (35) or α-tocopherol for overnight followed by 5 mM diethylmaleate (DEM) treatment. Cell viability was determined by trypan blue exclusion analysis at 3 h after DEM treatment. The acetate prodrugs of compounds C and tocopherol were both effective in maintaining cell viability following treatment with DEM, with the acetate of compound C being somewhat more effective.

Figure 17:
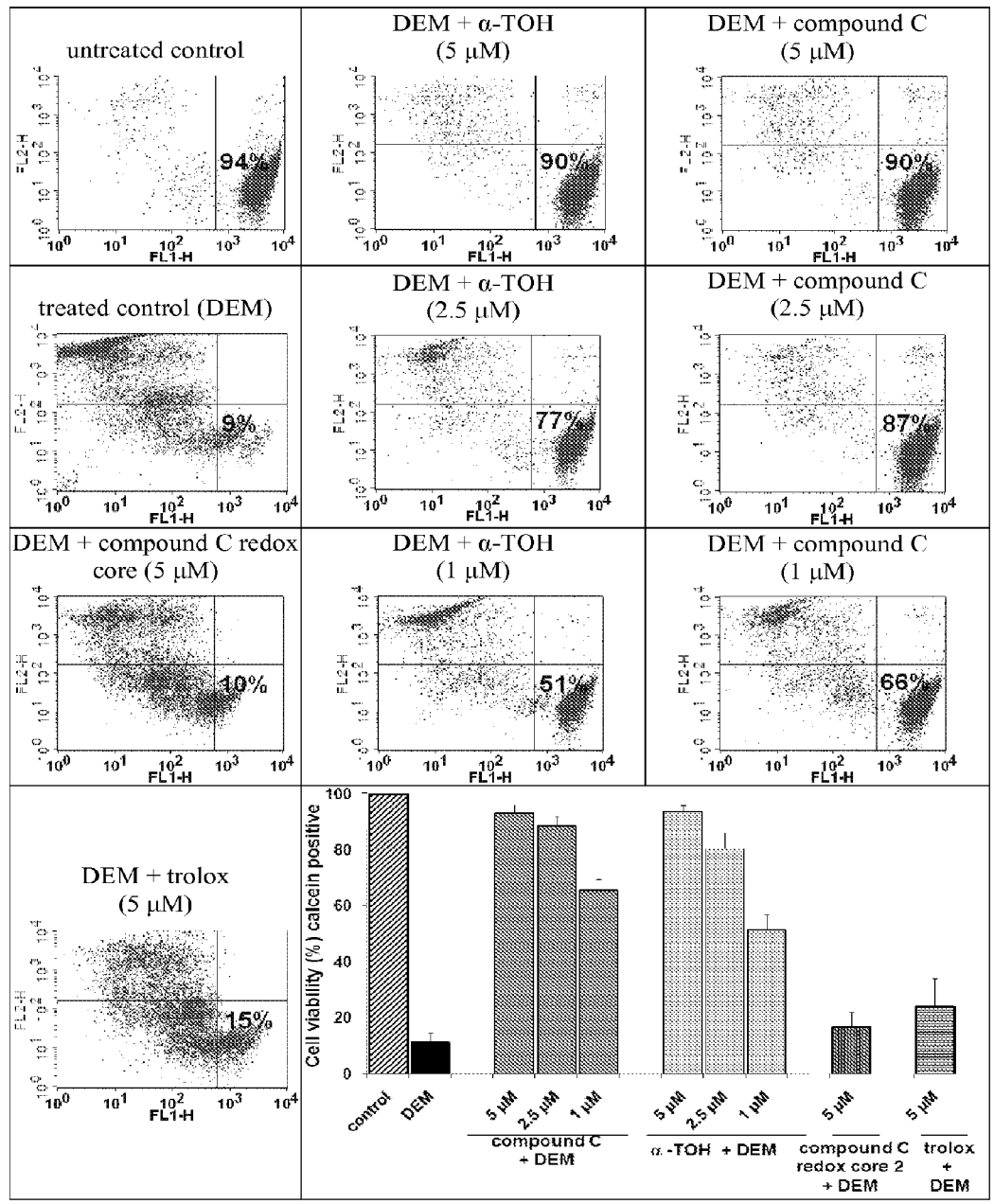

FIG. 17. Flow cytometry viability assay using the Live/Dead Viability/Cytotoxicity kit (Molecular Probes) where human CEM leukemia cells were incubated overnight in RPMI medium alone (control) or with α-tocopherol (α-TOH), compound C, compound C redox core or trolox and then treated with DEM for 3 hours. Compounds C and tocopherol were both effective in maintaining cell viability following treatment with DEM, with compound C being somewhat more effective. The redox cores of these compounds were quite ineffective.

Figure 18:
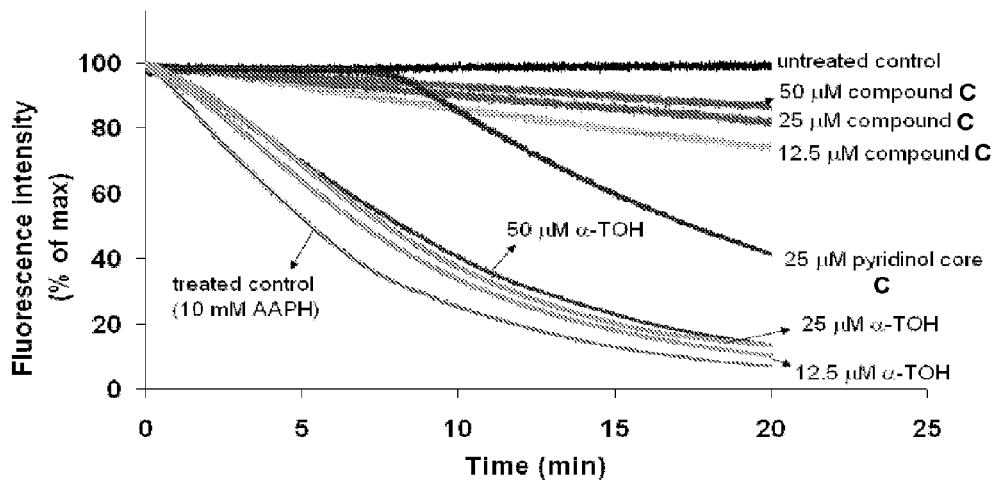
Figure 18:
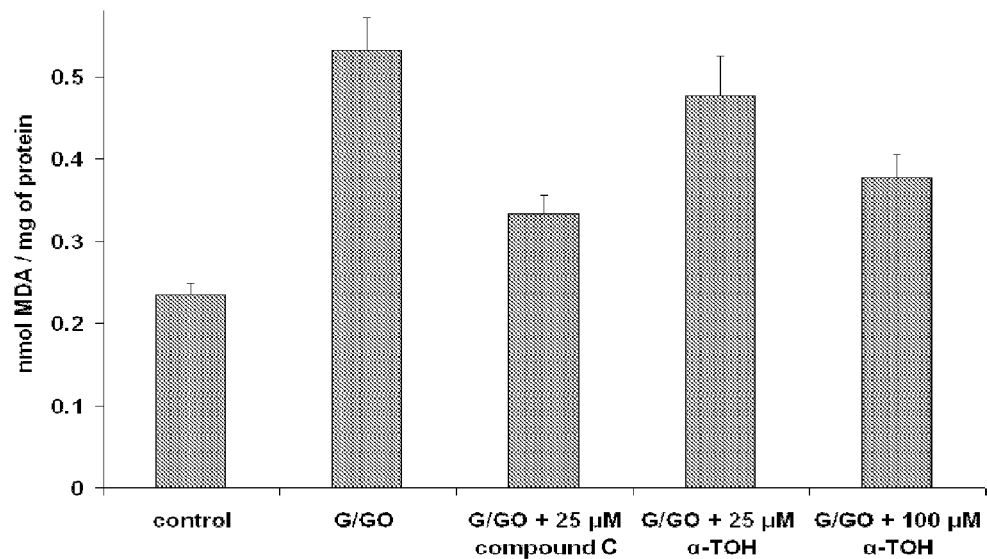
Figure 18:
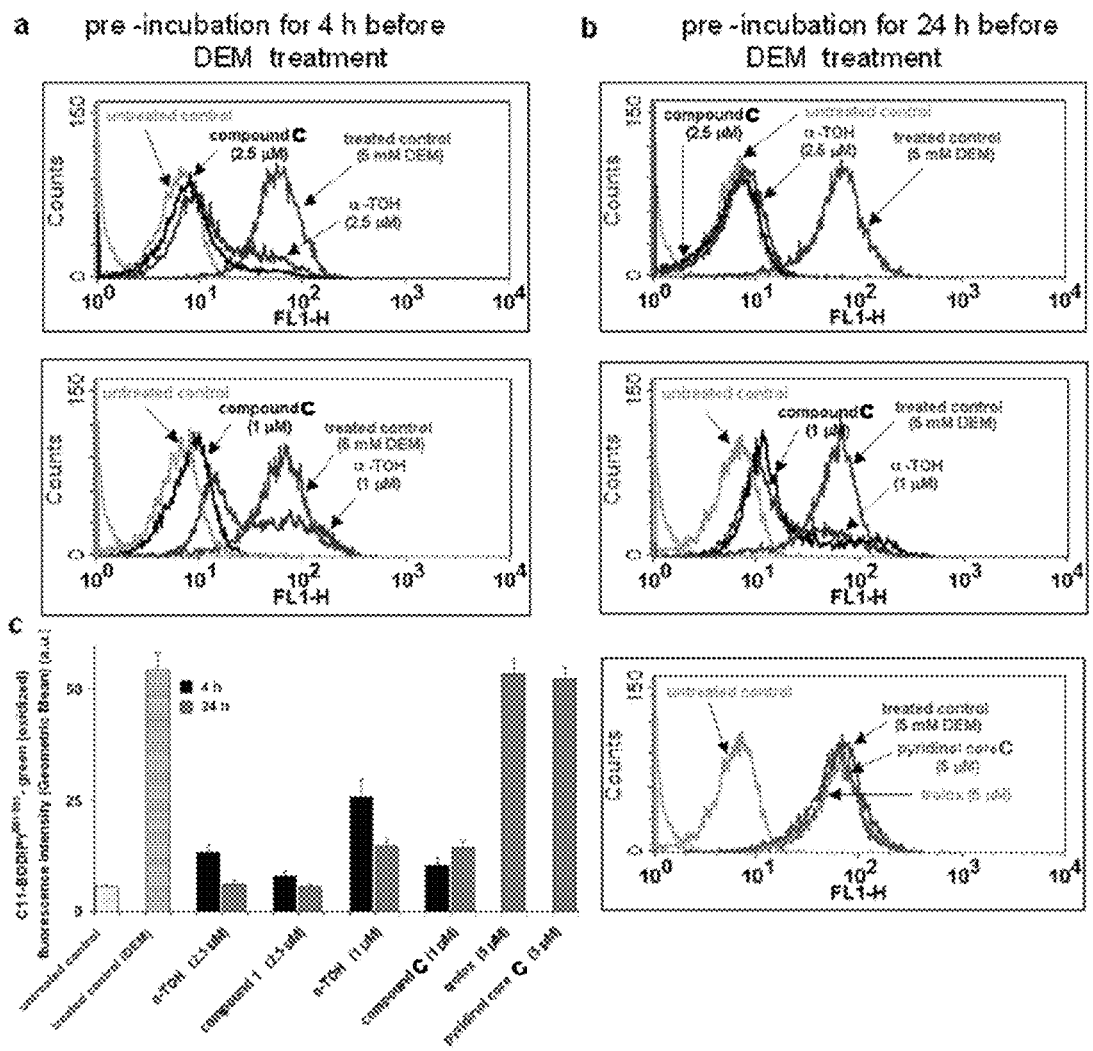

FIG. 18 A. Effect of compound C on lipid peroxidation induced by peroxyl radicals generated from thermal decomposition of AAPH in phospholipid liposomes in phosphate buffer at 40° C. The potency was measured directly by its ability to preserve the fluorescence of $C_{11}$-BODIPY$^{581/591}$ in presence of 10 mM AAPH. Relative fluorescence units are normalized to 100% intensity. Compound C prevents lipid peroxidation in a concentration-dependent fashion with scavenging activity much greater than that of α-tocopherol and compound C redox core.

FIG. 18 B. Compound C was found to be more effective in preventing TBARS formation in mitochondrial membranes stressed with $H_2O_2$ (generated using glucose oxidase (GO)) in bovine heart mitochondrial membranes.

FIG. 18 C. Lipid peroxidation in CEM leukemia cells depleted of glutathione. Representative flow cytometric histograms overlay showing lipid peroxidation in CEM cells following pretreatment with the indicated compounds (2.5 or 1 μM concentrations) for 4 (panel a) or 24 hours (panel b). Bottom left panel (c) shows a bar graph of mean $C_{11}$-BODIPY$^{581/591}$—green (oxidized form) fluorescence (a.u.) recorded by FACS and represents the geometric means of the above flow cytogram profiles calculated using CellQuest software. Data are expressed as means±SE (n=3). Compound C showed better protection against lipid peroxidation than α-tocopherol in a concentration and time-dependent fashion, while the compound C redox core and α-tocopherol (trolox) showed no protection.

Figure 19:
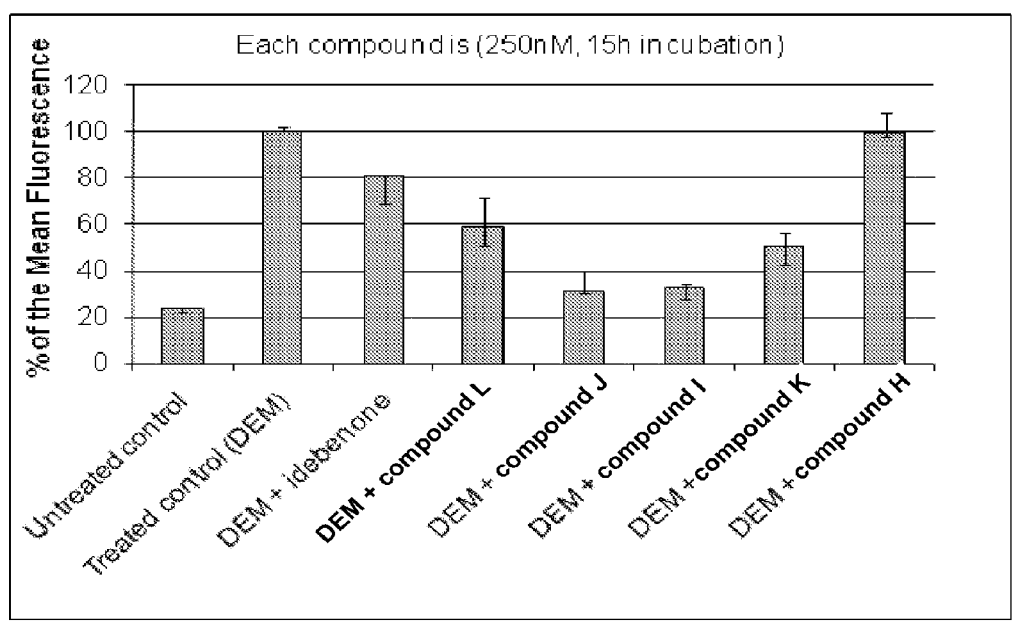

FIG. 19. Flow cytometric analysis of CCRF-CEM cells stained with DCFH-DA for 20 min, and pre-treated with the different compounds (Idebenone, compound L, compound J, Compound I, Compound K, and Compound H) at 0.25 μM for 15 hours, and then with the glutathione scavenger Diethyl Maleate (DEM) for 40 min. The most effective compounds at suppressing ROS in this assay were compounds I and J, which are side chain hydrocarbon derivatives of compound A.

Figure 20:
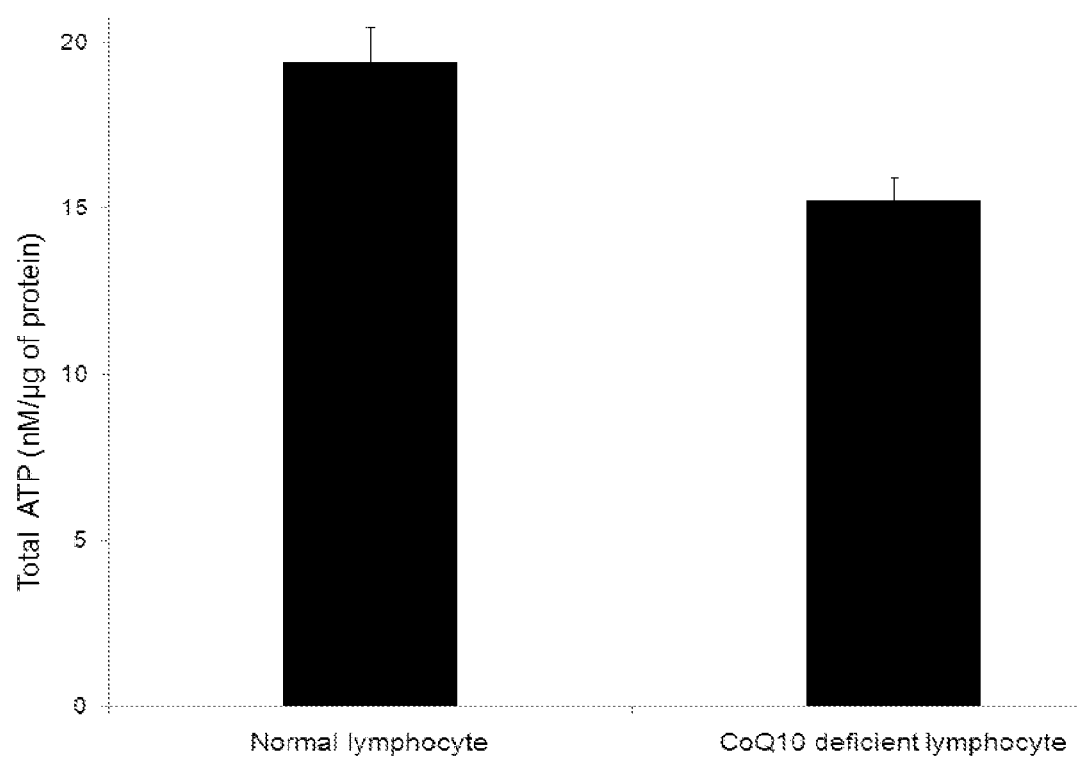

FIG. 20. Total intracellular ATP levels in $CoQ_{10}$ deficient and normal lymphocytes measured using the luciferin-luciferase reaction.

DETAILED DESCRIPTION OF THE INVENTION

In one aspect, the disclosure provides compounds of formula (I):

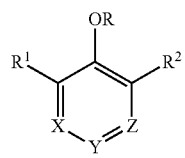

or a pharmaceutically acceptable salt thereof, wherein
R is hydrogen, or —CO($C_1$-$C_6$ alkyl);
$R^1$ is $C_1$-$C_6$ alkyl, $C_2$-$C_6$ alkenyl, $C_2$-$C_6$ alkynyl, or $C_1$-$C_6$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;
$R^2$ is $C_1$-$C_{20}$ alkyl, $C_2$-$C_{20}$ alkenyl, or $C_2$-$C_{20}$ alkynyl, each optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; where each $R^7$ independently is hydrogen, $C_1$-$C_6$ alkyl, or halo($C_1$-$C_6$ alkyl);
X is $CR^3$ or N; where $R^3$ is hydrogen, $C_1$-$C_6$ alkyl, halo($C_1$-$C_6$ alkyl), —$OR^7$, —$NR^7_2$, —$CO_2R^7$, or —$CON(R^7)_2$;
Y is $CR^4$ or N; where $R^4$ is hydrogen, $C_1$-$C_6$ alkyl, halo($C_1$-$C_6$ alkyl), —$OR^7$, —$NR^7_2$, —$CO_2R^7$, —$CON(R^7)_2$, aryl, heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; and
Z is $CR^5$ or N; where $R^5$ is hydrogen, $C_1$-$C_6$ alkyl, halo($C_1$-$C_6$ alkyl), —$OR^7$, —$NR^7_2$, —$CO_2R^7$, or —$CON(R^7)_2$, or
where $R^4$ and $R^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$,
provided that at least one of X, Y, and Z is N.

In one embodiment, the disclosure provides compounds of formula (I) wherein

R is hydrogen, or —CO($C_1$-$C_6$ alkyl);

$R^1$ is $C_1$-$C_6$ alkyl, $C_2$-$C_6$ alkenyl, $C_2$-$C_6$ alkynyl, or $C_1$-$C_6$ alkoxy, each optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$; where each $R^6$ independently is hydrogen or $C_1$-$C_6$ alkyl;

$R^2$ is $C_1$-$C_{20}$ alkyl, $C_2$-$C_{20}$ alkenyl, or $C_2$-$C_{20}$ alkynyl, each optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; where each $R^7$ independently is hydrogen, $C_1$-$C_6$ alkyl, or halo($C_1$-$C_6$ alkyl);

X is $CR^3$ or N; where $R^3$ is hydrogen, $C_1$-$C_6$ alkyl, halo($C_1$-$C_6$ alkyl), —$OR^7$, —$NR^7_2$, —$CO_2R^7$, or —$CON(R^7)_2$;

Y is $CR^4$ or N; where $R^4$ is hydrogen, $C_1$-$C_6$ alkyl, halo($C_1$-$C_6$ alkyl), —$OR^7$, —$NR^7_2$, —$CO_2R^7$, —$CON(R^7)_2$, heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; and Z is $CR^5$ or N; where $R^5$ is hydrogen, $C_1$-$C_6$ alkyl, halo($C_1$-$C_6$ alkyl), —$OR^7$, —$NR^7_2$, —$CO_2R^7$, or —$CON(R^7)_2$, or where $R^4$ and $R^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$, provided that at least one of X, Y, and Z is N.

In one embodiment, the disclosure provides compounds of formula (I) wherein R is hydrogen. Such compounds are hereinafter compounds of formula (II):

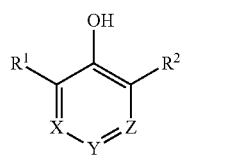

(II)

In another embodiment, the disclosure provides compounds of formulae (I) or (II), wherein $R^1$ is $C_1$-$C_6$ alkyl, optionally substituted with one to four substituents selected from halogen, cyano, nitro, $C_1$-$C_6$ alkyl, halo($C_1$-$C_6$ alkyl), —$OR^6$, —$NR^6_2$, —$CO_2R^6$, and —$CONR^6_2$, and where each $R^6$ independently is hydrogen or $C_1$-$C_6$ alkyl.

In yet another embodiment, the disclosure provides compounds as described above with reference to any of formulae (I) or (II), wherein $R^1$ is unsubstituted $C_1$-$C_6$ alkyl. In one embodiment, $R^1$ is methyl.

In yet another embodiment, the disclosure provides compounds as described above with reference to any of formulae (I) or (II), wherein $R^1$ is unsubstituted $C_1$-$C_6$ alkoxy.

In one embodiment, the disclosure provides compounds as described above with reference to any of formulae (I) or (II), wherein $R^2$ is $C_1$-$C_6$ alkyl or $C_2$-$C_{20}$ alkenyl, each optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$, where each $R^7$ independently is hydrogen, $C_1$-$C_6$ alkyl, or halo($C_1$-$C_6$ alkyl).

In another embodiment, the disclosure provides compounds of formulae (I) or (II), wherein $R^2$ is $C_1$-$C_{20}$ alkyl optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$, where each $R^7$ independently is hydrogen, $C_1$-$C_6$ alkyl, or halo($C_1$-$C_6$ alkyl).

One embodiment of the disclosure provides compounds of formulae (I) or (II), wherein $R^2$ is $C_1$-$C_6$ alkyl optionally substituted with one to four substituents selected from $C_1$-$C_6$ alkyl, halo($C_1$-$C_6$ alkyl), and —$OR^7$, where each $R^7$ independently is hydrogen, $C_1$-$C_6$ alkyl, or halo($C_1$-$C_6$ alkyl).

One embodiment of the disclosure provides compounds of formulae (I) or (II), wherein $R^2$ is $C_5$-$C_{20}$ alkyl optionally substituted with one to four substituents selected from $C_1$-$C_6$ alkyl, halo($C_1$-$C_6$ alkyl), and —$OR^7$, where each $R^7$ independently is hydrogen, $C_1$-$C_6$ alkyl, or halo($C_1$-$C_6$ alkyl).

Another embodiment of the disclosure provides compounds of formulae (I) or (II), wherein $R^2$ is $C_5$-$C_{20}$ alkyl optionally substituted with one to four —$OR^7$ groups, where each $R^7$ independently is hydrogen, $C_1$-$C_6$ alkyl, or halo($C_1$-$C_6$ alkyl). Yet another embodiment of the disclosure provides compounds of formulae (I) or (II), wherein $R^2$ is $C_7$-$C_{20}$ alkyl optionally substituted with one to four —$OR^7$ groups, where each $R^7$ independently is hydrogen, $C_1$-$C_6$ alkyl, or halo($C_1$-$C_6$ alkyl).

In one embodiment, the disclosure provides compounds of formulae (I) or (II), wherein $R^2$ is $C_7$-$C_{20}$ alkyl optionally substituted with one to four —OH groups. Another embodiment provides compounds where $R^2$ is hydroxydecyl or 3,7,11,15-tetramethyl-3-hydroxyhexadecanyl.

In one embodiment, the disclosure provides compounds of formulae (I) or (II), wherein $R^2$ is $C_5$-$C_{20}$ alkyl. Another embodiment provides compounds where $R^2$ is pentyl, decyl or hexadecyl.

In one embodiment, the disclosure provides compounds of formulae (I) or (II), wherein X is $CR^3$ or N; where $R^3$ is hydrogen, $C_1$-$C_6$ alkyl, halo($C_1$-$C_6$ alkyl), —$OR^7$, —$NR^7_2$, —$CO_2R^7$, or —$CON(R^7)_2$;

Y is $CR^4$ or N; where $R^4$ is hydrogen, $C_1$-$C_6$ alkyl, halo($C_1$-$C_6$ alkyl), —$OR^7$, —$NR^7_2$, —$CO_2R^7$, or —$CON(R^7)_2$; and Z is $CR^5$ or N; where $R^5$ is hydrogen, $C_1$-$C_6$ alkyl, halo($C_1$-$C_6$ alkyl), —$OR^7$, —$NR^7_2$, —$CO_2R^7$, or —$CON(R^7)_2$, or where $R^4$ and $R^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; and R, $R^1$, and $R^2$ are as defined above with reference to any preceding embodiments.

In one embodiment, the disclosure provides compounds of formula (III) wherein

X is N;

Y is $CR^4$, where $R^4$ is hydrogen, $C_1$-$C_6$ alkyl, halo($C_1$-$C_6$ alkyl), —$OR^7$, —$NR^7_2$, —$CO_2R^7$, or —$CON(R^7)_2$;

Z is N; and

R, $R^1$, and $R^2$ are as defined above with reference to any of the preceding embodiments.

In another embodiment, the disclosure provides compounds of formula (III) wherein $R^4$ is —$OR^7$, or —$NR^7_2$. Yet another embodiment provides compounds of formula (III) wherein $R^4$ is —OH, —O($C_1$-$C_6$ alkyl), —$NH_2$, —NH($C_1$-$C_6$ alkyl), or —N($C_1$-$C_6$ alkyl)$_2$. One embodiment of the disclosure provides compounds of formula (III) wherein $R^4$ is —$OCH_3$, or —N($CH_3$)$_2$. Another embodiment provides compounds of formula (III) where $R^4$ is —N($CH_3$)$_2$.

In one embodiment, the disclosure provides compounds of formula (IV) wherein
X is $CR^3$, where $R^3$ is hydrogen, $C_1$-$C_6$ alkyl, halo($C_1$-$C_6$ alkyl), —$OR^7$, —$NR^7_2$, —$CO_2R^7$, or —$CON(R^7)_2$;
Y is $CR^4$, where $R^4$ is hydrogen, $C_1$-$C_6$ alkyl, halo($C_1$-$C_6$ alkyl), —$OR^7$, —$NR^7_2$, —$CO_2R^7$, or —$CON(R^7)_2$;
Z is N; and
R, $R^1$, and $R^2$ are as defined above with reference to any of the preceding embodiments.

In another embodiment, the disclosure provides compounds of formula (IV) wherein $R^3$ is hydrogen or —$OCH_3$.

In one embodiment, the compounds of formula (IV) are those where $R^4$ is —$OR^7$, or —$NR^7_2$. Yet another embodiment provides compounds of formula (IV) wherein $R^4$ is —OH, —O($C_1$-$C_6$ alkyl), —$NH_2$, —NH($C_1$-$C_6$ alkyl), or —N($C_1$-$C_6$ alkyl)$_2$. One embodiment of the disclosure provides compounds of formula (IV) wherein $R^4$ is —$OCH_3$, or —$N(CH_3)_2$. Another embodiment provides compounds of formula (IV) where $R^4$ is —$N(CH_3)_2$.

In one embodiment, the disclosure provides compounds of formula (V) wherein
X is N; Y is $CR^4$; and Z is $CR^5$, where
$R^4$ and $R^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; and
R, $R^1$, and $R^2$ are as defined above with reference to any of the preceding embodiments.

In another embodiment, the disclosure provides compounds of formula (V) wherein $R^4$ and $R^5$ together with the atoms to which they are attached form 5 or 6 member heteroaryl or heterocyclyl ring, which contains at least one nitrogen atom, and is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$.

One embodiment of the disclosure provides compounds of formula (VI) and (VII):

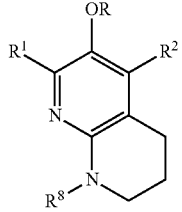
(VI)

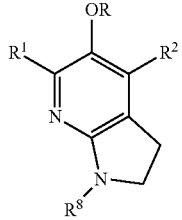
(VII)

$R^8$ is hydrogen or $C_1$-$C_6$ alkyl; and R, $R^1$, and $R^2$ are as defined above with reference to any of the preceding embodiments.

In one embodiment, the disclosure provides compounds of formula (VIII), wherein
X is $CR^3$ or N; where $R^3$ is hydrogen, $C_1$-$C_6$ alkyl, halo($C_1$-$C_6$ alkyl), —$OR^7$, —$NR^7_2$, —$CO_2R^7$, or —$CON(R^7)_2$;
Y is aryl, heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; and
Z is $CR^5$ or N; where $R^5$ is hydrogen, $C_1$-$C_6$ alkyl, halo($C_1$-$C_6$ alkyl), —$OR^7$, —$NR^7_2$, —$CO_2R^7$, or —$CON(R^7)_2$, or
where $R^4$ and $R^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; and
R, $R^1$, and $R^2$ are as defined above with reference to any preceding embodiments.

In another embodiment, the disclosure provides compounds of formula (VIII), wherein
X is $CR^3$ or N; where $R^3$ is hydrogen, $C_1$-$C_6$ alkyl, halo($C_1$-$C_6$ alkyl), —$OR^7$, —$NR^7_2$, —$CO_2R^7$, or —$CON(R^7)_2$;
Y is heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; and
Z is $CR^5$ or N; where $R^5$ is hydrogen, $C_1$-$C_6$ alkyl, halo($C_1$-$C_6$ alkyl), —$OR^7$, —$NR^7_2$, —$CO_2R^7$, or —$CON(R^7)_2$, or
where $R^4$ and $R^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; and
R, $R^1$, and $R^2$ are as defined above with reference to any preceding embodiments.

In one embodiment, the disclosure provides compounds of formula (VIII), wherein Y is heteroaryl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$. Another embodiment provides compounds wherein the heteroaryl ring is nitrogen-containing heteroaryl. In one embodiment the heteroaryl ring is pyrrolyl.

In one embodiment, the disclosure provides compounds of formula (VIII), wherein Y is heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$. Another embodiment provides compounds wherein the heterocyclyl ring is nitrogen-containing heterocyclyl. In one embodiment the heterocyclyl ring is pyrrolidinyl.

In another embodiment, the disclosure provides the following compounds:

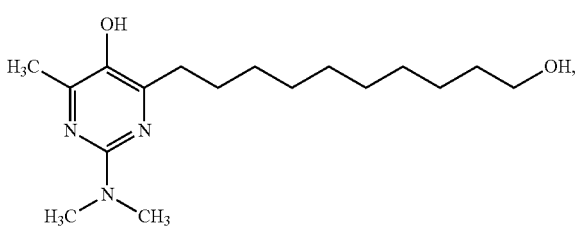

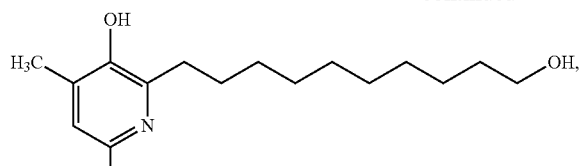
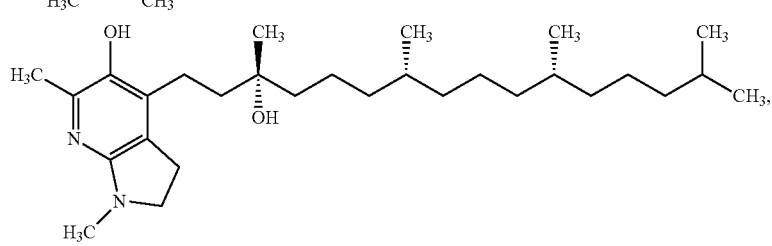
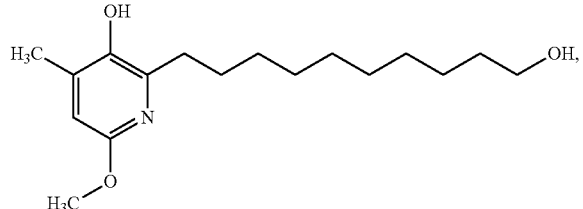
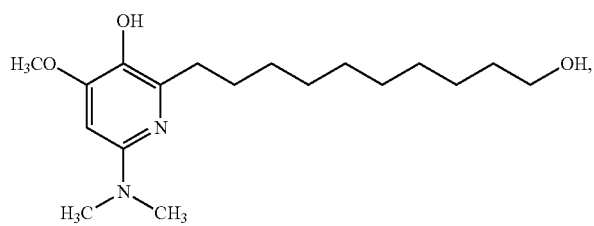
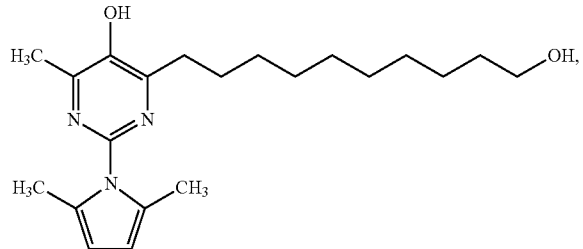
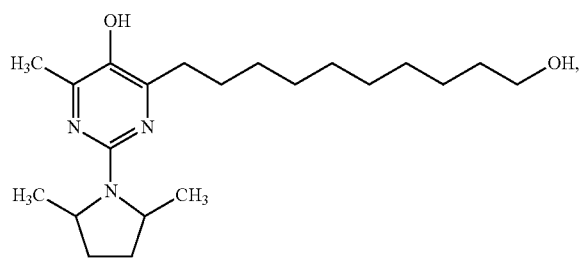
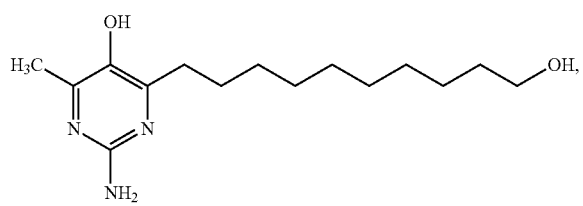

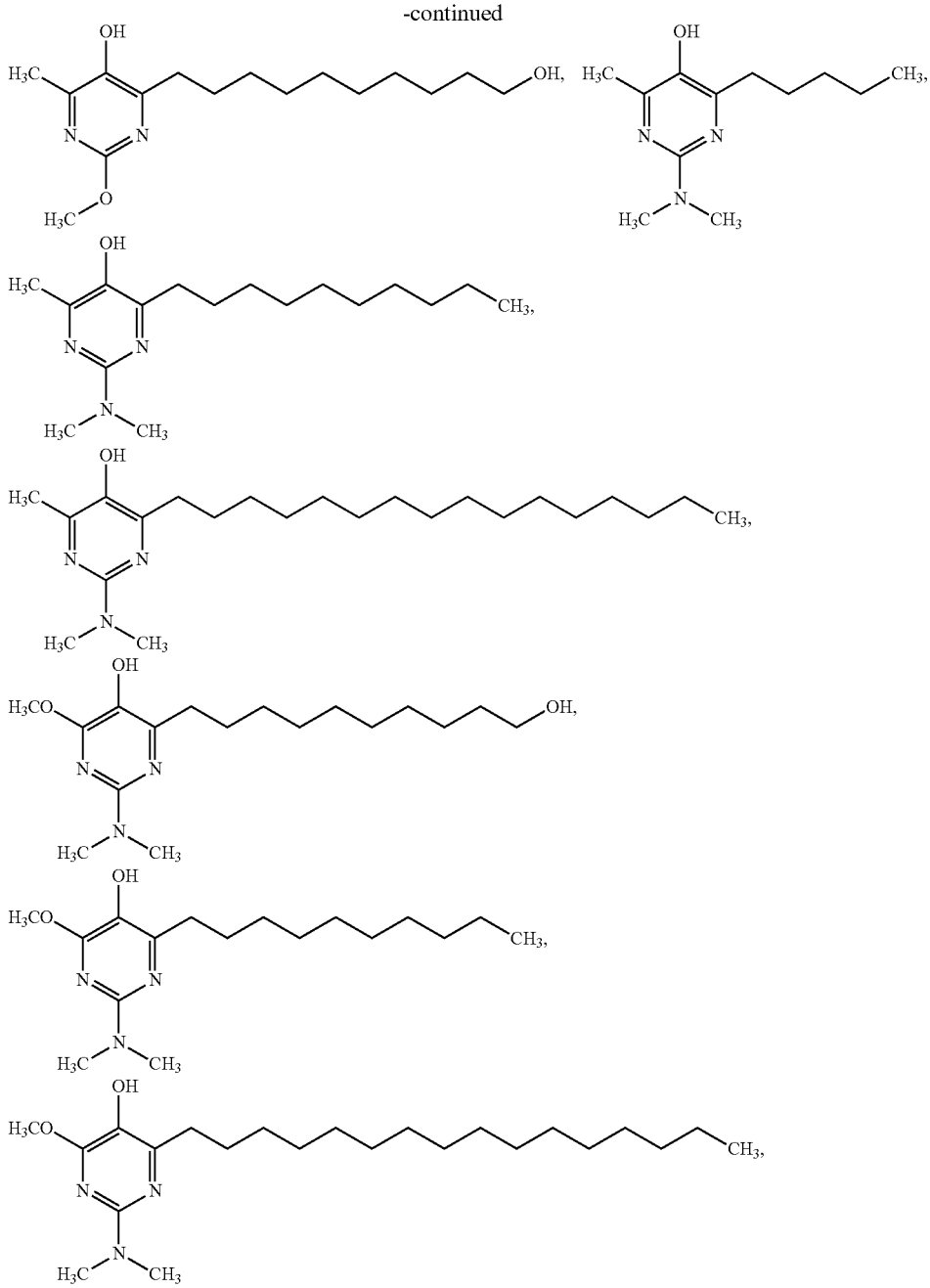

or a pharmaceutically acceptable salt thereof.

In another embodiment, the disclosure provides pharmaceutically acceptable salts of compounds of the disclosure. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, monofluoroacetic acid, difluoroacetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. For example, in one embodiment, the salt is a trifluoroacetic acid salt, p-toluenesulfonic acid salt, or hydrochloride salt.

Pharmaceutically acceptable salts also include salts formed when an acidic proton present in the parent compound is either replaced by an inorganic ion (e.g., an alkali metal ion such as $Na^+$, $K^+$ or $Li^+$, an alkaline earth ion such as $Ca^{2+}$ or $Mg^{2+}$ an aluminum ion, or an ammonium ion) or coordinates with an organic base (e.g., ethanolamine, diethanolamine, triethanolamine, N-methylglucamine, morpholine, piperidine, dimethylamine, diethylamine, etc.).

The compounds described herein, as well as the salts thereof, may also be in the form of hydrates, solvates and N-oxides, as are well-known in the art.

Therapeutic Applications

Compounds of the disclosure are useful, for example, for treating or suppressing diseases associated with decreased mitochondrial function resulting in diminished ATP production and/or oxidative stress and/or lipid peroxidation in a subject in need of treatment. The present disclosure provides methods of treating conditions including but not limited to Friedreich's ataxia, Leber's Hereditary Optic Neuropathy, Kearns-Sayre Syndrome, Mitochondrial Encephalomyopathy with Lactic Acidosis and Stroke-Like Episodes, and Leigh syndrome in a subject by administering an effective amount of a compound as described above with respect to any of formulae (I)-(VIII), including a salt or solvate or stereoisomer thereof.

The disclosure also provides methods of treating conditions including but not limited to obesity, atherosclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, and Leigh syndrome, in a subject by administering an effective amount of a compound as described above with respect to any of formulae (I)-(VIII), including a salt or solvate or stereoisomer thereof.

Friedreich's Ataxia

Friedreich's ataxia is a severe neurodegenerative and cardiodegenerative condition. It is characterized by progressive ataxia of the limbs, muscle weakness, dysarthria, skeletal deformities and cardiomyopathy. While the biochemical basis of the disease is still under investigation, it is strongly associated with insufficient frataxin (Wilson et al. (1997) *Nat. Genet.* 16, 352-357; Wilson et al. (2003) *J. Neurol. Sci.* 207, 103-105). In the majority of patients the insufficiency of frataxin is a consequence of an intronic GAA triplet repeat expansion in the gene for frataxin, which results in a significant decrease in its mRNA levels, and ultimately in protein levels as well (Campuzano et al. (1996) *Science* 271, 1423-1427; Campuzano et al. (1997) *Hum. Mol. Genet.* 6, 1771-1780). Frataxin acts as an iron chaperone during heme biosynthesis (Bencze et al. (2007) *J.C.S. Chem. Commun.* 1798-1800) and has been shown to be capable of stimulating the in vitro assembly of heme and Fe—S clusters (Park et al. (2003) *J. Biol. Chem.* 278, 31340-31351; Yoon et al. (2003) *J. Am. Chem. Soc.* 125, 6078-6084; Yoon et al. (2004) *J. Biol. Chem.* 279, 25943-25946). Frataxin can interact physically with mitochondrial electron transport chain proteins, as well as with mitochondrial aconitase (which contains an Fe—S cluster) (Bulteau et al. (2004) *Science* 305, 242-245; Gonzalez-Cabo et al. (2005) *Hum. Mol. Genet.* 14, 2091-2098). Therefore, frataxin deficiency results in disruption of cellular iron homeostasis, with a progressive iron accumulation in the mitochondrion, and a deficiency in heme and Fe—S clusters.

It is believed that a deficiency in frataxin leads to compromised mitochondrial respiratory chain function through a failure to assemble one or more Fe-utilizing proteins; one or more Fe—S clusters in the mitochondrial respiratory complexes are likely to represent a critical locus. In fact, diminished function of these complexes has been noted in Friedreich's ataxia patients (Bradley et al. (2000) *Hum. Mol. Genet.* 9, 275-282). The loss of mitochondrial respiratory chain function can lead to diminished ATP production, while the accumulation of Fe in the mitochondria makes the organelle highly susceptible to oxidative damage by reactive oxygen species, whose concentration increases concomitant with the decrease in respiratory chain function. There is compelling evidence that while oxidative damage is not the primary lesion in Friedreich's ataxia, oxidative stress helps to drive disease progression. Therefore, strategies to overcome oxidative stress should blunt disease progression and provide effective therapy.

Other Exemplary Mitochondrial Diseases

Leber hereditary optic neuropathy is associated with degeneration of retinal ganglion cells and causes progressive loss of vision resulting in various degrees of blindness. Leber hereditary optic neuropathy primarily affects men over the age of 20 and is maternally transmitted due to mutations in the mitochondrial (not nuclear) genome.

Kearns-Sayre syndrome is a rare neuromuscular disorder typically with onset usually before the age of 20. It is characterized by progressive external ophthalmoplegia (paralysis of the eye muscles) and mild skeletal muscle weakness, hearing loss, loss of coordination, heart problems, and cognitive delays. There are many other names for the Kearns-Sayre syndrome including: Chronic progressive external ophthalmoplegia CPEO with myopathy; CPEO with ragged-red fibers; KSS; Mitochondrial cytopathy, Kearns-Sayre type; Oculocraniosomatic syndrome; Ophthalmoplegia-plus syndrome; Ophthalmoplegia with myopathy; and Ophthalmoplegia with ragged-red fibers.

Mitochondrial Encephalomyopathy with Lactic Acidosis and Stroke-Like Episodes is a progressive mitochondrial disease that involves multiple organ systems including the central nervous system, cardiac muscle, skeletal muscle, and gastrointestinal system. Symptoms include muscle weakness, stroke-like events, eye muscle paralysis, and cognitive impairment. Leigh syndrome is a degenerative brain disorder is usually diagnosed at a young age (e.g. before age two). Deterioration is often rapid with symptoms such as seizures, dementia, feeding and speech difficulties, respiratory dysfunction, heart problems, and muscle weakness. Prognosis is poor with death typically occurring within a few years of diagnosis.

Mitochondrial Energy Production

Energy released from the citric acid (Krebs) cycle in the mitochondrial matrix enters the mitochondrial electron transport chain as NADH (complex I) and $FADH_2$ (complex II). These are the first two of five protein complexes involved in ATP production, all of which are located in the inner mitochondrial membrane. Electrons derived from NADH (by oxidation with a NADH-specific dehydrogenase) and $FADH_2$ (by oxidation with succinate dehydrogenase) travel down the respiratory chain, releasing their energy in discrete steps by driving the active transport of protons from the mitochondrial matrix to the intermembrane space (i.e., through the inner mitochondrial membrane). The electron carriers in the respiratory chain include flavins, protein-bound iron-sulfur centers, quinones, cytochromes and copper. There are two molecules that transfer electrons between complexes: coenzyme Q (complex I→III, and complex II→III) and cytochrome c (complex III→IV). The final electron acceptor in the respiratory chain is $O_2$, which is converted to $H_2O$ in complex IV.

In a functional mitochondrion, transport of two electrons through complex I results in the transport of $4H^+$ into the intermembrane space. Two more $H^+$ transfers to the intermembrane space result from electron transport through complex III, and four more $H^+$ transfers from electron transport through complex IV. The 10 electrons transported to the intermembrane space create a proton electrochemical gradient; they can return to the mitochondrial matrix via complex V (ATP synthase), with the concomitant conversion of ADP to ATP. It is interesting that no $H^+$ is transferred to the intermembrane space as a consequence of electron transport through complex II. Therefore, $2e^-$ transfer from $FADH_2$ (complex II→complex III→complex IV) results in the transport of only 6 protons, compared with 10 protons resulting from $2e^-$ transfer from NADH (complex I→complex III→complex IV), with correspondingly less ATP produced. Each glucose molecule metabolized by glycolysis produces 12 electrons; these are converted to 5 NADH molecules and 1 $FADH_2$ via the Krebs cycle in the mitochondrial matrix. The 5 NADH molecules employed in mitochondrial electron transport produce about 25 ATPs, while the single $FADH_2$ affords only about 3 ATP molecules. (There are another 4 molecules of ATP derived from glucose metabolism—2 during glycolysis and 2 in the Krebs cycle). While this analysis underscores the importance of complex I involvement in normal ATP production, it also tends to obscure certain metabolic realities/uncertainties that may offer important opportunities for therapeutic intervention. One metabolic reality is that complex I, while important quantitatively for ATP production in normal mitochondria, is not essential for all mitochondrial ATP production. Electrons can enter the electron transport chain at the level of coenzyme Q (either from complex II or from fatty acid oxidation), producing about 60% as much ATP as would have resulted had they entered the electron transport chain at complex I). While the flux of electrons that normally enter the individual mitochondrial complexes, ultimately passing through coenzyme Q, is probably dictated largely by the availability of electrons derived from NADH, $FADH_2$ and fatty acid oxidation, the actual intrinsic capacity of the individual pathways does not appear to have been studied carefully.

In functional mitochondria, a few experimental parameters can be measured readily, reflecting mitochondrial respiration. These include NADH and $O_2$ consumption, and ATP production. Less readily measured are the electrons that flow through the electron transport chain, thereby consuming oxygen, and producing $H_2O$ and ATP. The electrons within the mitochondria can really only be measured when they are associated with one of the mitochondrial electron carriers such as coenzyme Q. In humans, this mitochondrial coenzyme is present as coenzyme $Q_{10}$, which has a 50-carbon C-substituent that renders the molecule virtually insoluble in water (calculated octanol-water partition coefficient $>10^{20}$) (James et al. (2005) *J Biol. Chem.* 280, 21295-21312).

In dysfunctional mitochondria, one can still carry out the same types of measurements as noted above for functioning mitochondria. If the flow of electrons through complex I is interrupted, several measured parameters should change. These include diminished consumption of NADH (measured as increased lactate through pyruvate reduction) and diminished ATP production. Since electrons will not flow as efficiently from complex I to coenzyme Q, the concentration of this reduced coenzyme will diminish. Interestingly, a new pathway for oxygen consumption is created. While oxygen is not converted as efficiently to water in complex IV (an overall four electron reduction of each oxygen molecule), much of the flow of electrons into a defective complex I is redirected to oxygen, with the production of superoxide (a one electron reduction of each oxygen). Thus, the stoichiometry of oxygen utilization is altered. The production of superoxide by mitochondria actually occurs to some extent even in normal mitochondria, but is a much more frequent event in mitochondria containing defects in the respiratory chain. Superoxide is one form of reactive oxygen species (ROS). Superoxide itself is not believed to react readily with biological molecules such lipid membranes, proteins and DNA, and actually functions as a signaling molecule for the regulation of certain cellular processes. Biologically, the main fate of superoxide ($O^-_{.2}$) is a disproportionation reaction with itself to produce peroxide ($H_2O_2$) and oxygen, i.e.

$$2O^-_{.2} + 2H^+ \rightarrow H_2O_2 + O_2$$

This reaction occurs spontaneously, and can also be catalyzed by superoxide dismutase. Superoxide can also be reduced to peroxide in a monovalent process. Like superoxide, hydrogen peroxide is also not intrinsically deleterious to cellular macromolecules, and is actually essential to the function of a number of enzymes. However, in the presence of metal ions such as iron and copper, hydrogen peroxide is converted to hydroxyl radical (HO.) and hydroxide ion ($OH^-$) according to the Fenton reaction, i.e.

$$HOOH + Fe^{2+} \rightarrow Fe^{3+} + HO. + OH^-$$

Hydroxyl radicals are very highly reactive, capable of reacting with virtually any biological molecule, including DNA, proteins and lipids. Hydroxyl radicals can also diffuse through cells readily, and their ability to damage cells is limited only by the distance that they travel before they react. Hydroxyl radicals can also react with superoxide, producing singlet oxygen (($^1O_2$)+$OH^-$), another highly reactive form of ROS that damages cellular macromolecules and assemblies. One particularly deleterious and well studied reaction mediated by hydroxyl radicals is the abstraction of hydrogen atoms (H.) from membrane lipids, forming a carbon-centered radical (R.). This radical $$HO. + RH(lipid) \rightarrow R. + H_2O$$

$$R. + O_2 \rightarrow ROO.$$

$$ROO. + RH \rightarrow ROOH + R.$$

can readily react with oxygen, forming a hydroperoxy radical (ROO.). The hydroperoxy radical is also highly reactive, and can abstract another hydrogen atom from the membrane lipid, producing another carbon-centered radical (which can undergo precisely the same chemistry), ultimately producing a chain reaction affording many oxidative lesions in the membrane lipids from a single hydroxyl radical (lipid peroxidation). It is for this reason that lipid peroxidation likely represents a major process by which cellular and mitochondrial membranes are degraded in cells containing (partially) dysfunctional mitochondria. The observed accumulation of lipofuscin in Friedreich's ataxia patients is fully consistent with the thesis that lipid peroxidation is a central process that drives disease progression (La Marche et al. (1980) *Can. J. Neurosci.* 7, 389-396; Yin, D. (1996) *Free Rad. Biol. Med.* 21, 871-888; Yamada et al. (2001) *J. Lipid Res.* 42, 1187-1196).

It may be noted that while all lesions in the mitochondrial electron transport chain that affect mitochondrial dysfunction will result in elevated levels of superoxide, some types of lesions may be expected to produce more functional damage. The latter would certainly include Friedreich's ataxia, in which suboptimal levels of the protein frataxin (which is responsible for cellular iron homeostasis; Park et al. (2003) *J. Biol. Chem.* 278, 31340-31351; Yoon et al. (2003) *J. Am.*

Chem. Soc. 125, 6078-6084; Yoon et al. (2004) *J. Biol. Chem.* 279, 25943-25946; Bencze et al. (2007) *J.C.S. Chem. Commun.* 1798-1800) results in an accumulation of $Fe^{2+/3+}$ within the mitochondria, and contributes instead to the Fenton chemistry noted above. Likewise, disorders such as amyotrophic lateral sclerosis are associated with a deficiency in the detoxifying enzyme superoxide dismutase, and will have greatly enhanced concentrations of the ROS discussed above.

One poorly studied parameter of mitochondrial electron transport is whether the process is best characterized as involving one or two electron transfers. The is important because NADH is an obligatory two-electron donor, and coenzyme Q and cytochrome c participate in two-electron redox cycles, as does $FADH_2$. Virtually all publications represent the processes in which these species participate as involving a net two electron change. However, $FADH_2$ may (and generally does) transfer its reducing equivalents as single electrons. Further, the Q cycle in complex III clearly involves single-electron transfers. Reduced cytochrome c is known to transfer electrons one at a time to cytochrome c oxidase, the enzyme responsible for the final step in respiration. Finally, the accumulation of electrons within dysfunctional mitochondria (producing reductive stress) is relieved substantially by (one-electron) reduction of oxygen to superoxide (vide supra). Thus, while the electron transport chain has the capacity to transfer two electrons by virtue of the redox cycles of most of its participants, it is not clear that it necessarily must do so to function.

Given that the reductive stress (build-up of electrons) encountered initially in mitochondrial dysfunction is a one electron process, as is lipid peroxidation, carriers of single electrons could find utility in dealing with reductive stress, e.g. molecules in which the one-electron reduced intermediate is stabilized by dipole interactions, substituent effects, resonance effects or captodative effects. Molecules designed to traffic single electrons, and which can (i) accept electrons from superoxide (ii) donate electrons to complex III and (iii) quench carbon-centered lipid radicals are especially useful. Multifunctional Radical Quenchers (MRQs) of the invention can effectively protect mitochondria, cells and organisms from oxidative stress.

Pharmaceutical Compositions

In another aspect, the present disclosure provides compositions comprising one or more of compounds as described above with respect to any of formulae (I)-(VIII) and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

DEFINITIONS

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present invention can modulate atherosclerosis by stimulating the removal of cholesterol from atherosclerotic lesions in a human.

"Treating" or "treatment" as used herein covers the treatment of a disease or disorder described herein, in a subject, preferably a human, and includes:

i. inhibiting a disease or disorder, i.e., arresting its development;

ii. relieving a disease or disorder, i.e., causing regression of the disorder;

iii. slowing progression of the disorder; and/or iv. inhibiting, relieving, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Methods of Synthesis

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

EXAMPLES

The compounds and methods of the disclosure are illustrated further by the following examples, which are provided for illustrative purposes and are not intended to be construed as limiting the disclosure in scope or spirit to the specific compounds and methods described in them.

$^1$H-NMR spectra were recorded on a Varian Inova 500 MHz and 400 MHz, using chloroform-d. $^1$H-NMR chemical shifts were reported relative to residual $CHCl_3$ at 7.24 ppm. All solvents were analytical grade and were used without further purification. All chemicals were purchased from Aldrich Chemical Company and were used without further purification. The reactions were carried out under an atmosphere of argon unless specified otherwise. Column chromatography was carried out using silica gel (Silicycle R10030B, 60 particle size, 230-240 mesh). Analytical thin layer chromatography separations were carried out on glass plates coated with silica gel (60, particle size F254, E. Merck 5608/7). The TLC chromatograms were developed using UV (short wave) lamp irradiation or by immersing the plates in 2.5% potassium permanganate in ethanol or 2% anysaldehyde+5% sulfuric acid+1.5% of glacial acetic acid in ethanol fallowed by heating (heat gun).

Example 1

Preparation of 2-N,N-dimethylamino-5-hydroxy-4-methyl-6-(10-hydroxydecyl)-pyrimidine

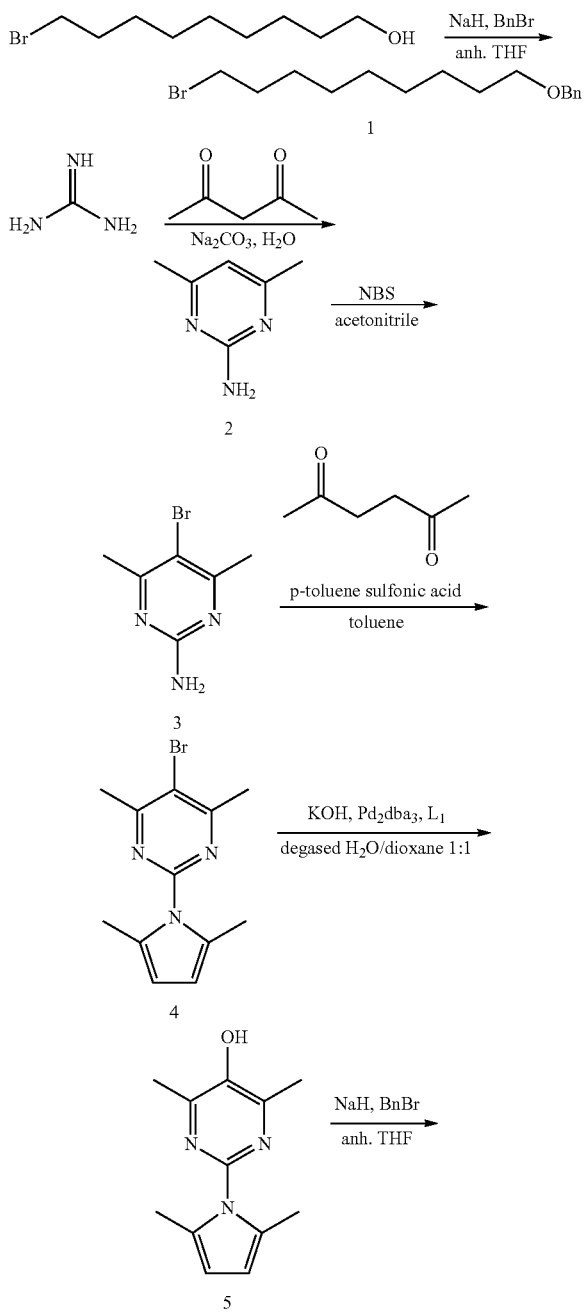

-continued

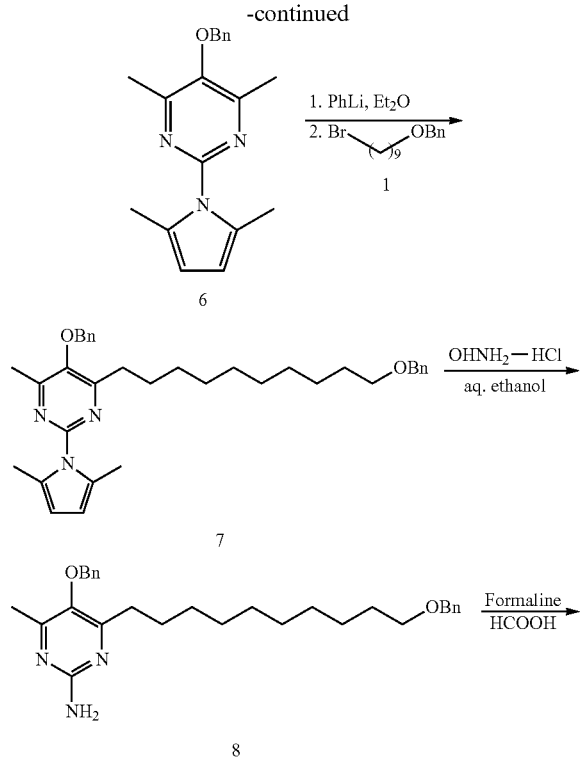

9-Bromo-1-(benzyloxy)nonane (1)

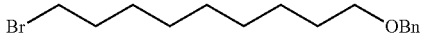 [SMILES: BrCCCCCCCCCOCc1ccccc1]

To a stirred solution containing 2.00 g (8.96 mmol) of 9-bromo-1-nonanol in 20 mL of anhydrous THF were added 1.55 mL (12.60 mmol) of benzyl bromide followed by 677 mg (16.94 mmol) of a 60% suspension of NaH in mineral oil. The reaction mixture was stirred overnight under argon atmosphere at room temperature. The reaction mixture was carefully quenched with saturated aqueous sodium bicarbonate. The mixture was poured into 100 nit of water and extracted with two portions of 100 mL of ether. The combined organic solution was washed with a portion of 100 mL of brine, dried (MgSO$_4$) and then concentrated under diminished pressure. The residue was purified by chromatography on a silica gel column. Elution with hexanes and then with hexanes-ethyl acetate 4:1 gave the expected product as colorless oil: yield 2.54 g (90%). $^1$H-NMR (CDCl$_3$) δ 7.86 (m, 5H), 4.51 (s, 2H), 3.47 (t, 2H, J=6.4), 3.40 (t, 2H, J=6.8), 1.85 (m, 2H), 1.62 (m, 2H), 1.39 (m, 10H); $^{13}$C-NMR (CDCl$_3$) δ 138.70, 128.34, 127.62, 127.47, 72.86, 70.46, 34.02, 32.83, 29.76, 29.38, 29.36, 28.71, 28.15, 28.16

2-Amino-4,6-dimethylpyrimidine (2)

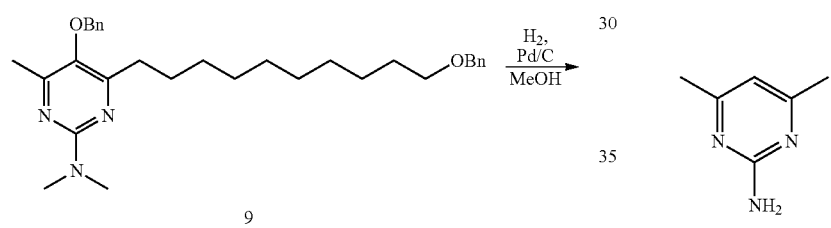

To a stirred solution containing 4.00 g (36.99 mmol) of guanidine sulfate and 8.40 g (79.25 mmol) of sodium carbonate in 25 mL of water were added 6.00 mL (58.12 mmol) of 2,4-pentadienone. The reaction mixture was stirred at 100° C. overnight. The reaction mixture was poured into 150 mL of water and then extracted with two portions of 150 mL of dichloromethane. The combined organic solution was washed with a 150 mL portion of brine, dried (MgSO$_4$) and then concentrated under diminished pressure to afford the expected product as a white solid: yield 4.31 g (95%). $^1$H-NMR (CDCl$_3$) δ 6.33 (s, 1H), 5.39 (br, 2H), 2.24 (s, 6H); $^{13}$C-NMR (CDCl$_3$) δ 167.72, 162.90, 110.45, 23.66.

2-Amino-5-bromo-4,6-dimethylpyrimidine (3)

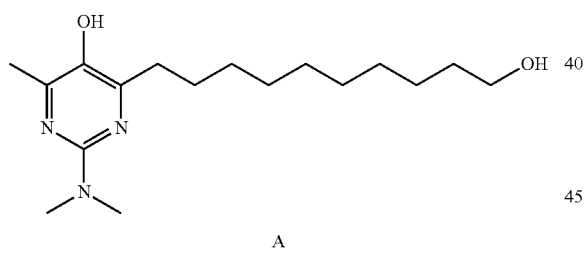

To a stirred solution containing 4.31 g (34.75 mmol) of 2-amino-4,6-dimethylpyrimidine (2) in 150 mL of acetonitrile were added 6.15 g (52.12 mmol) of N-bromosuccinim-

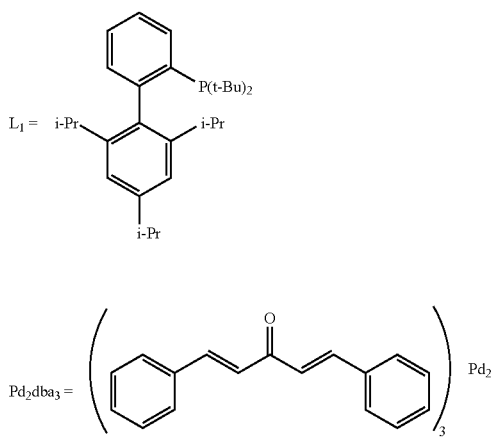

ide. The reaction mixture was stirred at room temperature under argon atmosphere for 3 h. The formed precipitate was filtered and dried to afford the expected product as a white solid: yield 5.93 g (83%). $^1$H-NMR (CDCl$_3$) δ 5.19 (br, 2H), 2.44 (s, 6H); $^{13}$C-NMR (CDCl$_3$) δ 166.28, 160.73, 109.60, 24.70.

2-(2,5-Dimethyl-1H-pyrrol-1-yl)-5-bromo-4,6-dimethylpyrimidine (4)

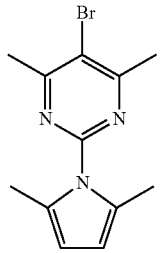

To a stirred solution containing 2.00 g (9.89 mmol) of 2-amino-5-bromo-4,6-dimethylpyrimidine (3) in 16 mL of anhydrous toluene were added 1.36 mL (11.5 mmol) of 2,5-hexadienone followed by 96 mg (0.50 mmol) of p-toluene sulfonic acid. The reaction mixture was stirred at reflux overnight under argon atmosphere. The reaction mixture was poured into 150 mL of water and then extracted with a portion of 200 mL of ethyl acetate. The organic solution was washed with a portion of 150 mL of brine, dried (MgSO$_4$) and then concentrated under diminished pressure. The residue was purified by chromatography on a silica gel column. Elution with hexanes-ethyl acetate 5:1 gave the expected product as light yellow crystals: yield 2.23 g (81%). $^1$H-NMR (CDCl$_3$) δ 5.90 (s, 2H), 2.67 (s, 6H), 2.34 (s, 6H); $^{13}$C-NMR (CDCl$_3$) δ 166.92, 155.32, 129.56, 118.62, 108.74, 24.90, 14.50.

2-(2,5-Dimethyl-1H-pyrrol-1-yl)-5-hydroxy-4,6-dimethylpyrimidine (5)

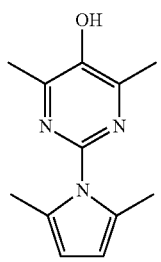

To a stirred solution containing 2.00 g (7.14 mmol) of 2-(2,5-dimethyl-1H-pyrrol-1-yl)-5-bromo-4,6-dimethylpyrimidine (4) in 16 mL of dioxane-degassed water 1:1 were added 132 mg (0.14 mmol) of Pd$_2$dba$_3$ followed by 242 mg (0.58 mmol) of 2-Di-tert-butylphosphino-2',4',6'-triisopropylbiphenyl (L1) and 1.2 g (21.42 mmol) of potassium hydroxide. The reaction mixture was stirred at 100° C. under argon atmosphere during 3 h. The reaction mixture was poured into 100 mL of water and extracted with two portions of 75 mL of ethyl acetate. The aqueous layer was acidified with HCl (pH 2-3) and then extracted with two portions of 100 mL of ethyl acetate. The combined organic solution was washed with a portion of 100 mL of brine, dried (MgSO$_4$) and the concentrated under diminished pressure to afford the expected product as a light yellow crystals: yield 1.62 g (100%). $^1$H-NMR (CDCl$_3$) δ 5.76 (s, 2H), 2.47 (s, 6H), 2.20 (s, 6H); $^{13}$C-NMR (CDCL$_3$) δ 154.15, 149.87, 145.13, 128.74, 107.32, 18.40, 13.50.

2-(2,5-Dimethyl-1H-pyrrol-1-yl)-5-benzyloxy-4,6-dimethylpyrimidine (6)

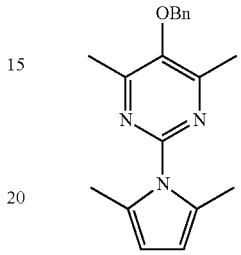

To a stirred solution containing 1.62 g (7.46 mmol) of 2-(2,5-dimethyl-1H-pyrrol-1-yl)-5-hydroxy-4,6-dimethylpyrimidine (5) in 30 mL of anhydrous THF were added 440 mg (11.00 mmol) of 60% sodium hydride suspension in mineral oil followed by 1.20 mL (10.10 mmol) of benzyl bromide. The reaction mixture was stirred at room temperature under argon atmosphere for 48 h. The reaction mixture was poured into 150 mL of water and extracted with two portions of 100 mL of ethyl acetate. The combined organic solution was washed with a portion of 100 of brine, dried (MgSO$_4$) and then concentrated under diminished pressure. The residue was purified by chromatography on a silica gel column. Elution with hexanes-ethyl acetate 4:1 gave the expected product as light yellow oil: yield 2.20 g (96%). $^1$H-NMR (CDCl$_3$) δ 7.42 (m, 5H), 5.86 (s, 2H), 4.92 (s, 2H), 2.47 (s, 6H), 2.29 (s, 6H); $^{13}$C-NMR (CDCl$_3$) δ 161.59, 152.34, 147.66, 136.05, 129.16, 128.59, 128.26, 107.90, 75.29, 19.10, 14.10.

2-(2,5-Dimethyl-1H-pyrrol-1-yl)-5-benzyloxy-4-methyl-6-(10-benzyloxydecyl)-pyrimidine (7)

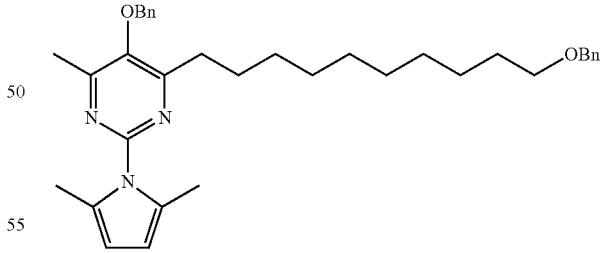

To a stirred solution at −78° C. containing 500 mg (1.62 mmol) of 2-(2,5-dimethyl-1H-pyrrol-1-yl)-5-benzyloxy-4,6-dimethylpyrimidine (6) in 10 mL of anhydrous THF were added 1.11 mL (1.76 mmol) of a 1.6 M solution of n-BuLi in pentane followed by 509 mg (1.62 mmol) of 9-bromo-1-(benzyloxy)nonane (1). The reaction mixture was stirred under argon atmosphere at −78° C. for 30 min. then the reaction mixture was warmed to room temperature slowly, and the reaction mixture was stirred overnight. The reaction was quenched with saturated aqueous NaHCO$_3$ and the poured into 70 mL of water. The mixture was then extracted with two portions of 70 mL of ethyl acetate. The combined organic solution was then washed with a portion of 100 mL of brine, dried (MgSO$_4$) and then concentrated under diminished pressure. The residue was purified by chromatography on a silica gel column. Elution with hexanes-ethyl acetate 5:1 gave the expected product as light yellow oil: yield 175 mg (20%). $^1$H-NMR (CDCl$_3$) δ 7.48-7.37 (m, 10H), 5.93 (s, 2H), 4.94 (s, 2H), 4.55 (s, 2H), 3.51 (t, 2H, J=6.8), 2.84 (t, 2H, J=7.6) 2.52 (s, 3H), 2.39 (s, 6H), 1.82 (m, 2H), 1.65 (m, 2H), 1.33 (m, 12H); $^{13}$C-NMR (CDCl$_3$) δ 165.16, 161.60, 152.48, 147.71, 138.79, 136.28, 129.16, 128.59, 128.26, 107.99, 75.29, 72.96, 70.70, 31.70, 29.85, 29.62, 29.52, 27.79, 26.27, 22.73, 19.32, 14.37

2-Amino-5-benzyloxy-4-methyl-6-(10-benzyloxydecyl)-pyrimidine (8)

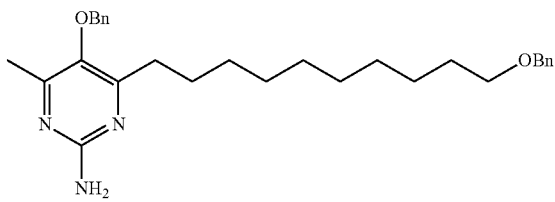 [SMILES: Cc1nc(N)nc(CCCCCCCCCCOCc2ccccc2)c1OCc1ccccc1]

To stirred solution containing 343 mg (0.63 mmol) of 2-(2,5-dimethyl-1H-pyrrol-1-yl)-5-benzyloxy-4-methyl-6-(10-benzyloxydecyl)-pyrimidine (7) in 10 mL of ethanol-water 9:1 were added 500 mg (7.19 mmol) of hydroxylamine hydrochloride followed by 400 mg (7.14 mmol) of potassium hydroxide. The reaction mixture was then stirred at reflux under argon atmosphere overnight. A second portion of 500 mg (7.19 mmol) of hydroxylamine hydrochloride was added and the reaction mixture was stirred overnight at reflux under argon atmosphere. The reaction mixture was then poured into 70 mL of water and then basified to a pH 9-10 with a 1N NaOH solution. The mixture was extracted with two portions of 70 mL of dichloromethane. The combined organic solution was washed with a portion of 70 mL of brine, dried (MgSO$_4$) and then concentrated under diminished pressure. The residue was purified by chromatography on a silica gel column. Elution with acetone-hexanes 2:1 gave the expected product as a colorless oil: yield 153 mg (52%). $^1$H-NMR (CDCl$_3$) δ 7.48-7.37 (m, 10H), 5.17 (br., 2H), 4.69 (s, 2H), 4.45 (s, 2H), 3.41 (t, 2H, J=6.8), 2.55 (t, 2H, J=7.6), 2.26 (s, 3H), 1.63-1.53 (m, 4H), 1.27 (m, 12H); $^{13}$C-NMR (CDCl$_3$) δ 164.85, 161.14, 158.88, 142.81, 138.71, 136.77, 129.16, 128.59, 128.26, 75.91, 72.83, 70.50, 31.90, 29.77, 29.22, 29.55, 29.45, 29.41, 28.44, 28.19, 19.00.

2-N,N-dimethylamino-5-benzyloxy-4-methyl-6-(10-benzyloxydecyl)-pyrimidine (9)

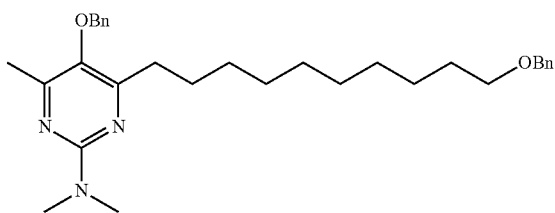

A stirred solution containing 188 mg (0.407 mmol) of 2-amino-5-benzyloxy-4-methyl-6-(10-benzyloxydecyl)-pyrimidine (8) in 35% aqueous formaldehyde-formic acid 1:1 was stirred at reflux overnight under argon atmosphere. The reaction mixture was poured into 50 mL of water and extracted with two portions of 40 mL of ethyl acetate. The combined organic solution was washed with portions of 40 mL of saturated aqueous NaHCO$_3$ and brine. The organic solution was dried (MgSO$_4$) and then concentrated under diminished pressure. The residue was purified by chromatography on a silica gel column. Elution with acetone-hexanes 1:2 gave the expected product as colorless oil: yield 82 mg (41%). $^1$H-NMR (CDCl$_3$) δ 7.48-7.37 (m, 10H), 4.70 (s, 2H), 4.49 (s, 2H), 3.45 (t, 2H, J=6.4), 3.15 (s, 6H), 2.61 (t, 2H, J=7.2), 2.34 (s, 3H), 1.63-1.53 (m, 4H), 1.27 (m, 12H); $^{13}$C-NMR (CDCl$_3$) δ 141.24, 138.71, 137.44, 129.16, 128.59, 128.26, 75.91, 72.83, 70.50, 31.90, 29.77, 29.22, 29.55, 29.45, 29.41, 28.44, 28.19, 19.00, 14.10.

2-N,N-dimethylamino-5-hydroxy-4-methyl-6-(10-hydroxydecyl)-pyrimidine (A)

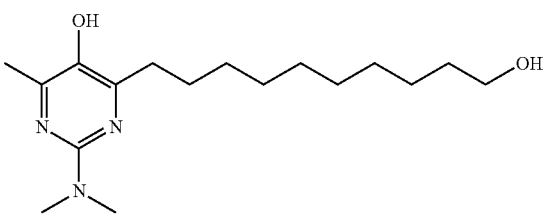 [SMILES: Cc1nc(N(C)C)nc(CCCCCCCCCCO)c1O]

To a stirred solution containing 82 mg (0.17 mmol) of 2-N,N-dimethylamino-5-benzyloxy-4-methyl-6-(10-benzyloxydecyl)-pyrimidine (9) in 5 mL of anhydrous methanol were added 3 mg of 10% palladium on carbon. The reaction mixture was stirred at room temperature under hydrogen atmosphere. The reaction mixture was filtered through celite and the filtrated was concentrated under diminished pressure. The residue was purified by chromatography on a silica gel column. Elution with hexanes-acetone 2:1 gave the expected product as colorless oil: yield 23 mg (44%). $^1$H-NMR (CDCl$_3$) δ 3.63 (t, 2H, J=6.8), 3.15 (br., 6H), 2.61 (br., 2H), 2.34 (br., 3H), 1.69-1.53 (m, 4H), 1.27 (m, 12H); $^{13}$C-NMR (CDCl$_3$) δ 141.24, 138.71, 137.44, 57.63, 31.90, 29.77, 29.22, 29.55, 29.45, 29.41, 28.44, 28.19, 19.00, 14.10.

Preparation of 2-N,N-dimethylamino-5-hydroxy-4,6-dimethylpyrimidine (12)

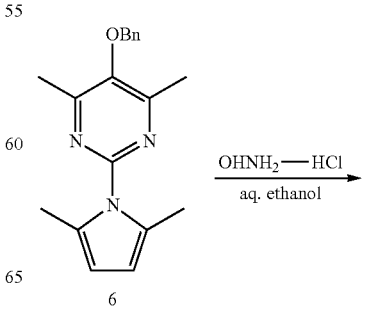

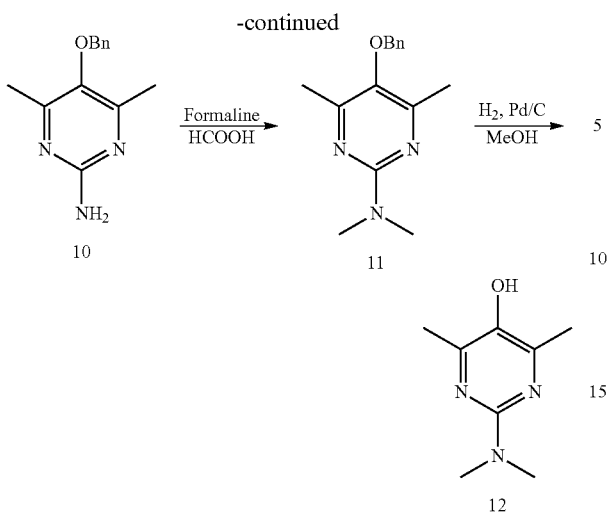

2-Amino-5-benzyloxy-4,6-dimethylpyrimidine (10)

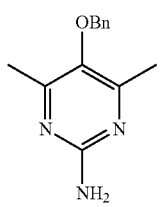

To a stirred solution containing 2.85 g (9.27 mmol) 2-(2,5-dimethyl-1H-pyrrol-1-yl)-5-benzyloxy-4,6-dimethylpyrimidine (6) in 30 mL of ethanol-water 1:1 were added 6.44 g (93 mmol) of hydroxylamine hydrochloride. The reaction mixture was stirred at reflux overnight under argon atmosphere. The pH of the solution was then brought to 10 and diluted with 20 mL of water. The mixture was extracted with two portions of 30 mL of dichloromethane. The combined organic solution was dried (MgSO$_4$) and then concentrate under diminished pressure. The residue was purified by chromatography on a silica gel column. Elution with acetone-hexanes 1:2 gave the expected product as white solid. Yield: 2.1 g (98%). $^1$H-NMR (CDCl$_3$) δ 7.39 (m, 5H), 4.80 (br. 2H), 4.74 (s, 2H), 2.29 (s, 6H). $^{13}$C-NMR (CDCl$_3$) 160.05, 158.45, 141.50, 137.02, 37.27, 19.22.

2-N,N-dimethylamino-5-benzyloxy-4,6-dimethylpyrimidine (11)

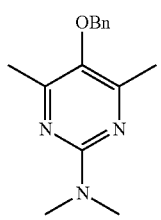

A stirred solution containing 500 mg (2.18 mmol) 2-amino-5-benzyloxy-4,6-dimethylpyrimidine (10) in 20 ml of formaline-formic acid 1:1 was stirred at reflux overnight under argon atmosphere. The reaction mixture was poured into 100 mL of 1N NaOH and extracted with two portions of 100 mL of dichloromethane. The combined organic solution was dried (MgSO$_4$) and then concentrate under diminished pressure. The residue was purified by chromatography on a silica gel column. Elution with hexanes-ethyl acetate 3:1 gave the expected product as colorless oil. Yield: 130 mg (23%). $^1$H-NMR (CDCl$_3$) δ7.41 (m, 5H), 4.74 (s, 2H), 3.14 (s, 6H), 2.31 (s, 6H). $^{13}$C-NMR (CDCl$_3$) δ 160.05, 158.45, 141.50, 137.02, 75.34, 37.27, 19.22.

2-N,N-dimethylamino-5-hydroxy-4,6-dimethylpyrimidine (12)

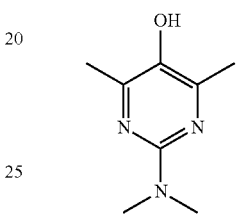

To a stirred solution containing 130 mg (0.50 mmol) 2-N,N-dimethylamino-5-benzyloxy-4,6-dimethylpyrimidine (11) in 4 ml of methanol were added 50 mg Pd/C (10%). The reaction mixture was stirred at room temperature 5 h under hydrogen atmosphere. The reaction mixture was filtered through celite and concentrated under diminished pressure to afford the expected product as a white solid: yield 82 mg (100%). $^1$H-NMR (CDCl$_3$) δ 3.13 (s, 6H), 2.35 (s, 6H). $^{13}$C-NMR (CDCl$_3$) δ 155.65, 155.35, 138.02, 37.89, 18.74.

Example 2

Preparation of 2-N,N-dimethylamino-5-hydroxy-4-methyl-6-(10-hydroxydecyl)-pyridine

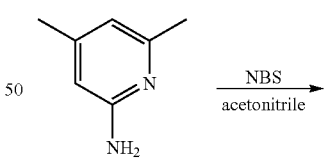

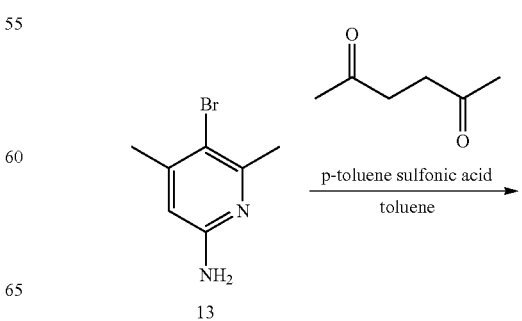

-continued

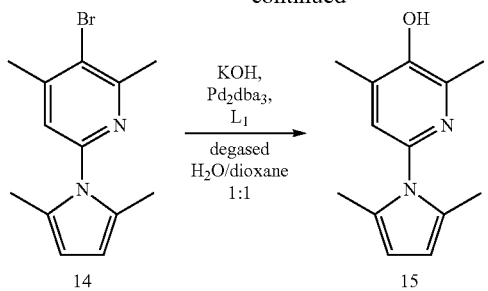

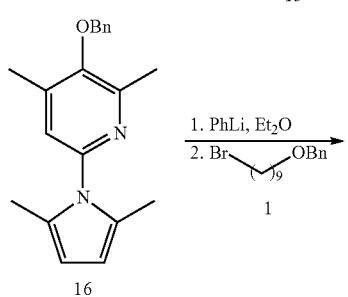

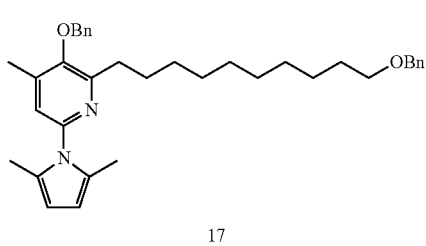

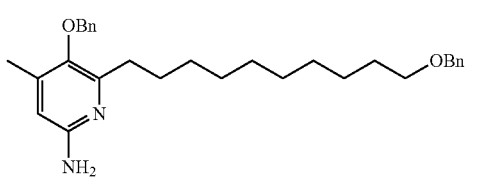

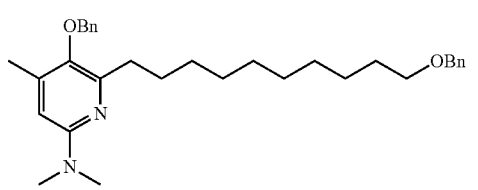

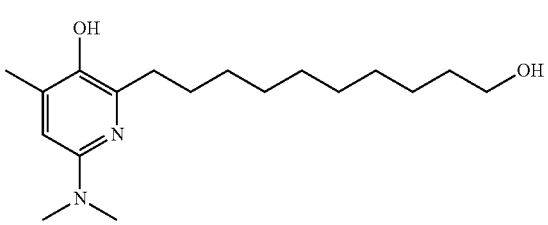

2-Amino-5-bromo-4,6-dimethylpyridine (13)

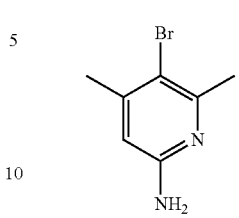

To a stirred solution containing 2.00 g (16.32 mmol) of 2-amino-4,6-dimethylpyridine in 25 mL of acetonitrile were added 2.90 g (16.32 mmol) of N-bromosuccinimide. The reaction mixture was stirred at room temperature under argon atmosphere for 5 h. The formed precipitate was filtered and dried to afford the expected product as a white solid: yield 2.76 g (84%). $^1$H-NMR (CDCl$_3$) δ 6.22 (s, 1H), 4.39 (br, 2H), 2.48 (s, 3H), 2.25 (s, 3H); $^{13}$C-NMR (CDCl$_3$) δ156.34, 155.23, 148.64, 112.26, 108.10, 25.10, 23.30.

2-(2,5-Dimethyl-1H-pyrrol-1-yl)-5-bromo-4,6-dimethylpyridine (14)

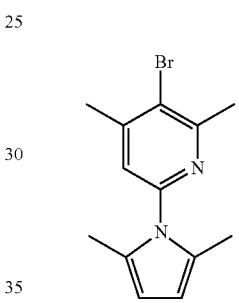

To a stirred solution containing 2.76 g (13.75 mmol) of 2-amino-5-bromo-4,6-dimethylpyridine (13) in 25 mL of toluene were added 2.02 mL (17.18 mmol) of 2,5-hexadienone followed by 130 mg (0.68 mmol) of p-toluene sulfonic acid. The reaction mixture was stirred at reflux overnight under argon atmosphere. The reaction mixture was poured into 150 mL of water and then extracted with a portion of 200 mL of ethyl acetate. The organic solution was washed with a portion of 150 mL of brine, dried (MgSO$_4$) and then concentrated under diminished pressure. The residue was purified by chromatography on a silica gel column. Elution with hexanes-ethyl acetate 5:1 gave the expected product as an orange oil: yield 2.37 g (62%). $^1$H-NMR (CDCl$_3$) δ 6.93 (s, 1H), 5.88 (s, 2H), 2.70 (s, 3H), 2.47 (s, 3H), 2.12 (s, 6H); $^{13}$C-NMR (CDCl$_3$) δ 157.35, 149.32, 128.42, 122.49, 121.22, 25.58, 23.41, 13.10.

2-(2,5-Dimethyl-1H-pyrrol-1-yl)-5-hydroxy-4,6-dimethylpyridine (15)

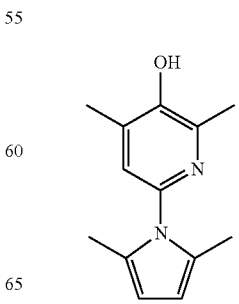

To a stirred solution containing 2.37 g (8.49 mmol) of 2-(2,5-dimethyl-1H-pyrrol-1-yl)-5-bromo-4,6-dimethylpyridine (14) in 30 mL of dioxane-degassed water 1:1 were added 311 mg (0.34 mmol) of Pd$_2$dba$_3$ followed by 288 mg (0.68 mmol) of 2-Di-tert-butylphosphino-2',4',6'-triisopropylbyphenyl (L1) and 1.42 g (25.46 mmol) of potassium hydroxide. The reaction mixture was stirred at 100° C. under argon atmosphere during 3 h. The reaction mixture was poured into 150 mL of water and extracted with two portions of 150 mL of ethyl acetate. The combined organic solution was washed with a portion of 100 mL of brine, dried (MgSO$_4$) and the concentrated under diminished pressure. The residue was purified by chromatography on a silica gel column. Elution with hexanes-ethyl acetate 3:1 gave the expected product as a white solid: yield 1.19 g (65%). $^1$H-NMR (CDCl$_3$) δ 6.89 (s, 1H), 5.75 (s, 2H), 2.45 (s, 3H), 2.22 (s, 3H), 2.05 (s, 6H); $^{13}$C-NMR (CDCl$_3$) δ 148.80, 145.03, 143.12, 135.51, 128.43, 122.32, 106.01, 18.48, 15.95, 12.80.

2-(2,5-Dimethyl-1H-pyrrol-1-yl)-5-benzyloxy-4,6-dimethylpyridine (16)

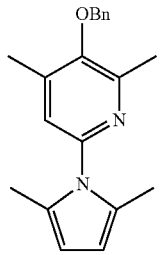

To a stirred solution containing 1.18 g (5.50 mmol) of 2-(2,5-dimethyl-1H-pyrrol-1-yl)-5-hydroxy-4,6-dimethylpyridine (15) in 20 mL of anhydrous THF were added 1.20 mL (10.10 mmol) of benzyl bromide followed by 440 mg (11.00 mmol) of 60% sodium hydride suspension in mineral oil. The reaction mixture was stirred at room temperature under argon atmosphere overnight. The reaction mixture was poured into 150 mL of water and extracted with two portions of 100 mL of ethyl acetate. The combined organic solution was washed with a portion of 100 mL of brine, dried (MgSO$_4$) and then concentrated under diminished pressure. The residue was purified by chromatography on a silica gel column. Elution with hexanes-ethyl acetate 4:1 gave the expected product as light yellow oil: yield 1.42 g (84%). $^1$H-NMR (CDCl$_3$) δ 6.98 (s, 1H), 5.91 (s, 2H), 4.94 (s, 2H), 2.58 (s, 3H), 2.37 (s, 3H), 2.17 (s, 6H); $^{13}$C-NMR (CDCl$_3$) δ 152.02, 151.03, 146.64, 141.95, 136.73, 128.60, 128.33, 127.89, 121.94, 106.44, 74.59, 19.48, 16.18, 13.08.

2-(2,5-Dimethyl-1H-pyrrol-1-yl)-5-benzyloxy-4-methyl-6-(10-benzyloxydecyl)-pyridine (17)

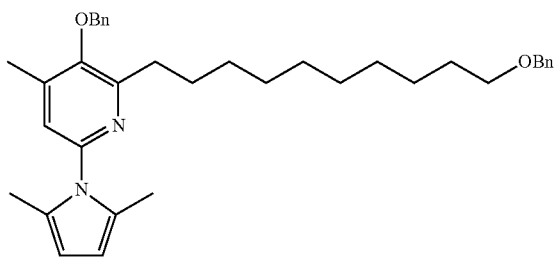 [SMILES: Cc1cc(-n2c(C)ccc2C)nc(CCCCCCCCCCOCc2ccccc2)c1OCc1ccccc1]

To a stirred solution at −78° C. containing 1.42 g (4.63 mmol) of 2-(2,5-dimethyl-1H-pyrrol-1-yl)-5-benzyloxy-4,6-dimethylpyridine (16) in 20 mL of anhydrous THF were added 5.15 mL (9.27 mmol) of a 1.8 M solution of PhLi in hexane followed by 1.45 g (4.63 mmol) of 9-bromo-1-(benzyloxy)nonane (1). The reaction mixture was stirred under argon atmosphere at −78° C. for 30 min. then the reaction mixture was warmed to room temperature slowly, and the reaction mixture was stirred 30 min. The reaction was quenched with saturated aqueous NaHCO$_3$ and the poured into 150 mL of water. The mixture was then extracted with two portions of 150 mL of ethyl acetate. The combined organic solution was then washed with a portion of 100 mL of brine, dried (MgSO$_4$) and then concentrated under diminished pressure. The residue was purified by chromatography on a silica gel column. Elution with hexanes-ethyl acetate 4:1 gave the expected product as light yellow oil: yield 1.22 g (49%) $^1$H-NMR (CDCl$_3$) δ 7.54-7.37 (m, 10H), 6.93, (s, 1H), 5.94 (s, 2H), 4.95 (s, 2H), 4.55 (s, 2H), 3.52 (t, 2H, J=6.4), 2.91 (t, 2H, J=8.0) 2.39 (s, 3H), 2.51 (s, 6H), 1.82 (m, 2H), 1.65 (m, 2H), 1.33 (m, 12H); $^{13}$C-NMR (CDCl$_3$) δ 155.94, 150.86, 146.89, 142.59, 138.80, 136.92, 128.69, 128.49, 128.38, 127.81, 127.65, 127.49, 121.75, 106.55, 75.30, 72.89, 70.55, 32.21, 29.85, 29.68, 29.63, 29.60, 29.59, 29.57, 29.53, 28.99, 26.27, 16.42, 13.30.

2-Amino-5-benzyloxy-4-methyl-6-(10-benzyloxydecyl)-pyridine (18)

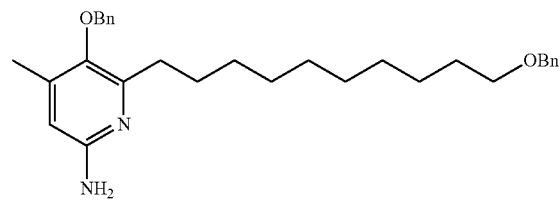

To stirred solution containing 1.22 g (2.26 mmol) of 2-(2,5-dimethyl-1H-pyrrol-1-yl)-5-benzyloxy-4-methyl-6-(10-benzyloxydecyl)-pyridine (17) in 40 mL of ethanol-water 4:1 were added 5.44 g (90.40 mmol) of hydroxylamine hydrochloride followed by 6.00 mL (45.20 mmol) of triethylamine. The reaction mixture was then stirred at reflux under argon atmosphere overnight. The reaction mixture was then poured into 100 mL of saturated aqueous NaHCO$_3$ and extracted with two portions of 100 mL of dichloromethane. The combined organic solution was washed with a portion of 100 mL of brine, dried (MgSO$_4$) and then concentrated under diminished pressure. The residue was purified by chromatography on a silica gel column. Elution with dichloromethane-methanol 9:1 gave the expected product as a yellowish oil: yield 722 mg (69%). $^1$H-NMR (CDCl$_3$) δ 7.38-7.24 (m, 10H), 6.24 (s, 1H), 4.72 (s, 2H), 4.48 (s, 2H), 3.44 (t, 2H, J=8.0), 2.63 (t, 2H, J=8.0), 2.19 (s, 3H), 2.04 (s, 3H), 1.63-1.53 (m, 4H), 1.27 (m, 12H); $^{13}$C-NMR (CDCl$_3$) δ 176.95, 153.85, 149.42, 146.90, 143.66, 138.66, 136.73, 128.62, 128.30, 127.77, 127.61, 127.44, 109.71, 75.86, 72.81, 70.50, 29.73, 29.58, 29.55, 29.52, 29.44, 29.42, 29.26, 26.16, 22.14, 16.73.

2-N,N-dimethylamino-5-benzyloxy-4-methyl-6-(10-benzyloxydecyl)-pyridine (19)

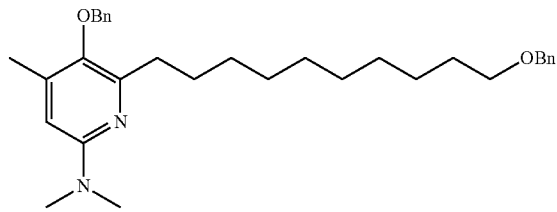 [SMILES: Cc1cc(N(C)C)nc(CCCCCCCCCCOCc2ccccc2)c1OCc1ccccc1]

A stirred solution containing 722 mg (1.57 mmol) of 2-amino-5-benzyloxy-4-methyl-6-(10-benzyloxydecyl)-pyridine (18) in 6 mL of anhydrous DMF were added 1.17 mL (18.84 mmol) of methyl iodide followed by 376 mg (9.40 mmol) of a 60% suspension of NaH in mineral oil. The reaction mixture was stirred at room temperature for 3 h under argon atmosphere. The reaction mixture was quenched with water and concentrated under diminished pressure. The residue was dissolved into 150 mL of dichloromethane and washed with a portion of 150 mL of brine. The organic solution was dried ($MgSO_4$) and then concentrated under diminished pressure. The residue was purified by chromatography on a silica gel column. Elution with n-pentane-ethyl acetate 3:1 gave the expected product as yellowish oil: yield 320 mg (42%) $^1$H-NMR ($CDCl_3$) δ 7.48-7.37 (m, 10H), 4.70 (s, 2H), 4.49 (s, 2H), 3.45 (t, 2H, J=6.4), 3.15 (s, 6H), 2.61 (t, 2H, J=7.2), 2.34 (s, 3H), 1.63-1.53 (m, 4H), 1.27 (m, 12H)

2-N,N-dimethylamino-5-hydroxy-4-methyl-6-(10-hydroxydecyl)-pyridine (B)

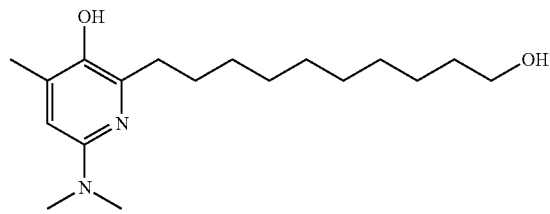

To a stirred solution at −78° C. containing 18 mg (0.045 mmol) of 2-N,N-dimethylamino-5-benzyloxy-4-methyl-6-(10-benzyloxydecyl)-pyridine (19) in 2 mL of anhydrous dichoromethane were added 17 mg (0.045 mmol) of n-$Bu_4$NI followed by 113 μL (0.113 mmol) of a 1M solution of $BCl_3$ in dichloromethane. The reaction mixture was stirred meanwhile was warmed slowly to room temperature during 30 minutes under argon atmosphere. The reaction mixture was quenched with water and poured into 20 mL of 2N HCl. The mixture was extracted with a 30 mL portion of DCM. The aqueous layer was basified (pH~11-12) with a 2N NaOH solution and extracted with two portions of 20 mL of DCM. The combined organic solution was washed with a portion of 40 mL of brine, dried ($MgSO_4$) and concentrated under diminished pressure to afford the expected product as a yellowish oil: yield 10.6 mg (76%). $^1$H-NMR ($CDCl_3$) δ 6.21 (br, H), 3.63 (t, 2H, J=6.4), 3.04 (br., 6H), 2.71 (br., 2H), 2.22 (br., 3H), 1.69-1.53 (m, 4H), 1.27 (m, 12H).

Preparation of 2-N,N-dimethylamino-5-hydroxy-4,6-dimethylpyrimidine (21)

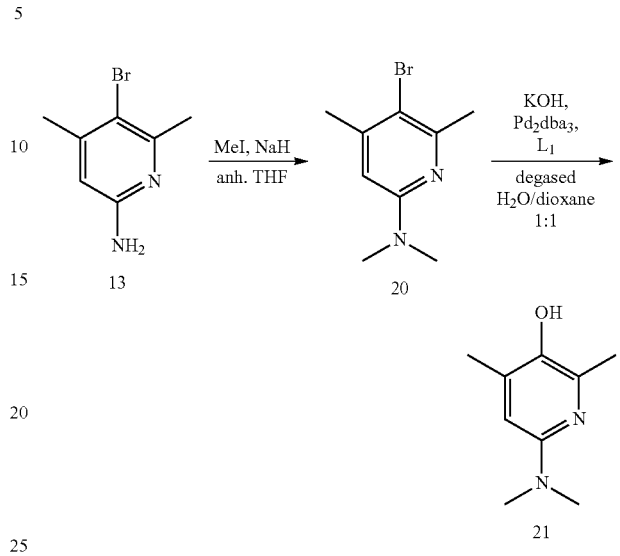

2-N,N-dimethylamino-5-bromo-4,6-dimethylpyridine (20)

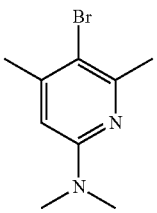

To a stirred solution containing 1.12 g (5.57 mmol) of 2-amino-5-bromo-4,6-dimethylpyridine (13) in 20 mL of anhydrous THF were added 1.04 mL (16.71 mmol) of methyl iodide followed by 668 mg (16.71 mmol) of 60% suspension of sodium hydride in mineral oil. The reaction mixture was stirred at room temperature under argon atmosphere overnight. The reaction mixture was poured into 100 mL of water and extracted with two portions 100 mL of ether. The combined organic solution was dried (MgSO4) and the concentrated under diminished pressure. The residue was purified by chromatography on a silica gel column. Elution with hexanes-ether 9:1 gave the expected product as colorless oil: yield 700 mg (55%). $^1$H-NMR ($CDCl_3$) δ 6.22 (s, 1H), 3.01 (s, 6H), 2.51 (s, 3H), 2.30 (s, 3H); $^{13}$C-NMR ($CDCl_3$) δ156.34, 155.23, 148.64, 112.26, 108.10, 74.40, 25.10, 23.30.

2-N,N-dimethylamino-5-hydroxy-4,6-dimethylpyridine (21)

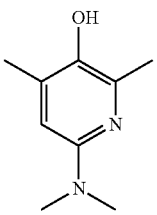

To a stirred solution containing 1.12 g (5.57 mmol) of 2-N,N-dimethylamino-5-bromo-4,6-dimethylpyridine (20) in 10 mL of dioxane-degassed water 1:1 were added 56 mg (0.06 mmol) of $Pd_2dba_3$ followed by 45 mg (0.10 mmol) of 2-Di-tert-butylphosphino-2',4',6'-triisopropylbyphenyl (L1) and 512 mg (9.15 mmol) of potassium hydroxide. The reaction mixture was stirred at 100° C. under argon atmosphere during 4 h. The reaction mixture was poured into 100 mL of water and extracted with a portion of 75 mL of ether. The aqueous layer was neutralized (pH ~7.0) with HCl and then extracted with two portions of 75 mL of ethyl acetate. The combined organic solution was washed with a portion of 75 mL of brine, dried ($MgSO_4$) and the concentrated under diminished pressure to afford the expected product as a light brownish solid: yield 200 mg (35%). $^1$H-NMR (Methanol-$d_4$) δ 6.27 (s, 1H), 2.90 (s, 6H), 2.29 (s, 3H), 2.16 (s, 3H)

Example 3

Preparation of 4-((3R,7R,11R)-3-hydroxy-3,7,11,15-tetramethylhexadecyl)-1,6-dimethyl-2,3-dihydro-1H-pyrrolo[2,3-b]pyridine-5-ol

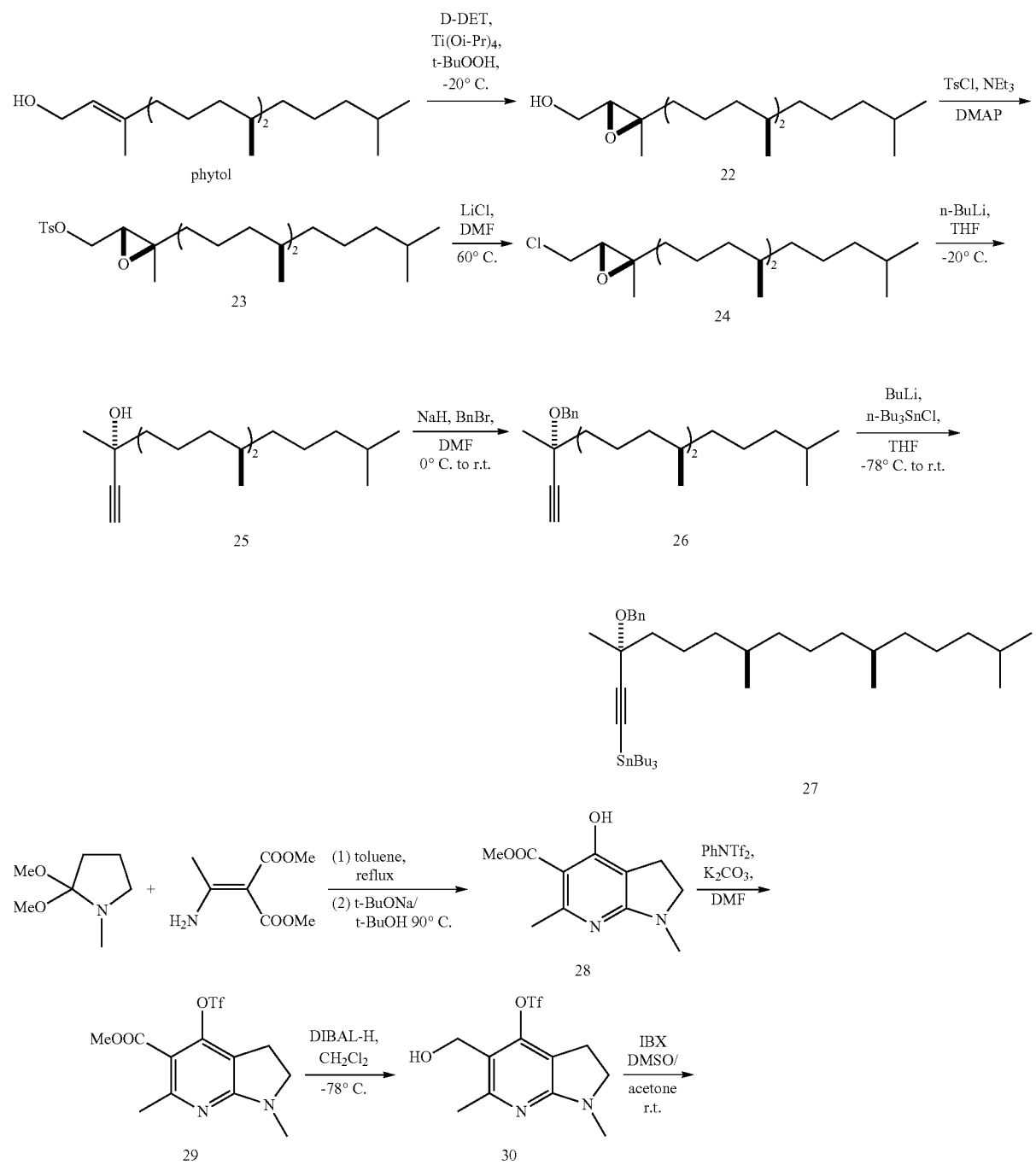

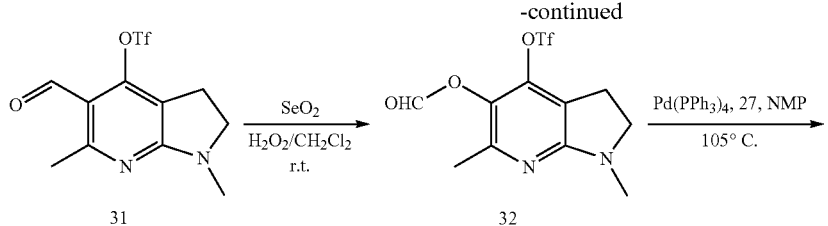
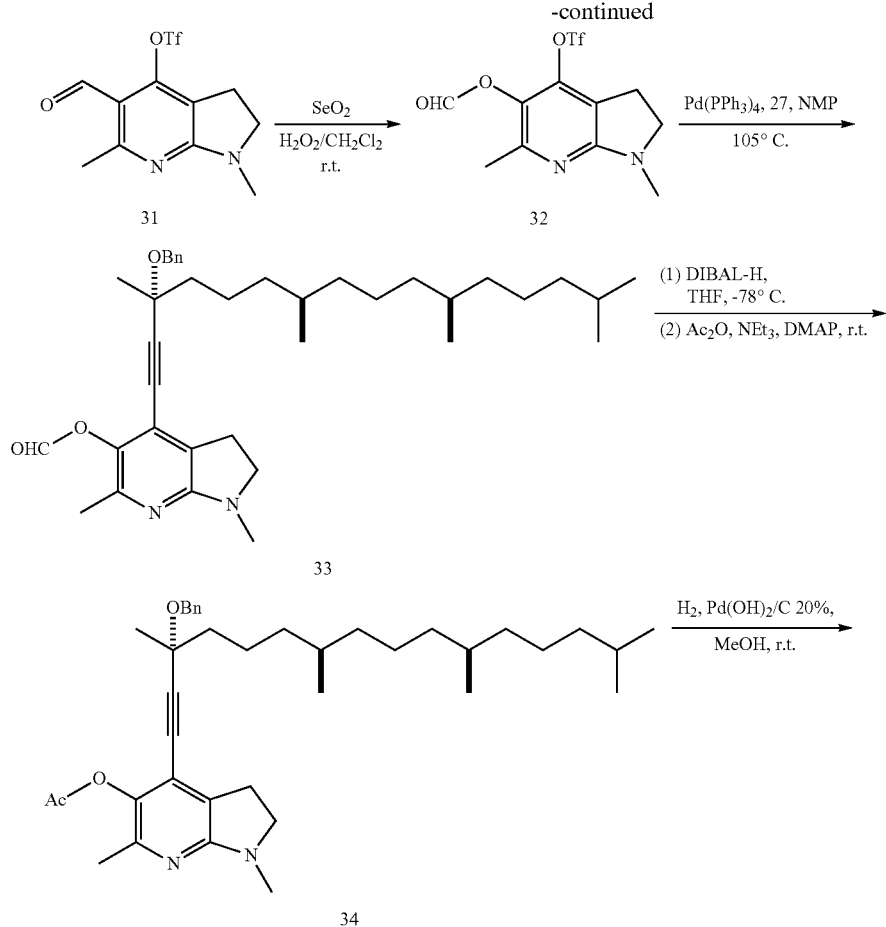
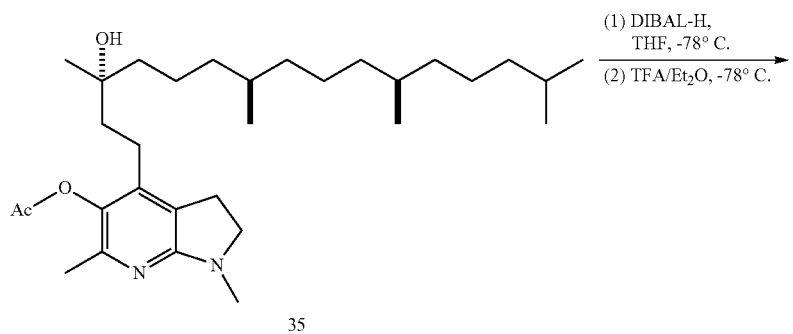
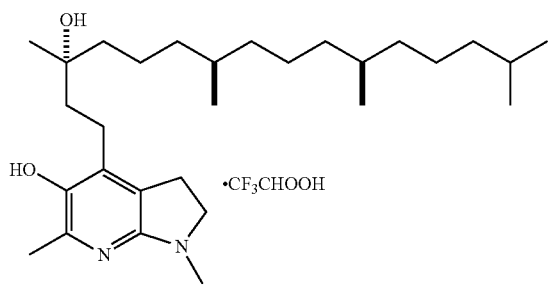

(2R,3R)-3-methyl-3-((4R,8R)-4,8,12-trimethyltridecyl)oxiran-2-yl)methanol ((R)-22)

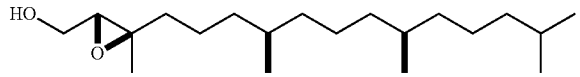

To a solution of 4.7 g of D-DET (22 mmol) and 3.5 g of 4 Å MS in 300 mL of dichloromethane was added 13.7 g of Ti(i-PrO)$_4$ (20 mmol) and 5.5 mL of t-BuOOH (5.5 M in nonane, 30 mmol) at −20° C. under argon protection. After 20 minutes a solution of 5.93 g of natural phytol (20 mmol) in 80 mL of dichloromethane was added to the reaction mixture. Then the reaction mixture was stirred at the same temperature for 3 h. TLC monitored all starting material was consumed. The reaction was quenched by adding 250 mL of 1N NaOH mixture with brine then the mixture was allowed to warm to room temperature. The mixture was filtered through celite then the mother liquid was separated, the solid was washed by two portions of 400 mL ethyl acetate. The combined organic layer was dried (Na$_2$SO$_4$) and concentrated under diminished pressure. The residue was purified by flash chromatography on a silica gel column (25×3.2 cm). Elution with 1:10 Et$_2$O-hexanes gave the product (R)-22 as colorless oil: yield 5.98 g, (96%); silica gel TLC R$_f$ 0.26 (1:1 Et$_2$O-hexane); $^1$H NMR (CDCl$_3$, ppm): δ 0.83-0.87 (m, 12H), 1.00-1.65 (m, 21H), 1.21 (s, 3H), 2.27 (br s, 1H), 2.97 (dd, J=3, 4.8 Hz, 1H), 3.68 (dd, J=5.4, 8.1 Hz, 1H), 3.83 (br d, J=8.7 Hz, 1H). $^{13}$C NMR (CDCl$_3$, ppm): δ 17.04, 19.92, 20.02, 22.82, 22.90, 23.00, 24.73, 25.06, 26.06, 28.24, 37.18, 37.53, 37.59, 37.66, 39.06, 39.61, 61.65, 61.71, 63.27, 80.86.

Toluene-4-sulfonic acid 3-methyl-3-(4,8,12-trimethyl-tridecyl)-oxiranylmethyl ester ((R)-23)

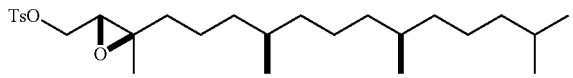

To a solution of 0.93 g of epoxide alcohol 22 (3.0 mmol) in 20 mL of dichloromethane was added 0.75 g of triethylamine and catalytic amount of DMAP. Then 0.68 g of TsCl was added by portions to the mixture. The reaction mixture was stirred at room temperature overnight then quenched by adding 30 mL of water. The organic layer was washed with brine and dried over Na$_2$SO$_4$. After the solvent was removed the residue was purified by flash chromatography on a silica gel column (25×3.2 cm). Elution with 1:100 to 1:10 Et$_2$O-hexanes gave the product (R)-23 as colorless oil: yield 1.12 g, (80%); silica gel TLC R$_f$ 0.20 (1:5 Et$_2$O-hexane); $^1$H NMR (CDCl$_3$, ppm): δ 0.82-0.86 (m, 12H), 0.99-1.92 (m, 21H), 1.19 (s, 3H), 2.44 (s, 3H), 2.96 (t, J=6.0 Hz, 1H), 4.09 (dd, J=6.0, 11.0 Hz, 1H), 4.15 (dd, J=5.5, 11.0 Hz, 1H), 7.34 (d, J=8.0 Hz, 2H), 7.80 (d, J=6.8 Hz, 2H).

(2R,3S)-3-(chloromethyl)-2-methyl-2-((4R,8R)-4,8,12-trimethyltridecyl)oxirane ((R)-24)

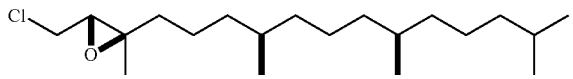

To a solution of 1.12 g of epoxide tosylate ester ((R)-23, 2.4 mmol) in 20 mL of DMF was added 0.12 g of lithium chloride (2.6 mmol). The reaction mixture was stirred at 60° C. for 1 hour. After cooled to room temperature, the mixture was poured into 40 mL of water and extracted with three portions of 30 mL of EtOAc. The combined organic layer was washed with saturated aqueous NaHCO$_3$ and brine then dried (Na$_2$SO$_4$) and concentrated under diminished pressure. The residue was purified by flash chromatography on a silica gel column (25×3.2 cm). Elution with 1:100 Et$_2$O-hexanes gave the product (R)-24 as colorless oil: yield 0.72 g, (91%); silica gel TLC R$_f$ 0.66 (1:5 Et$_2$O-hexanes); $^1$H NMR (CDCl$_3$, ppm): δ 0.83-0.88 (m, 12H), 1.00-1.70 (m, 21H), 1.31 (s, 3H), 3.03 (t, J=6.6 Hz, 1H), 3.45 (dd, J=7.2, 11.4 Hz, 1H), 3.70 (dd, J=6, 11.7 Hz, 1H).

(3R,7R,11R)-3,7,11,15-tetramethylhexadec-1-yn-3-ol ((R)-25)

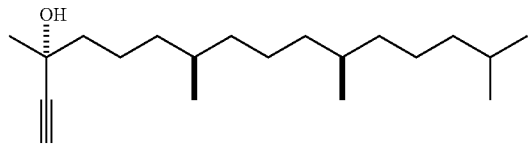 [SMILES: C#C[C@](C)(O)CCC[C@H](C)CCC[C@H](C)CCCC(C)C]

To a solution of 720 mg of epoxide chloride ((R)-24, 2.2 mmol) in 10 mL of dry THF was added 4.4 mL of butyl lithium (2.5 M in hexane, 11.0 mmol) at −20° C. under argon protection. After 20 min the reaction mixture was quenched by adding 10 mL of saturated aqueous ammonium chloride and warmed to room temperature. The reaction mixture was extracted by three portions of 10 mL ethyl acetate. The combined organic layer was washed with brine and dried over MgSO$_4$. After the solvent was removed under diminished pressure the residue was purified b flash chromatography on a silica gel column (20×3.2 cm). Elution with 1:5 Et$_2$O-hexanes gave the product (R)-25 as colorless oil: yield 640 mg, (100%); silica gel TLC R$_f$ 0.16 (1:1 Et$_2$O-hexanes); $^1$H NMR (CDCl$_3$, ppm): δ 0.82-0.87 (m, 12H), 0.99-1.72 (m, 21H), 1.49 (s, 3H), 2.12 (br s, 1H), 2.42 (s, 1H).

[1-Methyl-1-(4R,8R,12R)-4,8,12-trimethyl-tridecyl)-prop-2-ynyloxymethyl]-benzene ((R)-26)

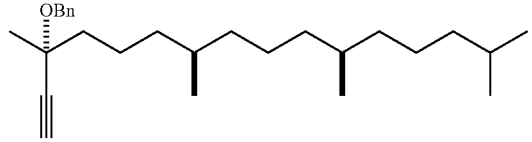 [SMILES: C#C[C@@](C)(CCC[C@H](C)CCC[C@H](C)CCCC(C)C)OCc1ccccc1]

To a solution of 718 mg of (R)-25 (2.4 mmol) in 20 mL of dry DMF was added 160 mg of sodium hydride (60% mixture of mineral oil, 4.0 mmol) and stirred at 0° C. for 20 min. 680 mg of benzyl bromide (4.0 mmol) was added to the reaction mixture by syringe. After addition, the reaction mixture was warmed to room temperature and stirred for 1 h. 20 mL of aqueous saturated ammonium chloride and 20 mL of water were added to quench this reaction. The reaction mixture was extracted by 3 portions of 50 mL ethyl acetate. The combined organic layer was washed with brine and dried (MgSO$_4$) then the solvent was removed under diminished pressure. The residue was purified by flash chromatography on a silica gel column (25×3.2 cm). Elution with 1:100 Et$_2$O-hexanes gave the product (R)-26 as colorless oil: yield 750 mg, (80%); silica gel TLC R$_f$ 0.95 (1:20 Et$_2$O-hexanes); $^1$H NMR (CDCl$_3$, ppm): δ 0.83-0.88 (m, 12H), 1.02-1.81 (m, 19H), 1.50 (s, 3H), 2.48 (s, 3H), 4.63 (dd, J=11.5, 32.5 Hz, 2H), 7.24-7.27 (m, 1H), 7.30-7.37 (m, 4H). $^{13}$C NMR (CDCl$_3$, ppm): δ 19.67, 19.83, 21.69, 22.65, 22.71, 24.47, 24.80, 26.32, 26.37, 27.97, 32.69, 32.79, 37.11, 37.29, 37.43, 39.37, 41.82, 66.19, 73.23, 73.67, 85.51, 127.27, 127.62, 128.25, 139.11; MALDI-TOF: m/z, M+Na$^+$, 407.2.

((3R,7R,11R)-3-(benzyloxy)-3,7,11,15-tetramethyl-hexadec-1-ynyl)tributylstannane (27)

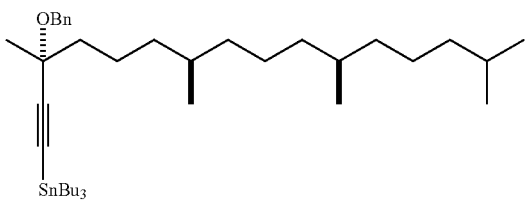

To a solution of 424 mg (1.4 mmol) of alkyne 26 in 6 mL of dry THF was added 1.12 mL (2.5 M in hexane, 2.8 mmol) at −78° C. After addition, the reaction mixture was warmed to 0° C. and stirred for 20 min then 470 mg (1.4 mmol) of n-Bu$_3$SnCl was added. The reaction mixture was warmed to room temperature and stirred for 4 h then poured into 10 mL of aqueous saturated NH$_4$Cl. The mixture was extracted with three 10 mL portions of ethyl ether. The combined organic layer was washed with brine, dried (Na$_2$SO$_4$) and concentrated under diminished pressure. The residue was purified by flash chromatography on a silica gel column (25×3.2 cm). Elution with pure hexanes gave the product 27 as colorless oil: yield 768 mg (100%); silica gel TLC R$_f$ 0.96 (1:20 Et$_2$O-hexanes); $^1$H NMR (CDCl$_3$): δ 0.78-0.92 (m, 39H), 0.96-1.84 (24H), 4.64 (q, J=16.4 Hz, 2H), 7.24-7.36 (m, 5H); $^{13}$C NMR (CDCl$_3$): δ 8.82, 11.15, 13.75, 13.80, 19.83, 22.16, 22.71, 22.81, 24.65, 24.92, 26.99, 27.51, 28.08, 29.04, 29.39, 29.85, 32.94, 37.63, 39.51, 66.24, 73.27, 74.60, 87.38, 127.12, 127.73, 128.18, 128.35, 139.77; mass spectrum, m/z 697.5 (M+Na$^+$) (theoretical 697.4).

4-Hydroxy-1,6-dimethyl-2,3-dihydro-1H-pyrrolo[2,3-b]pyridine-5-carboxylic acid methyl ester (28)

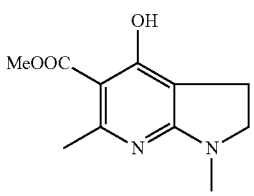

A mixture of 100 mg of 2-(1-Amino-ethylidene)-malonic acid dimethyl ester (57.7 µmol) and 168 mg of 2,2-dimethyl-1-methylpyrrolidine (115.4 µmol) in 2 mL of toluene was heated at reflux for 3 h then 160 mg of sodium tert butoxide (2.9 eq) and 1 mL of tert butanol was added. The resulting reaction mixture was heated at 90° C. and stirred for 16 h then cooled to room temperature. To this solution was added 5 mL of aqueous saturated ammonium chloride and was extracted with three portions of 10 mL of ethyl acetate. The combined organic layer was washed with brine and dried (MgSO$_4$). After the solvent was removed under diminished pressure, the residue was purified by flash chromatography on a silica gel column (15×2 cm). Elution with 1:20 to 1:10 EtOAc-hexanes gave product 28 as white solid: yield 115 mg, (90%); Silica gel TLC R$_f$ 0.46 (1:4 EtOAc-Hexane); $^1$H NMR (CDCl$_3$, ppm): δ 2.62 (s, 3H), 2.93 (t, J=8.4 Hz, 2H), 2.98 (s, 3H), 3.55 (t, J=9.0 Hz, 2H), 3.90 (s, 3H), 11.79 (s, 1H). $^{13}$C NMR (CDCl$_3$, ppm): δ 22.48, 27.82, 31.90, 51.98, 52.35, 101.09, 102.20, 162.20, 163.75, 165.64, 172.38; HRMS (ESI+) calculated for C$_{11}$H$_{14}$N$_2$O$_3$ 223.1077. found 223.1082.

Methyl 1,6-dimethyl-4-(trifluoromethylsulfonyloxy)-2,3-dihydro-1H-pyrrolo[2,3-b]pyridine-5-carboxylate (29)

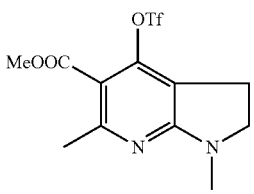 [SMILES: COC(=O)c1c(C)nc2c(c1OS(=O)(=O)C(F)(F)F)CCN2C]

To a solution of 74 mg of 4-Hydroxy-1,6-dimethyl-2,3-dihydro-1H-pyrrolo[2,3-b]pyridine-5-carboxylic acid methyl ester (28, 0.33 mmol) and 150 mg of potassium carbonate in 2.5 mL of dry DMF was added 180 mg of N-phenyl bis-triflormethane sulfonimide (0.50 mmol) at room temperature. The reaction mixture was stirred for 1.5 h then quenched by adding 5 mL of aqueous saturated ammonium chloride. The reaction mixture was extracted with three portions of 5 mL of ethyl acetate. The combined organic layer was washed with brine and dried (MgSO$_4$). The solvent was removed and the residue was purified by flash chromatography on a silica gel column (15×2 cm). Elution with 1:40 EtOAc-hexanes gave product 29 as white solid: yield 110 mg, (94%). Silica gel TLC R$_f$ 0.30 (1:1 EtOAc-hexanes); $^1$H NMR (CDCl$_3$, ppm): δ 2.54 (s, 3H), 3.01 (s, 3H), 3.11 (t, J=8.5 Hz, 2H), 3.62 (t, J=8.0 Hz, 2H), 3.85 (s, 3H); $^{13}$C NMR (CDCl$_3$, ppm): δ 23.54, 24.37, 51.33, 52.04, 108.54, 10.96, 111.88, 149.34, 161.78, 164.88, 165.60; HRMS (ESI+) calculated for C$_{12}$H$_{13}$N$_2$O$_5$SF$_3$ 355.0570. found 355.0566.

5-(Hydroxymethyl)-1,6-dimethyl-2,3-dihydro-1H-pyrrolo[2,3-b]pyridin-4-yl trifluoromethanesulfonate (30)

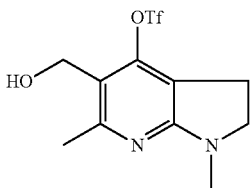 [SMILES: Cc1nc2c(c(OS(=O)(=O)C(F)(F)F)c1CO)CCN2C]

To a solution of 169.7 mg of methyl ester 29 in 2 mL of dichloromethane was added 1.43 mL of DIBAL-H (1M in toluene, 3 eq) dropwise at −78° C. under Ar protection. After addition, the reaction mixture was stirred at the same temperature and stirred for additional 2 h then 5 mL of aqueous saturated sodium potassium tartrate was added by syringe. The reaction mixture was allowed to warm to room temperature and stirred for additional 4 h. After separation, the aqueous layer was extracted with three portions of 5 mL of dichloromethane. The combined organic layer was washed with brine and dried over magnesium sulfate. After the solvent was removed, the residue was purified by flash chromatography on a silica gel column (15×2 cm). Elution with 1:2 EtOAc-hexanes gave product 30 as white solid: yield 148 mg, (95%). Silica gel TLC $R_f$ 0.20 (1:1 EtOAc-hexanes); $^1$H NMR (CDCl$_3$, ppm): δ 1.72 (br s, 1H), 2.52 (s, 3H), 2.96 (s, 3H), 3.08 (t, J=8.4 Hz, 2H), 3.54 (t, J=8.4 Hz, 2H), 4.58 (s, 2H). $^{13}$C NMR (CDCl$_3$, ppm): δ 22.01, 23.97, 32.29, 51.78, 76.68, 111.48, 114.08, 149.79, 159.93, 164.67; HRMS (ESI+) calculated for $C_{11}H_{13}N_2O_4SF_3$ (M+H$^+$) 327.0621. found 327.0622.

5-Formyl-1,6-dimethyl-2,3-dihydro-1H-pyrrolo[2,3-b]pyridin-4-yl trifluoromethanesulfonate (31)

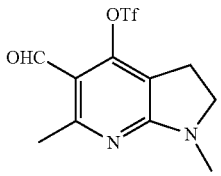 [SMILES: Cc1nc2c(c(OS(=O)(=O)C(F)(F)F)c1C=O)CCN2C]

To a solution of 134 mg of alcohol 30 in 2 mL of DMSO and 2 mL of acetone was added 116 mg of IBX. The reaction mixture was stirred at room temperature for 16 h then cooled to 0° C., 5 mL of a mixture of 5% NaHCO$_3$ and 5% of NaS$_2$O$_3$ was added by syringe slowly. After stirred for additional 20 min the mixture was extracted with three portions of 5 mL of ethyl acetate. The combined organic layer was washed with brine and dried over MgSO$_4$. After the solvent was removed under diminished pressure, the residue was purified by flash chromatography on a silica gel column (15×2 cm). Elution with 1:10 EtOAc-hexanes gave product 31 as white crystal: yield 121 mg, (91%). Silica gel TLC $R_f$ 0.20 (1:4 EtOAc-hexanes); $^1$H NMR (CDCl$_3$, ppm): δ 2.70 (s, 3H), 3.09 (s, 3H), 3.18 (t, J=8.5 Hz, 2H), 3.72 (t, J=8.5 Hz, 2H), 10.09 (s, 1H). $^{13}$C NMR (CDCl$_3$, ppm): 623.21, 24.06, 31.48, 51.19, 112.28, 112.40, 120.01, 151.18, 165.51, 166.54, 185.22; $^{19}$F NMR (CDCl$_3$, ppm): δ−73.54 (s, 3F); HRMS (APCI+) calculated for $C_{11}H_{12}N_2O_4SF_3$ (M+H$^+$) 325.0470. found 325.0465.

1,6-Dimethyl-4-(trifluoromethylsulfonyloxy)-2,3-dihydro-1H-pyrrolo[2,3-b]pyridin-5-yl formate (32)

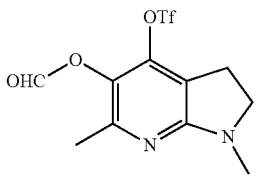 [SMILES: Cc1nc2c(c(OS(=O)(=O)C(F)(F)F)c1OC=O)CCN2C]

To a solution of 80 mg (0.24 mmol) of aldehyde 31 in 3 mL of dichloromethane was added 1 mg (0.09 mmol) of SeO$_2$ and 1.5 mL of H$_2$O$_2$ (30% in H$_2$O). The reaction mixture was stirred at room temperature for 16 h then cooled to 0° C., 12 mL of 5% of NaHCO$_3$ was added slowly. The mixture was stirred for additional 20 min then extracted with three portions of 15 mL of ethyl acetate. The combined organic layer was washed with brine and dried over Na$_2$SO$_4$. After solvent was removed, the residue was purified by flash chromatography on a silica gel column (15×2 cm). Elution with 1:10 EtOAc-hexanes gave product 32 as light yellow solid: yield 47.6 mg (57%). Silica gel TLC $R_f$ 0.28 (4:1 EtOAc-hexanes); $^1$H NMR (CDCl$_3$, ppm): δ 2.25 (s, 3H), 2.94 (s, 3H), 3.08 (t, J=8.4 Hz, 2H), 3.57 (t, J=8.4 Hz, 2H), 8.23 (s, 1H). $^{13}$C NMR (CDCl$_3$, ppm): δ 19.21, 23.69, 32.36, 52.10, 113.38, 116.76, 119.95, 126.71, 150.24, 158.20, 162.82; $^{19}$F NMR (CDCl$_3$, ppm): δ−73.77 (s, 3F); HRMS (ESI+) calculated for $C_{11}H_{11}N_2O_5SF_3$ (M+H$^+$) 340.0414. found 340.0413.

4-((3R,7R,11R)-3-(benzyloxy)-3,7,11,15-tetramethylhexadec-1-ynyl)-1,6-dimethyl-2,3-dihydro-1H-pyrrolo[2,3-b]pyridin-5-yl formate (33)

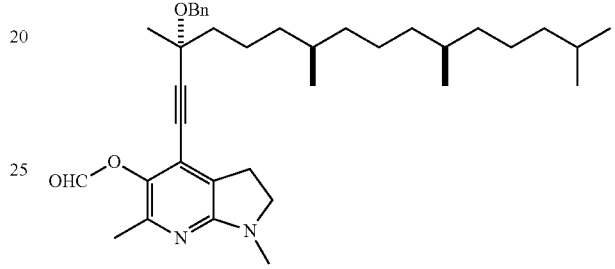

To a solution of 28.0 mg (0.082 mmol) of formate ester 32 in 2 mL of NMP was added 9.1 mg (0.008 mmol) of Pd(PPh$_3$)$_4$, 66.0 mg (0.098 mmol) of tributyltin side chain substitute 6. The reaction mixture was heated at 105° C. and stirred for 2 h then cooled to 0° C. Five mL of 5% NaHCO$_3$ was added slowly. The mixture was stirred at 0° C. for additional 20 min then extracted with three portions of 8 mL of ethyl acetate. The combined organic layer was washed with brine and dried over Na$_2$SO$_4$. After solvent was removed the residue was purified by flash chromatography on a silica gel column (20×1.7 cm). Elution with 1:10 EtOAc-hexanes gave the product 33 as colorless oil: yield 42.0 mg (88%); silica gel TLC $R_f$ 0.38 (1:4 EtOAc-hexanes); $^1$H NMR (CDCl$_3$, ppm): δ 0.84-0.89 (m, 12H), 1.05-1.83 (m, 21H), 1.56 (s, 3H), 2.47 (s, 3H), 2.92 (s, 3H), 2.96 (t, J=6.4 Hz, 2H), 3.50 (t, J=6.4 Hz, 2H), 4.65 (dd, J=9.2, 21.6 Hz, 2H), 7.27-7.39 (m, 5H), 8.16 (s, 1H). $^{13}$C NMR (CDCl$_3$, ppm): δ 19.08, 19.66, 19.74, 21.92, 22.63, 22.72, 24.50, 24.80, 25.47, 26.34, 27.97, 32.75, 32.77, 32.81, 37.12, 37.30, 37.47, 39.37, 41.86, 52.34, 66.47, 74.45, 100.95, 105.00, 106.43, 124.43, 127.38, 127.53, 128.32, 130.23, 135.21, 138.96, 146.38, 159.20; HRMS (ESI+) calculated for $C_{37}H_{54}N_2O_3$ (M+H$^+$) 575.4207. found 575.4244.

4-((3R,7R,11R)-3-hydroxy-3,7,11,15-tetramethylhexadecyl)-1,6-dimethyl-2,3-dihydro-1H-pyrrolo[2,3-b]pyridin-5-yl acetate (34)

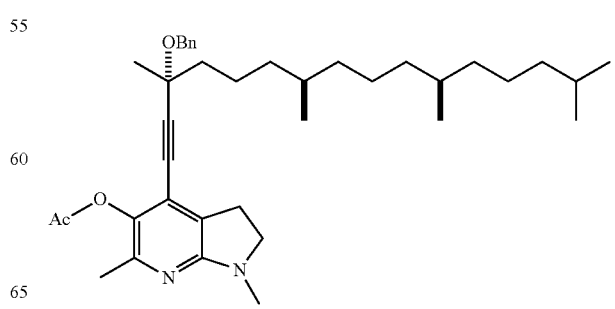

To a solution of 25 mg of formate ester 33 in 2 mL of CH₂Cl₂ was added 220 μL (1M in toluene, 5 eq) of DIBAL-H at −78° C. The reaction mixture was stirred at the same temperature for 1.5 h then 300 μL of triethylamine and 150 μL of acetic anhydride and catalytic amount of DMAP was added. The resulting reaction mixture was allowed to warm to room temperature and stirred for 24 h. The reaction was quenched with 2 mL of aqueous saturated ammonium chloride and extracted with three portions of 5-mL of ethyl acetate. The combined organic layer was washed with brine, dried (Na₂SO₄) and concentrated under diminished pressure. The residue was purified by flash chromatography on a silica gel column (20×1.7 cm). Elution with 6:100 EtOAc-hexanes gave the product 34 as yellowish oil: yield 20 mg, (78%); Silica gel TLC R$_f$ 0.48 (1:4 EtOAc-hexanes); $^1$H NMR (C₆H₆): δ 0.87-0.93 (m, 12H), 1.02-1.99 (m, 25H), 1.52 (s, 3H), 1.95 (s, 3H), 2.37 (s, 3H), 2.49 (t, J=8.0 Hz, 2H), 2.67 (s, 3H), 4.76 (dd, J=11.6, 55.2 Hz, 2H), 7.06-7.20 (m, 3H), and 7.44 (d, J=7.6 Hz, 2H); HRMS (ESI+) calculated for C₃₈H₅₆N₂O₃ (M+H⁺) 589.4364. found 589.4383.

4-((3R,7R,11R)-3-hydroxy-3,7,11,15-tetramethyl-hexadecyl)-1,6-dimethyl-2,3-dihydro-1H-pyrrolo[2,3-b]pyridine-5-yl acetate (35)

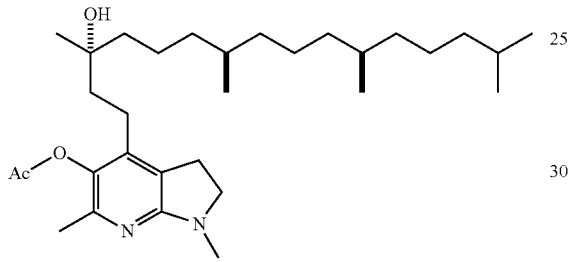

To a solution of 25.0 mg (0.05 mmol) of acetate ester 34 in 5 mL of methanol was added 13 mg of Pearlman catalyst. The reaction mixture was bubbled with hydrogen and stirred for 2 h then charged with a hydrogen balloon overnight. The mixture was filtered through a pad of celite and washed with methanol. The solvent was concentrated under diminished pressure and the residue was purified by flash chromatography on a silica gel column (20×1.7 cm). Elution with 1:5 EtOAc-hexanes gave the product 35 as colorless oil: yield 15.7 mg, (71%); Silica gel TLC R$_f$ 0.10 (1:4 EtOAc-hexanes); $^1$H NMR (CDCl₃): δ 0.83-0.87 (m, 12H), 1.00-1.56 (m, 23H), 1.20 (s, 3H), 2.20 (s, 3H), 2.30 (s, 3H), 2.38 (t, J=7.2 Hz, 2H), 2.87 (t, J=8.4 Hz, 2H), 2.89 (s, 3H) and 3.44 (t, J=8.0 Hz, 2H) with a proton of OH unidentified; HRMS (ESI+) calculated for C₃₁H₅₄N₂O₃ (M+H⁺) 503.4207. found 503.4213.

4-((3R,7R,11R)-3-hydroxy-3,7,11,15-tetramethyl-hexadecyl)-1,6-dimethyl-2,3-dihydro-1H-pyrrolo[2,3-b]pyridine-5-ol (Compound C)

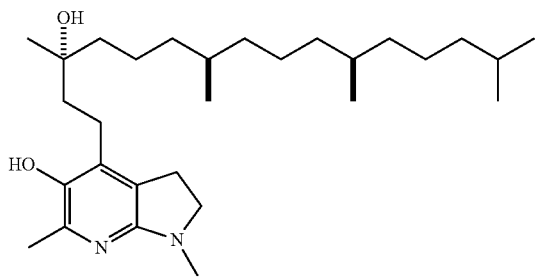 [SMILES: Cc1nc2c(c(CC[C@](C)(O)CCC[C@H](C)CCC[C@H](C)CCCC(C)C)c1O)CCN2C]

To a solution of 2.2 mg (4.4 μmol) acetyl ester 35 in 1 mL CH₂Cl₂ was added 17.5 μL (17.5 μmol) of DIBAL-H at −78° C. The reaction mixture was stirred at same temperature for 2 h than 1 mL of aqueous saturated sodium potassium tartrate was added slowly. The reaction mixture was allowed to warm to room temperature slowly add stirred for 3 h then separated. The aqueous layer was extracted with two portions of 5 mL of ethyl acetate. The combined organic layer was washed with brine, dried (Na₂SO₄) and concentrated under diminished pressure to give the product C as orange oil. HPLC found retain time in 21.82 min. This compound was degenerated after one day; mass spectrum, m/z 461.4 (M+H⁺) (theoretical 461.4).

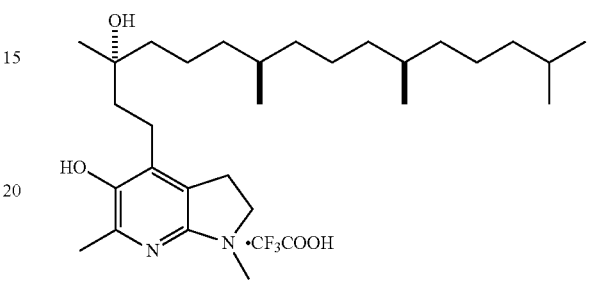

The above obtained compound was dissolved in 1 mL of ether and cooled to −78° C. To this solution was added 0.1 mL of TFA ether solution (0.1 M in ether). The mixture was stirred at same temperature for 1 h then solvent was removed. The residue was transferred by CH₃CN to vials and lyophilized to give product C as a TFA salt: yield 2.5 mg (100%).

Example 4

Preparation of 6-amino-2-(10-hydroxydecyl)-4-methylpyridin-3-ol

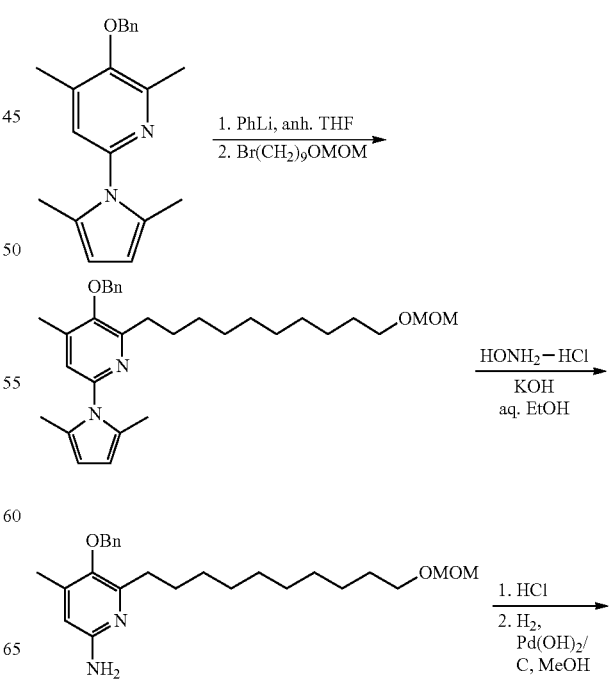

3-(Benzyloxy)-6-(2,5-dimethyl-1H-pyrrol-1-yl)-2-(10-(methoxymethoxy)decyl)-4-methylpyridine

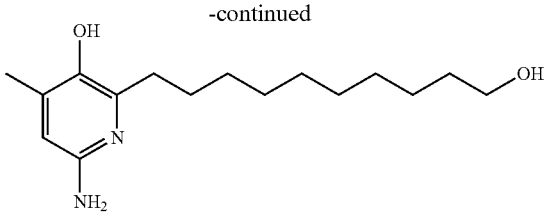

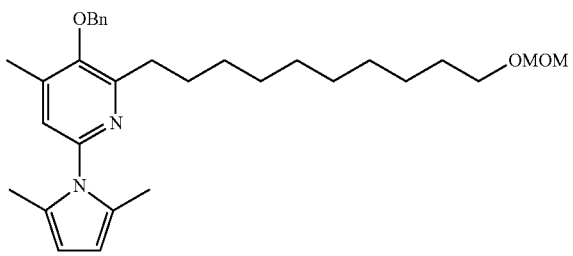

To a stirred solution at −78° C. containing 906 mg (2.95 mmol) of 3-(benzyloxy)-6-(2,5-dimethyl-1H-pyrrol-1-yl)-2,4-dimethylpyridine in 20 mL of anh. THF were added 789 mg (2.95 mmol) of 1-bromo-9-(methoxymethoxy)nonane followed by 1.99 mL (3.54 mmol) of a 1.80 M solution of PhLi in hexane. The reaction mixture was stirred at −78° C. for 30 min. then the reaction mixture was warmed to 23° C. slowly, and the reaction mixture was stirred 30 min. The reaction was quenched with satd aq ammonium chloride and then poured into 80 mL of water. The mixture was then extracted with two 80-mL portions of ethyl acetate. The combined organic layer was then washed with a 100-mL portion of brine, dried (MgSO$_4$) and then concentrated under diminished pressure. The residue was purified by chromatography on a silica gel column (15×5 cm). Elution with 4:1 hexanes-ethyl acetate afforded the expected product as a light yellow oil: yield 877 mg (60%); silica gel TLC R$_f$ 0.3 (9:1 hexanes-ethyl acetate); $^1$H NMR (CDCl$_3$) δ 1.18-1.22 (br m, 12H), 1.50 (quint, 2H, J=6.8 Hz), 1.65 (m, 2H), 2.06 (s, 6H), 2.26 (s, 3H), 2.75 (dd, 2H, J=7.6, 7.6 Hz), 3.28 (s, 3H), 3.43 (t, 2H, J=6.8 Hz), 4.53 (s, 2H), 4.82 (s, 2H), 5.78 (s, 2H), 6.79, (s, 1H) and 7.29-7.40 (m, 5H); $^{13}$C NMR (CDCl$_3$) δ 13.30, 13.30, 16.35, 26.19, 28.92, 29.40, 29.48, 29.50, 29.55, 29.61, 29.73, 32.13, 55.05, 67.86, 75.24, 96.36, 106.40, 106.40, 121.68, 121.68, 127.73, 127.90, 127.90, 128.89, 128.89, 138.83, 141.97, 141.97, 146.80, 150.76 and 155.88; mass spectrum (APCI), m/z 493.3426 (M+H)$^+$ (C$_{31}$H$_{45}$N$_2$O$_3$ requires 493.3430).

5-(Benzyloxy)-6-(10-(methoxymethoxy)decyl)-4-methylpyridin-2-amine

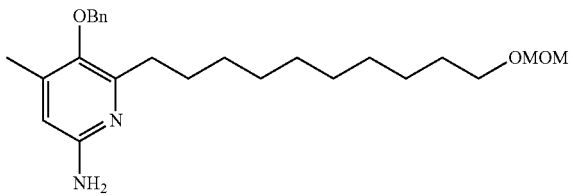

To stirred solution containing 240 mg (0.49 mmol) of 3-(benzyloxy)-6-(2,5-dimethyl-1H-pyrrol-1-yl)-2-(10-(methoxymethoxy)decyl)-4-methylpyridine in 10 mL of 9:1 ethanol-water were added 338 mg (4.87 mmol) of hydroxylamine hydrochloride followed by 273 mg (4.87 mmol) of potassium hydroxide. The reaction mixture was then stirred at reflux 6 h. then a second portion of 338 mg (4.87 mmol) of hydroxylamine hydrochloride followed by 273 mg (4.87 mmol) of potassium hydroxide was added and the mixture was stirred at reflux 16 h. The reaction mixture was then poured into 50 mL of water and extracted with two 50-mL portions of dichloromethane. The combined organic layer was washed with a 60-mL portion of brine, dried (MgSO$_4$) and then concentrated under diminished pressure. The residue was purified by chromatography on a silica gel column (10×3 cm). Elution with 9:1 dichloromethane-methanol afforded the expected product as a yellowish oil: yield 113 mg (56%); silica gel TLC R$_f$ 0.45 (9:1 dichloromethane-methanol); $^1$H NMR (CDCl$_3$) δ 1.24-1.31 (br m, 12H), 1.63-1.53 (m, 4H), 2.16 (s, 3H), 2.62 (dd, 2H, J=8.0, 8.0 Hz), 3.28 (s, 3H), 3.48 (t, 2H, J=6.8 Hz), 4.59 (s, 2H), 4.71 (s, 2H), 5.24 (br s, 2H), 6.16 (s, 1H) and 7.31-7.43 (m, 5H); $^{13}$C NMR (CDCl$_3$) δ 16.73, 29.19, 29.40, 29.46, 29.46, 29.48, 29.56, 29.72, 29.84, 32.24, 53.41, 67.85, 75.43, 96.34, 108.08, 127.73, 128.00, 128.00, 128.50, 128.50, 137.41, 142.46, 144.91, 153.46 and 154.13; mass spectrum (APCI), m/z 415.2957 (M+H)$^+$ (C$_{25}$H$_{39}$N$_2$O$_3$ requires 415.2961).

6-amino-2-(10-hydroxydecyl)-4-methylpyridin-3-ol

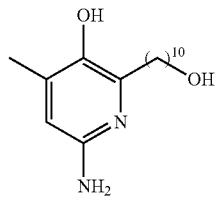

To a stirred solution containing 113 mg (0.27 mmol) of 5-(benzyloxy)-6-(10-(methoxymethoxy)decyl)-4-methylpyridin-2-amine in 10 mL of methanol were added two drops of concentrated HCl and the mixture was stirred at reflux for 16 h. To the mixture were added 5 mg of 20% palladium hydroxide on carbon (Degussa type E101 NE/N). The reaction mixture was stirred at 23° C. under hydrogen atmosphere for 15 min. The reaction mixture was filtered through celite and the filtrated was concentrated under diminished pressure. The residue was purified by chromatography on a silica gel column (10×1 cm). Elution with 17:3 dichloromethane-methanol afforded the expected product as white solid: yield 22 mg (29%); mp: 138-139° C.; silica gel TLC R$_f$ 0.20 (17:3 dichloromethane-methanol); $^1$H NMR (methanol-d$_4$) δ 1.28-1.35 (m, 12H), 1.48-1.58 (m, 4H), 2.13 (s, 3H), 2.60 (dd, 2H, J=7.6, 7.6 Hz), 3.51 (t, 2H, J=6.8 Hz) and 6.25 (s, 1H); $^{13}$C NMR (methanol-d$_4$) δ 15.21, 25.51, 28.78, 29.15, 29.20, 29.22, 29.22, 29.28, 31.49, 32.23, 61.58, 108.39, 139.23, 141.68, 146.88 and 152.45; mass spectrum (APCI+), m/z 281.2231 (M+H) (C$_{16}$H$_{29}$N$_2$O$_2$ requires 281.2229).

Example 5

Preparation of 2-(10-hydroxydecyl)-6-methoxy-4-methylpyridin-3-ol (Compound F)

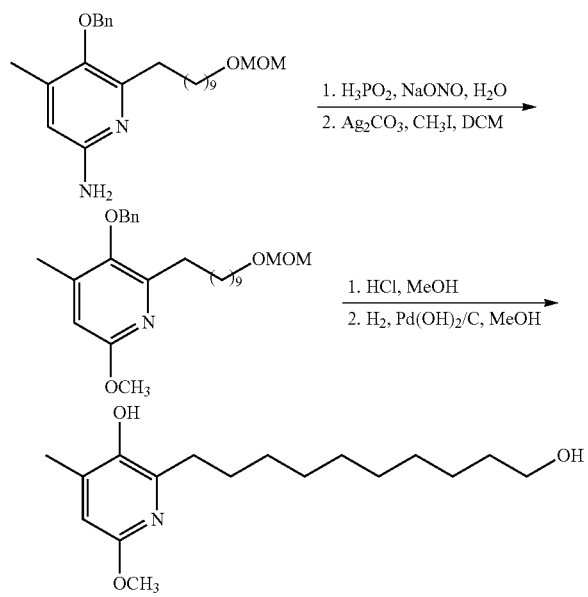

3-(benzyloxy)-6-methoxy-2-(10-(methoxymethoxy)decyl)-4-methylpyridine

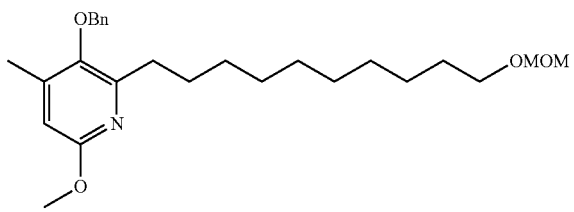

To a stirred solution at 0° C. containing 65 mg (0.16 mmol) of 5-(benzyloxy)-6-(10-(methoxymethoxy)decyl)-4-methylpyridin-2-amine in 2 mL of water-50% aqueous $H_3PO_2$ 1:1 were added 17 mg (0.24 mmol) of sodium nitrite. The reaction mixture was stirred at 0° C. for 30 min and then at 23° C. for 16 h. The reaction mixture was neutralized (pH~7) with aqueous NaOH and stirred for two hours. The reaction mixture was poured into 50 mL of water and extracted with two 40-mL portions of DCM. The combined organic layer was dried ($MgSO_4$) and concentrated under diminished pressure. The residue was dissolved into 5 mL of anhydrous DCM. To the solution were added 100 μL (1.60 mmol) of methyl iodide followed by 66 mg (0.24 mmol) of $Ag_2CO_3$. The reaction mixture was stirred overnight at 23° C. and protected from light. The reaction mixture was filtered and the filtrate was concentrated under diminished pressure. The residue was purified by chromatography on a silica gel column (8×1 cm). Elution with 3:1 hexanes-ethyl acetate afforded the expected product as colorless oil: yield 18 mg (26%); silica gel TLC $R_f$ 0.55 (4:1 hexanes-ethyl acetate) $^1$H NMR (CDCl$_3$) δ 1.24-1.24 (m, 12H), 1.56 (quint, 2H, J=7.6 Hz), 1.70 (quint, 2H, J=7.6 Hz), 2.22 (s, 3H), 2.70 (dd, 2H, J=7.6, 7.6 Hz), 3.34 (s, 3H), 3.49 (t, 2H, J=6.8 Hz), 3.86 (s, 3H), 4.60 (s, 2H), 4.74 (s, 2H), 6.37 (s, 1H) and 7.33-7.44 (m, 5H); $^{13}$C NMR (CDCl$_3$) δ 16.36, 26.19, 28.65, 29.42, 29.52, 29.54, 29.58, 29.65, 29.73, 31.77, 53.30, 55.05, 67.86, 75.31, 96.36, 108.75, 127.77, 128.07, 128.07, 128.53, 128.53, 137.29, 143.29, 146.62, 152.34 and 159.44; mass spectrum (APCI+), m/z 430.2965 (M+H) ($C_{16}H_{29}N_2O_2$ requires 430.2957).

2-(10-hydroxydecyl)-6-methoxy-4-methylpyridin-3-ol (Compound F)

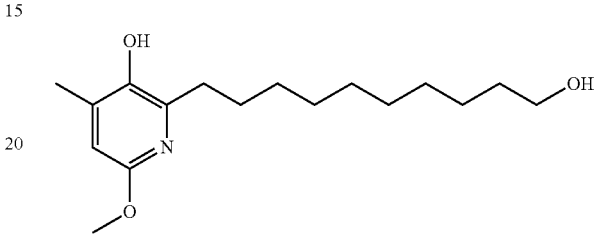

To a stirred solution containing 18 mg (0.04 mmol) of 3-(benzyloxy)-6-methoxy-2-(10-(methoxymethoxy)decyl)-4-methylpyridine in 3 mL of methanol were added two drops of concentrated HCl. The reaction mixture was stirred at reflux for 16 h. To the mixture were added 3 mg of 20% palladium hydroxide on carbon (Degussa type E101 NE/N). The reaction mixture was stirred at room temperature under hydrogen atmosphere for 15 min. The reaction mixture was filtered through celite and the filtrate was concentrated under diminished pressure. The residue was purified by chromatography on a silica gel column (5×1 cm). Elution with 3:1 hexanes-ethyl acetate afforded the expected product as white solid: yield 8 mg (67%); mp: 80-81° C.; silica gel TLC $R_f$ 0.50 (3:1 hexanes-ethyl acetate); $^1$H NMR (methanol-d$_4$) δ 1.27 (br s, 12H), 1.49 (br s, 2H), 1.64 (br s, 2H), 2.41 (br s, 3H), 2.81 (br s, 2H), 3.51 (br s, 3H), 4.02 (br s, 1H) and 7.05 (br s, 1H); $^{13}$C NMR (methanol-d$_4$) δ 16.59, 25.51, 28.13, 28.57, 28.92, 28.97, 29.09, 29.14, 29.24, 32.22, 56.39, 61.56, 107.60, 142.26, 145.27, 148.68 and 155.10; mass spectrum (APCI+), m/z 296.2220 (M+H) ($C_{17}H_{30}NO_3$ requires 296.2226).

Example 6

Preparation of 6-(dimethylamino)-2-(10-hydroxydecyl)-4-methoxypyridin-3-ol (Compound G)

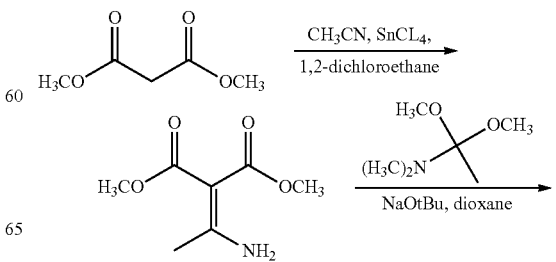

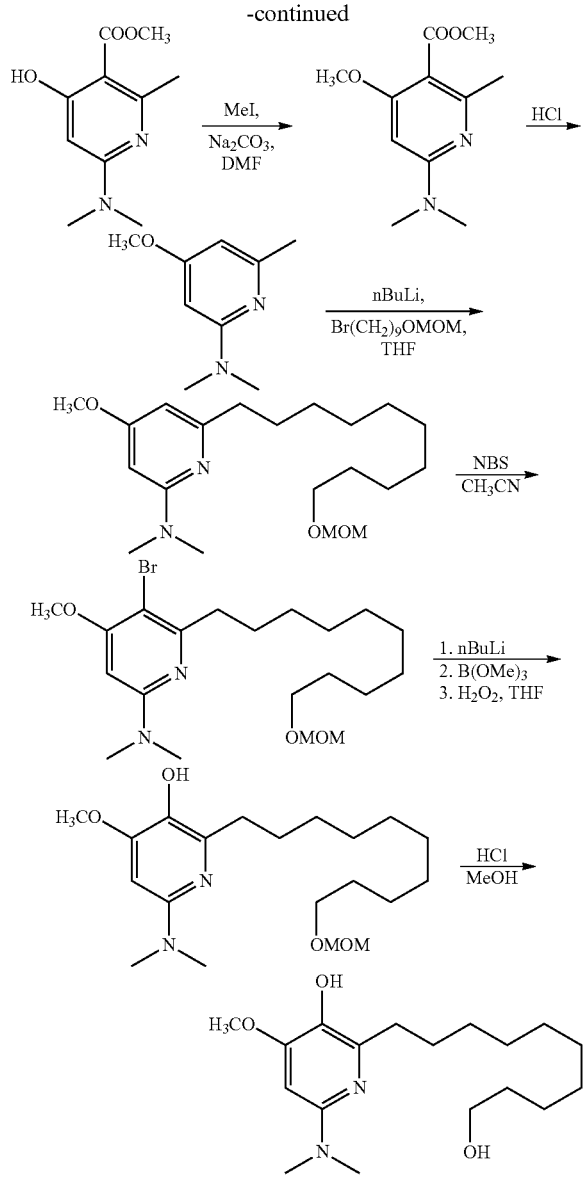

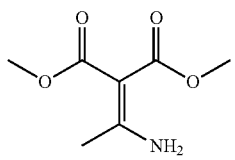

Dimethyl 2-(1-Aminoethylidene)malonate

To a stirred solution containing 4.36 mL (38.0 mmol) of dimethyl malonate and 2.00 mL (38.0 mmol) of acetonitrile in 20 mL of 1,2-dichloroethane were added 8.90 mL (76.0 mmol) of $SnCl_4$. The reaction mixture was stirred at reflux for 2 h. The reaction mixture was then concentrated under diminished pressure and the residue was dissolved into 100 mL of acetone. Then, 70 mL of satd. aq. sodium carbonate were added and the mixture was stirred for 20 minutes. The mixture was poured into 200 mL of satd. aq. sodium bicarbonate and extracted with two 200-mL portions of DCM. The combined organic solution was washed with a 200-mL portion of brine, dried ($MgSO_4$) and concentrated under diminished pressure. The residue was recrystallized in ethyl acetate/hexanes to afford the expected product as colorless crystals: yield 3.96 g (60%); mp: 81-82° C.; silica gel TLC $R_f$ 0.5 (1:1 ethyl acetate-hexanes); $^1$H NMR ($CDCl_3$) δ 2.10 (s, 3H), 3.66 (s, 3H), 3.69 (s, 3H), 5.29 (br s, 1H) and 8.94 (br s, 1H); $^{13}$C NMR ($CDCl_3$) δ 22.0, 51.0, 51.6, 92.4, 164.0, 168.7 and 168.9; mass spectrum (APCI), m/z 174.0760 $(M+H)^+$ ($C_7H_{12}NO_4$ requires 174.0766).

Methyl 6-(Dimethylamino)-4-hydroxy-2-methylnicotinate

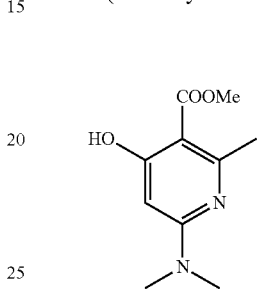

A solution containing 1.10 g (6.36 mmol) of dimethyl 2-(1-Aminoethylidene)malonate and 1.40 mL (9.56 mmol) of N,N'-dimethylacetamide dimethyl acetal in 10 mL of anhydrous dioxane was stirred at reflux for 3 h then 1.24 g (12.7 mmol) of sodium tert-butoxide were added and the mixture was stirred at reflux for 3 h. The reaction mixture was poured into 100 mL of water and extracted with two 80-mL portions of ethyl acetate. The combined organic solution was washed with one 80-mL portion of brine, dried ($MgSO_4$) and concentrated under diminished pressure. The residue was purified by chromatography on a silica gel column (4×10 cm). Elution with 3:1 hexanes-ethyl acetate afforded methyl the expected product as a white solid: yield 689 mg (51%); mp: 61-62° C.; silica gel TLC $R_f$ 0.47 (3:1 ethyl acetate-hexnanes); $^1$H NMR ($CDCl_3$) δ 2.58 (s, 3H), 3.06 (s, 6H), 3.87 (s, 3H), 5.97 (s, 1H) and 11.88 (s, 1H); $^{13}$C NMR ($CDCl_3$) δ 27.5, 37.4, 37.4, 51.6, 88.6, 99.3, 160.3, 161.9, 169.3 and 171.9; mass spectrum (APCI), m/z 211.1081 $(M+H)^+$ ($C_{10}H_{15}N_2O_3$ requires 211.1083).

Methyl 6-(Dimethylamino)-4-methoxy-2-methylnicotinate

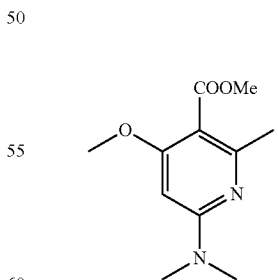

To a stirred solution containing 689 mg (3.27 mmol) of methyl 6-(Dimethylamino)-4-hydroxy-2-methylnicotinate in 10 mL of anhydrous DMF were added 1.91 g (18.0 mmol) of anhydrous sodium carbonate followed by 611 μL (9.81 mmol) of methyl iodide. The reaction mixture was stirred at 23° C. for 16 h. Then, the reaction mixture was poured into 80 mL of water and extracted with two 80-mL portions of ethyl acetate. The combined organic solution was washed with one 80-mL portion of brine, dried (MgSO$_4$) and concentrated under diminished pressure. The residue was purified by chromatography on a silica gel column (3×10 cm). Elution with 1:1 hexanes-diethyl ether afforded the expected product as a white solid: yield 340 mg (47%); mp: 65-66° C.; silica gel TLC R$_f$ 0.15 (1:1 hexanes-diethyl ether); $^1$H NMR (CDCl$_3$) δ 2.37 (s, 3H), 3.07 (s, 6H), 3.80 (s, 3H) and 5.72 (s, 1H), 3.82 (s, 3H); $^{13}$C NMR (CDCl$_3$) δ 168.4, 165.2, 160.3, 156.7, 107.6, 84.5, 55.2, 51.7, 37.8, 37.8 and 23.5; mass spectrum (APCI), m/z 225.1246 (M+H)$^+$ (C$_{11}$H$_{17}$N$_2$O$_3$ requires 225.1239).

4-Methoxy-N,N,6-trimethylpyridin-2-amine

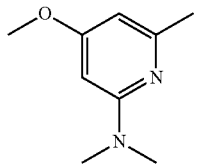

A solution containing 340 mg (1.52 mmol) of methyl 6-(Dimethylamino)-4-methoxy-2-methylnicotinate in 5 mL of 6N aq. HCl was stirred at reflux for 16 h. The reaction mixture was poured into 50 mL of water and the pH was set up to 12. The mixture was extracted with two 40-mL portions of ethyl acetate. The combined organic solution was washed with a 40-mL portion of brine, dried (MgSO$_4$) and concentrated under diminished pressure. The residue was purified by chromatography on a silica gel column (2×6 cm). Elution with 9:1 dichloromethane-methanol afforded the expected product as a colorless oil: yield 87 mg (34%); silica gel TLC R$_f$ 0.25 (9:1 dichloromethane-methanol); $^1$H NMR (CDCl$_3$) δ 2.33 (s, 3H), 3.02 (s, 6H), 3.75 (s, 3H), 5.77 (s, 1H) and 6.03 (s, 1H); $^{13}$C NMR (CDCl$_3$) δ 24.8, 38.0, 38.0, 54.7, 87.4, 98.5, 157.9, 160.8, 167.5; mass spectrum (APCI), m/z 167.1183 (M+H)$^+$ (C$_9$H$_{15}$N$_2$O requires 167.1184).

4-Methoxy-6-(10-(methoxymethoxy)decyl)-N,N-dimethylpyridin-2-amine

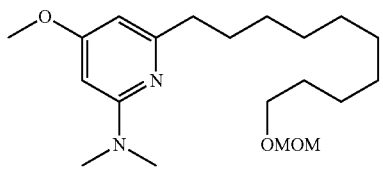

To a stirred solution containing 156 mg (0.94 mmol) of 4-methoxy-N,N,6-trimethylpyridin-2-amine in 5 mL of anhydrous THF were added 252 mg (0.94 mmol) of 1-bromo-9-(methoxymethoxy)nonane followed by 650 μL (1.04 mmol) of 1.6M n-BuLi in pentane. The reaction mixture was stirred at 23° C. for 15 min. The reaction was quenched with satd. aq. ammonium chloride and poured into 50 mL of water. The mixture was extracted with two 50-mL portions of ethyl acetate. The combined organic solution was washed with a 50-mL portion of brine, dried (MgSO$_4$) and concentrated under diminished pressure. The residue was purified by chromatography on a silica gel column (3×10 cm). Elution with 1:1 hexanes-ethyl acetate afforded the expected product as yellowish oil: yield 235 mg (70%); silica gel TLC R$_f$ 0.47 (1:1 hexanes-ethyl acetate); $^1$H NMR (CDCl$_3$) δ 1.24 (br m, 12H), 1.55 (quint, 2H, J=6.4 Hz), 1.68 (quint, 2H, J=7.6 Hz), 2.55 (dd, 2H, J=7.6, 7.6 Hz), 3.03 (s, 6H), 3.46 (s, 3H), 3.49 (t, 2H, J=6.8 Hz), 3.76 (s, 3H), 4.59 (s, 2H), 5.77 (s, 1H) and 6.01 (s, 1H); $^{13}$C NMR (CDCl$_3$) δ 26.17, 29.25, 29.39, 29.48, 29.50, 29.55, 29.60, 29.62, 29.72, 37.96, 37.96, 54.63, 55.01, 67.85, 87.44, 96.36, 97.86, 160.77, 162.05 and 167.41; mass spectrum (APCI), m/z (M+H)$^+$353.2808 (C$_{20}$H$_{37}$N$_2$O$_3$ requires 353.2804).

5-Bromo-4-methoxy-6-(10-(methoxymethoxy)decyl)-N,N-dimethylpyridin-2-amine

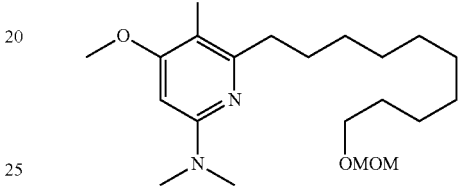

To a stirred solution containing 213 mg (0.60 mmol) of 4-methoxy-6-(10-(methoxymethoxy)decyl)-N,N-dimethylpyridin-2-amine in 5 mL of acetonitrile were added 107 mg (0.60 mmol) of N-bromosuccinimide. The reaction mixture was stirred at 23° C. protected from light for 3 h. The reaction mixture was poured into 50 mL of satd. aq. sodium bicarbonate and extracted two 50-mL portions of ethyl acetate. The combined organic layer was washed with one 50-mL portion of brine, dried (MgSO$_4$) and concentrated under diminished pressure. The residue was purified by chromatography on a silica gel column (3×10 cm). Elution with 4:1 hexanes-ethyl acetate afforded the expected product as a yellowish oil: yield 114 mg (44%); silica gel TLC R$_f$ 0.45 (4:1 hexanes-ethyl acetate); $^1$H NMR (CDCl$_3$) δ 1.29 (br m, 12H), 1.56 (quint, 2H, J=7.2 Hz), 1.68 (quint, 2H, J=7.2 Hz), 2.55 (dd, 2H, J=7.6, 7.6 Hz), 3.03 (s, 6H), 3.33 (s, 3H), 3.48 (t, 2H, J=6.8 Hz), 3.85 (s, 3H), 4.59 (s, 2H) and 5.76 (s, 1H); $^{13}$C NMR (CDCl$_3$) δ 26.17, 28.08, 29.40, 29.47, 29.51, 29.57, 29.65, 29.72, 37.31, 38.05, 38.05, 55.02, 55.65, 67.87, 86.47, 96.35, 97.29, 158.80, 159.11 and 162.60; mass spectrum (APCI), m/z (M+H)$^+$431.1913 (C$_{20}$H$_{36}$N$_2$O$_3$Br requires 431.1909).

6-(Dimethylamino)-4-methoxy-2-(10-(methoxymethoxy)decyl)pyridin-3-ol

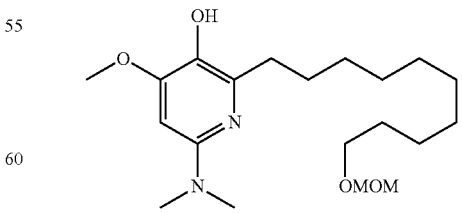

To a stirred solution containing 114 mg (0.26 mmol) of 5-Bromo-4-methoxy-6-(10-(methoxymethoxy)decyl)-N,N-dimethylpyridin-2-amine in 5 mL of anhydrous THF were added 413 μL (0.66 mmol) of 1.6M n-BuLi in pentane. The reaction mixture was stirred at 23° C. for 10 minutes. Then, were added 89.0 μL (0.79 mmol) of trymethyl borate and the mixture was stirred at 23° C. for 30 minutes. Then, were added 684 μL (12.6 mmol) of 35% aq $H_2O_2$ followed by 684 μL of 1N NaOH. The reaction mixture was stirred at 23° C. for 2 h and then poured into 20 mL of water. The mixture was extracted with two 20-mL portions of ethyl acetate. The combined organic layer was washed with one 20-mL portion of brine, dried ($MgSO_4$) and concentrated under diminished pressure. The residue was purified by chromatography on a silica gel column (2×10 cm). Elution with 1:1 hexanes-ethyl acetate afforded the expected product as a yellowish oil: yield 20 mg (21%); silica gel TLC $R_f$ 0.1 (1:1 hexanes-ethyl acetate); $^1$H NMR (methanol) δ 1.29 (br s, 12H), 1.56 (br m, 4H), 2.66 (dd, 2H, J=7.6, 7.6 Hz), 3.00 (s, 6H), 3.29 (s, 3H), 3.48 (t, 2H, J=6.8 Hz), 3.90 (s, 3H), 4.56 (s, 2H) and 6.11 (s, 1H); $^{13}$C NMR (methanol-$d_4$) δ 25.85, 28.06, 29.07, 29.11, 29.19, 29.24, 29.37, 30.10, 35.20, 38.17, 38.17, 53.94, 54.93, 67.46, 87.91, 95.98, 132.79, 143.67, 153.94 and 157.39; mass spectrum (APCI), m/z (M+H)$^+$369.2760 ($C_{20}H_{37}N_2O_4$ requires 369.2753)

6-(Dimethylamino)-2-(10-hydroxydecyl)-4-methoxypyridin-3-ol (Compound G)

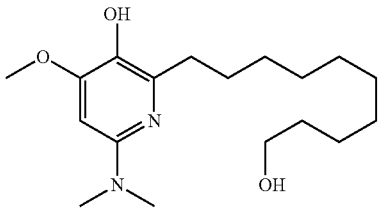 [SMILES: COc1cc(N(C)C)nc(CCCCCCCCCCO)c1O]

To a stirred solution containing 6-(Dimethylamino)-4-methoxy-2-(10-(methoxymethoxy)decyl)pyridin-3-ol in 5 mL of methanol was added a drop of conc HCl. The reaction mixture was stirred at reflux for 2 h. A drop of conc $NH_4OH$ was added and the mixture was concentrated under diminished pressure. The residue was purified by chromatography on a silica gel column (1×10 cm). Elution with 9:1 dichloromethane-methanol afforded the expected product as a yellowish oil: yield 7 mg (40%); silica gel TLC $R_f$ 0.2 (9:1 dichloromethane-methanol); $^1$H NMR (methanol) δ 1.29 (br m, 12H), 1.49 (quint, 2H, J=6.8 Hz), 1.62 (quint, 2H, J=7.2 Hz), 2.66 (dd, 2H, J=7.6, 7.6 Hz), 3.00 (s, 6H), 3.49 (t, 2H, J=6.8 Hz), 3.90 (s, 3H) and 6.11 (s, 1H); $^{13}$C NMR (methanol) δ 25.50, 28.06, 29.08, 29.13, 29.14, 29.20, 29.28, 30.09, 32.22, 38.16, 38.16, 54.90, 61.57, 87.88, 132.75, 143.86, 154.04 and 157.27; mass spectrum (APCI), m/z (M+H)$^+$ 325.2489 ($C_{18}H_{33}N_2O_3$ requires 325.2491).

Example 7

Alternative preparation of 2-N,N-dimethylamino-5-hydroxy-4-methyl-6-(10-hydroxydecyl)-pyrimidine (Compound A)

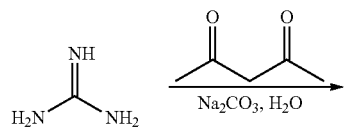

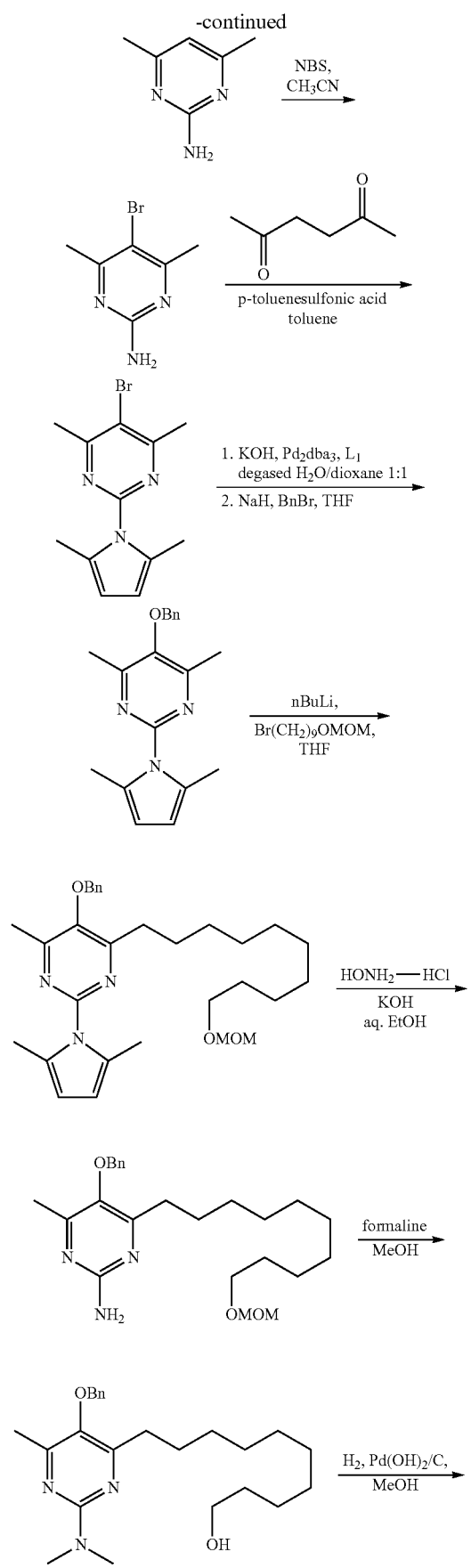

-continued

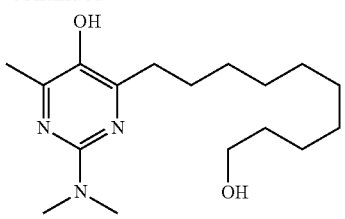

2-Amino-4,6-dimethylpyrimidine

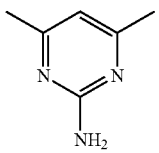

To a stirred solution containing 4.00 g (37.0 mmol) of guanidine sulfate and 8.40 g (79.3 mmol) of sodium carbonate in 25 mL of water were added 6.00 mL (58.1 mmol) of 2,4-pentanedione. The reaction mixture was stirred at 100° C. overnight. The reaction mixture was poured into 150 mL of water and then extracted with two 150-mL portions of dichloromethane. The combined organic phase was washed with 150 mL of brine, dried (MgSO$_4$) and then concentrated under diminished pressure to afford the expected product as a colorless solid: yield 4.31 g (95%); mp 152-153° C.; silica gel TLC R$_f$ 0.50 (9:1 dichloromethane-methanol); $^1$H NMR (CDCl$_3$) δ 2.24 (s, 6H), 5.39 (br s, 2H) and 6.33 (s, 1H); $^{13}$C NMR (CDCl$_3$) δ 23.7, 23.7, 110.5, 162.9, 162.9 and 167.7; mass spectrum (APCI), m/z 124.0869 (M+H)$^1$ (C$_6$H$_{10}$N$_3$ requires 124.0875).

2-Amino-5-bromo-4,6-dimethylpyrimidine

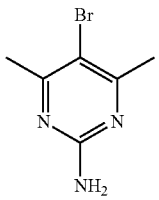

To a stirred solution containing 4.31 g (34.8 mmol) of 2-amino-4,6-dimethylpyrimidine in 150 mL of acetonitrile was added 6.15 g (52.1 mmol) of N-bromosuccinimide. The reaction mixture was stirred at 23° C. for 3 h. The formed precipitate was filtered and dried to afford the expected product as a colorless solid: yield 5.93 g (83%); mp 183-185° C.; silica gel TLC R$_f$ 0.15 (2:1 ethyl acetate-hexanes); $^1$H NMR (CDCl$_3$) δ 2.44 (s, 6H) and 5.19 (br s, 2H); $^{13}$C NMR (CDCl$_3$) δ 24.7, 24.7, 109.6, 160.7, 160.7 and 166.3; mass spectrum (APCI), m/z 201.9982 (M+H)$^+$ (C$_6$H$_9$N$_3$Br requires 201.9980).

5-Bromo-2-(2,5-dimethyl-1H-pyrrol-1-yl)-4,6-dimethylpyrimidine

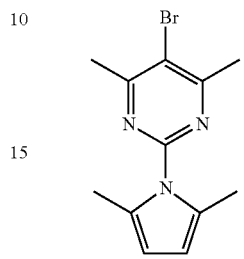

To a stirred solution containing 2.00 g (9.89 mmol) of 2-amino-5-bromo-4,6-dimethylpyrimidine in 16 mL of anhydrous toluene was added 1.36 mL (11.5 mmol) of 2,5-hexanedione followed by 96 mg (0.50 mmol) of p-toluenesulfonic acid. The reaction mixture was heated and stirred at reflux for 12 h. The reaction mixture was poured into 150 mL of water and then extracted with 200 mL of ethyl acetate. The organic solution was washed with 150 mL of brine, dried (MgSO$_4$) and concentrated under diminished pressure. The residue was purified by chromatography on a silica gel column (15×5 cm). Elution with 5:1 hexanes-ethyl acetate afforded the expected product as light yellow crystals: yield 2.23 g (81%); mp 64-65° C.; silica gel TLC R$_f$ 0.65 (6:1 hexanes-ethyl acetate); $^1$H NMR (CDCl$_3$) δ 2.34 (s, 6H), 2.67 (s, 6H) and 5.89 (s, 2H); $^{13}$C NMR (CDCl$_3$) δ 14.5, 14.5, 24.9, 24.9, 108.7, 108.7, 118.6, 129.5, 129.5, 155.3, 155.3 and 166.9; mass spectrum (APCI), m/z 280.0458 (M+H)$^+$ (C$_{12}$H$_{15}$N$_3$Br requires 280.0449).

5-(Benzyloxy)-2-(2,5-dimethyl-1H-pyrrol-1-yl)-4,6-dimethylpyrimidine

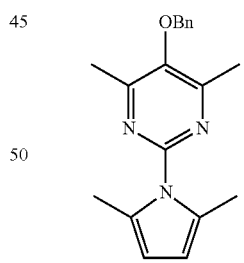

To a stirred solution containing 4.87 g (17.4 mmol) of 5-bromo-2-(2,5-dimethyl-1H-pyrrol-1-yl)-4,6-dimethylpyrimidine in 50 mL of 1:1 dioxane-degassed water was added 632 mg (0.69 mmol) of Pd$_2$dba$_3$ followed by 293 mg (0.69 mmol) of 2-di-tert-butylphosphino-2',4',6'-triisopropylbiphenyl (L$_1$) and 2.92 g (52.1 mmol) of KOH. The reaction mixture was stirred at 100° C. for 3 h. The cooled reaction mixture was poured into 200 mL of water and extracted with 100 mL of ethyl acetate. The aqueous layer was acidified with HCl (pH 2-3) and then extracted with two 150-mL portions of ethyl acetate. The combined organic layer was washed with 150 mL of brine, dried (MgSO$_4$) and concentrated under diminished pressure. The residue was dissolved in 50 mL of anhydrous THF and treated with 3.10 mL (26.0 mmol) of benzyl bromide followed by 1.40 g (34.8 mmol) of a 60% suspension of NaH in mineral oil. The reaction mixture was stirred at 23° C. for 48 h. The reaction mixture was quenched with satd aq sodium bicarbonate and poured into 150 mL of water and extracted with two 150-mL portions of ether. The combined organic layer was washed with 150 mL of brine, dried (MgSO$_4$) and concentrated under diminished pressure. The residue was purified by chromatography on a silica gel column (20×6 cm). Elution with 9:1 hexanes-ethyl acetate afforded the expected product as a light yellow oil: yield 4.09 g (76%); silica gel TLC R$_f$ 0.6 (6:1 hexanes-ethyl acetate); $^1$H NMR (CDCl$_3$) δ2.29 (s, 6H), 2.47 (s, 6H), 4.92 (s, 2H), 5.86 (s, 2H) and 7.42 (m, 5H); $^{13}$C NMR (CDCl$_3$) δ 14.1, 14.1, 19.1, 19.1, 75.3, 107.9, 107.9, 128.3, 128.6, 128.6, 129.0, 129.0, 129.2, 129.2, 136.0, 147.7, 152.3, 152.3 and 161.6; mass spectrum (APCI), m/z 307.1675 (M)$^+$ (C$_{19}$H$_{21}$N$_3$O requires 307.1685).

5-(Benzyloxy)-2-(2,5-dimethyl-1H-pyrrol-1-yl)-4-(10-(methoxymethoxy)decyl)-6-methylpyrimidine

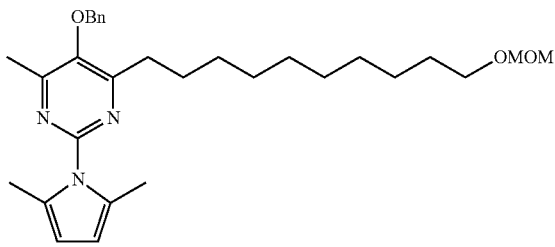

To a stirred solution at −78° C. containing 486 mg (1.58 mmol) of 5-(benzyloxy)-2-(2,5-dimethyl-1H-pyrrol-1-yl)-4,6-dimethylpyrimidine and 281 mg (1.05 mmol) of 1-bromo-9-(methoxymethoxy)nonane in 10 mL of anhydrous THF was added 987 µL (1.58 mmol) of a 1.6 M solution of n-BuLi in pentane. The reaction mixture was stirred under argon atmosphere at 23° C. for 30 min. The reaction was quenched with saturated aqueous ammonium chloride and then poured into 50 mL of water. The mixture was then extracted with two 50-mL portions of ethyl acetate. The combined organic layer was washed with 80 mL of brine, dried (MgSO$_4$) and concentrated under diminished pressure. The residue was purified by chromatography on a silica gel column (15×3 cm). Elution with 5:1 hexanes-ethyl acetate afforded the expected product as a light yellow oil: yield 289 mg (56%); silica gel TLC R$_f$ 0.55 (5:1 hexanes-ethyl acetate); $^1$H NMR (CDCl$_3$δ1.33 (m, 12H), 1.60 (m, 2H), 1.82 (m, 2H), 2.33 (s, 6H), 2.49 (s, 3H), 2.79 (dd, 2H, J=7.6, 7.6 Hz), 3.36 (s, 3H), 3.52 (t, 2H, J=6.4 Hz), 4.62 (s, 2H), 4.90 (s, 2H), 5.87 (s, 2H) and 7.37-7.48 (m, 5H); $^{13}$C NMR (CDCl$_3$) δ14.4, 14.4, 19.3, 26.2, 27.7, 29.4, 29.4, 29.5, 29.5, 29.6, 29.8, 31.6, 55.1, 67.9, 75.7, 96.4, 108.0, 108.0, 128.0, 128.58, 128.62, 128.7, 129.3, 136.2, 147.4, 147.4, 152.6, 161.6, 161.6 and 165.1; mass spectrum (APCI), m/z 494.3395 (M+H)$^1$ (C$_{30}$H$_{44}$N$_3$O$_3$ requires 494.3383).

5-(Benzyloxy)-4-(10-(methoxymethoxy)decyl)-6-methylpyrimidin-2-ylamine

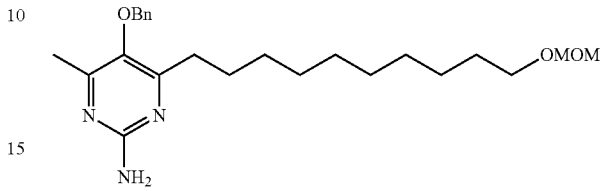

To a stirred solution containing 230 mg (0.47 mmol) of 5-(benzyloxy)-2-(2,5-dimethyl-1H-pyrrol-1-yl)-4-(10-(methoxymethoxy)decyl)-6-methylpyrimidine in 15 mL of 9:1 ethanol-water was added 327 mg (4.70 mmol) of hydroxylamine hydrochloride followed by 263 mg (4.70 mmol) of KOH. The reaction mixture was then heated and stirred at reflux for 5 h. A second portion of 327 mg (4.70 mmol) of hydroxylamine hydrochloride followed by 263 mg (4.70 mmol) of KOH was added and the reaction mixture was heated and stirred at reflux for 12 h. The reaction mixture was poured into 70 mL of water and then treated with 1N NaOH until pH 9-10 was reached. The reaction mixture was extracted with two 70-mL portions of ethyl acetate. The combined organic layer was washed with 70 mL of brine, dried (MgSO$_4$) and concentrated under diminished pressure. The residue was purified by chromatography on a silica gel column (10×3 cm). Elution with 2:1 hexanes-ethyl acetate afforded the expected product as a colorless oil: yield 133 mg (76%); silica gel TLC R$_f$ 0.76 (9:1 dichloromethane-methanol); $^1$H NMR (CDCl$_3$) δ1.27 (m, 12H), 1.53-1.63 (m, 4H), 2.26 (s, 3H), 2.54 (dd, 2H, J=7.6, 7.6 Hz), 3.31 (s, 3H), 3.46 (t, 2H, J=6.8 Hz), 4.57 (s, 2H), 4.69 (s, 2H), 5.19 (br s, 2H) and 7.35-7.37 (m, 5H); $^{13}$C NMR (CDCl$_3$) δ 18.9, 26.2, 28.4, 29.36, 29.40, 29.5, 29.67, 29.70, 31.9, 55.0, 67.8, 75.9, 96.3, 127.9, 128.3, 128.3, 128.6, 128.6, 136.8, 142.8, 158.9, 161.1, 161.1 and 164.8; mass spectrum (APCI), m/z 416.2908 (M+H)$^+$ (C$_{24}$H$_{38}$N$_3$O$_3$ requires 416.2913).

10-(5-(Benzyloxy)-2-(dimethylamino)-6-methylpyrimidin-4-yl)decan-1-ol

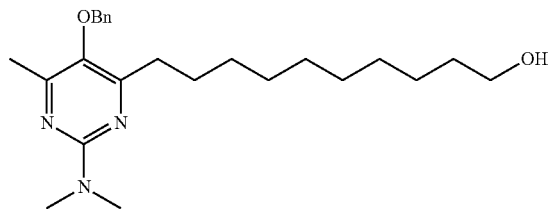 [SMILES: Cc1nc(N(C)C)nc(CCCCCCCCCCO)c1OCc1ccccc1]

A stirred solution containing 180 mg (0.43 mmol) of 5-(benzyloxy)-4-(10-(methoxymethoxy)decyl)-6-methylpyrimidin-2-ylamine in 10 mL of 35% aq 1:1 formaldehyde-formic acid was heated and stirred at reflux for 16 h. The reaction mixture was poured into 20 mL of water and extracted with two 40-mL portions of ethyl acetate. The combined organic layer was washed with 40 mL of satd aq NaHCO₃ and then 40 mL of brine. The organic solution was dried (MgSO₄) and concentrated under diminished pressure. The residue was purified by chromatography on a silica gel column (8×3 cm). Elution with 1:2 acetone-hexanes afforded the expected product as a colorless oil: yield 44 mg (44%); silica gel TLC $R_f$ 0.58 (1:2 acetone-hexanes); ¹H NMR (methanol-d₄) δ1.27 (m, 12H), 1.53-1.73 (m, 4H), 2.26 (s, 3H), 2.55 (dd, 2H, J=7.6, 7.6 Hz), 3.09 (s, 6H), 3.50 (t, 2H, J=6.8 Hz), 4.71 (s, 2H) and 7.35-7.37 (m, 5H); ¹³C NMR (methanol-d₄) δ 14.0, 17.8, 25.5, 27.6, 29.1, 29.2, 29.3, 31.3, 32.3, 36.3, 36.3, 61.6, 75.5, 127.9, 128.3, 128.3, 128.6, 128.6, 137.1, 141.0, 158.4, 160.5, 161.5 and 163.7; mass spectrum (APCI), m/z 400.2969 (M+H)⁺ ($C_{24}H_{38}N_3O_2$ requires 400.2964).

2-N,N-dimethylamino-5-hydroxy-4-methyl-6-(10-hydroxydecyl)-pyrimidine (Compound A)

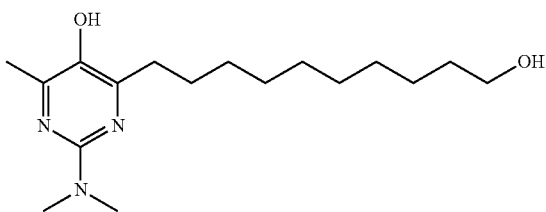 [SMILES: Cc1nc(N(C)C)nc(CCCCCCCCCCO)c1O]

To a stirred solution containing 44.0 mg (0.11 mmol) of 10-(5-(benzyloxy)-2-(dimethylamino)-6-methylpyrimidin-4-yl)decan-1-ol in 3 mL of methanol was added 3 mg of 20% palladium hydroxide on carbon (Degussa type E101 NE/N). The reaction mixture was stirred at 23° C. under a hydrogen atmosphere for 15 min. The reaction mixture was filtered through Celite and the filtrate was concentrated under diminished pressure to afford 2-(dimethylamino)-4-(10-hydroxydecyl)-6-methylpyrimidin-5-ol as a colorless oil: yield 33 mg (100%). An analytical sample was obtained by chromatography on a silica gel column (10×1 cm). Elution with 2:1 toluene-ethyl acetate afforded the purified product as a colorless oil; silica gel TLC $R_f$ 0.25 (2:1 toluene-ethyl acetate); ¹H NMR (methanol-d₄) δ1.29-1.35 (m, 12H), 1.49 (m, 2H), 1.65 (m, 2H), 2.26 (s, 3H), 2.62 (dd, 2H, J=7.2, 7.2 Hz), 3.06 (s, 6H) and 3.51 (t, 2H, J=6.4 Hz); ¹³C NMR (methanol-d₄) δ 17.8, 25.5, 27.3, 29.13, 29.15, 29.15, 29.18, 29.3, 31.2, 32.2, 36.5, 36.5, 61.6, 138.0, 155.6, 157.3 and 159.4; mass spectrum (APCI), m/z 310.2490 (M+H)⁺ ($C_{17}H_{32}N_3O_2$ requires 310.2495).

Example 8

Preparation of 2-(2,5-dimethyl-1H-pyrrol-1-yl)-4-(10-hydroxydecyl)-6-methylpyrimidin-5-ol

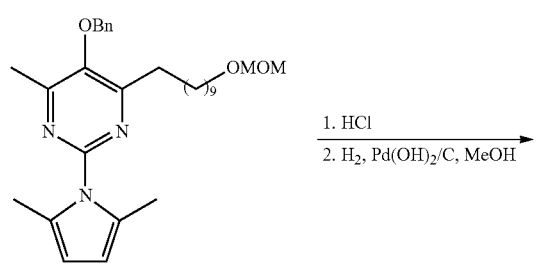

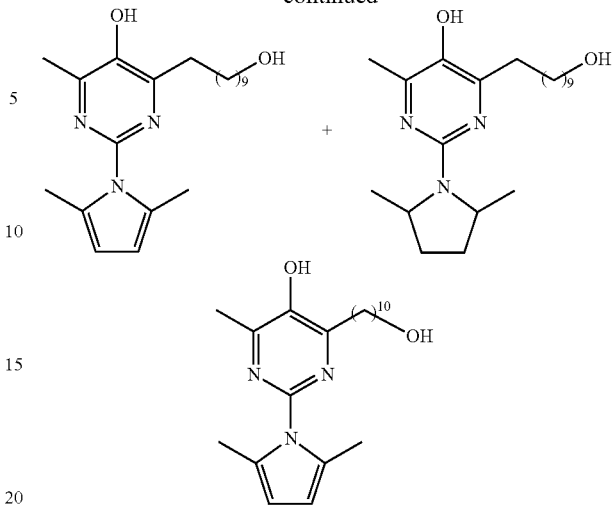

To a stirred solution containing 240 mg (0.48 mmol) of 5-(Benzyloxy)-2-(2,5-dimethyl-1H-pyrrol-1-yl)-4-(10-(methoxymethoxy)decyl)-6-methylpyrimidine in 10 mL of methanol were two drops of concentrated HCl and the mixture was stirred at reflux overnight. To the mixture were added 10 mg of 20% palladium hydroxide on carbon (Degussa type E101 NE/E). The reaction mixture was stirred at 23° C. under hydrogen atmosphere for 15 min. The reaction mixture was filtered through celite and the filtrated was concentrated under diminished pressure. The residue was purified by chromatography on a silica gel column (13×3 cm). Elution with 2:1 toluene-ethyl acetate afforded the expected product as colorless oil: yield 13 mg (8%); silica gel TLC $R_f$ 0.40 (2:1 toluene-ethyl acetate); ¹H NMR (methanol-d₄) 61.29-1.35 (m, 12H), 1.49 (m, 2H), 1.71 (m, 2H), 2.11 (s, 6H), 2.45 (s, 3H), 2.80 (dd, 2H, J=7.2, 7.2 Hz), 3.50 (t, 2H, J=6.4 Hz) and ~5.74 (s, 2H); ¹³C NMR (methanol-d₄) δ 11.96, 11.96, 17.50, 25.49, 27.27, 28.93, 29.05, 29.12, 29.18, 29.22, 31.00, 32.22, 61.56, 106.34, 106.34, 128.37, 128.37, 146.20, 148.84, 155.40 and 158.94; mass spectrum (APCI), m/z 360.2659 (M+H)⁺ ($C_{21}H_{34}N_3O_2$ requires 360.2651).

Example 9

Preparation of 2-(2,5-dimethylpyrrolidin-1-yl)-4-(10-hydroxydecyl)-6-methylpyrimidin-5-ol

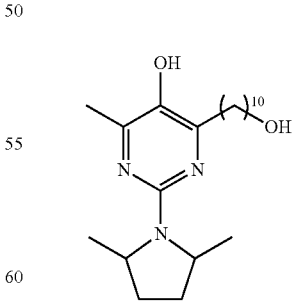

This compound was obtained as side product in the reaction for the preparation of 2-(2,5-dimethyl-1H-pyrrol-1-yl)-4-(10-hydroxydecyl)-6-methylpyrimidin-5-ol. Colorless oil: yield 25 mg (14%); silica gel TLC $R_f$ 0.46 (2:1 toluene-ethyl acetate); ¹H NMR (methanol-d₄) δ 1.26-1.35 (m, 16H), 1.51

(m, 2H), 1.69 (m, 4H), 1.98 (m, 2H), 2.25 (s, 3H), 2.61 (dd, 2H, J=7.2, 7.2 Hz), 3.51 (t, 2H, J=6.8 Hz) and 4.11 (m, 2H); $^{13}$C NMR (methanol-$d_4$) δ 17.62, 17.62, 20.98, 20.98, 25.50, 27.11, 29.08, 29.14, 29.16, 29.16, 29.28, 31.00, 31.50, 32.22, 54.52, 54.52, 61.58, 137.80, 155.46, 155.46 and 159.12; mass spectrum (APCI), m/z 364.2954 (M+H)$^+$ ($C_{21}H_{38}N_3O_2$ requires 364.2964).

Example 10

Preparation of 2-amino-4-(10-hydroxydecyl)-6-methylpyrimidin-5-ol

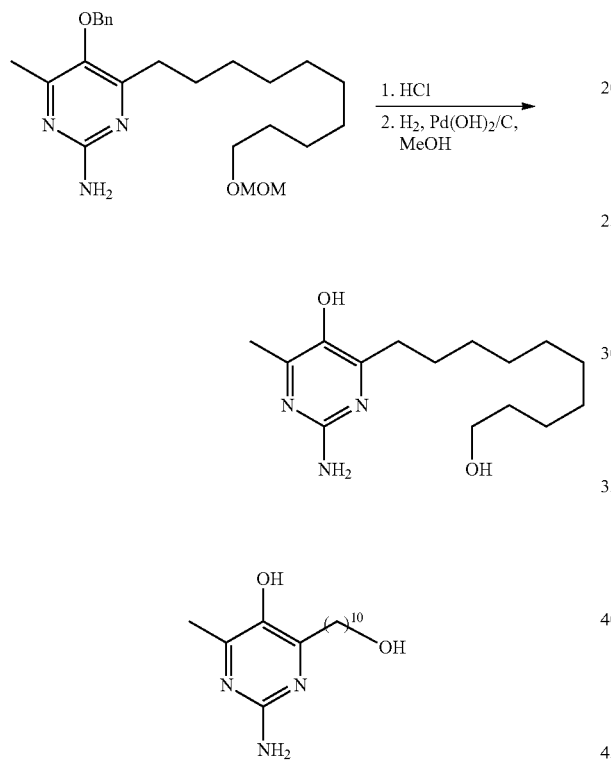

To a stirred solution containing 133 mg (0.48 mmol) of 5-(benzyloxy)-4-(10-(methoxymethoxy)decyl)-6-methylpyrimidin-2-amine in 10 mL of methanol were added two drops of concentrated HCl and the mixture was stirred at reflux for 16 h. To the mixture were added 10 mg of 20% palladium hydroxide on carbon (Degussa type E101 NE/N). The reaction mixture was stirred at 23° C. under hydrogen atmosphere for 15 min. The reaction mixture was filtered through celite and the filtrated was concentrated under diminished pressure. The residue was purified by chromatography on a silica gel column (13×3 cm). Elution with 17:3 dichloromethane-methanol afforded the expected product as white solid: yield 68 mg (69%); mp: 103-104° C.; silica gel TLC R$_f$ 0.20 (17:3 dichloromethane-methanol); $^1$H NMR (methanol-$d_4$) δ 1.29-1.35 (m, 12H), 1.50 (quint, 2H, J=6.8 Hz), 1.64 (quint, 2H, J=7.6 Hz), 2.37 (s, 3H), 2.71 (dd, 2H, J=7.6, 7.6 Hz) and 3.51 (t, 2H, J=6.4); $^{13}$C NMR (methanol-$d_4$) δ 16.42, 25.50, 27.07, 29.00, 29.02, 29.08, 29.13, 29.25, 30.72, 32.22, 61.56, 138.97, 153.46, 157.60 and 160.84; mass spectrum (APCI+), m/z 282.2170 (M+H) ($C_{15}H_{28}N_3O_2$ requires 282.2182).

Example 11

Preparation of 4-(10-hydroxydecyl)-2-methoxy-6-methylpyrimidin-5-ol (Compound E)

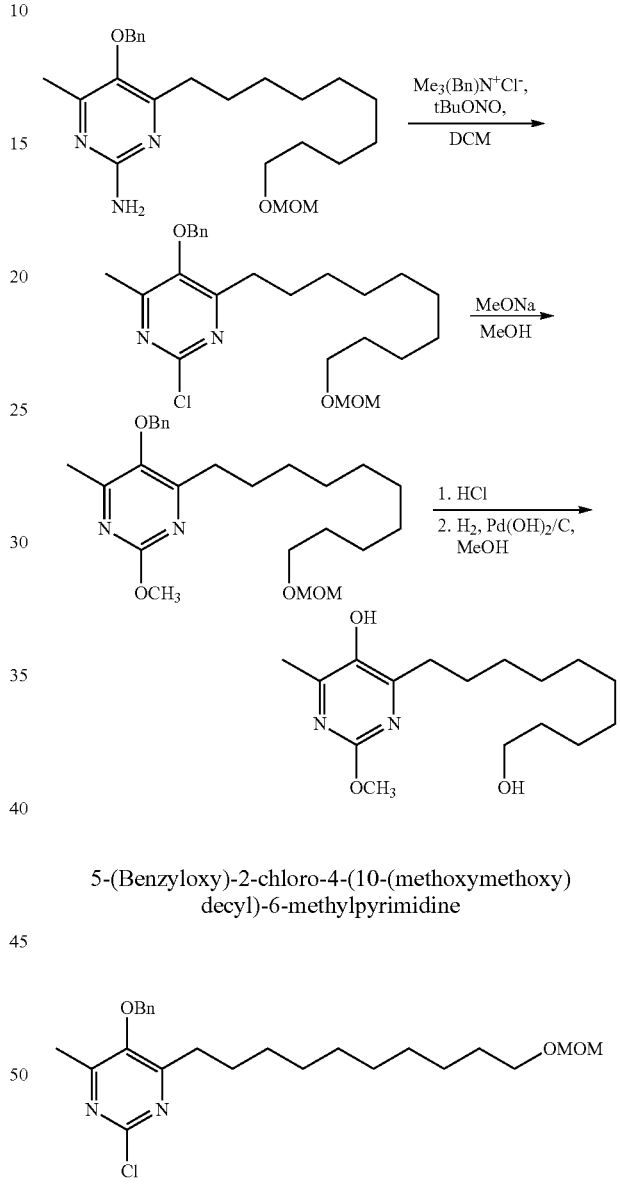

5-(Benzyloxy)-2-chloro-4-(10-(methoxymethoxy)decyl)-6-methylpyrimidine

To a stirred solution containing 240 mg (0.58 mmol) of 5-(benzyloxy)-4-(10-(methoxymethoxy)decyl)-6-methylpyrimidin-2-amine in 10 mL of anhydrous DCM were added 1.10 g (5.80 mmol) of benzyltrimethylammonium chloride followed by 696 μL (5.80 mmol) of t-butyl nitrite. The reaction mixture was stirred at 23° C. protected from light for 15 h. The mixture was filtered and the filtrate was concentrated under diminished pressure. The residue was purified by chromatography on a silica gel column (3×10 cm). Elution with 4:1 hexanes-ethyl acetate afforded the expected product as a colorless oil: yield 44 mg (16%); silica gel TLC R$_f$ 0.45 (4:1 hexanes-ethyl acetate); $^1$H NMR (CDCl$_3$) δ 1.24 (br s, 12H), 1.55 (quint, 2H, J=7.2 Hz), 1.65 (quint, 2H, J=6.8 Hz), 2.42 (s, 3H), 2.67 (dd, 2H, J=8.0, 8.0 Hz), 3.33 (s, 3H), 3.47 (t, 2H, J=6.8 Hz), 4.59 (s, 2H), 4.83 (s, 2H) and 7.37 (m, 5H); $^{13}$C NMR (CDCl$_3$) δ 19.32, 26.16, 28.14, 29.25, 29.35, 29.35, 29.47, 29.51, 29.71, 31.92, 55.04, 67.85, 76.03, 96.36, 128.08, 128.73, 128.73, 128.77, 128.77, 135.73, 149.01, 154.24, 163.79 and 167.41; mass spectrum (APCI), m/z (M+H)$^+$ 435.2411 (C$_{24}$H$_{36}$N$_2$O$_3$Cl requires 435.2415)

5-(Benzyloxy)-2-methoxy-4-(10-(methoxymethoxy)decyl)-6-methylpyrimidine

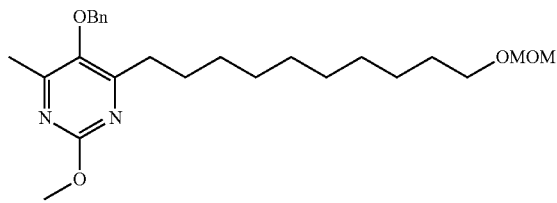

To a stirred solution containing 41.0 mg (0.09 mmol) of 5-(benzyloxy)-2-chloro-4-(10-(methoxymethoxy)decyl)-6-methylpyrimidine in 5 mL of anhydrous methanol were added 22 mg (0.94 mmol) of sodium. The mixture was then stirred at reflux for 16 h. The reaction was quenched with water and poured into 50 mL of water. The mixture was extracted with two 50-mL portions of ethyl acetate. The combined organic solution was washed with one 50-mL portion of brine, dried (MgSO$_4$) and concentrated under diminished pressure. The residue was purified by chromatography on a silica gel column (2×6 cm). Elution with 1:1 hexanes-ethyl acetate afforded the expected product as a colorless oil: yield 30 mg (74%); silica gel TLC R$_f$ 0.65 (1:1 hexanes-ethyl acetate); $^1$H NMR (CDCl$_3$) δ 1.24 (br m, 12H), 1.55 (quint, 2H, J=6.8 Hz), 1.68 (quint, 2H, J=7.6 Hz), 2.37 (s, 3H), 2.65 (dd, 2H, J=7.6, 7.6 Hz), 3.33 (s, 3H), 3.48 (t, 2H, J=6.8 Hz), 3.93 (s, 3H), 4.59 (s, 2H), 4.83 (s, 2H) and 7.37 (m, 5H); $^{13}$C NMR (CDCl$_3$) δ 19.21, 26.16, 27.85, 29.36, 29.40, 29.51, 29.53, 29.71, 31.71, 54.69, 55.02, 67.85, 75.80, 96.36, 127.49, 128.38, 128.38, 128.63, 128.63, 136.50, 145.14, 160.61, 162.38 and 165.87; mass spectrum (APCI), m/z (M+H)$^+$ 431.2910 (C$_{25}$H$_{39}$N$_2$O$_4$ requires 431.2910).

4-(10-hydroxydecyl)-2-methoxy-6-methylpyrimidin-5-ol (Compound E)

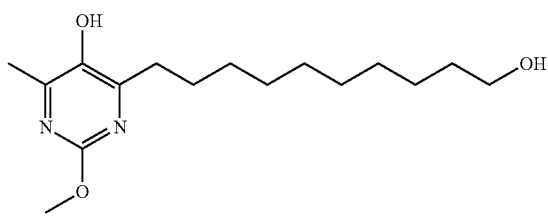 [SMILES: COc1nc(C)c(O)c(CCCCCCCCCCO)n1]

To a stirred solution containing 30.0 mg (0.07 mmol) of 5-(Benzyloxy)-2-methoxy-4-(10-(methoxymethoxy)decyl)-6-methylpyrimidine in 3 mL of methanol was added a drop of concentrated HCl. The mixture was stirred at reflux for 16 h. Then, were added 2 mg of 20% palladium hydroxide on carbon (Degussa type E101 NE/N) and the mixture was stirred at 23° C. for 20 min. The mixture was filtered through celite and concentrated under diminished pressure to afford the expected product as a yellowish oil: yield 20 mg (97%); silica gel TLC R$_f$ 0.45 (4:1 hexanes-ethyl acetate); $^1$H NMR (methanol) δ 1.30 (br m, 12H), 1.50 (br m, 2H), 1.74 (br m, 2H), 2.56 (s, 3H), 2.89 (dd, 2H, J=7.6, 7.6 Hz), 3.51 (t, 2H, J=6.4 Hz) and 4.15 (s, 3H); $^{13}$C NMR (methanol) δ 16.16, 25.49, 26.83, 28.94, 29.04, 29.11, 29.18, 29.22, 30.82, 32.20, 56.14, 61.56, 143.11, 143.11, 152.95 and 152.95; mass spectrum (APCI), m/z (M+H)$^+$ 297.2180 (C$_{16}$H$_{29}$N$_2$O$_3$ requires 297.2178).

Example 12

Preparation of 2-(dimethylamino)-4-methyl-6-pentylpyrimidin-5-ol (Compound H)

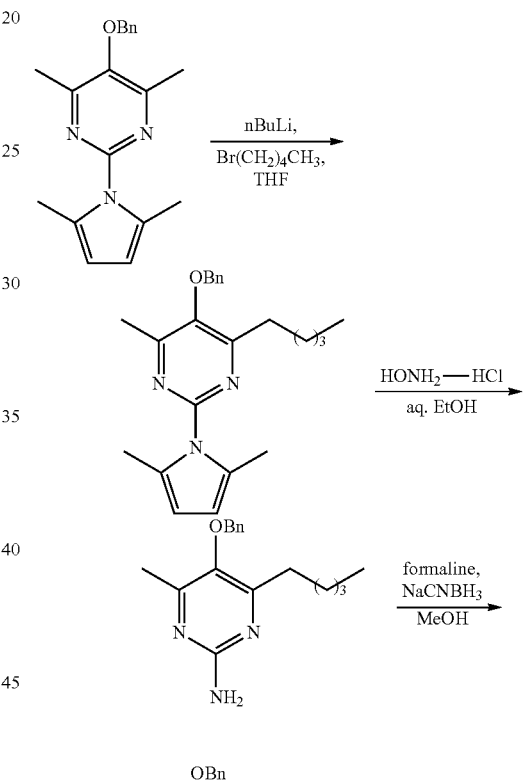

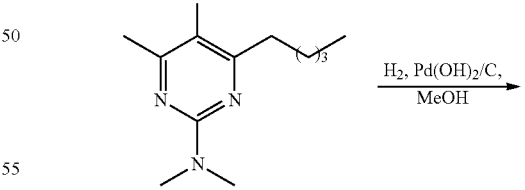

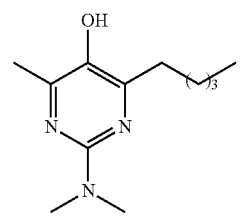

5-(benzyloxy)-2-(2,5-dimethyl-1H-pyrrol-1-yl)-4-methyl-6-pentylpyrimidine

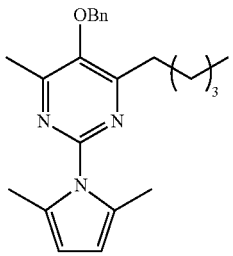

To a stirred solution at −78° C. containing 1.00 g (3.25 mmol) of 5-(Benzyloxy)-2-(2,5-dimethyl-1H-pyrrol-1-yl)-4,6-dimethylpyrimidine and 233 µL (2.16 mmol) of 4-bromobutane in 30 mL of anhydrous THF were added 2.70 mL (4.32 mmol) of a 1.6 M solution of n-BuLi in pentane. The reaction mixture was stirred at 23° C. for 30 min. The reaction was quenched with saturated aqueous ammonium chloride and then poured into 70 mL of water. The mixture was then extracted with two 70-mL portions of diethyl ether. The combined organic layer was then washed with a 100-mL portion of brine, dried (MgSO$_4$) and then concentrated under diminished pressure. The residue was purified by chromatography on a silica gel column (15×5 cm). Elution with 4:1 hexanes-diethyl ether afforded the expected product as a colorless oil: yield 533 mg (69%); silica gel TLC R$_f$ 0.50 (4:1 hexanes-diethyl ether); $^1$H NMR (CDCl$_3$) δ 0.90 (t, 3H, J=7.2 Hz), 1.34 (m, 2H), 1.77 (m, 2H), 2.33 (s, 6H), 2.49 (s, 3H), 2.79 (dd, 2H, J=7.6, 7.6 Hz), 4.91 (s, 62), 5.88 (s, 2H) and 7.40-7.44 m, 5H); $^{13}$C NMR (CDCl$_3$) δ 13.95, 14.34, 19.29, 22.47, 27.41, 31.59, 31.73, 75.72, 107.94, 107.94, 128.01, 128.01, 128.22, 128.72, 129.30, 136.22, 147.38, 147.38, 152.60, 161.62, 161.62 and 165.08; mass spectrum (APCI), m/z 364.2394 (M+H)$^+$ (C$_{23}$H$_{30}$N$_3$O requires 364.2389).

5-(benzyloxy)-4-methyl-6-pentylpyrimidin-2-amine

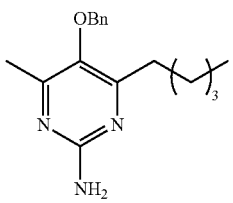

To stirred solution containing 533 mg (1.46 mmol) of 5-(benzyloxy)-2-(2,5-dimethyl-1H-pyrrol-1-yl)-4-methyl-6-pentylpyrimidine in 10 mL of ethanol-water 9:1 were added 1.0 g (14.60 mmol) of hydroxylamine hydrochloride. The reaction mixture was then stirred at reflux during 5 h. A second portion of 1.0 g (14.60 mmol) of hydroxylamine hydrochloride was added and the reaction mixture was stirred at reflux for 16 h. The reaction mixture was then poured into 70 mL of water and then basified to a pH 9-10 with a 1N NaOH aqueous solution. The mixture was extracted with two 70-mL portions of ethyl acetate. The combined organic layer was washed with a 70-mL portion of brine, dried (MgSO$_4$) and then concentrated under diminished pressure. The residue was purified by chromatography on a silica gel column (10×3 cm). Elution with 2:1 hexanes-ethyl acetate afforded the expected product as a colorless oil: yield 334 mg (80%); silica gel TLC R$_f$ 0.25 (2:1 hexanes-ethyl acetate); $^1$H NMR (CDCl$_3$) δ 0.86 (t, 3H, J=6.8 Hz), 1.27 (m, 4H), 1.63 (m, 2H), 2.28 (s, 3H), 2.56 (dd, 2H, J=8.0, 8.0 Hz), 4.71 (s, 2H), 5.15 (br s, 2H) and 7.35-7.37 (m, 5H); $^{13}$C NMR (CDCl$_3$) δ 13.94, 18.85, 22.41, 28.04, 31.86, 75.90, 127.90, 128.26, 128.26, 128.58, 128.58, 136.76, 142.80, 156.18, 158.79, 161.13 and 164.89; mass spectrum (APCI), m/z 286.1914 (M+H)$^+$ (C$_{34}$H$_{52}$N$_3$O requires 286.1919).

5-(benzyloxy)-N,N,4-trimethyl-6-pentylpyrimidin-2-amine

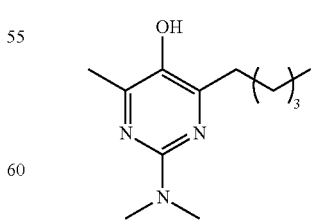

To a stirred solution containing 334 mg (1.17 mmol) of 5-(benzyloxy)-4-methyl-6-pentylpyrimidin-2-amine in 4 mL of methanol were added 4 mL of 35% aq. formaldehyde followed by 588 mg (9.35 mmol) of NaCNBH$_3$. The reaction mixture was stirred at 23° C. for 3 h. The reaction mixture was quenched with acetic acid until bubbling ceased then poured into 20 mL of water and extracted with two 40-mL portions of ethyl acetate. The combined organic layer was washed with one 40-mL portion of saturated aq. NaHCO$_3$ and one 40-mL portion of brine. The organic solution was dried (MgSO$_4$) and then concentrated under diminished pressure. The residue was purified by chromatography on a silica gel column (8×3 cm). Elution with 2:1 hexanes-ethyl acetate afforded the expected product as colorless oil: yield 150 mg (41%); silica gel TLC R$_f$ 0.7 (2:1 hexanes-ethyl acetate); $^1$H NMR (CDCl$_3$) δ 0.88 (t, 3H, J=7.2 Hz), 1.33 (m, 4H), 1.69 (quint, 2H, J=7.6 Hz), 2.32 (s, 3H), 2.62 (dd, 2H, J=8.0, 8.0 Hz), 3.15 (s, 6H), 4.70 (s, 2H) and 7.33-7.44 (m, 5H); $^{13}$C NMR (CDCl$_3$) δ 14.00, 19.31, 22.54, 27.52, 31.67, 31.81, 37.22, 37.22, 75.73, 127.94, 128.13, 128.13, 128.55, 128.55, 137.15, 141.26, 158.60, 160.01 and 163.48; mass spectrum (APCI), m/z 314.2224 (M+H)$^1$ (C$_{19}$H$_{28}$N$_3$O requires 314.2232).

2-(dimethylamino)-4-methyl-6-pentylpyrimidin-5-ol (Compound H)

To a stirred solution containing 150 mg (0.48 mmol) of 5-(benzyloxy)-N,N,4-trimethyl-6-pentylpyrimidin-2-amine in 5 mL of methanol were added 5 mg of 20% palladium hydroxide on carbon (Degussa typy E101 NE/E). The reac-

77 tion mixture was stirred at 23° C. under hydrogen atmosphere for 15 min. The reaction mixture was filtered through celite and the filtrated was concentrated under diminished pressure. The residue was purified by chromatography on a silica gel column (8×3 cm). Elution with 2:1 hexane-ethyl acetate afforded the expected product as white solid: yield 60 mg (56%); mp: 61-62° C.; silica gel TLC $R_f$ 0.50 (2:1 hexanes-ethyl acetate); $^1$H NMR (methanol-$d_4$) δ 0.89 (t, 3H, J=5.6 Hz), 1.33 (m, 4H), 1.66 (quint, 2H, J=7.2 Hz), 2.26 (s, 3H), 2.62 (dd, 2H, J=7.6, 7.6 Hz) and 3.05 (s, 6H); $^{13}$C NMR (methanol-$d_4$) δ 12.93, 17.53, 22.16, 27.00, 31.21, 31.43, 36.49, 138.01, 155.64, 157.33 and 159.44; mass spectrum (APCI), m/z 224.1769 (M+H)$^+$ ($C_{12}H_{22}N_3O$ requires 224.1763).

Example 13

Preparation of 4-decyl-2-(dimethylamino)-6-methylpyrimidin-5-ol (Compound I)

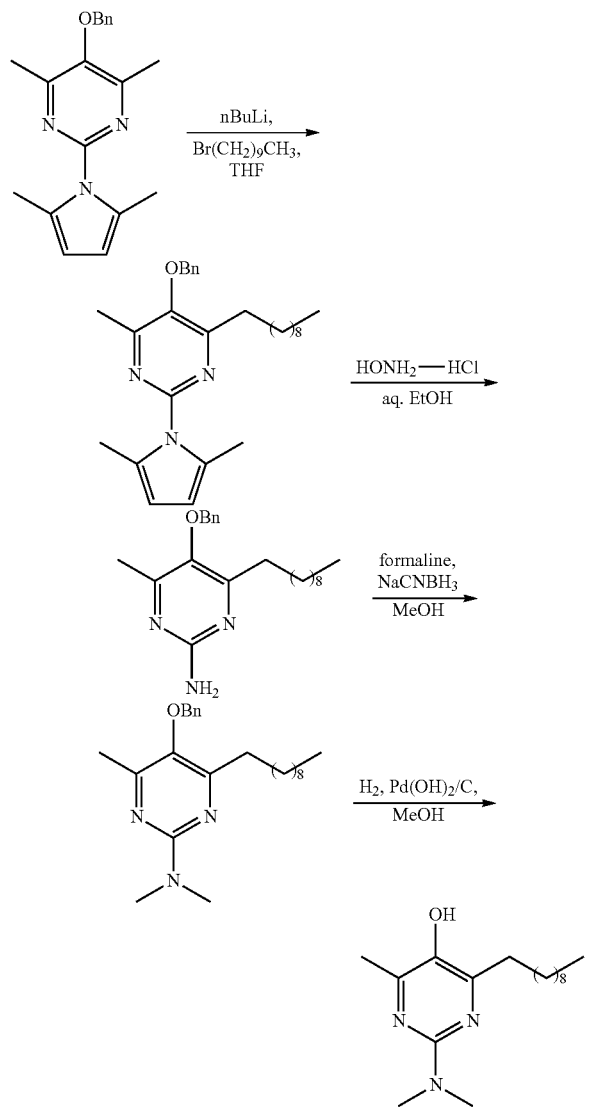

78

5-(benzyloxy)-4-decyl-2-(2,5-dimethyl-1H-pyrrol-1-yl)-6-methylpyrimidine

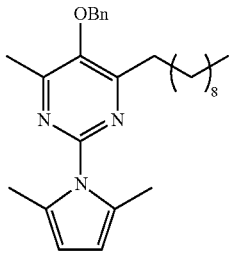

To a stirred solution at −78° C. containing 1.00 g (3.25 mmol) of 5-(Benzyloxy)-2-(2,5-dimethyl-1H-pyrrol-1-yl)-4,6-dimethylpyrimidine and 415 mg (2.16 mmol) of 1-bromononane in 30 mL of anhydrous THF were added 2.70 mL (4.32 mmol) of a 1.60 M solution of n-BuLi in pentane. The reaction mixture was stirred at 23° C. for 30 min. The reaction was quenched with saturated aqueous ammonium chloride and then poured into 70 mL of water. The mixture was then extracted with two 70-mL portions of diethyl ether. The combined organic layer was then washed with a 100-mL portion of brine, dried (MgSO$_4$) and then concentrated under diminished pressure. The residue was purified by chromatography on a silica gel column (15×5 cm). Elution with 4:1 hexanes-diethyl ether afforded the expected product as light colorless oil: yield 502 mg (53%); silica gel TLC $R_f$ 0.60 (4:1 hexanes-diethyl ether); $^1$H NMR (CDCl$_3$) δ0.89 (t, 3H, J=7.2 Hz), 1.20-1.30 (m, 14H), 1.75 (m, 2H), 2.31 (s, 6H), 2.48 (s, 3H), 2.77 (dd, 2H, J=7.6, 7.6 Hz), 4.90 (s, 2H), 5.86 (s, 2H) and 7.40-7.44 (m, 5H); $^{13}$C NMR (CDCl$_3$) δ 14.10, 14.33, 19.28, 22.67 27.74, 29.29, 29.29, 29.41, 29.51, 29.57, 31.62, 31.88, 75.72, 107.91, 128.01, 128.22, 128.72, 129.30, 129.30, 136.22, 147.35, 147.35, 152.59, 161.59 and 165.09; mass spectrum (APCI), m/z 434.3172 (M+H)$^+$ ($C_{28}H_{40}N_3O$ requires 434.3171).

5-(benzyloxy)-4-decyl-6-methylpyrimidin-2-amine

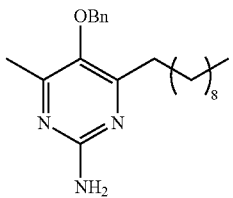

To stirred solution containing 502 mg (1.15 mmol) of 5-(benzyloxy)-4-decyl-2-(2,5-dimethyl-1H-pyrrol-1-yl)-6-methylpyrimidine in 10 mL of ethanol-water 9:1 were added 800 mg (11.50 mmol) of hydroxylamine hydrochloride. The reaction mixture was then stirred at reflux during 5 h. A second portion of 800 mg (11.50 mmol) of hydroxylamine hydrochloride was added and the reaction mixture was stirred at reflux for 16 h. The reaction mixture was then poured into 70 mL of water and then basified to a pH 9-10 with a 1N NaOH aqueous solution. The mixture was extracted with two 70-mL portions of ethyl acetate. The combined organic layer was washed with a 70-mL portion of brine, dried (MgSO$_4$) and then concentrated under diminished pressure. The residue was purified by chromatography on a silica gel column (10×3 cm). Elution with 3:2 hexanes-ethyl acetate afforded the expected product as a colorless oil: yield 305 mg (75%); silica gel TLC $R_f$ 0.25 (3:2 hexanes-ethyl acetate); $^1$H NMR (CDCl$_3$) δ 0.85 (t, 3H, J=6.4 Hz), 1.26 (m, 14H), 1.61 (m, 2H), 2.27 (s, 3H), 2.56 (dd, 2H, J=8.0, 8.0 Hz), 4.71 (s, 2H), 5.24 (br s, 2H) and 7.35-7.40 (m, 5H); $^{13}$C NMR (CDCl$_3$) δ 13.94, 18.86, 22.64, 28.41, 29.27, 29.39, 29.50, 29.55, 29.71, 31.87, 31.88, 75.88, 127, 88, 128.24, 128.24, 128.58, 128.58, 136.79, 142.8, 158.92, 161.09 and 162.82; mass spectrum (APCI), m/z 356.2704 (M+H)$^+$ (C$_{22}$H$_{34}$N$_3$O requires 356.2702).

5-(benzyloxy)-4-decyl-N,N,6-trimethylpyrimidin-2-amine

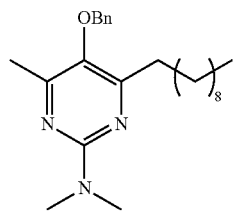

To a stirred solution containing 305 mg (0.86 mmol) of 5-(benzyloxy)-4-decyl-6-methylpyrimidin-2-amine in 3 mL of methanol were added 3 mL of 35% aq. formaldehyde followed by 271 mg (4.30 mmol) of NaCNBH$_3$. The reaction mixture was stirred at 23° C. for 3 h. The reaction mixture was quenched with acetic acid until bubbling ceased then poured into 20 mL of water and extracted with two 40-mL portions of ethyl acetate. The combined organic layer was washed with one 40-mL portion of saturated aq. NaHCO$_3$ and one 40-mL portion of brine. The organic solution was dried (MgSO$_4$) and then concentrated under diminished pressure. The residue was purified by chromatography on a silica gel column (8×3 cm). Elution with 2:1 hexanes-ethyl acetate afforded the expected product as colorless oil: yield 154 mg (46%); silica gel TLC $R_f$ 0.8 (2:1 hexanes-ethyl acetate); $^1$H NMR (CDCl$_3$) δ 0.87 (t, 3H, J=6.4 Hz), 1.33 (m, 14H), 1.69 (quint, 2H, J=7.2 Hz), 2.32 (s, 3H), 2.61 (dd, 2H, J=7.6, 7.6 Hz), 3.14 (s, 6H), 4.70 (s, 2H) and 7.33-7.44 (m, 5H); $^{13}$C NMR (CDCl$_3$) δ 14.07, 19.29, 22.65, 27.85, 29.30, 29.50, 29.55, 29.59, 29.62, 31.71, 31.89, 37.21, 37.21, 75.72, 127.91, 128.11, 128.11, 128.54, 128.54, 137.17, 141.27, 158.60, 159.01 and 163.49; mass spectrum (APCI), m/z 384.3003 (M+H)$^+$ (C$_{24}$H$_{38}$N$_3$O requires 384.3015).

4-decyl-2-(dimethylamino)-6-methylpyrimidin-5-ol (Compound I)

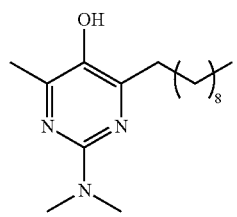

To a stirred solution containing 150 mg (0.48 mmol) 5-(benzyloxy)-4-decyl-N,N,6-trimethylpyrimidin-2-amine in 5 mL of methanol were added 5 mg of 20% palladium hydroxide on carbon (Degussa type E101 NE/E). The reaction mixture was stirred at 23° C. under hydrogen atmosphere for 15 min. The reaction mixture was filtered through celite and the filtrated was concentrated under diminished pressure. The residue was purified by chromatography on a silica gel column (8×3 cm). Elution with 4:1 hexane-ethyl acetate afforded the expected product as white solid: yield 33 mg (28%); mp: 71-72° C.; silica gel TLC $R_f$ 0.25 (4:1 hexanes-ethyl acetate); $^1$H NMR (methanol-d$_4$) δ 0.87 (t, 3H, J=6.8 Hz), 1.21-1.31 (m, 14H), 1.65 (quint, 2H, J=7.2 Hz), 2.26 (s, 3H), 2.62 (dd, 2H, J=7.2, 7.2 Hz) and 3.05 (s, 6H); $^{13}$C NMR (methanol-d$_4$) δ 13.01, 17.55, 22.29, 27.27, 29.02, 29.15, 29.17, 29.26, 29.29, 31.24, 31.64, 36.52, 36.52, 138.04, 155.59, 157.31 and 159.41; mass spectrum (APCI), m/z 294.2554 (M+H)$^+$ (C$_{17}$H$_{32}$N$_3$O requires 294.2545).

Example 14

Preparation of 2-(dimethylamino)-4-hexadecyl-6-methylpyrimidin-5-ol (Compound J)

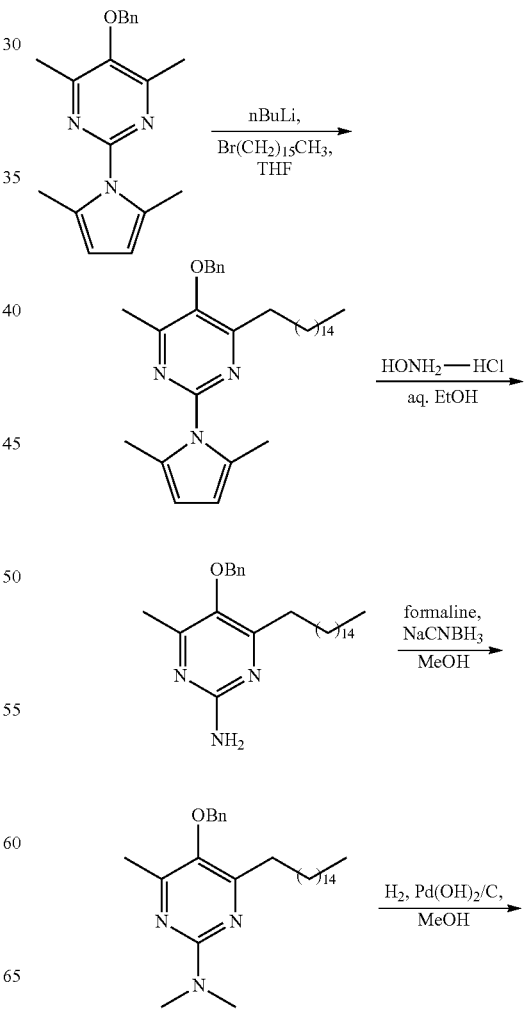

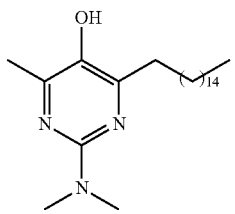

5-(benzyloxy)-2-(2,5-dimethyl-1H-pyrrol-1-yl)-4-hexadecyl-6-methylpyrimidine

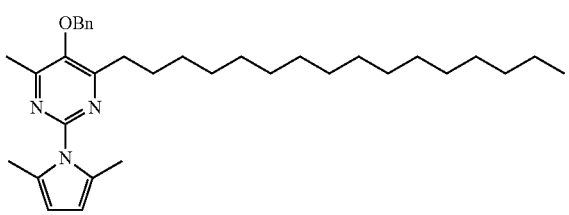 [SMILES: CCCCCCCCCCCCCCCCc1nc(-n2c(C)ccc2C)nc(C)c1OCc1ccccc1]

To a stirred solution at −78° C. containing 1.00 g (3.25 mmol) of 5-(Benzyloxy)-2-(2,5-dimethyl-1H-pyrrol-1-yl)-4,6-dimethylpyrimidine and 630 μL (2.16 mmol) of 1-bromopentadecane in 20 mL of anhydrous THF were added 2.70 mL (4.32 mmol) of a 1.60 M solution of n-BuLi in pentane. The reaction mixture was stirred at 23° C. for 30 min. The reaction was quenched with saturated aqueous ammonium chloride and then poured into 70 mL of water. The mixture was then extracted with two 70-mL portions of diethyl ether. The combined organic layer was then washed with a 100-mL portion of brine, dried (MgSO$_4$) and then concentrated under diminished pressure. The residue was purified by chromatography on a silica gel column (15×5 cm). Elution with 4:1 hexanes-diethyl ether afforded the expected product as a colorless oil: yield 269 mg (24%); silica gel TLC $R_f$ 0.5 (4:1 hexanes-diethyl ether); $^1$H NMR (CDCl$_3$) δ0.89 (t, 3H, J=7.2 Hz), 1.20-1.30 (m, 26H), 1.75 (quint, 2H, J=7.2 Hz), 2.29 (s, 6H), 2.47 (s, 3H), 2.76 (dd, 2H, J=8.0, 8.0 Hz), 4.89 (s, 2H), 5.85 (s, 2H) and 7.30-7.42 (m, 5H); $^{13}$C NMR (CDCl$_3$) δ 14.08, 14.30, 14.30, 19.27, 22.66 27.72, 29.33, 29.40, 29.50, 29.55, 29.63, 29.63, 29.63, 29.67, 29.67, 29.67, 29.67, 31.61, 31.89, 75.72, 107.91, 128.01, 128.22, 128.72, 129.30, 129.30, 136.22, 147.35, 147.35, 152.59, 161.59 and 165.09; mass spectrum (APCI), m/z 518.4113 (M+H)$^+$ (C$_{34}$H$_{52}$N$_3$O requires 518.4110).

5-(benzyloxy)-4-hexadecyl-6-methylpyrimidin-2-amine

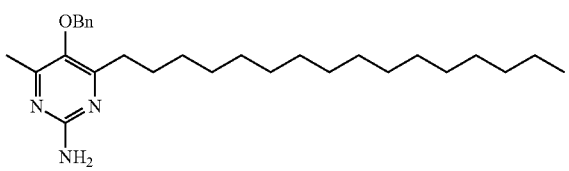 [SMILES: CCCCCCCCCCCCCCCCc1nc(N)nc(C)c1OCc1ccccc1]

To stirred solution containing 269 mg (0.52 mmol) of 5-(benzyloxy)-2-(2,5-dimethyl-1H-pyrrol-1-yl)-4-hexadecyl-6-methylpyrimidine in 10 mL of ethanol were added 723 mg (10.40 mmol) of hydroxylamine hydrochloride. The reaction mixture was then stirred at reflux during 5 h. The reaction mixture was then poured into 70 mL of water and then basified to a pH 9-10 with a 1N NaOH aqueous solution. The mixture was extracted with two 70-mL portions of ethyl acetate. The combined organic layer was washed with a 70-mL portion of brine, dried (MgSO$_4$) and then concentrated under diminished pressure. The residue was purified by chromatography on a silica gel column (10×3 cm). Elution with 3:2 hexanes-ethyl acetate afforded the expected product as a colorless oil: yield 231 mg (100%); silica gel TLC $R_f$ 0.25 (1:1 hexanes-ethyl acetate); $^1$H NMR (CDCl$_3$) δ 0.85 (t, 3H, J=6.8 Hz), 1.26 (m, 26H), 1.61 (quint, 2H, J=7.2 Hz), 2.28 (s, 3H), 2.56 (dd, 2H, J=7.6, 7.6 Hz), 4.72 (s, 2H), 5.03 (br s, 2H) and 7.35-7.40 (m, 5H); $^{13}$C NMR (CDCl$_3$) δ 14.08, 18.91, 22.66, 28.42, 29.33, 29.41, 29.52, 29.63, 29.63, 29.63, 29.63, 29.67, 29.67, 29.67, 29.67, 29.73, 31.90, 75.88, 127, 88, 128.24, 128.24, 128.58, 128.58, 136.79, 142.87, 158.79, 161.12 and 164.87; mass spectrum (APCI), m/z 440.3646 (M+H)$^+$ (C$_{28}$H$_{46}$N$_3$O requires 440.3641).

5-(benzyloxy)-4-hexadecyl-N,N,6-trimethylpyrimidin-2-amine

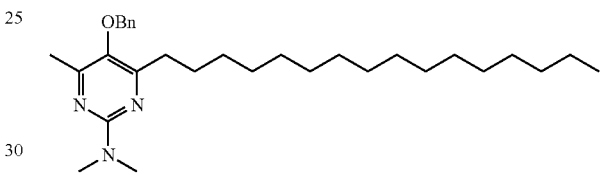

To a stirred solution containing 230 mg (0.52 mmol) of 5-(benzyloxy)-4-hexadecyl-6-methylpyrimidin-2-amine in 4 mL of methanol were added 4 mL of 35% aq. formaldehyde followed by 263 mg (4.18 mmol) of NaCNBH$_3$. The reaction mixture was stirred at 23° C. for 3 h. The reaction mixture was quenched with acetic acid until bubbling ceased then poured into 20 mL of water and extracted with two 40-mL portions of ethyl acetate. The combined organic layer was washed with one 40-mL portion of saturated aq. NaHCO$_3$ and one 40-mL portion of brine. The organic solution was dried (MgSO$_4$) and then concentrated under diminished pressure. The residue was purified by chromatography on a silica gel column (8×3 cm). Elution with 4:1 hexanes-ethyl acetate afforded the expected product as colorless oil: yield 100 mg (41%); silica gel TLC $R_f$ 0.75 (4:1 hexanes-ethyl acetate); $^1$H NMR (CDCl$_3$) δ 0.86 (t, 3H, J=6.8 Hz), 1.23-1.28 (br m, 26H), 1.68 (quint, 2H, J=6.8 Hz), 2.31 (s, 3H), 2.61 (dd, 2H, J=7.6, 7.6 Hz), 3.14 (s, 6H), 4.69 (s, 2H) and 7.40-7.46 (m, 5H); $^{13}$C NMR (CDCl$_3$) δ 14.05, 19.29, 22.64, 27.72, 27.84, 29.31, 29.50, 29.55, 29.62, 29.64, 29.64, 29.64, 29.66, 29.66, 29.66, 31.59, 31.70, 31.89, 37.21, 37.21, 75.67, 127.90, 128.16, 128.16, 128.54, 128.54, 137.17, 141.27, 158.60, 159.01 and 163.62; mass spectrum (APCI), m/z 468.3950 (M+H)$^+$ (C$_{30}$H$_{50}$N$_3$O requires 468.3954).

2-(dimethylamino)-4-hexadecyl-6-methylpyrimidin-5-ol (Compound J)

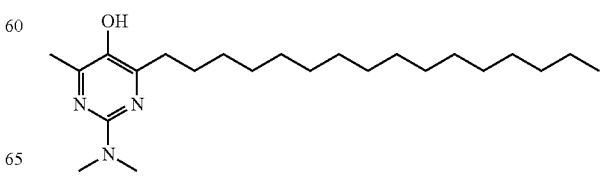

To a stirred solution containing 100 mg (0.21 mmol) 5-(benzyloxy)-4-hexadecyl-N,N,6-trimethylpyrimidin-2-amine in 5 mL of methanol were added 5 mg of 20% palladium hydroxide on carbon (Degussa type E101 NE/E). The reaction mixture was stirred at 23° C. under hydrogen atmosphere for 15 min. The reaction mixture was filtered through celite and the filtrated was concentrated under diminished pressure. The residue was purified by chromatography on a silica gel column (8×3 cm). Elution with 4:1 hexane-ethyl acetate afforded the expected product as white solid: yield 20 mg (25%); mp: 86-87° C.; silica gel TLC $R_f$ 0.45 (4:1 hexanes-ethyl acetate); $^1$H NMR (methanol-d$_4$) δ 0.89 (t, 3H, J=6.8 Hz), 1.28-1.34 (m, 26H), 1.67 (quint, 2H, J=7.2 Hz), 2.28 (s, 3H), 2.63 (dd, 2H, J=7.6, 7.6 Hz) and 3.07 (s, 6H); $^{13}$C NMR (methanol-d$_4$) δ 12.96, 17.52, 22.27, 27.23, 29.00, 29.12, 29.12, 29.20, 29.20, 29.20, 29.30, 29.30, 29.30, 29.30, 29.30, 31.21, 31.61, 36.50, 36.50, 138.02, 155.61, 157.31 and 159.41; mass spectrum (APCI), m/z 378.3491 (M+H)$^+$ (C$_{23}$H$_{44}$N$_3$O requires 378.3484).

Example 15

Preparation of 2-(dimethylamino)-4-(10-hydroxydecyl)-6-methoxypyrimidin-5-ol (Compound D)

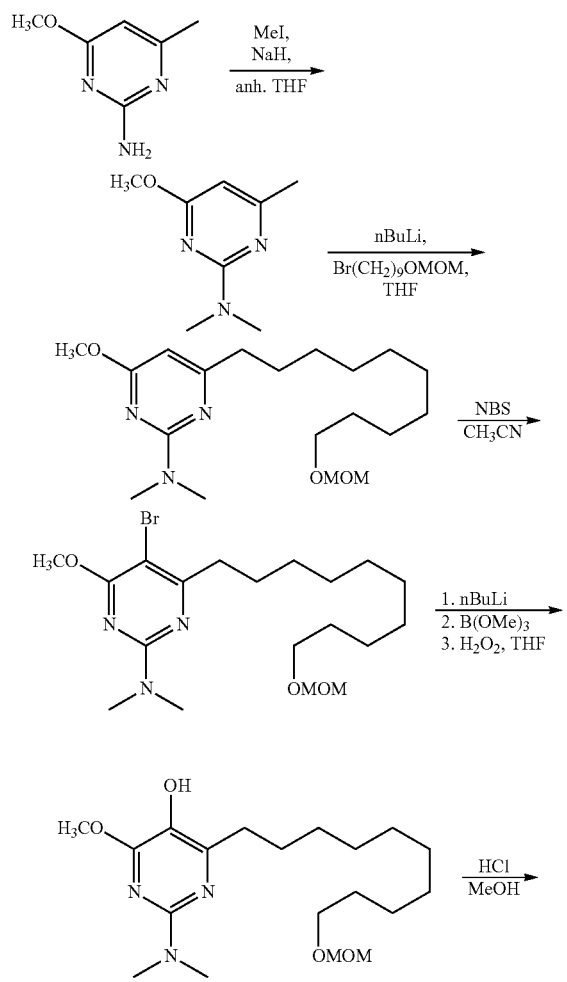

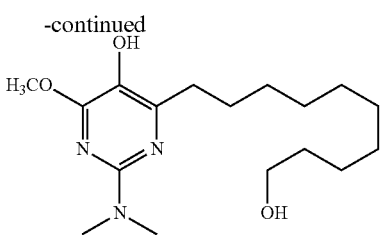

4-methoxy-N,N,6-trimethylpyrimidin-2-amine

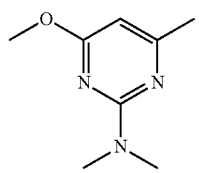

To a stirred solution containing 1.0 g (7.19 mmol) of 4-methoxy-6-methylpyrimidin-2-amine in 10 mL of anf DMF were added 1.35 mL (21.6 mmol) of methyl iodide followed by 853 mg (21.6 mmol) of 60% suspension of sodium hydride in mineral oil. The reaction mixture was stirred at 23° C. for 20 min. The reaction mixture was quenched with water and concentrated under diminished pressure in order to remove as much DMF as possible. The residue was dissolved in 70 mL of ethyl acetate and washed with 50-mL portions of water and brine respectively. The organic solution was dried (MgSO$_4$) and concentrated under diminished pressure. The residue was purified by chromatography on a silica gel column (15×5 cm). Elution with 4:1 hexanes-ethyl acetate afforded the expected product as colorless oil: yield 755 mg (63%); silica gel TLC $R_f$ 0.25 (4:1 hexanes-ethyl acetate); $^1$H NMR (CDCl$_3$) δ 2.22 (s, 3H), 3.12 (s, 6H), 3.83 (s, 3H) and 5.76 (s, 1H); $^{13}$C-NMR (CDCl$_3$) δ 24.07, 36.76, 36.76, 52.68, 93.74, 162.24, 167.70 and 170.24; mass spectrum (APCI+), m/z 168.1135 (M+H) (C$_8$H$_{14}$N$_3$O requires 168.1137).

4-methoxy-6-(10-(methoxymethoxy)decyl)-N,N-dimethylpyrimidin-2-amine

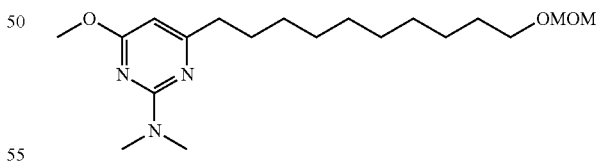

To a stirred solution containing 933 mg (5.58 mmol) of 4-methoxy-N,N,6-trimethylpyrimidin-2-amine and 1.5 g (5.58 mmol) of 1-Bromo-9-(methoxymethoxy)nonane in 20 mL of anhydrous THF were added 5.23 mL (8.37 mmol) of 1.6 M n-BuLi in hexanes. The reaction mixture was stirred at 23° C. for 20 min. The reaction mixture was quenched with saturated aqueous ammonium chloride and poured into 100 mL of water. The compound was extracted with two 80-mL portions of ethyl acetate. The combined organic layer was washed with one 80-mL portion of brine, dried (MgSO$_4$) and concentrated under diminished pressure. The residue was purified by chromatography on a silica gel column (15×5 cm). Elution with 9:1 hexanes-ethyl acetate afforded the expected product as colorless oil: yield 1.41 g (71%); silica gel TLC $R_f$ 0.45 (9:1 hexanes-ethyl acetate); $^1$H-NMR (CDCl$_3$) δ 1.24-1.32 (br m, 10H), 1.82 (m, 4H), 2.48 (dd, 2H, J=8.0, 8.0 Hz), 3.14 (s, 6H), 3.33 (s, 3H), 3.48 (t, 2H, J=6.8 Hz), 3.85 (s, 3H), 4.59 (s, 2H) and 5.76 (s, 1H); $^{13}$C NMR (CDCl$_3$) δ 26.18, 28.46, 28.66, 29.29, 29.39, 29.45, 29.54, 29.72, 36.77, 37.81, 37.81, 52.74, 55.04, 67.85, 93.03, 96.35, 162.35, 170.25 and 172.03; mass spectrum (APCI+), m/z 354.2766 (M+H) (C$_{19}$H$_{36}$N$_3$O$_3$ requires 254.2757).

5-bromo-4-methoxy-6-(10-(methoxymethoxy)decyl)-N,N-dimethylpyrimidin-2-amine

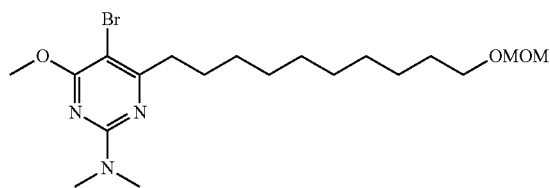

To a stirred solution containing 1.41 g (3.99 mmol) of 4-methoxy-6-(10-(methoxymethoxy)decyl)-N,N-dimethylpyrimidin-2-amine in 10 mL of acetonitrile were added 852 mg (4.79 mmol) of N-bromosuccinimide. The reaction mixture was stirred at 23° C. and protected from light for 5 h. The reaction mixture was concentrated under diminished pressure and the residue was dissolved into 100 mL of ethyl acetate. The organic solution was washed with a 100-mL portion of brine, dried (MgSO$_4$) and concentrated under diminished pressure. The residue was purified by chromatography on a silica gel column. Elution with 9:1 hexanes-ethyl acetate afforded the expected product as colorless oil: yield 910 mg (53%); silica gel TLC $R_f$ 0.65 (9:1 hexanes-ethyl acetate); $^1$H NMR (CDCl$_3$) δ 1.31-1.26 (br m, 10H), 1.54-1.64 (m, 4H), 2.67 (dd, 2H, J=7.6, 7.6 Hz), 3.11 (s, 6H), 3.33 (s, 3H), 3.48 (t, 2H, J=6.8 Hz), 3.92 (s, 3H) and 4.59 (s, 2H); $^{13}$C-NMR (CDCL$_3$) δ 26.18, 27.59, 29.34, 29.40, 29.40, 29.47, 29.55, 29.72, 36.68, 36.93, 53.96, 55.04, 67.85, 91.16, 96.35, 160.06, 165.05 and 169.04; mass spectrum (APCI+), m/z 432.1857 (M+H) (C$_{19}$H$_{35}$N$_3$O$_3$Br requires 432.1862).

2-(dimethylamino)-4-methoxy-6-(10-(methoxymethoxy)decyl)pyrimidin-5-ol

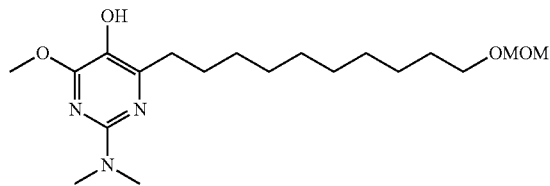

To a stirred solution at −5° C. containing 120 mg (0.25 mmol) of 5-bromo-4-methoxy-6-(10-(methoxymethoxy)decyl)-N,N-dimethylpyrimidin-2-amine in 3 mL of anhydrous THF were added 390 μL (0.62 mmol) of 1.6 M solution of n-BuLi in hexanes. The reaction mixture was stirred at −5° C. for 20 min. Then to the mixture were added 84 μL (0.75 mmol) of trimethoxy boron and the reaction mixture was stirred for 1 h. Then to reaction mixture were added 0.55 mL of 30% aq. H$_2$O$_2$ followed by 0.18 mL of 3N aq. NaOH. The reaction mixture was stirred for 30 min and poured into 50-mL of water. The mixture was neutralized with diluted aq. HCl and extracted with two 50-mL portions of ethyl acetate. The combined organic solution was washed with a 80-mL portion of brine, dried (MgSO$_4$) and concentrated under diminished pressure. The residue was purified by chromatography on a silica gel column (10×3 cm). Elution with 2:1 hexanes-ethyl acetate afforded the expected product as colorless oil: yield 47 mg (51%); silica gel TLC $R_f$ 0.50 (2:1 hexanes-ethyl acetate); $^1$H NMR (CDCl$_3$) δ 1.29-1.21 (br m, 10H), 1.64-1.54 (m, 4H), 2.58 (br s, 2H), 3.07 (s, 6H), 3.33 (s, 3H), 3.48 (t, 2H, J=6.8 Hz), 3.92 (s, 3H) and 4.59 (s, 2H); $^{13}$C NMR (CDCl$_3$) δ 26.14, 27.65, 29.29, 29.37, 29.42, 29.45, 29.52, 29.69, 31.19, 37.21, 37.21, 53.24, 55.03, 67.86, 96.32, 126.92, 154.98, 155.94 and 158.04; mass spectrum (APCI+), m/z 370.2700 (M+H) (C$_{19}$H$_{36}$N$_3$O$_3$ requires 370.2706).

2-(dimethylamino)-4-(10-hydroxydecyl)-6-methoxypyrimidin-5-ol (Compound D)

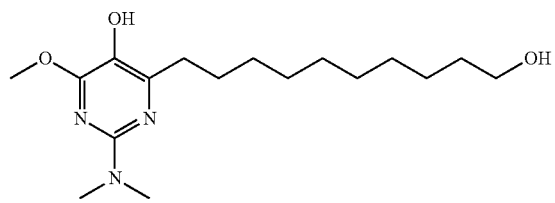 [SMILES: COc1nc(N(C)C)nc(CCCCCCCCCCO)c1O]

To a stirred solution containing 20 mg (0.054 mmol) of 2-(dimethylamino)-4-methoxy-6-(10-(methoxymethoxy)decyl)pyrimidin-5-ol in 5 mL of methanol were added 2 drops of concentrated HCl. The reaction mixture was stirred at reflux for 16 h. The reaction mixture was concentrated under diminished pressure and the residue was purified by chromatography on a silica gel column (8×1 cm). Elution with 1:2 hexanes-ethyl acetate afforded the expected product as white solid: yield 7 mg (40%); mp: 104-105° C.; silica gel TLC $R_f$ 0.15 (1:2 hexanes-ethyl acetate); $^1$H NMR (methanol-d$_4$) δ 1.28-1.32 (br m, 10H), 1.49 (m, 2H), 1.64 (m, 2H), 2.76 (dd, 2H, J=7.6, 7.6 Hz), 3.22 (s, 6H), 3.51 (t, 2H, J=6.8 Hz) and 4.07 (s, 3H); $^{13}$C NMR (methanol-d$_4$) δ 25.55, 27.49, 27.72, 29.02, 29.03, 29.17, 29.19, 29.31, 32.26, 37.20, 37.20, 54.45, 61.59, 128.10, 146.40, 151.34 and 162.67; mass spectrum (APCI+), m/z 326.2442 (M+H) (C$_{17}$H$_{32}$N$_3$O$_3$ requires 326.2444).

Example 16

Preparation of 4-decyl-2-(dimethylamino)-6-methoxypyrimidin-5-ol (Compound L)

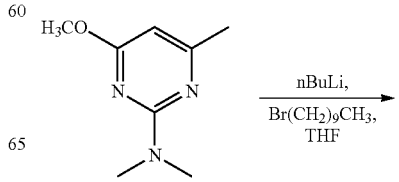

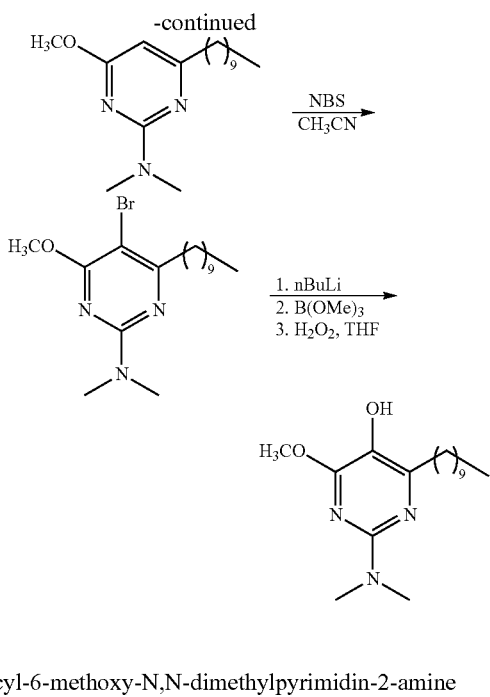

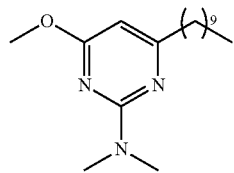

4-decyl-6-methoxy-N,N-dimethylpyrimidin-2-amine

To a stirred solution containing 1.06 g (6.34 mmol) of 4-methoxy-N,N,6-trimethylpyrimidin-2-amine and 1.32 g (6.34 mmol) of 1-bromononane in 20 mL of anhydrous THF were added 5.15 mL (8.34 mmol) of 1.6 M n-BuLi in hexanes. The reaction mixture was stirred at 23° C. for 20 min. The reaction mixture was quenched with saturated aqueous ammonium chloride and poured into 100 mL of water. The compound was extracted with two 80-mL portions of ethyl acetate. The combined organic layer was washed with one 80-mL portion of brine, dried (MgSO$_4$) and concentrated under diminished pressure. The residue was purified by chromatography on a silica gel column (15×5 cm). Elution with 9:1 hexanes-ethyl acetate afforded the expected product as colorless oil: yield 1.22 g (66%); silica gel TLC R$_f$ 0.7 (9:1 hexanes-ethyl acetate); $^1$H-NMR (CDCl$_3$) δ 0.85 (t, 3H, J=6.8 Hz), 1.28-1.23 (br m, 14H), 1.82 (quint, 2H, J=7.2 Hz), 2.46 (dd, 2H, J=7.6, 7.6 Hz), 3.14 (s, 6H), 3.85 (s, 3H) and 5.77 (s, 1H); $^{13}$C NMR (CDCl$_3$) δ 14.09, 22.66, 28.46, 29.31, 29.32, 29.48, 29.54, 29.59, 31.88, 36.78, 37.83, 37.83, 52.75, 93.03, 162.29, 170.25 and 173.93.

5-bromo-4-decyl-6-methoxy-N,N-dimethylpyrimidin-2-amine

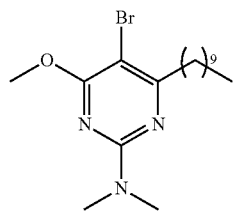

To a stirred solution containing 1.22 g (4.16 mmol) of 4-decyl-6-methoxy-N,N-dimethylpyrimidin-2-amine in 20 mL of acetonitrile were added 808 mg (4.54 mmol) of N-bromosuccinimide. The reaction mixture was stirred at 23° C. and protected from light for 5 h. The reaction mixture was concentrated under diminished pressure and the residue was dissolved into 100 mL of ethyl acetate. The organic solution was washed with a 100-mL portion of brine, dried (MgSO$_4$) and concentrated under diminished pressure. The residue was purified by chromatography on a silica gel column. Elution with 9:1 hexanes-ethyl ether afforded the expected product as white solid: yield 1.27 g (82%); mp: 45-46° C.; silica gel TLC R$_f$ 0.75 (9:1 hexanes-ethyl ether); $^1$H-NMR (CDCl$_3$) δ 0.86 (t, 3H, J=6.8 Hz), 1.33-1.24 (br m, 14H), 1.65 (quint, 2H, J=7.2 Hz), 2.68 (dd, 2H, J=7.6, 7.6 Hz), 3.12 (s, 6H) and 3.92 (s, 3H); $^{13}$C NMR (CDCl$_3$) δ 14.09, 22.67, 27.62, 29.32, 29.37, 29.45, 29.57, 29.60, 31.89, 36.70, 36.94, 36.94, 53.97, 91.17, 160.07, 165.06 and 169.05.

4-decyl-2-(dimethylamino)-6-methoxypyrimidin-5-ol: (Compound L)

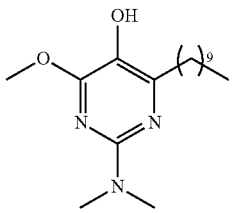

To a stirred solution at −5° C. containing 500 mg (1.34 mmol) of 5-bromo-4-decyl-6-methoxy-N,N-dimethylpyrimidin-2-amine in 10 mL of anhydrous THF were added 202 μL (1.34 mmol) of N,N,N,N-tretamethyl ethylenediamine followed by 2.09 mL (3.35 mmol) of 1.6 M solution of n-BuLi in hexanes. The reaction mixture was stirred at −5° C. for 20 min. Then to the mixture were added 440 μL (4.02 mmol) of trimethoxy boron and the reaction mixture was stirred at 23° C. for 1 h. Then to reaction mixture were added 3.46 mL of 30% aq H$_2$O$_2$. The reaction mixture was then stirred for 30 min and poured into 100 mL of water. The mixture was neutralized with diluted aq. HCl and extracted with two 100-mL portions of ethyl acetate. The combined organic solution was washed with a 100-mL portion of brine, dried (MgSO$_4$) and concentrated under diminished pressure. The residue was purified by chromatography on a silica gel column (10×3 cm). Elution with 4:1 hexanes-ethyl acetate afforded the expected product as white solid: yield 111 mg (27%); mp: 59-60° C.; silica gel TLC R$_f$=0.60 (4:1 hexanes-ethyl acetate); $^1$H-NMR (methanol-d$_4$) δ 0.87 (t, 3H, J=6.4 Hz), 1.33-1.24 (br m, 14H), 1.62 (quint, 2H, J=7.2 Hz), 2.58 (dd, 2H, J=7.6, 7.6 Hz), 3.09 (s, 6H) and 3.91 (s, 3H); $^{13}$C NMR (methanol-d$_4$) δ 13.05, 22.32, 27.62, 29.05, 29.15, 29.17, 29.29, 29.31, 30.58, 31.67, 36.32, 36.32, 52.23, 126.96, 155.92, 155.94 and 159.48.

Example 17

Preparation of 2-(dimethylamino)-4-hexadecyl-6-methoxypyrimidin-5-ol (Compound K)

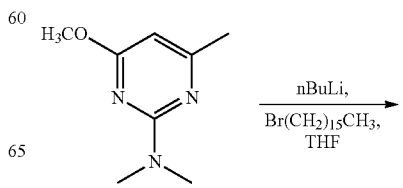

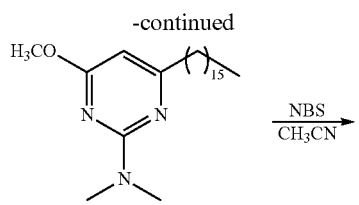

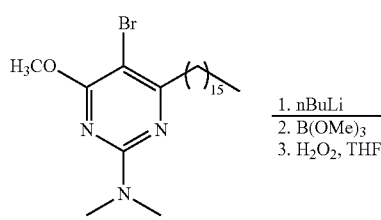

4-hexadecyl-6-methoxy-N,N-dimethylpyrimidin-2-amine

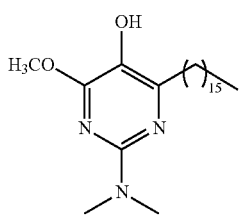

To a stirred solution containing 1.12 g (6.70 mmol) of 4-methoxy-N,N,6-trimethylpyrimidin-2-amine and 2.62 g (6.70 mmol) of 1-pentadecane in 20 mL of anhydrous THF were added 6.28 mL (10.1 mmol) of 1.6 M n-BuLi in hexanes. The reaction mixture was stirred for 20 min at 23° C. The reaction mixture was quenched with saturated aqueous ammonium chloride and poured into 100 mL of water. The compound was extracted with two 80-mL portions of ethyl acetate. The combined organic layer was washed with one 80-mL portion of brine, dried (MgSO$_4$) and concentrated under diminished pressure. The residue was purified by chromatography on a silica gel column (15×5 cm). Elution with 9:1 hexanes-ethyl acetate afforded the expected product as white solid: yield 1.58 g (62%); mp: 49-50° C.; silica gel TLC R$_f$ 0.5 (9:1 hexanes-ethyl ether); $^1$H-NMR (CDCl$_3$) δ 0.86 (t, 3H, J=6.8 Hz), 1.30-1.20 (br m, 26H), 1.63 (quint, 2H, J=7.2 Hz), 2.46 (dd, 2H, J=7.6, 7.6 Hz), 3.14 (s, 6H), 3.85 (s, 3H) and 5.77 (s, 1H); $^{13}$C NMR (CDCl$_3$) δ 14.10, 22.67, 28.49, 29.33, 29.49, 29.55, 29.64, 29.68, 29.68, 29.68, 29.68, 29.68, 29.68, 31.90, 36.78, 37.83, 37.83, 52.75, 93.03, 162.28, 179.25 and 171.93.

5-bromo-4-hexadecyl-6-methoxy-N,N-dimethylpyrimidin-2-amine

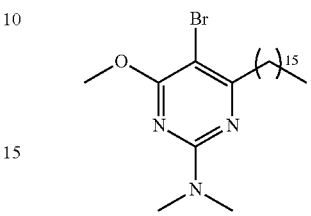

To a stirred solution containing 1.56 g (4.13 mmol) of 4-hexadecyl-6-methoxy-N,N-dimethylpyrimidin-2-amine in 30 mL of acetonitrile were added 888 mg (4.99 mmol) of N-bromosuccinimide. The reaction mixture was stirred at 23° C. and protected from light for 5 h. The reaction mixture was concentrated under diminished pressure and the residue was dissolved into 100 mL of ethyl acetate. The organic solution was washed with a 100-mL portion of brine, dried (MgSO$_4$) and concentrated under diminished pressure. The residue was purified by chromatography on a silica gel column. Elution with 9:1 hexanes-ethyl ether afforded the expected product as white solid: yield 1.80 g (95%); mp: 66-67° C.; silica gel TLC R$_f$ 0.60 (9:1 hexanes-ethyl ether); 0.86 (t, 3H, J=6.8 Hz), 1.34-1.20 (br m, 26H), 1.65 (quint, 2H, J=7.2 Hz), 2.68 (dd, 2H, J=7.6, 7.6 Hz), 3.12 (s, 6H) and 3.93 (s, 3H); $^{13}$C NMR (CDCl$_3$) δ14.10, 26.67, 27.62, 29.34, 39.37, 29.45, 29.57, 29.63, 29.65, 29.68, 29.68, 29.68, 29.68, 29.68, 31.90, 36.71, 36.95, 36.95, 53.98, 91.17, 160.08, 165.07 and 169.06.

2-(dimethylamino)-4-hexadecyl-6-methoxypyrimidin-5-ol (Compound K)

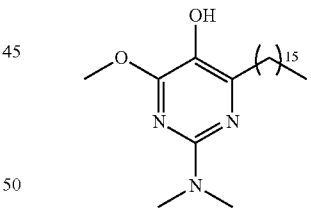

To a stirred solution at −5° C. containing 500 mg (1.10 mmol) of 5-bromo-4-hexadecyl-6-methoxy-N,N-dimethylpyrimidin-2-amine in 10 mL of anhydrous THF were added 166 μL (1.10 mmol) of N,N,N,N-tretamethyl ethylenediamine followed by 1.72 mL (2.75 mmol) of 1.6 M solution of n-BuLi in hexanes. The reaction mixture was stirred at −5° C. for 20 min. Then to the mixture were added 369 μL (3.30 mmol) of trimethoxy boron and the reaction mixture was stirred at 23° C. for 1 h. Then to reaction mixture were added 2.84 mL of 30% aq. H$_2$O$_2$ The reaction mixture was then stirred for 30 min and poured into 100 mL of water. The mixture was neutralized with diluted aq. HCl and extracted with two 100-mL portions of ethyl acetate. The combined organic solution was washed with a 100-mL portion of brine, dried (MgSO$_4$) and concentrated under diminished pressure.

The residue was purified by chromatography on a silica gel column (10×3 cm). Elution with 4:1 hexanes-ethyl acetate afforded the expected product as white solid: yield 240 mg (55%); mp: 78-79° C.; silica gel TLC $R_f$=0.50 (4:1 hexanes-ethyl acetate); $^1$H-NMR (dmso-d$_6$) δ 0.81 (t, 3H, J=6.0 Hz), 1.23-1.19 (br m, 26H), 1.52 (quint, 2H, J=6.8 Hz), 2.46 (dd, 2H, J=7.2, 7.2 Hz), 2.97 (s, 6H) and 3.82 (s, 3H); $^{13}$C NMR (dmso-d$_6$) δ 14.38, 22.53, 27.65, 29.14, 29.27, 29.32, 29.38, 29.43, 29.46, 29.46, 29.46, 29.46, 29.46, 29.46, 31.20, 31.73, 37.27, 37.27, 53.13, 127.10, 155.54, 156.81 and 159.70.

Example 18

I. Lipid Peroxidation Assay

Cis-Parinaric Acid Oxidation to Measure Lipid Peroxidation

Several methods for assaying lipid peroxidation in vitro have been developed (Kuypers et al. (1987) *Biochim Biophys Acta*. 25, 266-274; Pap et al. (1999) *FEBS Lett* 453, 278-282; Drummen et al. (2002) *Free Radic Biol Med*. 33, 473-490). Almost all of these methods are based on inhibition of free radical-induced oxidation reactions. A widely used fluorescence assay for lipid peroxidation uses lipid soluble cis-parinaric acid as a probe. cis-parinaric acid loses its fluorescence ($λ_{ex/em}$: 320/432 nm) upon interaction with peroxyl radicals and retains its fluorescence in the presence of radical quenchers. cis-parinaric acid is, however, air sensitive, photolabile and absorbs light in the UV region of the spectrum (at ~320 nm). However, this region of the spectrum is where most compounds have also been found to absorb and emit light. In practical terms, the results obtained using cis-parinaric as a probe for lipid peroxidation are confounded due to the overlapping of the compounds emission spectra with the cis-parinaric emission spectrum.

$C_{11}$-BODIPY$^{581/591}$ Oxidation to Measure Lipid Peroxidation

To overcome the problem of spectral overlap using cis-parinaric acid, a fluorescence assay for lipid peroxidation using a lipophilic probe belonging to the BODIPY class of fluorescent dyes was used. $C_{11}$-BODIPY$^{581/591}$ (4,4-difluoro-5-(4-phenyl-1,3-butadienyl)-4-bora-3a,4a-diaza-s-indacene-3-propionic acid) fluorescence shifts from red to green upon oxidation. $C_{11}$-BODIPY$^{581/591}$ (Molecular Probes, Eugene, Oreg., USA) stock solution concentrations were determined by measuring the absorption of $C_{11}$-BODIPY$^{581/591}$ at 582 nm using a molar extinction coefficient of 140,000 mol$^{-1}$ cm$^{-1}$(R. P. Haugland, (1999) Handbook of Fluorescent Probes and Research Chemicals, Molecular Probes, Inc., Eugene, Oreg.). The lipid peroxidation inducer 2,2'-Azobis (2-amidino-propane dihydrochloride) (AAPH) and the antioxidant compound α-tocopherol were obtained from Sigma (St. Louis, Mo., USA). Phospholipid bilayers were prepared from 1-stearoyl-2-oleoyl-phosphatidylcholine (SOPC) and 1,2-dilinoleoyl-phosphatidylcholine (DLPC) and were purchased from Avanti® polar lipids, INC (Alabaster, Ala., USA).

Preparation of Liposomes

Phosphotidylcholine (PC) liposomes were prepared as described before (Guey-Shuang et al. (1982) *Lipids*. 17, 403-413). Briefly, DLPC (25 mg) and SOPC (25 mg) were dissolved in chloroform and the solvent was removed by nitrogen evaporation (~2 hours to give a thin film of PC in a round bottom flask. The lipid film was hydrated with 50 mL of 10 mM Tris-HCl (pH 7.4), 100 mM KCl, shaken and sonicated for 15 seconds. The liposomes obtained were filtered several times through 0.2 µM membrane filter.

Measurement of $C_{11}$-BODIPY$^{581/591}$ Oxidation $C_{11}$ BODIPY$^{581/591}$ was incorporated into liposomes and oxidized by peroxyl radicals derived from the decomposition of AAPH in presence and absence of the compounds. Liposomes (1 mg/mL), suspended in 10 mM Tris-HCl (pH 7.4), 100 mM KCl, were transferred to a quartz 1 mL cuvette and placed in a Varian Cary Eclipse fluorometer (Varian, Cary, N.C.) equipped with a thermostatted cuvette holder at 40° C. Liposomes were pre-incubated for 10 min with 200 nM $C_{11}$ BODIPY$^{581/591}$ to allow their incorporation into the lipid phase of the liposomes. After the addition of AAPH (10 mM) the decay of red fluorescence was followed at λ exc=570 nm, λ em=600 nm. Relative fluorescence units were normalized to 100% intensity. Results obtained were verified by repeating experiments N=3 independent experiments.

Measurement of $C_{11}$-BODIPY$^{581/591}$ Oxidation in Cell Culture

Lipid peroxidation in CEM leukemia cells was detected by utilizing the oxidant-sensitive lipophilic probe $C_{11}$ BODIPY$^{581/591}$. Briefly, CEM cells (5×10$^5$ cell/mL) were treated with the test compounds at final concentrations of 1 and 2.5 µM, and incubated at 37° C. for 4 or 24 h in a humidified atmosphere containing 5% $CO_2$ in air. Cells were treated with 500 nM $C_{11}$ BODIPY$^{581/591}$ in phenol red-free RPMI-1640 media and incubated at 37° C. in the dark for 30 minutes. The cells were washed twice with phosphate buffered saline and oxidative stress was induced with 5 mM DEM in phenol red-free RPMI-1640 media for 90 minutes. Treated cells were collected by centrifugation at 300×g for 3 minutes and then washed twice with phosphate buffered saline. Cells were resuspended in 250 µL of phosphate buffered saline and were analyzed by FACS (FACS Calibur flow cytometer, Becton Dickinson) to monitor the change in intensity of the $C_{11}$ BODIPY$^{581/591}$-green (oxidized) fluorescence signal.

Assay for Thiobarbituric Acid Reactive Species (TSARS)

Lipid peroxidation by hydrogen peroxide in bovine heart mitochondrial membranes was determined by measuring the amount of thiobarbituric acid reactive substances released. Bovine heart mitochondria (1 mg protein) prepared as described by Smith (38) were added to 800 µL of 50 mM phosphate buffer, pH 8.0, and subjected to oxidative stress by the addition of 25 mM glucose and 1 U/mL glucose oxidase from *Aspergillus niger*. Samples were incubated with or without test compounds at 37° C. for 30 minutes. Two hundred µL each of 1% (w/v) thiobarbituric acid and 35% (v/v) perchloric acid, as well as 0.1% (w/v) butylated hydroxytoluene (from a 2% stock solution in DMSO) were added. Samples were heated at 100° C. for 15 minutes. One-mL aliquots of each sample were taken and diluted in 2 mL of water, then extracted once with 2 mL of n-butanol. Triplicate 500-µL aliquots were taken from the butanol phase and transferred to a quartz cuvette. TBARS were determined fluorometrically from the emission spectrum ($λ_{ex}$ 515 nm; $λ_{em}$ 550 nm) using a Varian fluorimeter. The malondialdehyde concentration was determined based on a standard curve created using serial dilutions of 10 mM 1,1,3,3-tetraethoxypropane hydrolyzed in 1% (v/v) $H_2SO_4$ at 4° C. overnight. The malondialdehyde concentration was expressed as nmoles manoldialdehyde per mg protein. Protein in aliquots of the homogenates was determined by the bicinchoninic acid method.

II. Reactive Oxygen Species (ROS) Assay

Cellular ROS production can be monitored using 2',7'-dichlorodihydrofluorescein diacetate (DCFH-DA) (LeBel et al. (1992) *Chem. Res. Toxicol*. 5, 227-231) (Molecular Probes, Eugene, Oreg., USA), a membrane permeable and oxidant-sensitive fluorescent dye. DCFH-DA is a non-fluorescent derivative of fluorescein that emits fluorescence after being oxidized by hydrogen peroxide and other ROS. The emitted fluorescence is directly proportional to the concentration of hydrogen peroxide. DCFH-DA is nonionic and nonpolar and is easily taken up by cells. Once inside the cell, DCFH-DA is hydrolyzed by cellular esterases to non-fluorescent DCFH which traps the dye in the cell. In the presence of ROS including hydrogen peroxide, DCFH is oxidized to the highly fluorescent compound dichlorofluorescein (DCF). The intracellular DCF fluorescence is used as an index of cellular ROS production.

Cellular oxidative stress was induced by pharmacological depletion of glutathione (GSH) using the chemical diethylmaleate (DEM). ROS production was assessed by monitoring DCF fluorescence. Leukemic CEM cells (ATCC®, catalogue number CRL-2264) were cultured in RPMI (GIBCO, Grand island, N.Y., USA) with 10% FCS, 2 mM glutamine (Hy-Clone, South Logan, Utah, USA) and 1% penicillin-streptomycin mix antibiotics (Cellgro, Manassan, Va., USA) supplements. Cells were maintained in the log phase at a concentration of between $1 \times 10^5$ and $1 \times 10^6$ cells/mL. CEM cells ($1 \times 10^6$ cell/mL) were plated (1 mL) in twelve well plate and treated with the invention compounds (final concentration 1 and 5 µM), and incubated for two hours at 37° C., 5% $CO_2$. The compounds tested were prepared by first making stock solutions (2.5 mM) in dimethylsulfoxide (DMSO). Cells were treated with 5 mM DEM for 30 minutes and collected by centrifugation at 300×g for 3 min and then washed twice with Hanks' Balanced Salt Solution (HSSB) buffer (Sigma, St. Louis, Mo. USA). Cells were resuspended in HSSB buffer+10 mM glucose and incubated at 37° C. in the dark for 20 min with 10 µM DCFH-DA. Cells were collected by centrifugation at 300×g for 3 min and then washed twice with HSSB buffer. The samples were analyzed immediately by flow cytometry (Becton-Dickinson FACS Caliber), (Cell Quest software, BD Biosciences) using 488 nm excitation laser and FL1-H channel 538 nm emission filter. In each analysis, 10,000 events were recorded after cell debris were electronically gated out. Results obtained were verified by repeating experiments N=3 independent experiments. Authentic hydrogen peroxide was used as a positive control.

III. Mitochondrial Membrane Potential ($\Delta_{\psi m}$) Assay

Measurement of Mitochondrial Membrane Potential ($\Delta_{\psi m}$)(FACS). For the determination of $\Delta_{\psi m}$, CEM leukemia cells were pre-treated with or without the test compounds. The cells were treated with 5 mM DEM for 120 minutes, collected by centrifugation at 300×g for 3 minutes and then washed twice with phosphate buffered saline. The cells were re-suspended in HSSB buffer and incubated at 37° C. in the dark for 15 minutes with 250 nM TMRM (a cationic dye which accumulates within mitochondria in accordance with the $\Delta_{\psi m}$ Nernst potential). Cells were collected by centrifugation at 300×g for 3 minutes and then washed twice with phosphate buffered saline. The samples were analyzed immediately by flow cytometry using 488 nm excitation laser and the FL2-H channel. The results obtained were verified in three independent experiments. The protonophore FCCP (30 µM) was used to dissipate the chemiosmotic proton gradient ($\Delta\mu H^+$) and served as a control for loss of $\Delta_{\psi m}$. In each analysis, 10,000 events were recorded.

IV. Trypan Blue Cell Viability Assay

Cell viability determined by trypan blue exclusion assay: This technique was used to assess the cytoprotective effects of the invention compounds in cultured cells pharmacologically treated to induce cell death by GSH depletion. DEM was used to deplete cellular GSH and induce oxidative stress. The viability of DEM-treated CEM cells was determined by their ability to exclude the dye trypan blue. Viable cells exclude trypan blue; whereas, non-viable cells take up the dye and stain blue. Briefly, CEM cells were grown in RPMI 1640 medium (GIBCO, Grand island, N.Y., USA) supplemented with 10% fetal calf serum, 2 mM glutamine (HyClone, South Logan, Utah, USA), 1% penicillin-streptomycin mix (Cellgro, Manassan, Va., USA). Cells were seeded at a density of $1 \times 10^6$ cells/mL and treated with different concentrations of the invention compounds. Cells were incubated at 37° C. in a humidified atmosphere of 5% $CO_2$ in air for three hours with 5 mM DEM. Cell viability was determined by staining cells with 0.4% trypan blue using a hemacytometer. At least 500 cells were counted for each experimental group. At the time of assay, >95% of DEM-treated cells were trypan blue positive; whereas, in non-DEM treated control cell cultures >95% cells were viable. Cell viability was expressed as the percentage of control. Data are expressed as means±S.E.M (n=3).

V. Cell Viability Assays (FACS)

Cell viability and cytotoxicity were determined by simultaneous staining live and dead cells using a two-color fluorescence assay, the Live/Dead® Viability/Cytotoxicity Kit (Molecular Probes). This assay is used to measure two recognized parameters of cell viability, intracellular esterase activity and plasma integrity. The membrane-impermeant DNA dye ethidium homodimer-1 (EthD-1) was used to identify dead cells whose plasma membrane integrity was disrupted. The membrane-permeant dye calcein-AM was used to label live cells. It penetrates into the cells where it is metabolized by cytoplasmic esterases and becomes a fluorescent but membrane-impermeant probe which is retained in viable cells. Human CEM leukemia cells were incubated overnight in RPMI medium (control) and in the presence of test compound and then treated with DEM for 3 hours. Cells were stained with 0.2 µM calcein-AM and 0.4 µM EthD-1. After 15 minutes, flow cytometry analysis was carried out using excitation at 488 nm. The green-fluorescent (539 nm) FL1-H channel, live-cell population appears in the lower right quadrant and the red-fluorescent (585 nm) FL2-H channel dead-cell population appears in the upper left quadrant (FIG. 11). In each analysis, 10,000 events were recorded. Results obtained were verified in three independent experiments.

VI. Calcein-AM Cell Viability Assay

A cell viability assay using the dye calcein acetoxymethyl (AM) was used to determine the effects of invention compounds on GSH-mediated cell death in primary FRDA patient derived fibroblasts (Jauslin et al. (2002) *Human Molecular Genetics.* 11, 3055-3063) FRDA fibroblasts were treated with L-buthionine (S,R)-sulfoximine (BSO) to inhibit de novo synthesis of GSH (Griffith et al. (1979) *J. Biol. Chem.* 254, 7558-7560) causing oxidative stress, plasma membrane damage and cell death. Fibroblasts from Friedreich Ataxia patients, but not control cells, die after GSH depletion on incubation with BSO (Jauslin et al. (2002) *Human Molecular Genetics.* 11, 3055-3063). Cell viability was determined using calcein-AM (Molecular Probe, Eugene, Oreg.). In live cells, non-fluorescent calcein AM is hydrolyzed by intracellular esterases to produce the strongly green fluorescent anion calcein.

Cell culture and reagents: Primary fibroblasts were derived from a patient donor with a molecular diagnosis of FRDA and control donor with no mitochondrial disease. These cell lines were obtained from Coriell Cell Repositories (Camden, N.J., USA; catalog numbers GM04078 and GM08402, respectively). Fibroblasts were cultured in 64% (v/v) Eagle's Minimal Essential Medium (MEM), no phenol red with Eagle's balanced salt (EBS) and 25% M199 with EBS (GIBCO, Grand island, N.Y., USA) supplemented with 10% (v/v) Fetal Calf Serum (HyClone, South Logan, Utah, USA), 1% penicillin-streptomycin mix antibiotics (Cellgro, Manassan, Va., USA), 10 ng/mL insulin (Sigma, St. Louis, Mo., USA), 10 ng/mL basic fibroblast growth factor βFGF (Lonza, Walkersville, Md., USA) and 2 mM glutamine (HyClone, South Logan, Utah, USA). BSO (L-buthionine (S,R)-sulfoximine) and (+)-alpha-tocopherol were purchased from Sigma Chemicals and calcein AM was purchased from Molecular Probes. Cell were grown in 75 cm² culture flasks (T75) and incubated at 37° C. in a humidified atmosphere of 5% $CO_2$ in air. Cells were fed twice a week and split every third day at a ratio of 1:3 upon reaching confluency. The invention compounds and reduced and oxidized forms of idebenone and alpha-tocopherol were reconstituted in DMSO or ethanol to provide 2.5 mM stock solutions.

Generation of Idebenol from Idebenone

Idebenol ($\epsilon_{290}$=3.94 mM⁻¹ cm⁻¹) was prepared by chemical reduction of idebenone ($\epsilon_{275}$=14 mM⁻¹ cm⁻¹ in absolute ethanol) as described by Trounce (Trounce et al. (1996) *Methods Enzymol.* 264, 484-509). Briefly, 5 mg of idebenone was added to 2 mL of ethanol reduced with excess potassium borohydride (color change yellow to colorless). The resulting solution was acidified to pH 2 with 6 M HCl. The idebenol was recovered in diethyl ether cyclohexane (2:1, v/v) and evaporated to dryness under nitrogen gas, dissolved in 1 mL of ethanol acidified to pH 2 with 0.1 N HCl and stored at −80° C.

Intervention compounds were screened according to the previous protocol (Jauslin et al. (2002) *Human Molecular Genetics.* 11, 3055-3063): Fibroblasts were seeded in 96 well microtiter black-walled cell culture plates (Costar, Corning, N.Y., USA) at a density of 3000 cells per well (100 μL). The plates were incubated overnight at 37° C. in a humidified atmosphere of 5% $CO_2$ in air to allow attachment of the cells to the culture plate. Serial dilutions of intervention and references compounds were made from their respective stock solutions to give a total volume of 150 μL in each well. Plates were incubated overnight in cell culture. The following day, 50 μL of a 4 mM BSO solution (in culture media) was added to each well to provide a final BSO concentration of 1 mM. Cell viability was assessed after first signs of toxicity appeared in BSO-treated cells (typically after 24-30 hours) by examining cultures under phase-contrast microscopy. The cell culture medium was discarded by aspiration and each well of the cell culture plate washed with pre-warmed HSSB to remove serum esterase activity. Cells were then treated in with 200 μL of 1.2 μM calcein-AM in HSSB for 60 min at 37° C. in the dark to allow the dye to enter the cell and be cleaved by esterases. The negative control/background was 200 μL of HSSB buffer. Fluorescence intensities were measured with a Spectramax M5 spectrofluorometer (Molecular Devices, Sunnyvale, Calif., USA) using excitation and emission of 485 nm and 525 nm respectively. The intervention compounds were assayed in triplicate. The solvent vehicles used either DMSO or ethanol did not affect cell viability at the concentrations (0.5-1%) used in the assay. The viability of non-BSO treated fibroblasts was set as 100%, and the viability of the BSO-treated and sample-treated cells was calculated relative to this value. Cell viability was expressed as the percentage of control. Data are expressed as means±S.E.M (n=3).

VII. Cytochrome c Reduction Assay

The rate of cytochrome c (10 μM) reduction was measured by monitoring the change in absorbance at 550 nm. Briefly the reaction was initiated by addition of 100 μM of the invention compounds to a mixture containing 50 mM phosphate buffer, 0.1 mM EDTA, pH 7.8, and 10 μM cytochrome c (Sigma, St. Louis, Mo. USA). For cytochrome c reduction by superoxide, xanthine oxidase (0.01 IU/mL) (Sigma, St. Louis, Mo. USA) was used in presence of xanthine (50 μM).

VIII. Total Intercellular ATP Concentration Assay

The reductions of mitochondrial respiratory chain activity in $CoQ_{10}$ deficient patients have been reported (Quinzii G M, Lopez L C, Von-Moltke J, Naini A, Krishna S, Schuelke M, Salviati L, Navas P, DiMauro S, and Hirano, M. Respiratory chain dysfunction and oxidative stress correlate with severity of primary CoQ10 deficiency. FASEB J. 2008; 22:1874-1885). The use of $CoQ_{10}$ analogues to normalize and restore the respiratory chain activities could provide valuable therapeutic approach. We have evaluated the efficiency of oxidative phosphorylation in $CoQ_{10}$ deficient lymphocyte (GM17932) in presence of tested $CoQ_{10}$ analogues by measuring total cellular ATP content using (ViaLight® Plus ATP monitoring reagent kit, Lonza).

$CoQ_{10}$ deficient lymphocyte and normal lymphocyte cell lines were obtained from Coriell Cell Repositories (Camden, N.J.; catalog number GM-17932, GM-158151, respectively). $CoQ_{10}$ deficient lymphocytes were cultured under glucose-free media supplemented with galactose for two weeks to force energy production predominantly through oxidative phosphorylation rather than glycolysis (Quinzii et al.; Robinson B H, Petrova-Benedict R, Buncic J R, Wallace D C. Nonviability of cells with oxidative defects in galactose medium: A screening test for affected patient fibroblast. Biochem. Med. Metab. Biol. 1992; 48:122-126). Lymphocytes were cultured in RPMI 1640 medium glucose-free (Gibco, Grand Island, N.Y.) supplemented with 25 mM galactose, 2 mM glutamine and 1% penicillin-streptomycin (Cellgro), and 10%, dialyzed fetal bovine serum FBS 0.5 μg/mL) (GEMINI, Bio-Product), Briefly, lymphocytes ($2 \times 10^5$ cell/mL), were plated (1 mL in 12-well plates) and treated with the test compounds at final concentrations of 5, 10 μM, and 25 μM and incubated at 37° C. for 48 h in a humidified atmosphere containing 5% $CO_2$ in air. The test compounds were prepared by first making 20 mM stock solutions in DMSO. Cells were transferred (100 μL) to 96-well microtiter black-walled cell culture plates (Costar, Corning, N.Y.). The total intracellular ATP level was measured in a luminator (Clarity™ luminescence microplate reader) with the ATP Bioluminescence Assay Kit (ViaLight® Plus ATP monitoring reagent kit, Lonza) following the manufacturer's instructions. The standard curve of ATP was obtained by serial dilution of 1 mM ATP solution. After calibration against the ATP standard, the ATP content of the cell extract was determined and normalized for protein content in the cell. FIG. 1 shows that the cellular content of ATP are significantly lower in $CoQ_{10}$ deficient than normal lymphocyte.

IX. NADH Oxidase Inhibition Assay

Beef heart mitochondria were obtained by a large-scale procedure. Inverted submitochondrial particles (SMP) were prepared by the method of Matsuno-Yagi and Hatefi (J. Biol. Chem. 260 (1985), p. 14424), and stored in a buffer containing 0.25 M sucrose and 10 mM Tris-HCl (pH 7.4) at −80° C. Inhibitory effects of compounds on bovine heart mitochondrial complex (I, III, IV) were evaluated. Maximal dimethyl sulfoxide concentration never exceeded 2% and had no influence on the control enzymatic activity. Beef heart SMP were diluted to 0.5 mg/mL. The enzymatic activities were assayed at 30° C. and monitored spectrophotometrically with a Beckman Coulter DU-530 (340 nm, c=6.22 mM$^{-1}$ cm$^{-1}$). NADH oxidase activity was determined in a reaction medium (2.5 mL) containing 50 mM Hepes, pH 7.5, containing 5 mM MgCl$_2$. The final mitochondrial protein concentration was 30 μg. After the pre-equilibration of SMP with inhibitor for 5 min, the initial rates were calculated from the linear portion of the traces.

Results

Figure 1A:
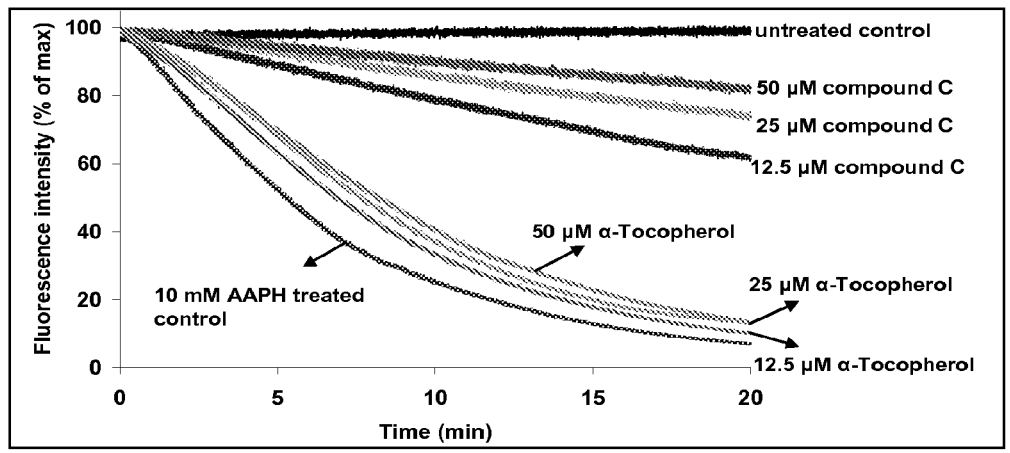
FIGS. 1A-C. Effect of multifunctional radical quenchers (MRQs) on lipid peroxidation induced by peroxyl radicals generated from thermal decomposition of AAPH in phospholipid liposomes in phosphate buffer at 40° C. The potency of these MRQs is directly measured by their ability to retain the fluorescence of $C_{11}$-BODIPY$^{581/591}$ in presence of AAPH. Relative fluorescence units are normalized to 100% intensity. An independent repeat gave identical results.
Figure 1B:
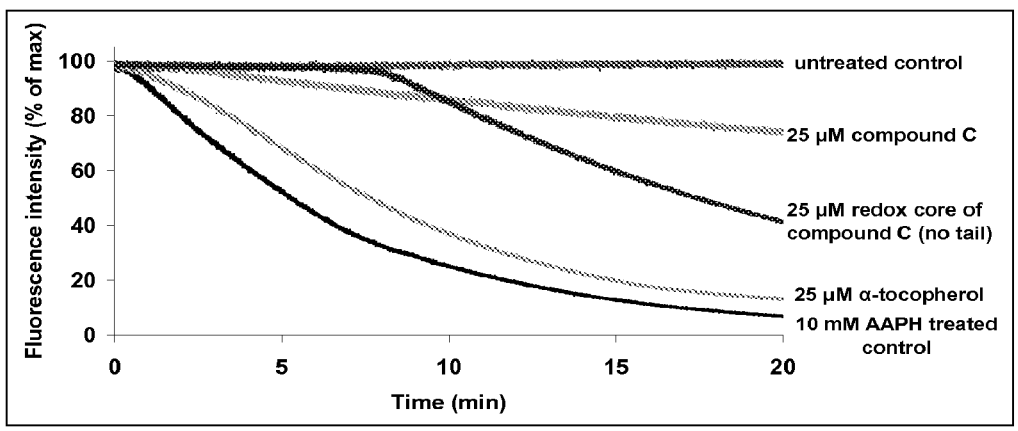
Figure 1C:
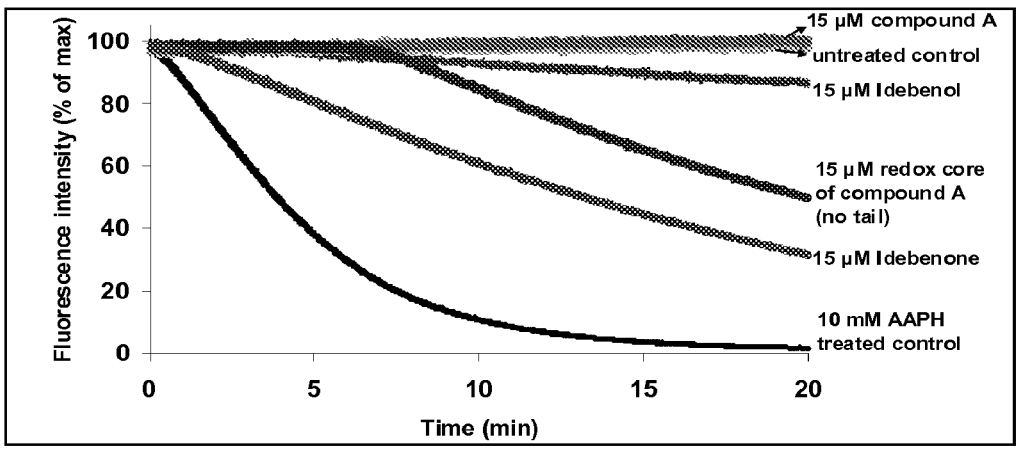
Figure 2:
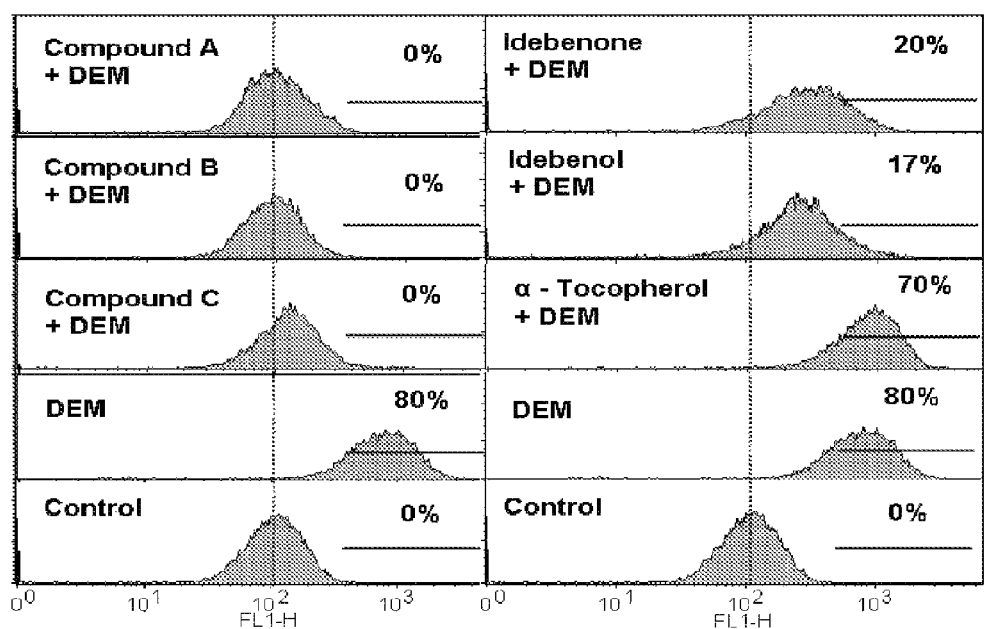
FIG. 2. Representative flow cytometric histograms showing ROS production in CEM cells. CEM cells were treated with media alone control (basal ROS level); diethylmaleate (DEM) (5 mM) (oxidative stress induced by glutathione depletion), diethylmaleate (5 mM)+MRQ compound A (5 μM); diethylmaleate (5 mM)+MRQ compound B (5 μM)

Compounds A, B, and C (Examples 1-3) have been tested for their ability to quench lipid peroxidation using $C_{11}$-BO-DIPY$^{581/591}$-liposome system as illustrated in FIG. 1. Compound C (FIG. 1A) was much more effective than α-tocopherol in quenching lipid peroxidation, as would have been predicted (Wijtmans et al. (2004) *J. Org. Chem.* 69, 9215-9223). The phytol side chain in C was found to be very important for quenching lipid peroxidation in this assay system; the core redox structure (1,4,6-trimethyl-2,3-dihydro-1H-pyrrolo[2,3-b]pyridin-5-ol) was much less effective in the same assay system (FIG. 1B). Compound B was about as effective as C, but compound A afforded complete protection at 15 μM concentration (FIG. 1C). Compound A was much more effective than idebenone and its reduced form in preventing lipid peroxidation. Again the redox core of compound A (compound 12) by itself was less active than its counterpart compound A (with aliphatic tail). Compounds A, B and C were also studied for their ability to quench superoxide ROS. This was done by assaying the effects of A-C on CEM cells that had been treated with 5 mM diethyl maleate (DEM) to chemically deplete glutathione in the cells, thus exposing them to increased oxidative stress. As shown in FIG. 2, A-C all protected the cells when used at 5 μM concentration. In comparison, α-tocopherol (a lipid peroxidation quencher) was ineffective, and both the oxidized and reduced forms of idebenone had only limited effect. Compound A also afforded complete protection when used at 1 μM concentration (FIG. 3). The quenching of ROS had the expected cytoprotective effect on the cultured CEM cells; as shown in FIG. 4, compounds A and B were superior to that achieved with idebenone (EC$_{50}$ values for A, and idebenone were 202±23 nM, 300±22 nM and 765±36 nM, respectively). The effects of A, B and C in protecting cells from ROS and the cytotoxic effects of oxidative stress at high nM/low μM concentrations contrasts sharply with the mM concentrations of the endogenous reagent glutathione that nature uses for the same purpose. It suggests that MRQs such as A, B and C must function catalytically to achieve their effects.

The ability of compound A to protect Friedreich's ataxia skin fibroblasts from oxidative damage (BSO-treated FRDA fibroblast) is illustrated in FIG. 5. Once again, this compound A (solid diamond) was more effective than idebenone (solid triangle), and much more effective than the compound A analogue lacking the idebenone side chain (asterisk) (EC$_{50}$ values for A and idebenone were 390±28 nM and 710±80 nM respectively). Compound C and α-tocopherol were also tested for their ability to rescue BSO-treated FRDA fibroblast model (Jauslin et al. (2002) *Human Molecular Genetics.* 11, 3055-3063) as illustrated in FIG. 5. Compound C (solid square) was slightly more effective than α-tocopherol (solid circle) (EC$_{50}$ values at high nM/low μM concentrations for compound C and α-tocopherol were 833±75 nM and 1030±116 nM respectively).

MRQs are not only a potent antioxidant, but also they reduce cytochrome c (FIG. 6). It should be noted that the reduction potentials of mediators in the mitochondrial electron transport chain become more positive as one proceeds down the chain. Thus cytochrome c, the carrier of electrons between mitochondrial complexes III and IV, has a redox potential of +0.23V, and is capable of accepting electrons from superoxide (redox potential −0.16V). This is illustrated in FIG. 6, in which superoxide is generated by the use of xanthine oxidase, and efficiently reduces cytochrome c. While the reduction of cytochrome c by superoxide does not result in the optimal production of ATP (4 protons are pumped across the mitochondrial membrane by virtue of two electron transiting through complexes I and IV, protons are pumped for two electrons transiting through complex III), the reduction of cytochrome c by superoxide will serve to relive potential reductive stress, and can produce up to 40% as much ATP as that produced by fully functional mitochondria. Compound A and B do clearly reduce cytochrome c (FIG. 6). It would be possible for MRQs to bypass blocked points of electron flow in the respiratory chain (complex III) by shuttling electrons directly to cytochrome c thus enhancing metabolic rate and cell respiration.

Figure 7:
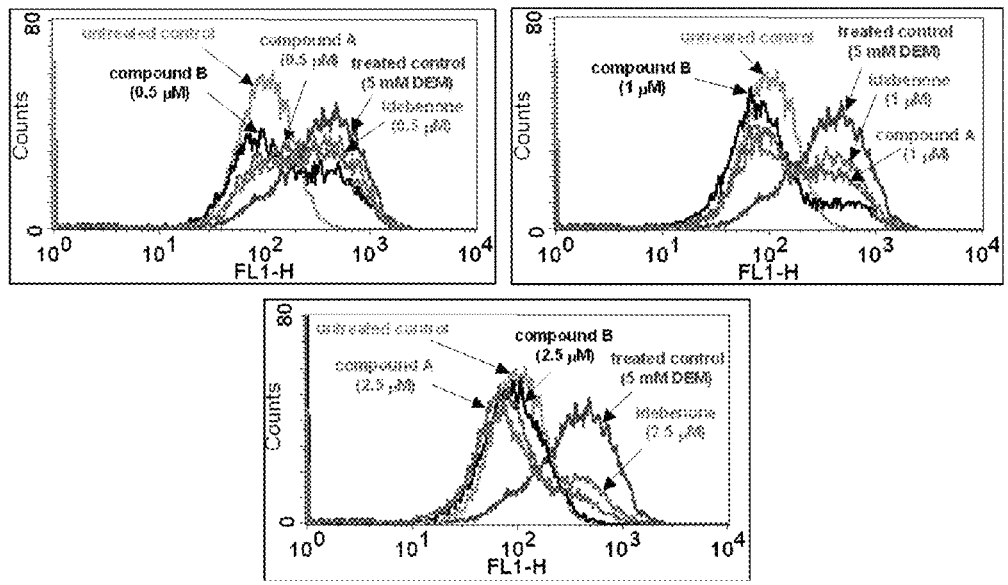
Figure 7:
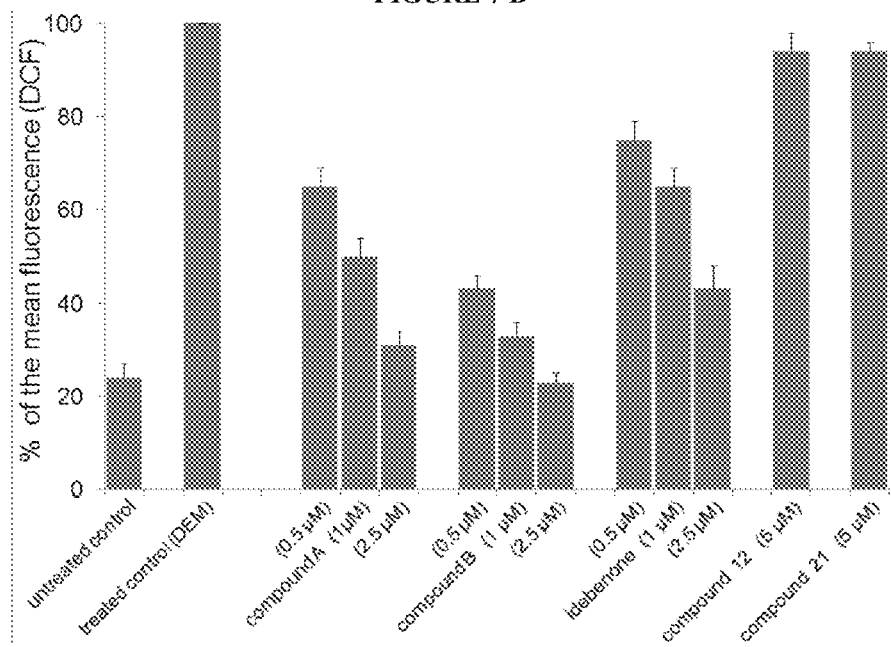
Figure 10:
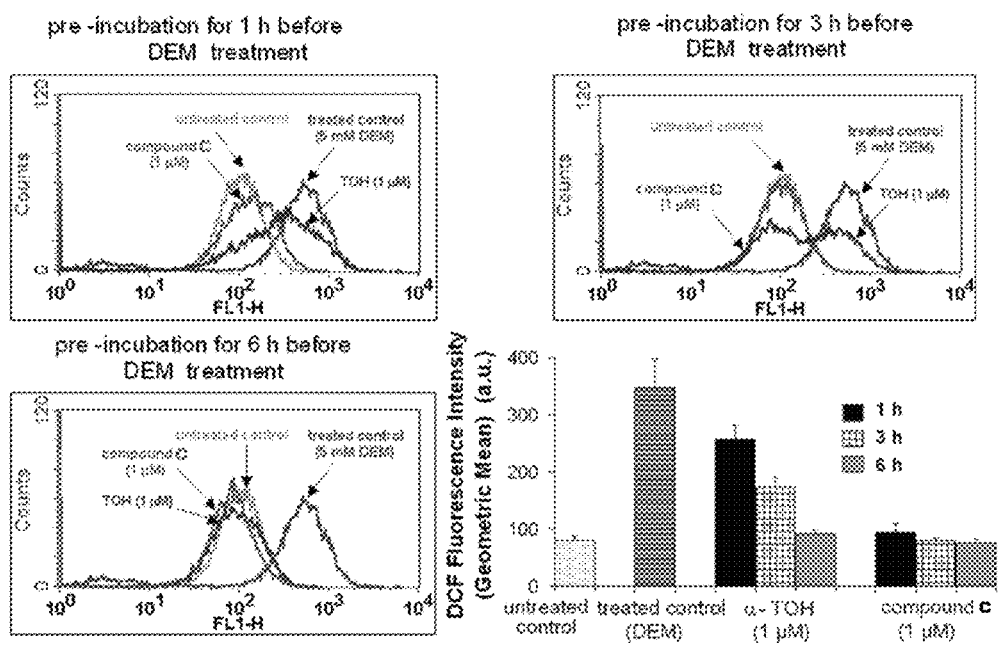

FIG. 7 illustrates that compounds A and B are more effective than idebenone in suppressing ROS in a dose-dependent fashion in DEM-treated cells, and that the side chains of these compounds are essential to that activity. FIGS. 9 and 10 illustrate the same comparison for compounds C and α-tocopherol, with the same conclusions. As shown in FIG. 8, compound D is also very effective in suppressing ROS. FIGS. 11 and 12 illustrate the very favorable properties of compounds A, B and D in maintaining mitochondrial membrane potential in cells treated with DEM, whereas idebenone was less effective in this regard. FIG. 13 illustrates the same principle for compound C, which is superior to tocopherol in maintaining mitochondrial membrane potential. FIG. 14 shows that compounds A, B and D are superior to idebenone in maintaining the viability of DEM-treated cells. FIGS. 15 and 17 make the same comparison between compound C and α-tocopherol, which demonstrate the superiority of compound C, as well as the need for the alkyl side chain. The same comparison is made in FIG. 16 for the O-acetate prodrugs of both compounds, again illustrating the superiority of compound C. FIG. 18 shows that compound C is clearly superior to α-tocopherol in quenching lipid peroxidation in a time- and dose-dependent fashion. FIG. 19 compares several analogues for their ability to suppress ROS and shows that compounds I and J are especially effective, and can work at quite low (250 nm) concentration. FIG. 20 shows the difference in total cellular ATP concentrations in normal and CoQ$_{10}$ deficient lymphocytes grown in the absence of glucose (to assure that all ATP production is mitochondrial in origin).

Table 1 shows total ATP concentration (as % of control) in the CoQ$_{10}$ deficient lymphocyte cell line as determined from the intracellular ATP levels using the luciferin-luciferase reaction. To enforce the respiratory chain-dependent ATP synthesis, cells were grown for 48 hours in glucose free media supplemented with 25 mM galactose and 10% dialyzed fetal bovine serum (glucose concentration less than 0.5 μg/mL). FIG. 20 illustrates total intracellular ATP levels in CoQ$_{10}$ deficient and normal lymphocytes measured using the luciferin-luciferase reaction. The levels of ATP shown in Table 1 are relative to the 100% value obtained for the CoQ$_{10}$ deficient cells in FIG. 20.

TABLE 1
| Compound | Total ATP concentration (% of control) | | |
|---|---|---|---|
| | 5 μM | 10 μM | 25 μM |
| 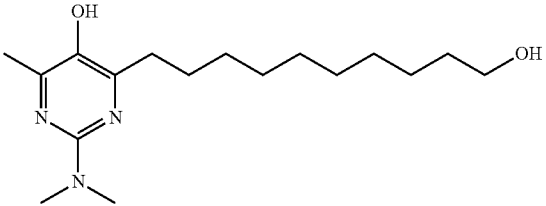 [SMILES: Cc1nc(N(C)C)nc(CCCCCCCCCCO)c1O] | 102.4 ± 1.2 | 87.9 ± 4.3 | 46.1 ± 1.2 |
| 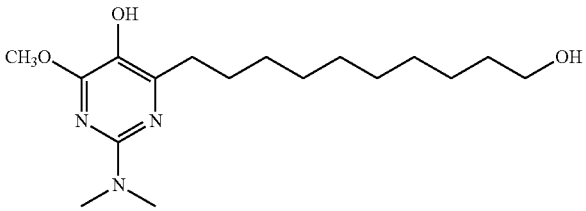 | 101.6 ± 1.4 | 96.8 ± 4.0 | 48.7 ± 0.8 |
| 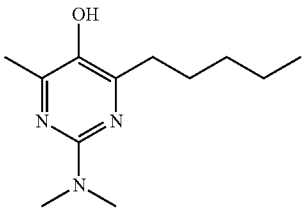 [SMILES: CCCCCc1nc(N(C)C)nc(C)c1O] | 109.3 ± 2.3 | 111.1 ± 1.5 | 105.6 ± 2.4 |
| 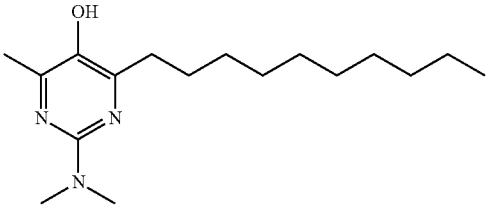 [SMILES: CCCCCCCCCCc1nc(N(C)C)nc(C)c1O] | 106.6 ± 2.7 | 98.7 ± 1.1 | 75.3 ± 1.8 |
| 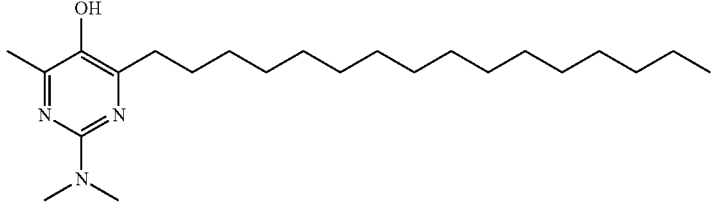 [SMILES: CCCCCCCCCCCCCCCCc1nc(N(C)C)nc(C)c1O] | 111.5 ± 1.8 | 106.9 ± 2.7 | 101.6 ± 3.1 |
| 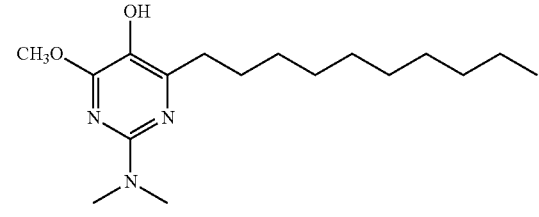 | 109.4 ± 5.0 | 110.5 ± 6.5 | 68.3 ± 2.7 |
| 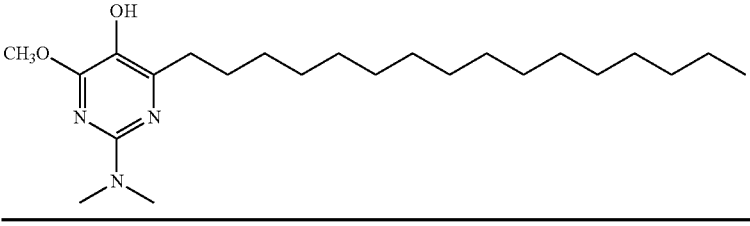 | 122.3 ± 1.9 | 116.4 ± 0.5 | 113.0 ± 1.6 |

Table 2 shows cytoprotective effects of compounds of the disclosure on cultured FRDA cells. The cells were pretreated with the compounds and then depleted of glutathione. The cell viability is expressed as percentage of total number of cells.

TABLE 2

| Compound | Viable Cells (%) | | |
|---|---|---|---|
| | 0.1 μM | 0.5 μM | 2.5 μM |
| (pyrimidine with OH, methyl, C9-OH chain, N(CH3)2) | 63.6 ± 8.4 | 83.5 ± 0.7 | 82.7 ± 8.1 |
| (pyridine with OH, methyl, C9-OH chain, N(CH3)) | 54.0 ± 5.2 | 76.5 ± 2.1 | 81.7 ± 5.0 |
| (pyrimidine with OH, H3CO, C9-OH chain, N(CH3)2) | 55.6 ± 5.7 | 80.0 ± 4.0 | 78.3 ± 7.5 |
| (pyridine with OH, H3CO, C9-OH chain, N(CH3)) | 33.0 ± 4.2 | 28.3 ± 2.1 | 29.5 ± 2.1 |
| (pyrimidine with OH, methyl, pentyl, N(CH3)2) | 46.0 ± 3.5 | 78.7 ± 4.0 | 81.3 ± 5.1 |
| (pyrimidine with OH, methyl, nonyl, N(CH3)2) | 54.5 ± 3.3 | 84.0 ± 3.6 | 76.3 ± 5.0 |

TABLE 2-continued

| Compound | Viable Cells (%) | | |
|---|---|---|---|
| | 0.1 μM | 0.5 μM | 2.5 μM |
| 4-methyl-6-tetradecyl-2-(dimethylamino)-5-hydroxypyrimidine (structure) | 61.3 ± 2.9 | 84.4 ± 3.4 | 88.0 ± 1.0 |
| 4-methoxy-6-decyl-2-(dimethylamino)-5-hydroxypyrimidine (structure) | 40.3 ± 1.5 | 83.7 ± 1.5 | 82.7 ± 2.5 |
| 4-methoxy-6-pentadecyl-2-(dimethylamino)-5-hydroxypyrimidine (structure) | 43.7 ± 3.1 | 66.3 ± 1.5 | 80.5 ± 5.0 |

Table 3 shows NADH oxidase inhibition activity of compounds on bovine heart mitochondrial complexes I, II and III. The activity is expressed as percentage of control.

TABLE 3

| Compound | Control | NADH oxidase activity (%) | | | | IC$_{50}$ (μM) |
|---|---|---|---|---|---|---|
| | | 10 μM | 5 μM | 2.5 μM | 1 μM | |
| (structure: 4-methyl-6-pentyl-2-(dimethylamino)-5-hydroxypyrimidine) | 100 | | | | 85 | |
| (structure: 4-methyl-6-decyl-2-(dimethylamino)-5-hydroxypyrimidine) | 100 | | | | 40 | 0.829 |

TABLE 3-continued
| Compound | Control | NADH oxidase activity (%) 10 μM | 5 μM | 2.5 μM | 1 μM | IC$_{50}$ (μM) |
|---|---|---|---|---|---|---|
| 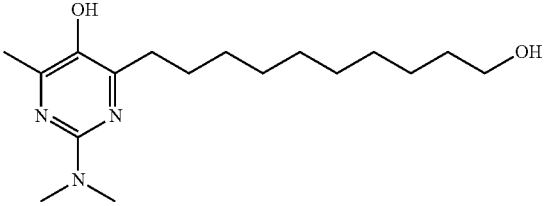 | 100 | 15 | 22 | 42 | 50 | 2.23 |
| 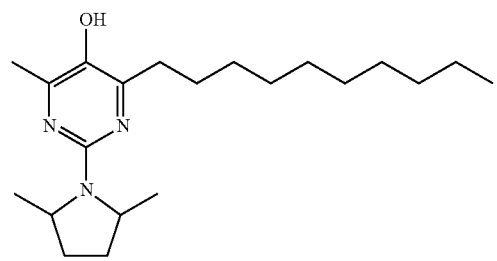 [SMILES: CCCCCCCCCCc1nc(N2C(C)CCC2C)nc(C)c1O] | 100 | | | | 40 | 10.7 |
| 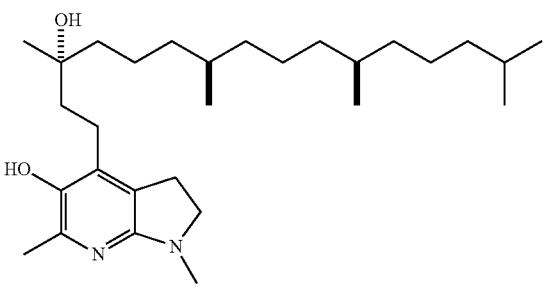 [SMILES: Cc1nc2c(c(CC[C@](C)(O)CCC[C@H](C)CCC[C@H](C)CCCC(C)C)c1O)CCN2C] | 100 | 15 | | 50 | 50 | |
| 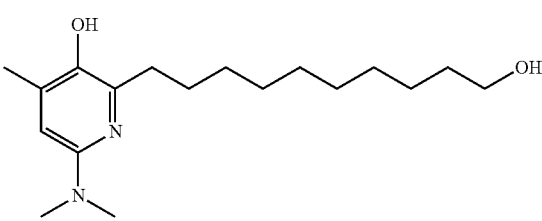 [SMILES: Cc1cc(N(C)C)nc(CCCCCCCCCCO)c1O] | 100 | 20 | 38 | 58 | 90 | |
| 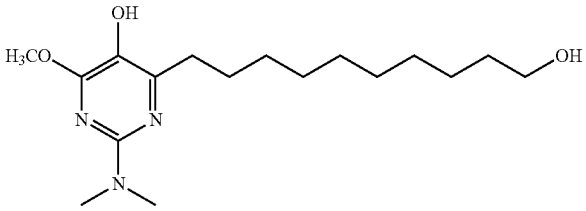 [SMILES: COc1nc(N(C)C)nc(CCCCCCCCCCO)c1O] | 100 | 25 | 50 | 40 | 62.5 | |
| 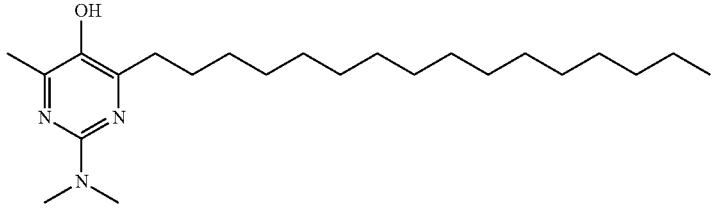 [SMILES: CCCCCCCCCCCCCCCCc1nc(N(C)C)nc(C)c1O] | 100 | 62 | 62 | 62 | 62 | |

TABLE 3-continued

| Compound | Control | NADH oxidase activity (%) | | | | IC$_{50}$ (μM) |
| --- | --- | --- | --- | --- | --- | --- |
| | | 10 μM | 5 μM | 2.5 μM | 1 μM | |
| (structure) | 100 | 70 | 70 | 70 | 90 | |
| (structure) | 100 | 10 | 38 | | 38 | |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A compound of formula:

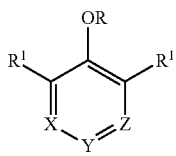

or a pharmaceutically acceptable salt thereof, wherein
R is hydrogen, or —CO($C_1$-$C_6$ alkyl);
$R^1$ is $C_1$-$C_6$ alkyl, $C_2$-$C_6$ alkenyl, $C_2$-$C_6$ alkynyl, or $C_1$-$C_6$ alkoxy, each optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$; where each R$^6$ independently is hydrogen or $C_1$-$C_6$ alkyl;
$R^2$ is $C_7$-$C_{20}$ alkyl, $C_7$-$C_{20}$ alkenyl, or $C_7$-$C_{20}$ alkynyl, each optionally substituted with one to four substituents selected from halogen, cyano, nitro, $C_1$-$C_6$ alkyl, halo($C_1$-$C_6$ alkyl), —OR$^7$, —NR$^7{}_2$, —CO$_2$R$^7$, and —CON(R$^7$)$_2$; where each R$^7$ independently is hydrogen, $C_1$-$C_6$ alkyl, or halo($C_1$-$C_6$ alkyl);
X is CR$^3$ or N; where R$^3$ is hydrogen, $C_1$-$C_6$ alkyl, halo($C_1$-$C_6$ alkyl), —OR$^7$, —NR$^7{}_2$, —CO$_2$R$^7$, or —CON(R$^7$)$_2$;
Y is CR$^4$; where R$^4$ is hydrogen, $C_1$-$C_6$ alkyl, halo($C_1$-$C_6$ alkyl), —OR$^7$, —NR$^7{}_2$, —CO$_2$R$^7$, —CON(R$^7$)$_2$, aryl, heteroaryl or heterocyclyl ring, which is optionally substituted with one to four substituents selected from halogen, cyano, nitro, $C_1$-$C_6$ alkyl, halo($C_1$-$C_6$ alkyl), —OR$^7$, —NR$^7{}_2$, —CO$_2$R$^7$, and —CON(R$^7$)$_2$; and Z is CR$^5$ or N; where R$^5$ is hydrogen, $C_1$-$C_6$ alkyl, halo($C_1$-$C_6$ alkyl), —OR$^7$, —NR$^7{}_2$, —CO$_2$R$^7$, or —CON(R$^7$)$_2$, or
where R$^4$ and R$^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —OR$^7$, —NR$^7{}_2$, —CO$_2$R$^7$, and —CON(R$^7$)$_2$,
provided that at least one of X and Z is N.

2. A compound according to claim 1, wherein R is hydrogen.

3. A compound according to claim 1, wherein
$R^1$ is $C_1$-$C_6$ alkyl, optionally substituted with one to four substituents selected from halogen, cyano, nitro, $C_1$-$C_6$ alkyl, halo($C_1$-$C_6$ alkyl), —OR$^6$, —NR$^6{}_2$, —CO$_2$R$^6$, and —CONR$^6{}_2$, and where each R$^6$ independently is hydrogen or $C_1$-$C_6$ alkyl.

4. A compound according to claim 3, wherein R$^1$ is unsubstituted $C_1$-$C_6$ alkyl.

5. A compound according to claim 4, wherein R$^1$ is methyl.

6. A compound according to claim 1, wherein R$^1$ is unsubstituted $C_1$-$C_6$ alkoxy.

7. A compound according to claim 1, wherein
$R^2$ is $C_7$-$C_{20}$ alkyl or $C_7$-$C_{20}$ alkenyl, each optionally substituted with one to four substituents selected from halogen, cyano, nitro, $C_1$-$C_6$ alkyl, halo($C_1$-$C_6$ alkyl), —OR$^7$, —NR$^7{}_2$, —CO$_2$R$^7$, and —CON(R$^7$)$_2$, where each R$^7$ independently is hydrogen, $C_1$-$C_6$ alkyl, or halo($C_1$-$C_6$ alkyl).

8. A compound according to claim 7, wherein
$R^2$ is $C_7$-$C_{20}$ alkyl optionally substituted with one to four substituents selected from halogen, cyano, nitro, $C_1$-$C_6$ alkyl, halo($C_1$-$C_6$ alkyl), —OR$^7$, —NR$^7{}_2$, —CO$_2$R$^7$, and —CON(R$^7$)$_2$, where each R$^7$ independently is hydrogen, $C_1$-$C_6$ alkyl, or halo($C_1$-$C_6$ alkyl).

9. A compound according to claim 8, wherein
$R^2$ is $C_7$-$C_{20}$ alkyl optionally substituted with one to four substituents selected from $C_1$-$C_6$ alkyl, halo($C_1$-$C_6$ alkyl), and —OR$^7$, where each R$^7$ independently is hydrogen, $C_1$-$C_6$ alkyl, or halo($C_1$-$C_6$ alkyl).

10. A compound according to claim 9, wherein $R^2$ is $C_7$-$C_{20}$ alkyl optionally substituted with one to four —$OR^7$ groups, where each $R^7$ independently is hydrogen, $C_1$-$C_6$ alkyl, or halo($C_1$-$C_6$ alkyl).

11. A compound according to claim 10, wherein $R^2$ is decyl or hexadecyl.

12. A compound according to claim 10, wherein $R^2$ is $C_7$-$C_{20}$ alkyl optionally substituted with one to four —OH groups.

13. A compound according to claim 12, wherein $R^2$ is hydroxydecyl or 3,7,11,15-tetramethyl-3-hydroxyhexadecanyl.

14. A compound according to claim 1, wherein
X is $CR^3$ or N; where $R^3$ is hydrogen, $C_1$-$C_6$ alkyl, halo($C_1$-$C_6$ alkyl), —$OR^7$, —$NR^7_2$, —$CO_2R^7$, or —$CON(R^7)_2$;
Y is $CR^4$; where $R^4$ is hydrogen, $C_1$-$C_6$ alkyl, halo($C_1$-$C_6$ alkyl), —$OR^7$, —$NR^7_2$, —$CO_2R^7$, —$CON(R^7)_2$, heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$; and
Z is $CR^5$ or N; where $R^5$ is hydrogen, $C_1$-$C_6$ alkyl, halo($C_1$-$C_6$ alkyl), —$OR^7$, —$NR^7_2$, —$CO_2R^7$, or —$CON(R^7)_2$, or
where $R^4$ and $R^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$.

15. A compound according to claim 1, wherein
X is $CR^3$ or N; where $R^3$ is hydrogen, $C_1$-$C_6$ alkyl, halo($C_1$-$C_6$ alkyl), —$OR^7$, —$NR^7_2$, —$CO_2R^7$, or —$CON(R^7)_2$;
Y is $CR^4$; where $R^4$ is hydrogen, $C_1$-$C_6$ alkyl, halo($C_1$-$C_6$ alkyl), —$OR^7$, —$NR^7_2$, —$CO_2R^7$, or —$CON(R^7)_2$; and
Z is $CR^5$ or N; where $R^5$ is hydrogen, $C_1$-$C_6$ alkyl, halo($C_1$-$C_6$ alkyl), —$OR^7$, —$NR^7_2$, —$CO_2R^7$, or —$CON(R^7)_2$, or
where $R^4$ and $R^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$.

16. A compound according to claim 1, wherein
X is N;
Y is $CR^4$, where $R^4$ is hydrogen, $C_1$-$C_6$ alkyl, halo($C_1$-$C_6$ alkyl), —$OR^7$, —$NR^7_2$, —$CO_2R^7$, or —$CON(R^7)_2$; and
Z is N.

17. A compound according to claim 16, wherein $R^4$ is —$OR^7$, or —$NR^7_2$.

18. A compound according to claim 17, wherein $R^4$ is —OH, —O($C_1$-$C_6$ alkyl), —$NH_2$, —NH($C_1$-$C_6$ alkyl), or —N($C_1$-$C_6$ alkyl)$_2$.

19. A compound according to claim 18, wherein $R^4$ is —$OCH_3$, or —$N(CH_3)_2$.

20. A compound according to claim 18, wherein $R^4$ is —$N(CH_3)_2$.

21. A compound according to claim 1, wherein
X is $CR^3$, where $R^3$ is hydrogen, $C_1$-$C_6$ alkyl, halo($C_1$-$C_6$ alkyl), —$OR^7$, —$NR^7_2$, —$CO_2R^7$, or —$CON(R^7)_2$;
Y is $CR^4$, where $R^4$ is hydrogen, $C_1$-$C_6$ alkyl, halo($C_1$-$C_6$ alkyl), —$OR^7$, —$NR^7_2$, —$CO_2R^7$, or —$CON(R^7)_2$; and
Z is N.

22. A compound according to claim 21, wherein $R^3$ is hydrogen or —$OCH_3$.

23. A compound according to claim 21, wherein $R^4$ is —$OR^7$, or —$NR^7_2$.

24. A compound according to claim 23, wherein $R^4$ is —OH, —O($C_1$-$C_6$ alkyl), —$NH_2$, —NH($C_1$-$C_6$ alkyl), or —N($C_1$-$C_6$ alkyl)$_2$.

25. A compound according to claim 24, wherein $R^4$ is —$OCH_3$, or —$N(CH_3)_2$.

26. A compound according to claim 24, wherein $R^4$ is —$N(CH_3)_2$.

27. A compound according to claim 1, wherein
X is N; Y is $CR^4$; and Z is $CR^5$, where
$R^4$ and $R^5$ together with the atoms to which they are attached form 5-7 member heteroaryl or heterocyclyl ring, which is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$.

28. A compound according to claim 27, wherein $R^4$ and $R^5$ together with the atoms to which they are attached form 5 or 6 member heteroaryl or heterocyclyl ring, which contains at least one nitrogen atom, and is optionally substituted with one to four substituents selected from halogen, cyano, nitro, $C_1$-$C_6$ alkyl, halo($C_1$-$C_6$ alkyl), —$OR^7$, —$NR^7_2$, —$CO_2R^7$, and —$CON(R^7)_2$.

29. A compound according to claim 28, having the following structure:

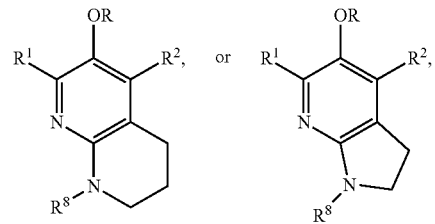

where $R^8$ is hydrogen or $C_1$-$C_6$ alkyl.

30. A compound according to claim 1, which is:

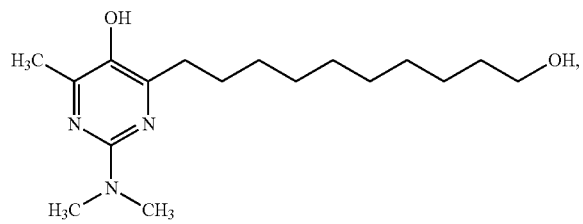

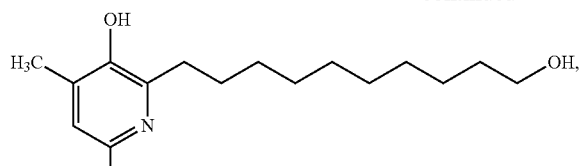
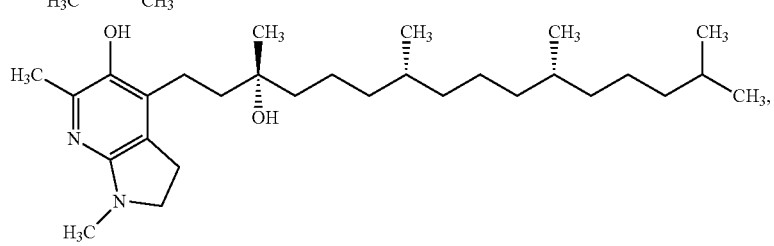
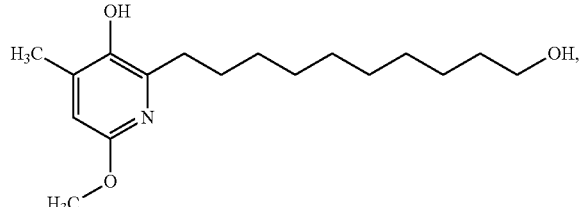
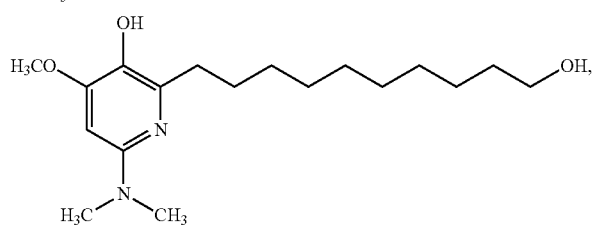
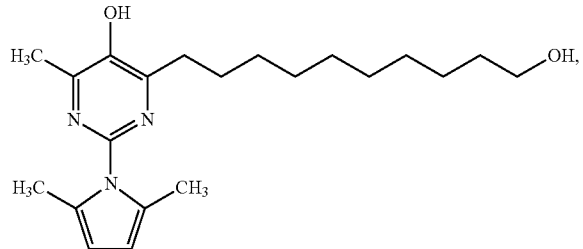
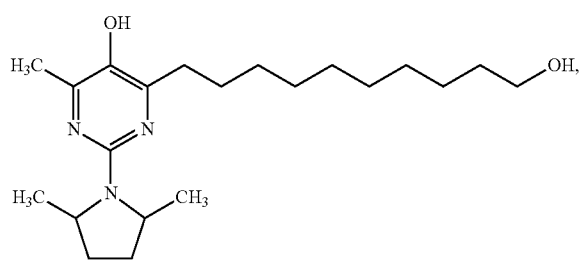
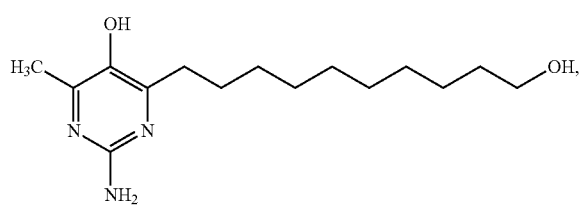

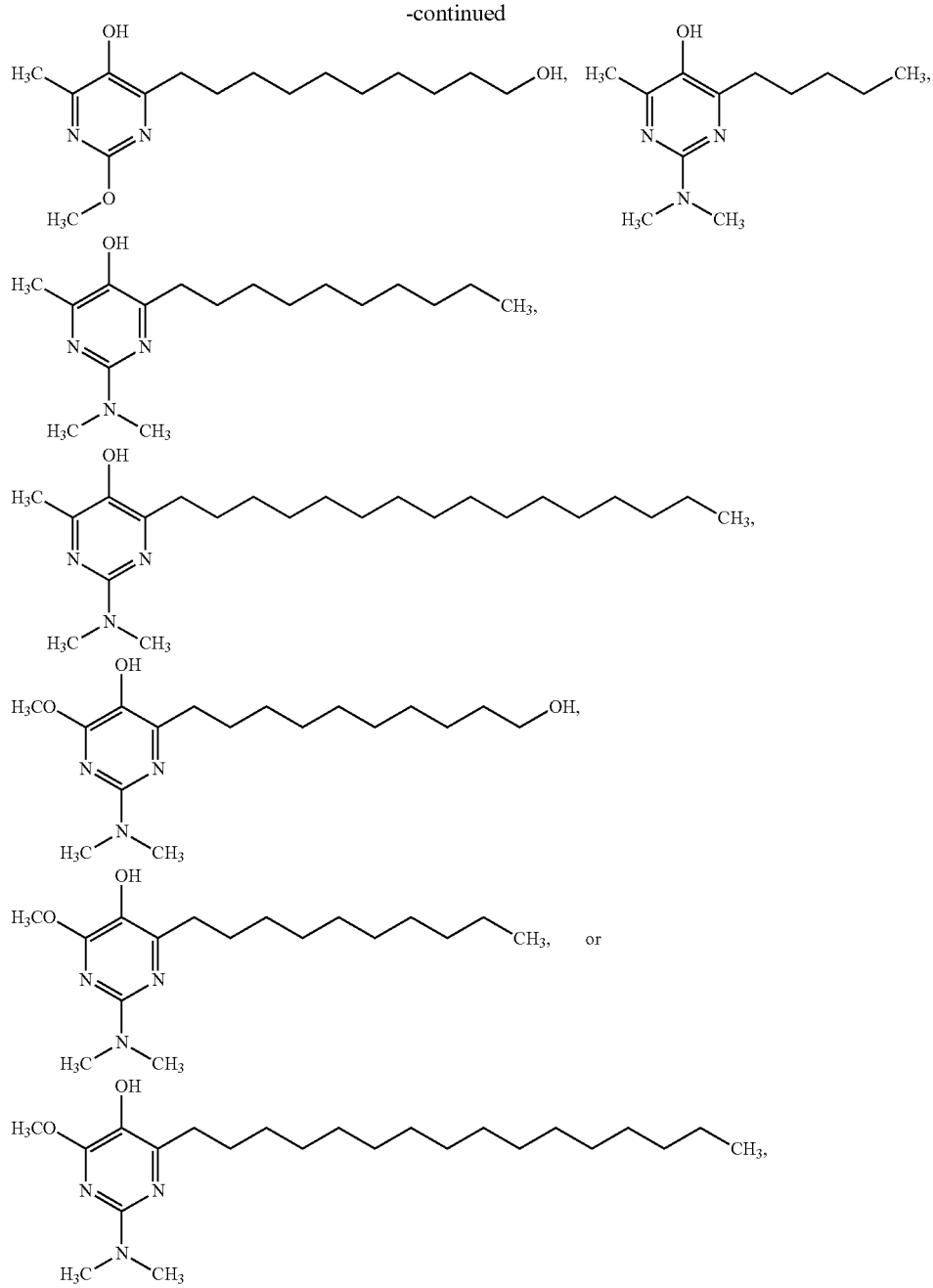
or a pharmaceutically acceptable salt thereof.
31. A pharmaceutical composition comprising a compound or a pharmaceutically acceptable salt according to claim 1 and an acceptable carrier, excipient and/or diluent.
* * * * *